(12) United States Patent
Kwon et al.

(10) Patent No.: US 11,145,825 B2
(45) Date of Patent: Oct. 12, 2021

(54) CONDENSED CYCLIC COMPOUND AND ORGANIC LIGHT-EMITTING DEVICE INCLUDING THE SAME

(71) Applicants: Samsung Electronics Co., Ltd.; Samsung SDI Co., Ltd., Yongin-si (KR)

(72) Inventors: Eunsuk Kwon, Suwon-si (KR); Sangmo Kim, Hwaseong-si (KR); Jongsoo Kim, Seoul (KR); Jhunmo Son, Yongin-si (KR); Soonok Jeon, Suwon-si (KR); Yeonsook Chung, Seoul (KR); Yongsik Jung, Yongin-si (KR); Jun Chwae, Seoul (KR)

(73) Assignees: SAMSUNG ELECTRONICS CO., LTD., Gyeonggi-Do (KR); SAMSUNG SDI CO., LTD., Gyeonggi-Do (KR)

(*) Notice: Subject to any disclaimer, the term of this patent is extended or adjusted under 35 U.S.C. 154(b) by 348 days.

(21) Appl. No.: 16/206,198

(22) Filed: Nov. 30, 2018

(65) Prior Publication Data

US 2019/0334095 A1  Oct. 31, 2019

(30) Foreign Application Priority Data

Apr. 27, 2018  (KR) .................. 10-2018-0049245

(51) Int. Cl.
| | | |
|---|---|---|
| *H01L 51/00* | (2006.01) | |
| *H01L 51/50* | (2006.01) | |
| *C09K 11/06* | (2006.01) | |
| *C07D 403/14* | (2006.01) | |
| *C09B 23/14* | (2006.01) | |
| *C09B 57/10* | (2006.01) | |

(52) U.S. Cl.
CPC ........ *H01L 51/0072* (2013.01); *C07D 403/14* (2013.01); *C09B 23/148* (2013.01); *C09B 57/10* (2013.01); *C09K 11/06* (2013.01); *H01L 51/0067* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| | | | |
|---|---|---|---|
| 9,960,365 B2 | 5/2018 | Jeon et al. | |
| 2012/0205636 A1* | 8/2012 | Kim | H01L 51/0072 257/40 |
| 2013/0341602 A1* | 12/2013 | Hikime | H01L 51/0074 257/40 |
| 2015/0144924 A1 | 5/2015 | Shin et al. | |
| 2015/0357576 A1* | 12/2015 | Kawamura | C07D 403/10 257/40 |

(Continued)

FOREIGN PATENT DOCUMENTS

| | | |
|---|---|---|
| JP | 2009-286980 A | 12/2009 |
| JP | 2010-238880 A | 10/2010 |

(Continued)

*Primary Examiner* — Robert S Loewe
(74) *Attorney, Agent, or Firm* — Cantor Colburn LLP

(57) ABSTRACT

A condensed cyclic compound represented by Formula 1:

$$Ar_1\text{-}(L_1)_{m1}\text{-}Ar_2 \quad \text{Formula 1}$$

wherein, in Formula 1, $Ar_1$, $Ar_2$, $L_1$, and m1 are the same as described in the specification.

19 Claims, 1 Drawing Sheet

(56) References Cited

U.S. PATENT DOCUMENTS

| | | | |
|---|---|---|---|
| 2016/0093811 A1* | 3/2016 | Jeon | C09K 11/025 257/40 |
| 2017/0133602 A1* | 5/2017 | Lee | H01L 51/0072 |
| 2017/0186974 A1 | 6/2017 | Jung et al. | |

FOREIGN PATENT DOCUMENTS

| | | | | |
|---|---|---|---|---|
| KR | 2017-0076474 A | 7/2017 | | |
| WO | 2014-011477 A1 | 1/2014 | | |
| WO | WO-2017104242 A1 * | 6/2017 | | G09F 9/30 |

\* cited by examiner

10

| 19 |
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2018-0049245, filed on Apr. 27, 2018, in the Korean Intellectual Property Office, and all the benefits accruing therefrom under 35 U.S.C. § 119, the content of which is incorporated herein in its entirety by reference.

BACKGROUND

1. Field

One or more embodiments relate to a condensed cyclic compound and an organic light-emitting device including the same.

2. Description of the Related Art

Organic light-emitting devices (OLEDs) are self-emission devices, that have wide viewing angles, high contrast ratios, short response times, as well as excellent characteristics in terms of brightness, driving voltage, and response speed, and that produce full-color images.

In an example, an organic light-emitting device includes an anode, a cathode, and an organic layer disposed between the anode and the cathode, wherein the organic layer includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as holes and electrons, recombine in the emission layer to produce excitons. These excitons transit from an excited state to a ground state, thereby generating light.

Various types of organic light emitting devices are known. However, there still remains a need in OLEDs having low driving voltage, high efficiency, high brightness, and long lifespan.

SUMMARY

One or more embodiments include a condensed cyclic compound and an organic light-emitting device including the same.

Additional aspects will be set forth in part in the description which follows and, in part, will be apparent from the description, or may be learned by practice of the presented embodiments.

An aspect provides a condensed cyclic compound represented by Formula 1 below:

$Ar_1$—$(L_1)_{m1}$—$Ar_2$   Formula 1

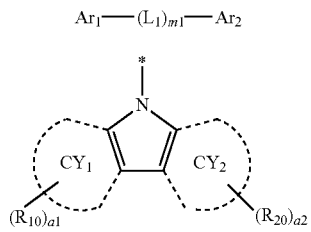

Formula 2

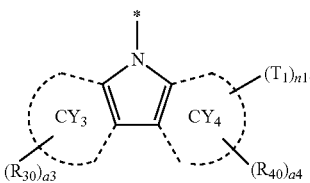

Formula 3

In Formulae 1 to 3, $L_1$ may be a substituted or unsubstituted $C_6$-$C_{60}$ carbocyclic group or a $C_2$-$C_{60}$ heterocyclic group, m1 may be an integer of 1 to 5, $Ar_1$ may be a group represented by Formula 2, $Ar_2$ may be a group represented by Formula 3, $T_1$ may be a substituted or unsubstituted 5-membered N-containing heterocyclic group, n1 may be an integer of 1 to 5, ring $CY_1$ to ring $CY_4$ may each independently be a $C_5$-$C_{60}$ carbocyclic group or a $C_2$-$C_{60}$ heterocyclic group, wherein ring $CY_1$ is a $C_6$-$C_{60}$ carbocyclic group having two or more rings or a $C_2$-$C_{60}$ heterocyclic group having two or more rings, $R_{10}$, $R_{20}$, $R_{30}$, and $R_{40}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$Si(Q_1)(Q_2)(Q_3)$, —$N(Q_4)(Q_5)$, and —$B(Q_6)(Q_7)$, a1 to a4 may each independently be an integer of 1 to 10,

* indicates a binding site to a neighboring atom, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, and a C$_1$-C$_{60}$ alkoxy group;

a C$_1$-C$_{60}$ alkyl group, a C$_2$-C$_{60}$ alkenyl group, a C$_2$-C$_{60}$ alkynyl group, and a C$_1$-C$_{60}$ alkoxy group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{11}$)(Q$_{12}$)(Q$_{13}$), —N(Q$_{14}$)(Q$_{15}$), and —B(Q$_{16}$)(Q$_{17}$);

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group;

a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), and —B(Q$_{26}$)(Q$_{27}$); and —Si(Q$_{31}$)(Q$_{32}$)(Q$_{33}$), —N(Q$_{34}$)(Q$_{35}$), and —B(Q$_{36}$)(Q$_{37}$), and Q$_1$ to Q$_7$, Q$_{11}$ to Q$_{17}$, Q$_{21}$ to Q$_{27}$, and Q$_{31}$ to Q$_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted heterocycloalkenyl group, a substituted or unsubstituted C$_8$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

Another aspect provides an organic light-emitting device including:

a first electrode;
a second electrode; and
an organic layer disposed between the first electrode and the second electrode, wherein the organic layer includes an emission layer, and
wherein the organic layer includes at least one of the condensed cyclic compound described above.

The emission layer may include the condensed cyclic compound, the emission layer may further include a dopant, and the condensed cyclic compound may be a host.

BRIEF DESCRIPTION OF THE DRAWING

These and/or other aspects will become apparent and more readily appreciated from the following description of the embodiments, taken in conjunction with FIGURE which is a schematic cross-sectional view of an organic light-emitting device according to an embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

The term "or" means "and/or." It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Unless otherwise defined, all terms (including technical and scientific terms) used herein have the same meaning as commonly understood by one of ordinary skill in the art to which this general inventive concept belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

A condensed cyclic compound according to an embodiment may be represented by Formula 1 illustrated below:

Formula 1

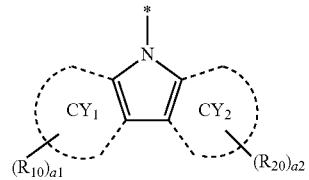

Formula 2

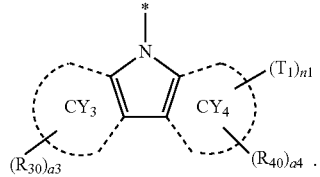

Formula 3

In Formula 1, $L_1$ may be a substituted or unsubstituted $C_5$-$C_{60}$ carbocyclic group or a $C_2$-$C_{60}$ heterocyclic group.

In an embodiment, $L_1$ may be a group represented by one selected from Formulae 4-1 to 4-3:

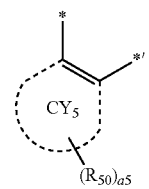

Formula 4-1

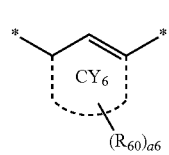

Formula 4-2

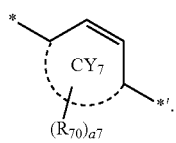

Formula 4-3

In Formulae 4-1 to 4-3, $CY_5$ to $CY_7$ may each independently be selected from a $C_5$-$C_{30}$ carbocyclic group and a $C_2$-$C_{60}$ heterocyclic group, $R_{50}$, $R_{60}$, and $R_{70}$ may each independently be selected from hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{41}$)($Q_{42}$)($Q_{43}$), —N($Q_{44}$)($Q_{45}$), and —B($Q_{46}$)($Q_{47}$), $Q_{41}$ to $Q_{47}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group, a5 to a7 may be an integer of 0 to 10, and \* and \*' each indicate a binding site to a neighboring atom.

In an embodiment, in Formulae 4-1 to 4-3, $CY_5$ to $CY_7$ may each independently be selected from a benzene group, a naphthalene group, and a fluorene group, a carbazole group, a dibenzofuran group, and a dibenzothiophene group, but embodiments of the present disclosure are not limited thereto.

In one or more embodiments, $L_1$ may be a group represented by one selected from Formulae 40-1 to 40-12:

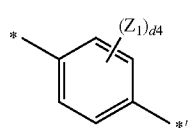

40-1

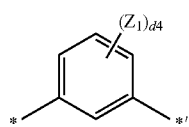

40-2

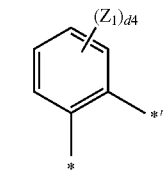

40-3

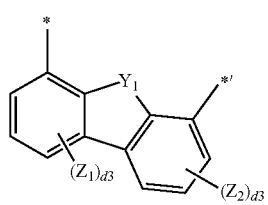

40-4

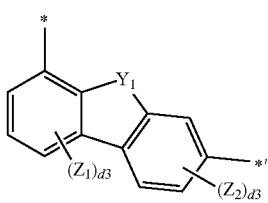

40-5

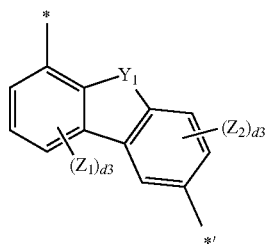

40-6

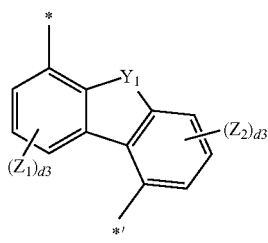

40-7

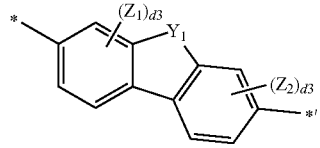

40-8

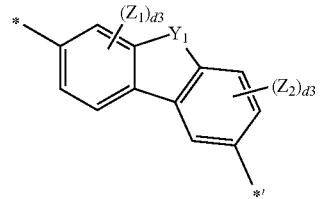

40-9

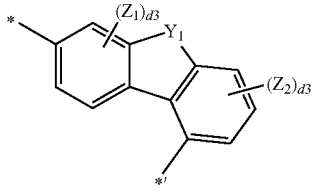

40-10

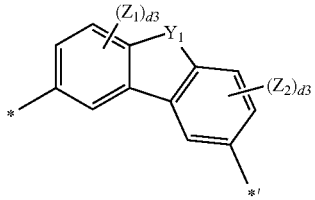

40-11

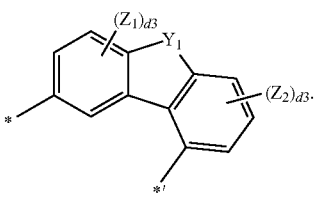

40-12

In Formulae 40-1 to 40-12, $Y_1$ may be O, S, C($Z_3$)($Z_4$), N($Z_5$), or Si($Z_6$)($Z_7$), $Z_1$ to $Z_7$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —Si($Q_{53}$)($Q_{54}$)($Q_{55}$), $Q_{53}$ to $Q_{55}$ may each independently be selected from a $C_1$-$C_{10}$ alkyl group, a $C_1$-$C_{10}$ alkoxy group, a phenyl group, a biphenyl group, a terphenyl group, and a naphthyl group, d3 may be an integer of 1 to 3, d4 may be an integer of 1 to 4, and

* and *' each indicate a binding site to a neighboring atom.

In Formula 1, m1 may be an integer of 1 to 5.

In an embodiment, m1 may be an integer of 1 to 3, but embodiments of the present disclosure are not limited thereto.

In Formula 1, $Ar_1$ may be a group represented by Formula 2, and $Ar_2$ may be a group represented by Formula 3.

In Formula 3, $T_1$ may be a substituted or unsubstituted 5-membered heterocyclic group containing nitrogen (N).

In an embodiment, $T_1$ may be a group represented by one selected from Formulae 5-1 to 5-7:

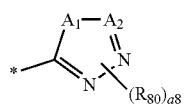

5-1

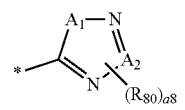

5-2

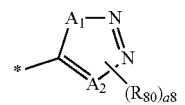

5-3

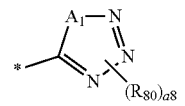

5-4

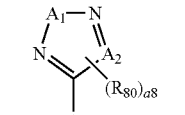

5-5

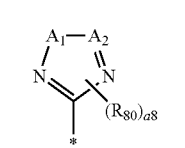

5-6

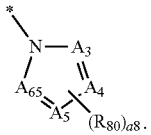

5-7

In Formulae 5-1 to 5-7, $A_1$ may be O, S, or N, $A_2$ may be C or Si, $A_3$ to $A_6$ may be N, C, or Si, wherein at least two selected from $A_3$ to $A_6$ may each be N, $R_{80}$ may be selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a phenyl group, a biphenyl group, a terphenyl group, a naphthyl group, a fluorenyl group, a carbazolyl group, a dibenzofuranyl group, and a dibenzothiophenyl group; and a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, and a naphthyl group, a8 may be an integer of 1 to 3, and

* indicates a binding site to a neighboring atom.

In one or more embodiments, $T_1$ may be a group represented by one selected from Formulae 6-1 to 6-8:

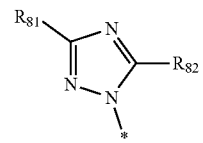

6-1

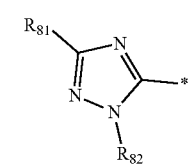

6-2

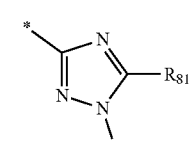

6-3

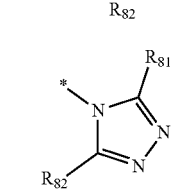

6-4

-continued

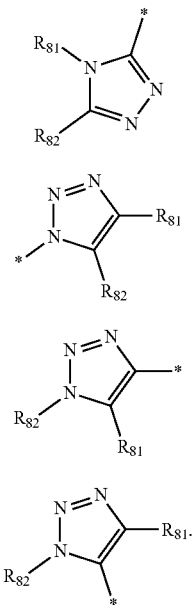

6-5

6-6

6-7

6-8

In Formulae 6-1 to 6-8, $R_{81}$ and $R_{82}$ may each independently be selected from: hydrogen, deuterium, —F, —Cl, —Br, —I, a cyano group, a $C_1$-$C_{20}$ alkyl group, and a alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a phenyl group, a biphenyl group, a terphenyl group, a naphthyl group, a fluorenyl group, a carbazolyl group, a dibenzofuranyl group, and a dibenzothiophenyl group; and a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, and a naphthyl group, and

* indicates a binding site to a neighboring atom.

For example, $T_1$ may be a group represented by one selected from Formulae 7-1 to 7-4:

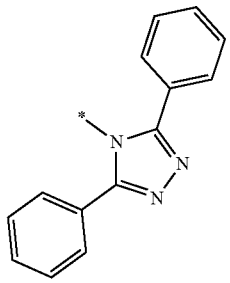

7-1

7-2

-continued

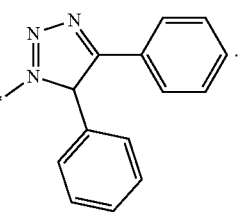

7-3

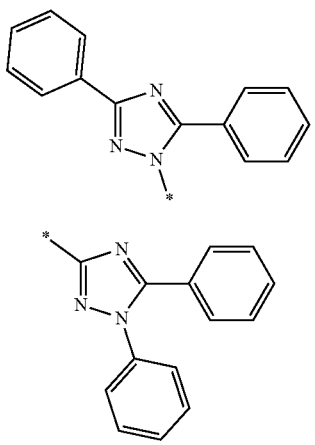

7-4

In Formulae 7-1 to 7-4,

* indicates a binding site to a neighboring atom.

In Formula 3, n1 may be an integer of 1 to 5.

For example, n1 may be an integer of 1 to 3.

In an embodiment, n1 may be 1, but embodiments of the present disclosure are not limited thereto.

In Formulae 2 and 3, ring $CY_1$ to ring $CY_4$ may each independently be a $C_5$-$C_{60}$ carbocyclic group or a $C_2$-$C_{60}$ heterocyclic group, wherein ring $CY_1$ may be a $C_6$-$C_{60}$ carbocyclic group including at least two rings or a $C_2$-$C_{60}$ heterocyclic group including at least two rings.

For example, $CY_1$ may be selected from a naphthalene group, a fluorene group, a carbazole group, a dibenzofuran group, and a dibenzothiophene group.

In one or more embodiments, $CY_2$ to $CY_4$ may each independently be selected from a benzene group, a naphthalene group, a fluorene group, a carbazole group, a dibenzofuran group, and a dibenzothiophene group.

In an embodiment, $CY_1$ may be selected from a naphthalene group, a fluorene group, a carbazole group, a dibenzofuran group, and a dibenzothiophene group, and $CY_2$ and $CY_3$ may each independently be selected from a benzene group, a naphthalene group, a fluorene group, a carbazole group, a dibenzofuran group, and a dibenzothiophene group.

In one or more embodiments, $CY_1$ may be selected from a naphthalene group, a fluorene group, a carbazole group, a dibenzofuran group, and a dibenzothiophene group, and $CY_2$ may be a benzene group.

In one or more embodiments, $CY_4$ may be a benzene group.

In one or more embodiments, $CY_3$ and $CY_4$ may each be a benzene group.

In an embodiment, $Ar_1$ may be selected from groups represented by Formulae 2-1 to 2-6, and $Ar_2$ may be selected from groups represented by Formulae 3-1 to 3-7:

2-1
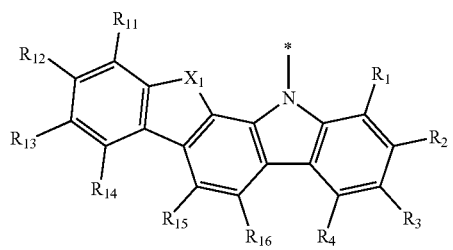
2-2
2-3
2-4
2-5
2-6
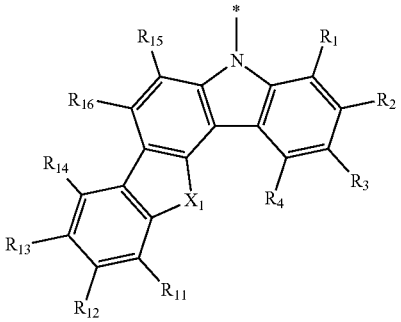
3-1
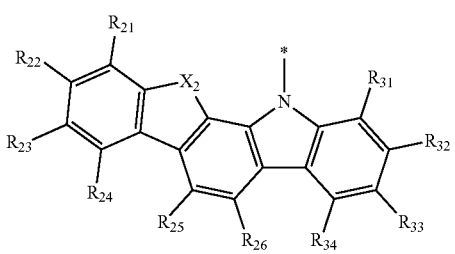
3-2
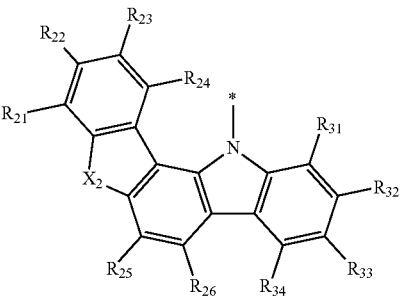
3-3
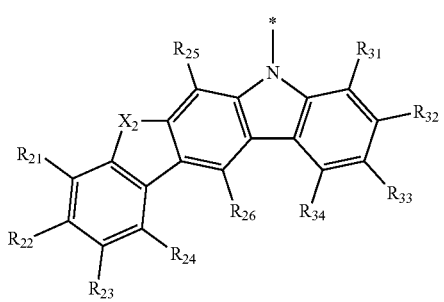
3-4
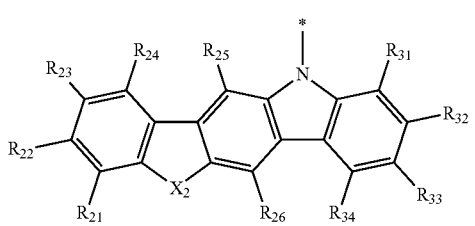

-continued 3-5
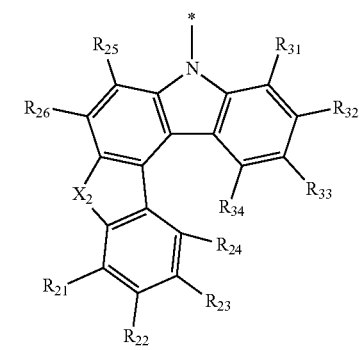

3-6
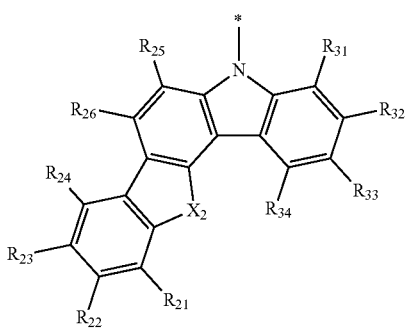

3-7
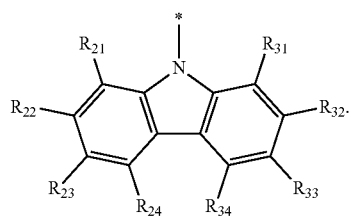

In Formulae 2-1 to 2-7 and 3-1 to 3-7:

$X_1$ may be $C(R_{17})(R_{18})$, $N(R_{19})$, O, or S, $X_2$ may be $C(R_{27})(R_{26})$, $N(R_{29})$, O, or S, $Z_5$ may be $C(R_5)(R_6)$, $R_1$ to $R_6$, $R_{11}$ to $R_{19}$, $R_{21}$ to $R_{29}$, and $R_{31}$ to $R_{34}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienoyrimidinyl group, a phenoxazinyl group, a pyridobenzoxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienoyrimidinyl group, a phenoxazinyl group, a pyridobenzoxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), $Q_1$ to $Q_7$ and $Q_{31}$ to $Q_{37}$ may each independently be selected from hydrogen, a $C_1$-$C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, and

* indicates a binding site to a neighboring atom.

In an embodiment, in Formulae 2-1 to 2-6 and 3-1 to 3-7, $R_1$ to $R_6$, $R_{11}$ to $R_{19}$, $R_{21}$ to $R_{29}$, and $R_{31}$ to $R_{34}$ may each independently be selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), and $Q_1$ to $Q_3$ and $Q_{31}$ to $Q_{33}$ may each independently be selected from hydrogen, a $C_1$-$C_{20}$ alkyl group, a $C_1$-$C_{20}$ alkoxy group, a phenyl group, a biphenyl group, a terphenyl group, and a naphthyl group, but embodiments of the present disclosure are not limited thereto.

In an embodiment, in Formulae 2-1 to 2-6 and Formulae 3-1 to 3-7, $X_1$ may be N($R_{19}$), O, or S.

In an embodiment, in Formula 1, $Ar_2$ may be a group represented by Formula 3-7, but embodiments of the present disclosure are not limited thereto.

In Formulae 2 and 3, $R_{10}$, $R_{20}$, $R_{30}$, and $R_{40}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$).

In Formulae 2 and 3, a1 to a4 may each independently be an integer of 1 to 10.

At least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_5$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{16}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, —CD$_3$, —CD$_2$H, —CDH$_2$, —CF$_3$, —CF$_2$H, —CFH$_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_1$-C$_{10}$ heterocycloalkyl group, a C$_3$-C$_{10}$ cycloalkenyl group, a C$_1$-C$_{10}$ heterocycloalkenyl group, a C$_6$-C$_{60}$ aryl group, a C$_6$-C$_{60}$ aryloxy group, a C$_6$-C$_{60}$ arylthio group, a C$_1$-C$_{60}$ heteroaryl group, a monovalent non-aromatic condensed polycyclic group, a monovalent non-aromatic condensed heteropolycyclic group, —Si(Q$_{21}$)(Q$_{22}$)(Q$_{23}$), —N(Q$_{24}$)(Q$_{25}$), and —B(Q$_{26}$)(Q$_{27}$); and —Si(Q$_{31}$)(Q$_{32}$)(Q$_{33}$), —N(Q$_{34}$)(Q$_{35}$), and —B(Q$_{36}$)(Q$_{37}$), and Q$_1$ to Q$_7$, Q$_{11}$ to Q$_{17}$, Q$_{21}$ to Q$_{27}$, and Q$_{31}$ to Q$_{37}$ may each independently be selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted C$_1$-C$_{60}$ alkyl group, a substituted or unsubstituted C$_2$-C$_{60}$ alkenyl group, a substituted or unsubstituted C$_2$-C$_{60}$ alkynyl group, a substituted or unsubstituted C$_1$-C$_{60}$ alkoxy group, a substituted or unsubstituted C$_3$-C$_{10}$ cycloalkyl group, a substituted or unsubstituted C$_1$-C$_{10}$ heterocycloalkyl group, a substituted or unsubstituted C$_3$-C$_{10}$ cycloalkenyl group, a substituted or unsubstituted C$_1$-C$_{10}$ heterocycloalkenyl group, a substituted or unsubstituted C$_6$-C$_{60}$ aryl group, a substituted or unsubstituted C$_6$-C$_{60}$ aryloxy group, a substituted or unsubstituted C$_6$-C$_{60}$ arylthio group, a substituted or unsubstituted C$_1$-C$_{60}$ heteroaryl group, a substituted or unsubstituted monovalent non-aromatic condensed polycyclic group, and a substituted or unsubstituted monovalent non-aromatic condensed heteropolycyclic group.

In an embodiment, the condensed cyclic compound represented by Formula 1 may be selected from Compounds 1 to 638, but embodiments of the present disclosure are not limited thereto:

1

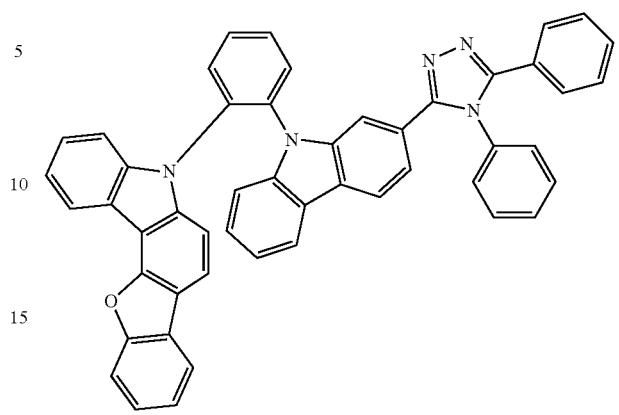

2

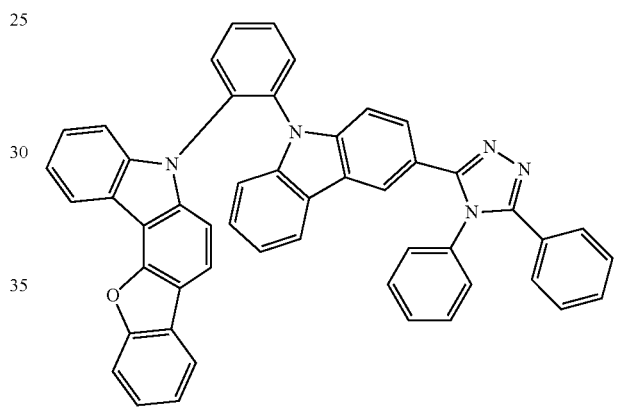

3

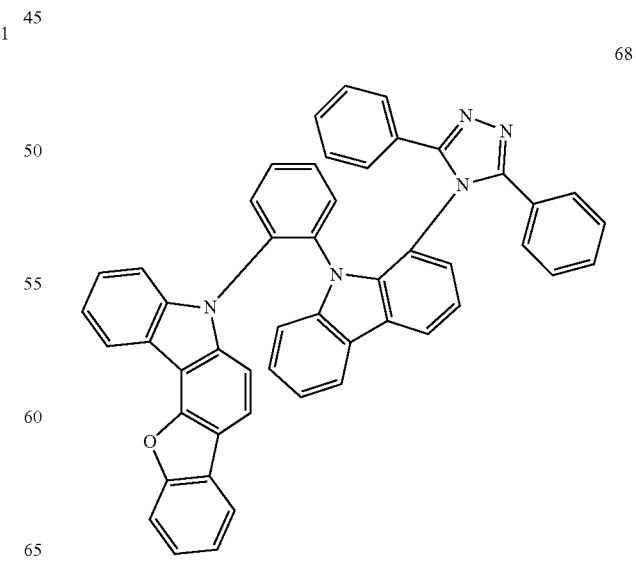

68

67
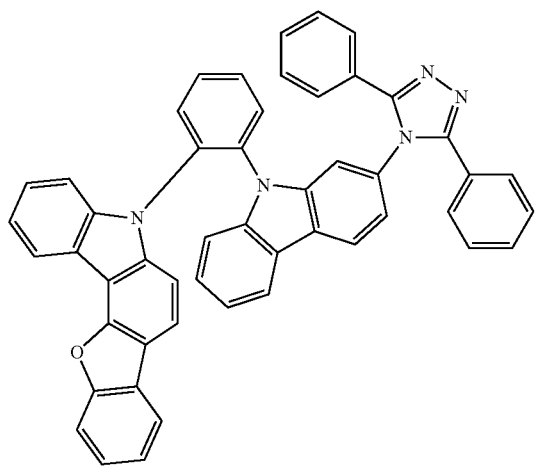
70
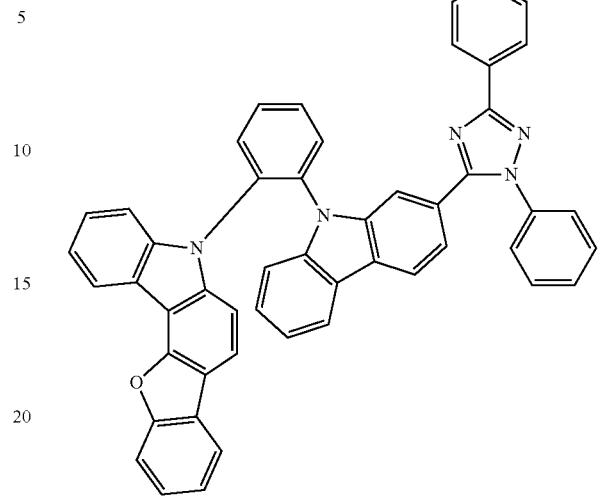
66
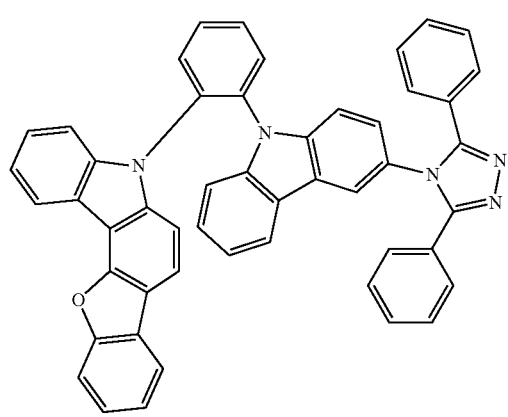
71
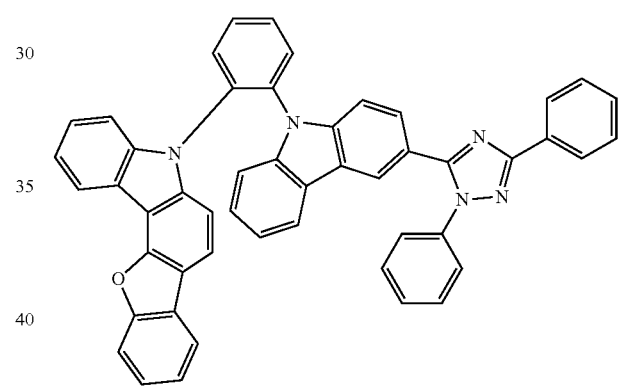
69
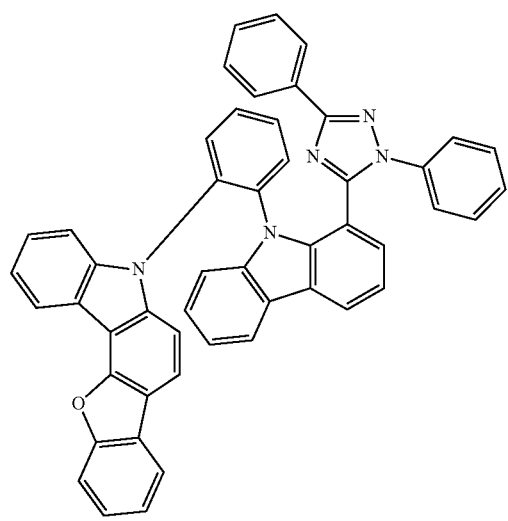
132
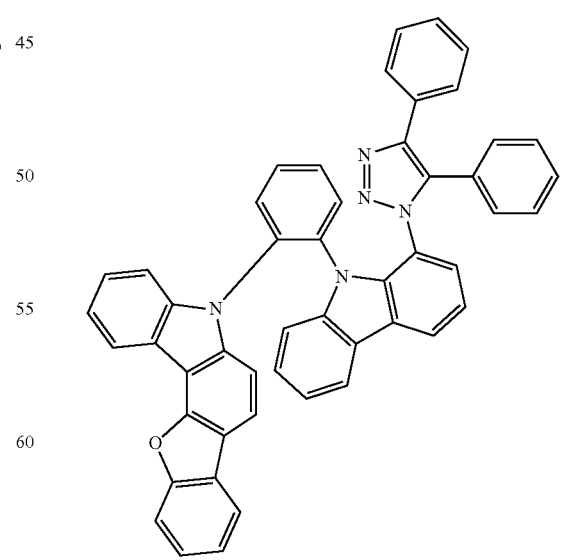

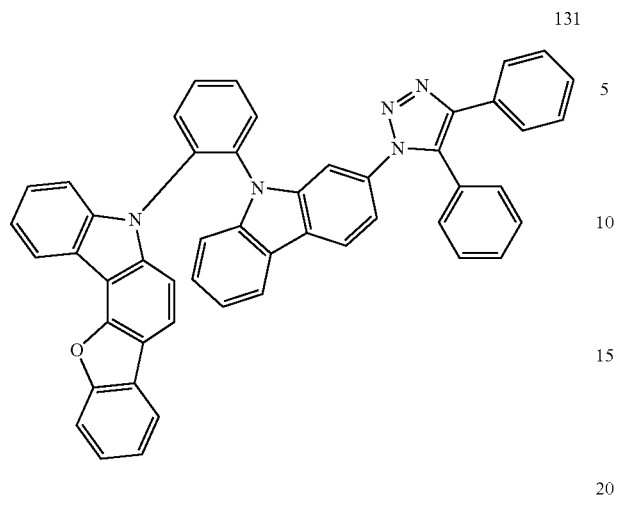
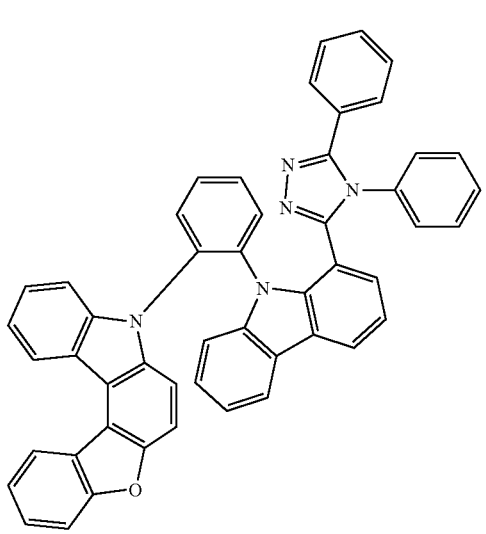
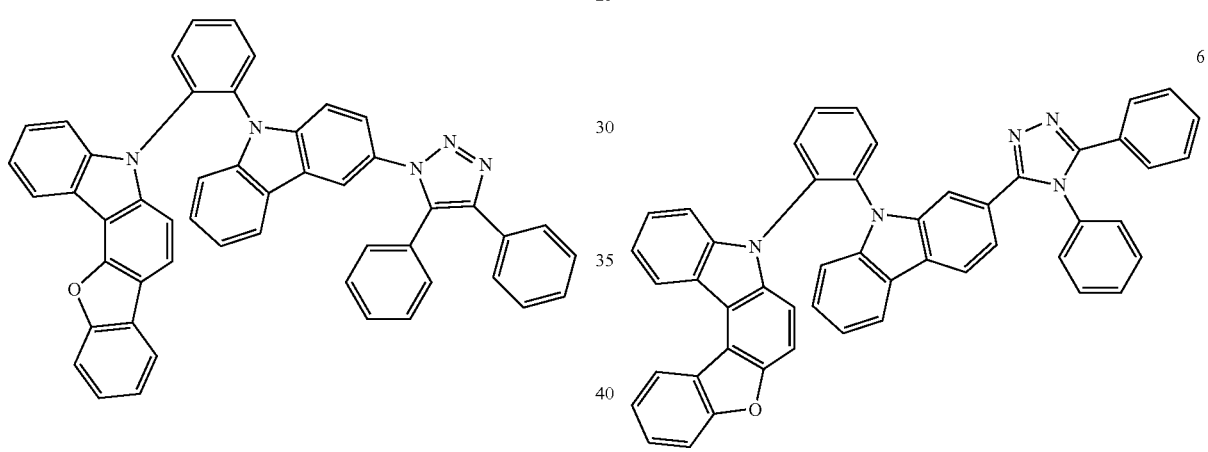
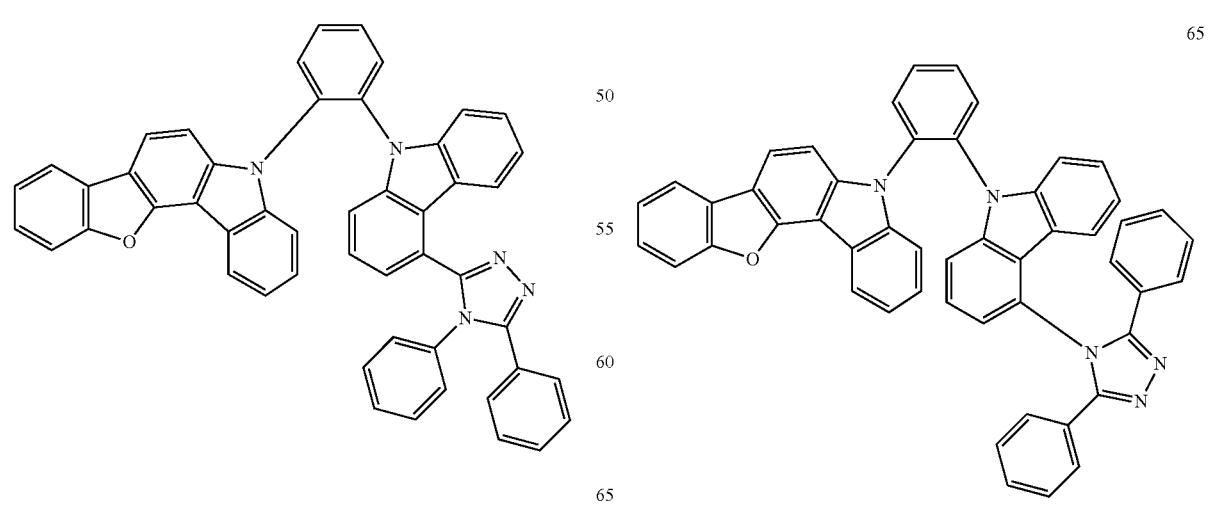

64
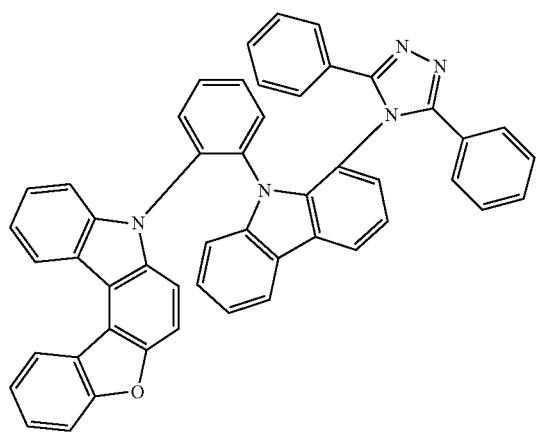
73
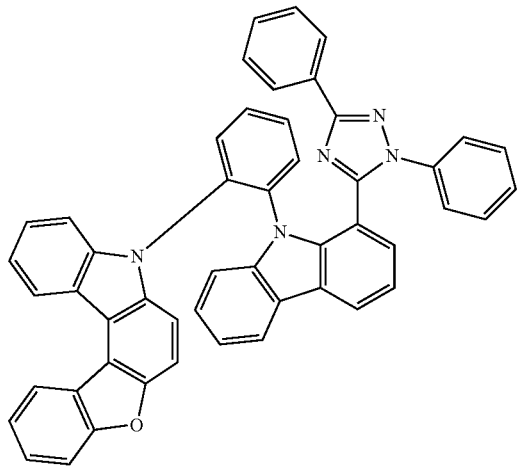
63
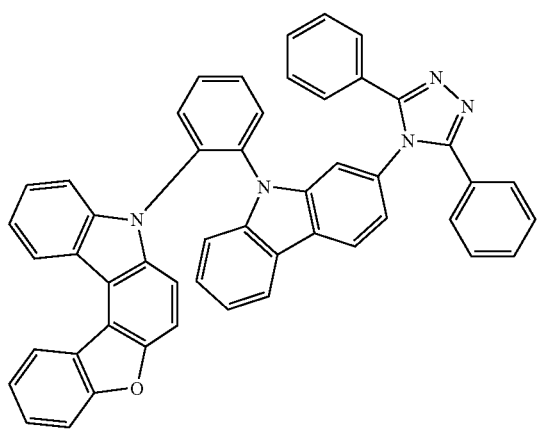
74
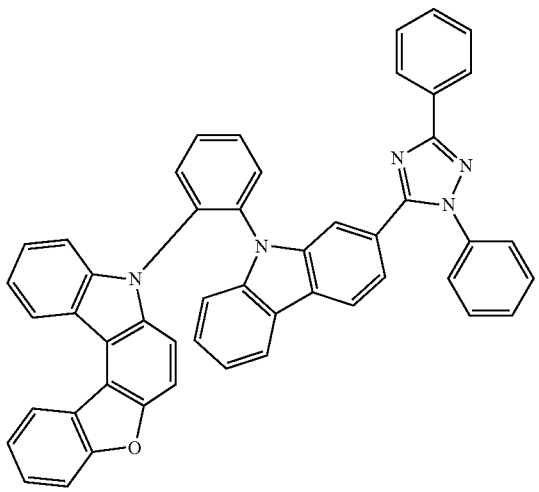
72
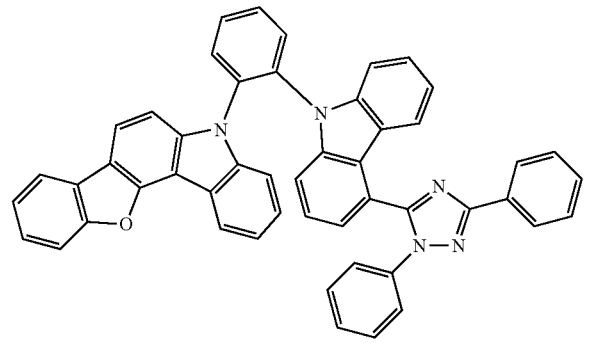
129
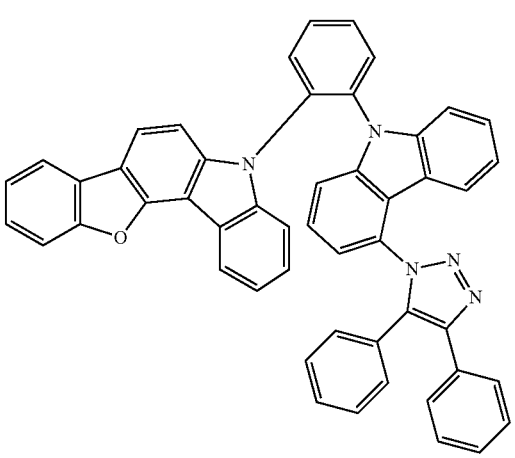

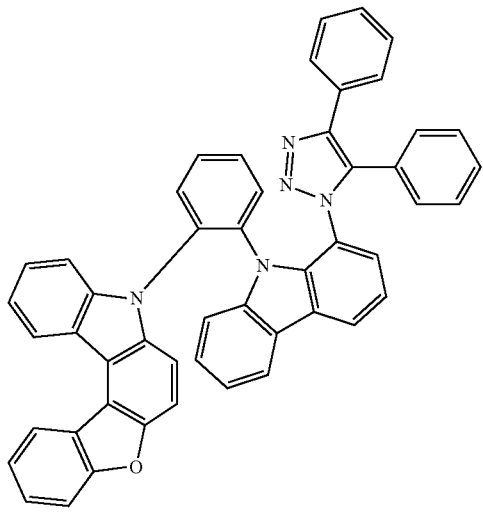
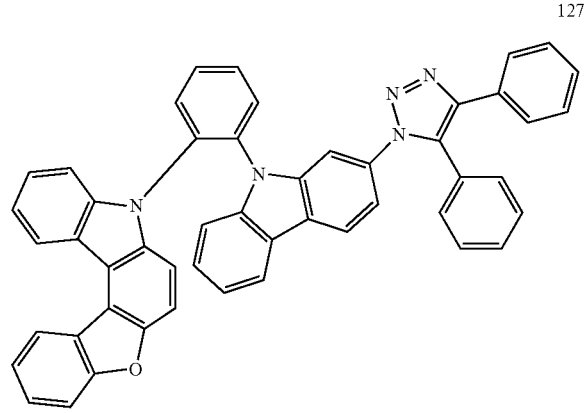
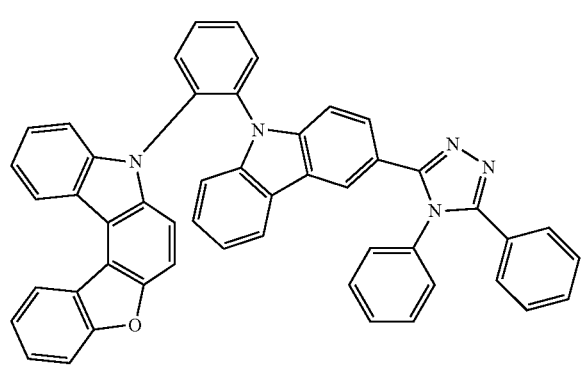
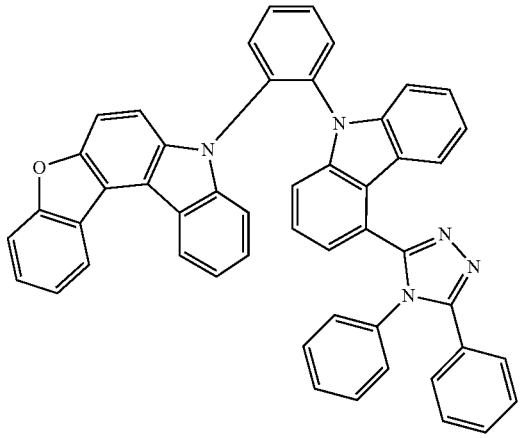
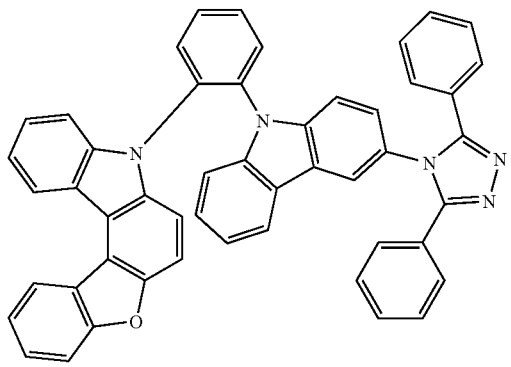

-continued
61
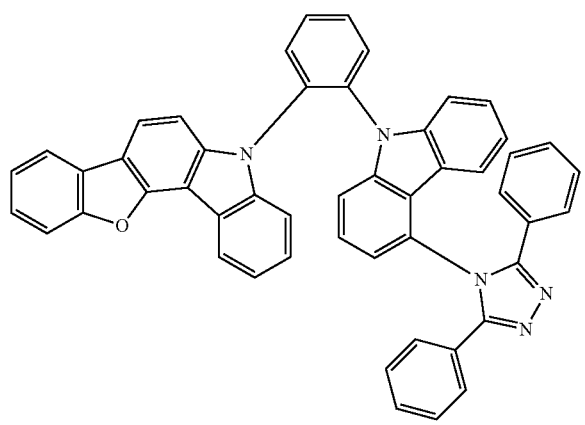
60
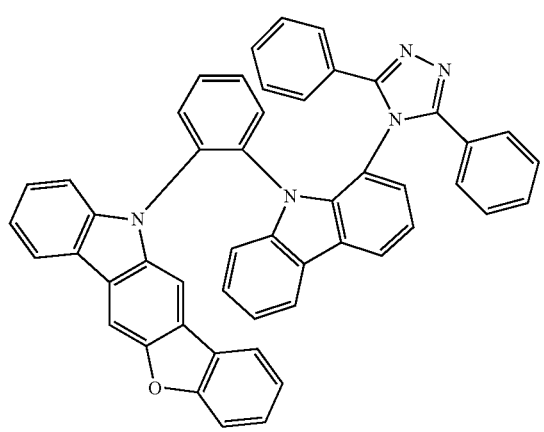
75
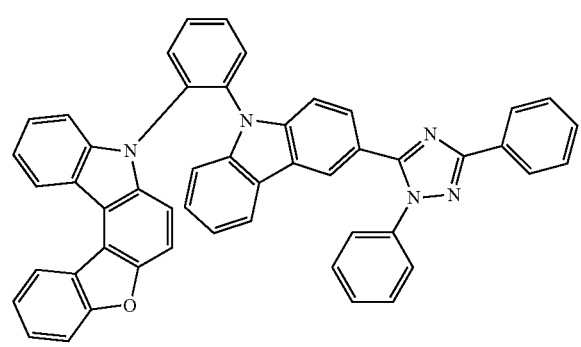
-continued
77
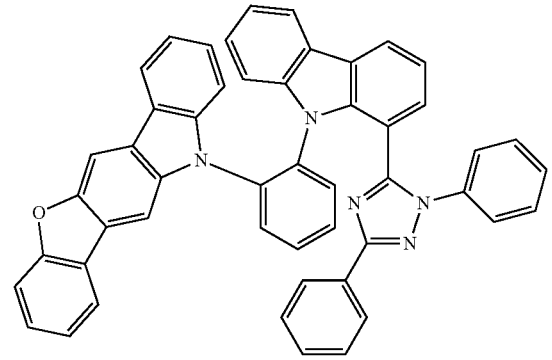
126
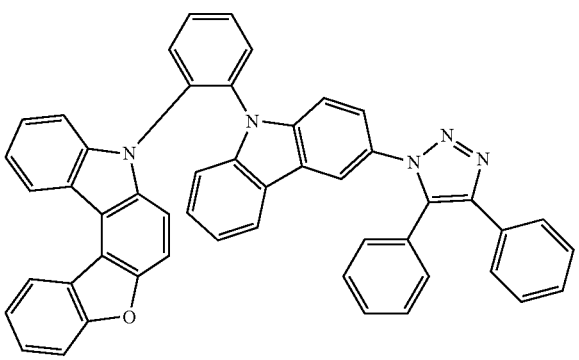
125
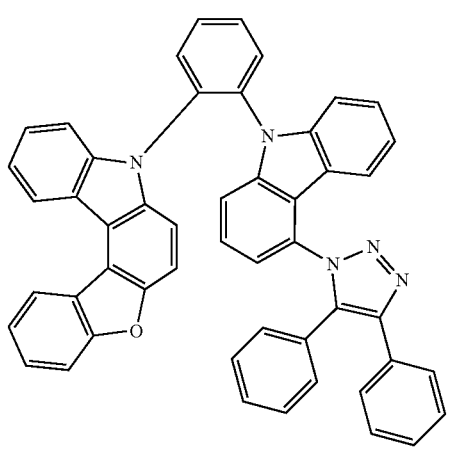
76

31
-continued
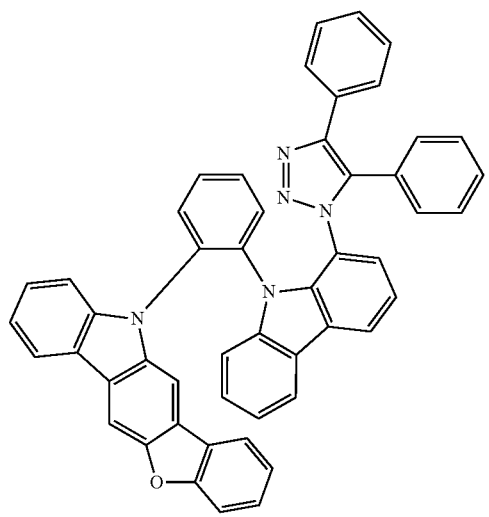
124
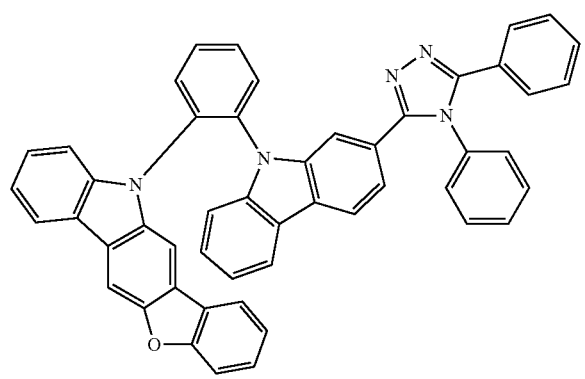
10
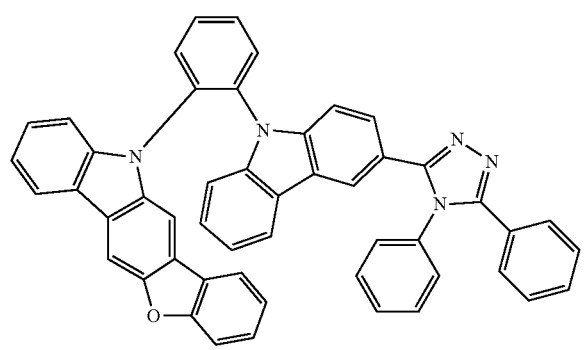
11
32
-continued
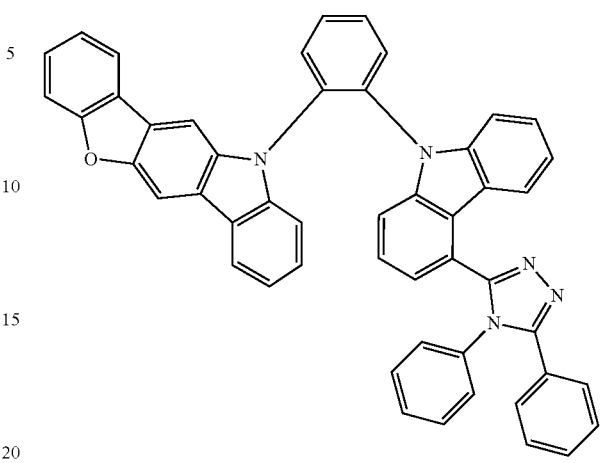
12
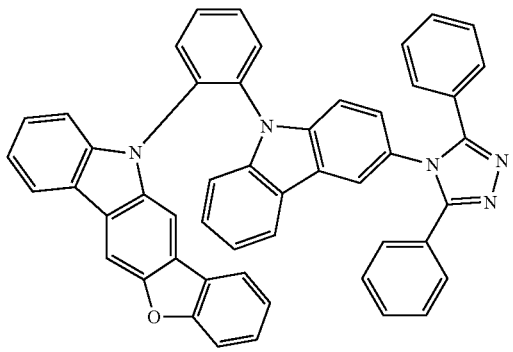
58

-continued
57
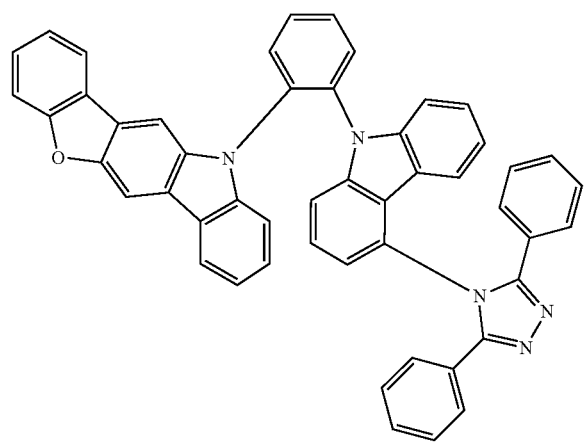
78
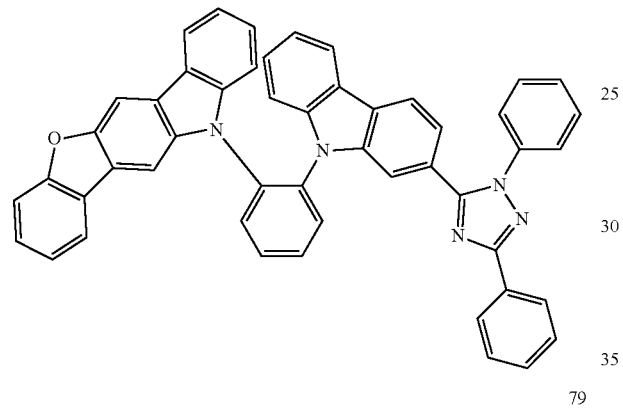
79
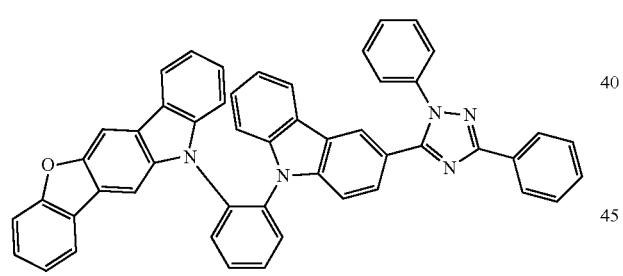
80
-continued
123
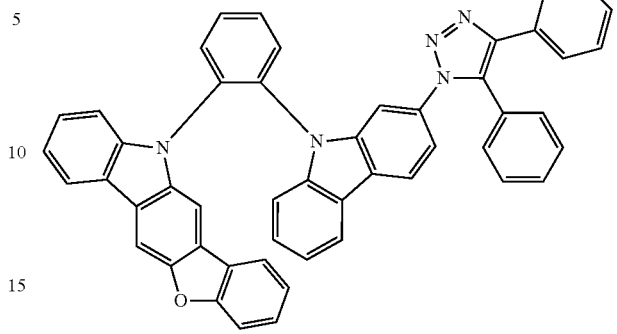
122
121
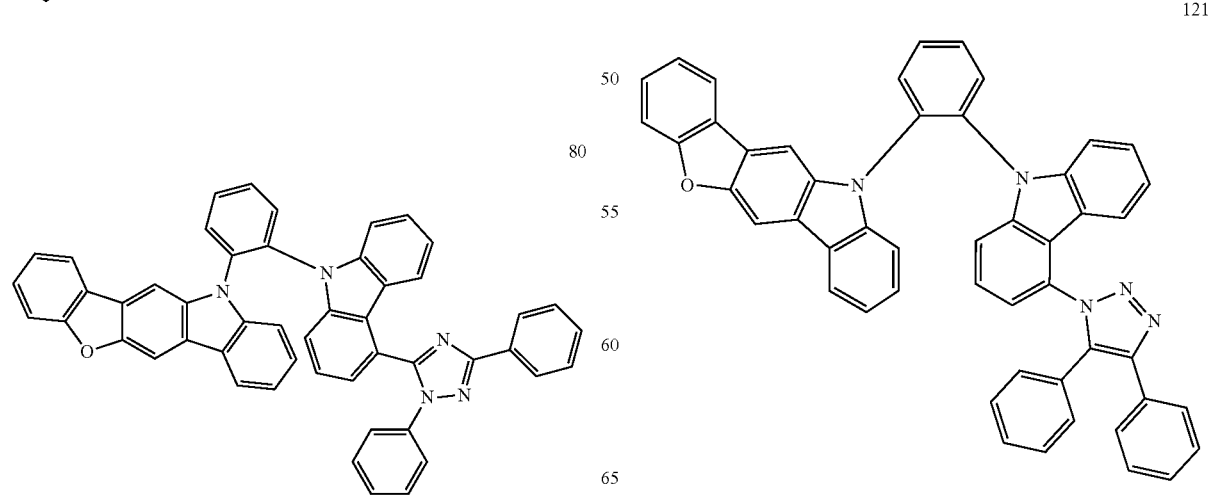

13
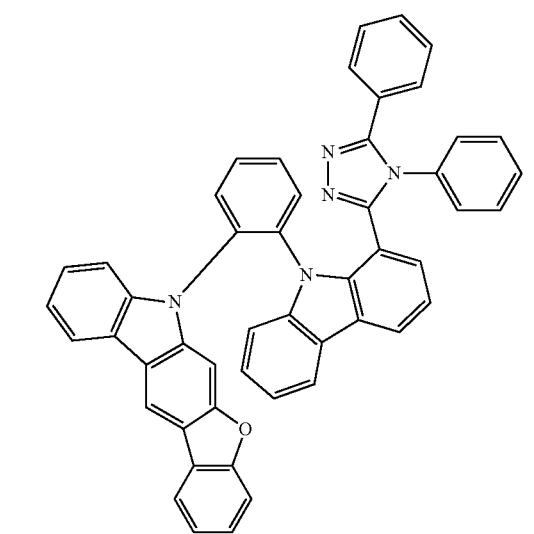
14
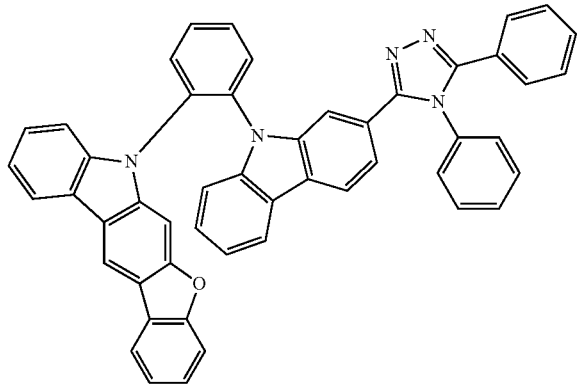
15
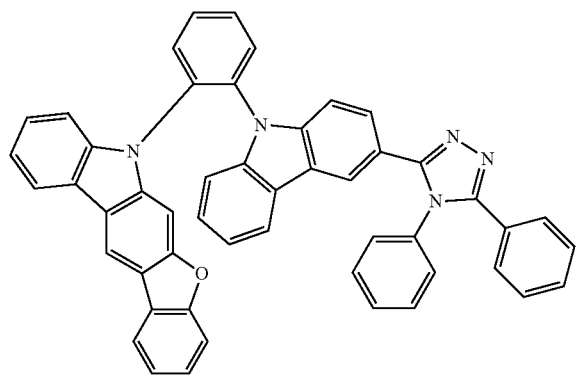
56
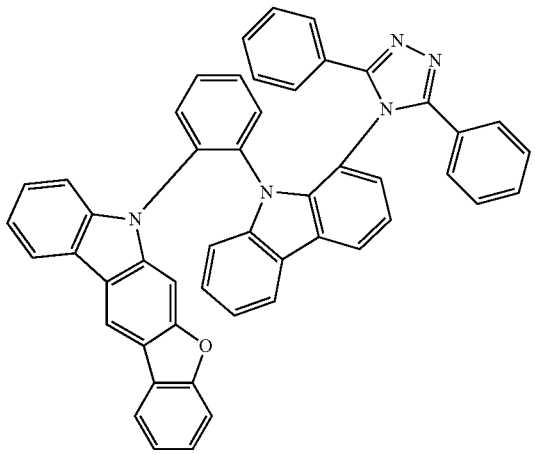
55
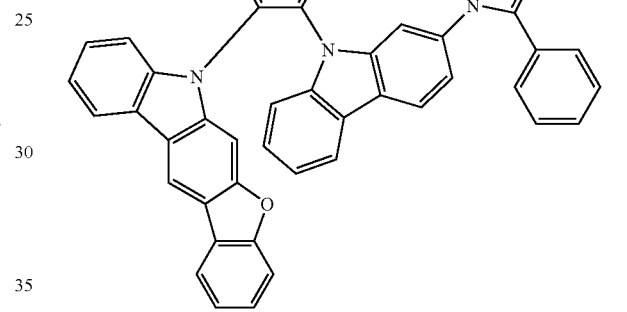
54
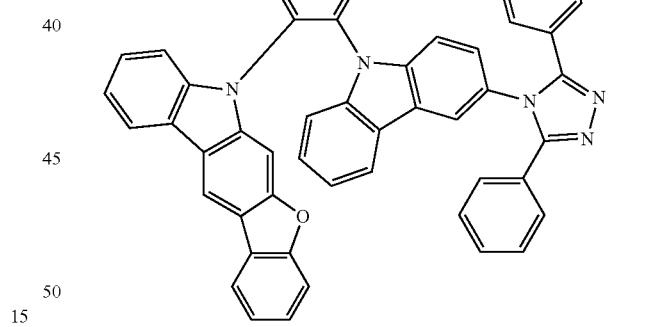
81
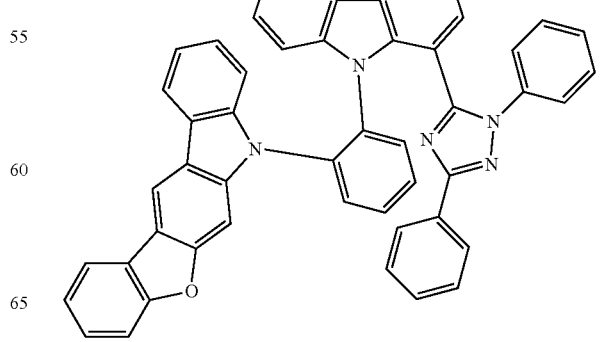

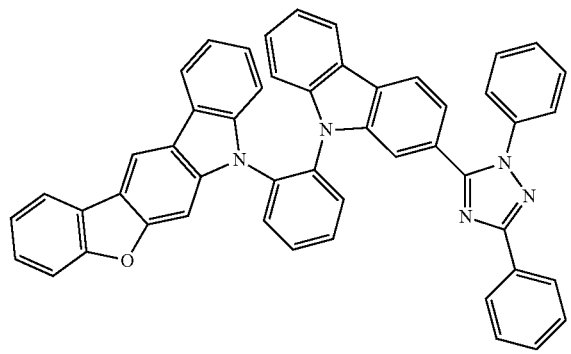
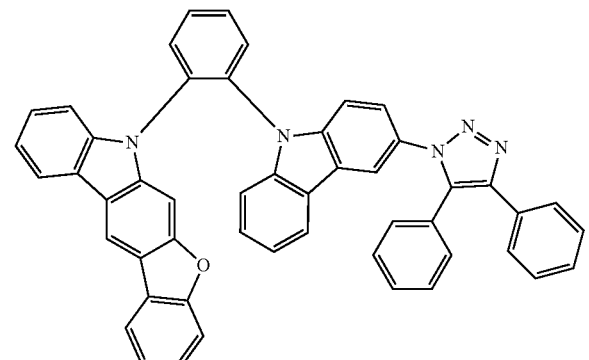
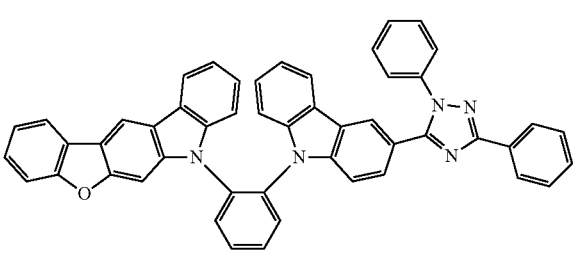
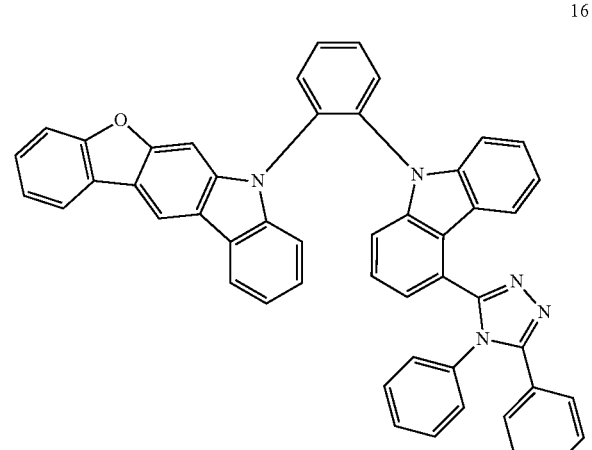
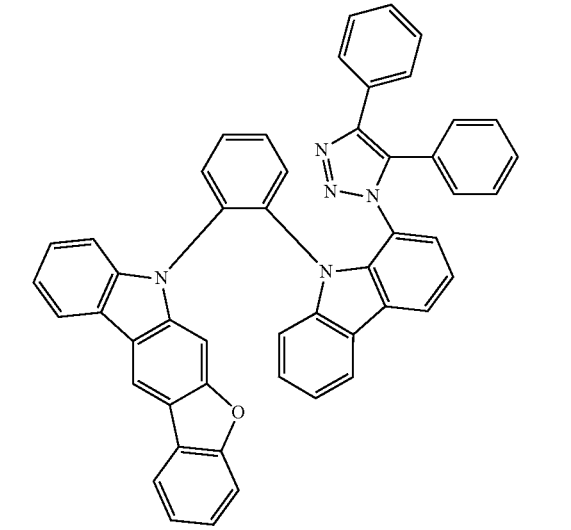
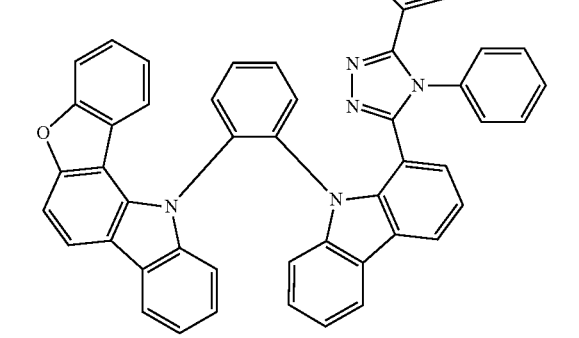
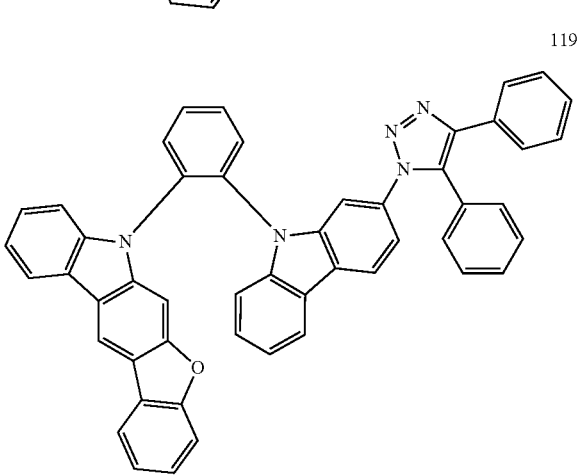
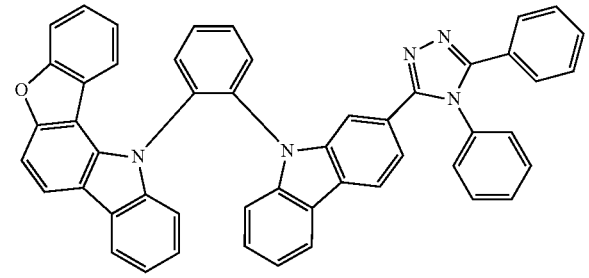

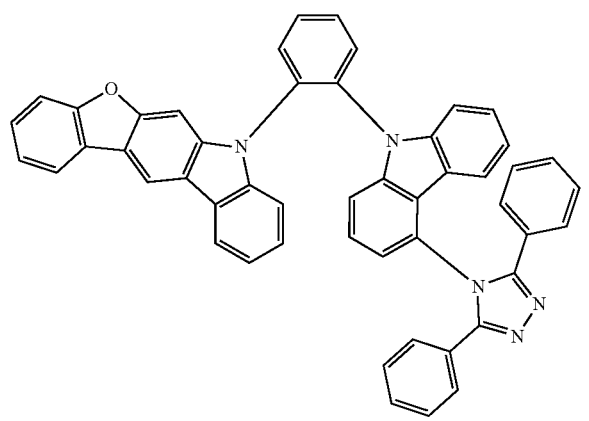
53
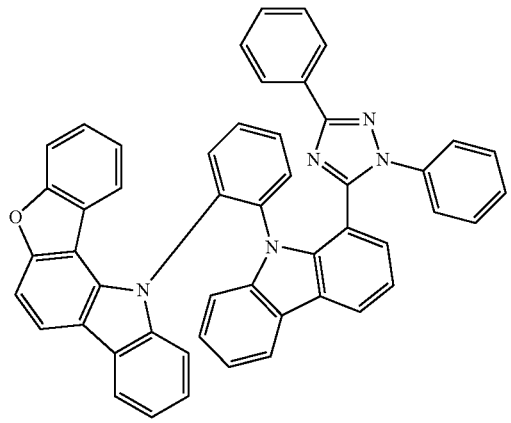
85
52
51
84
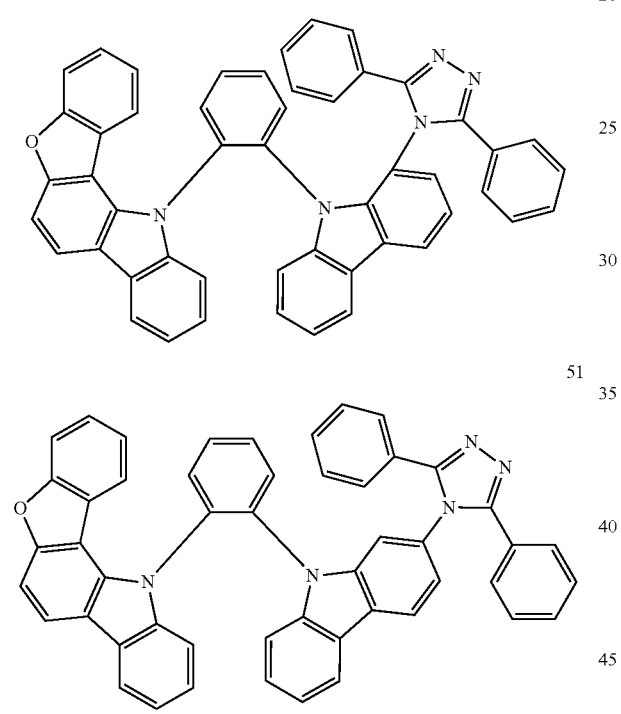
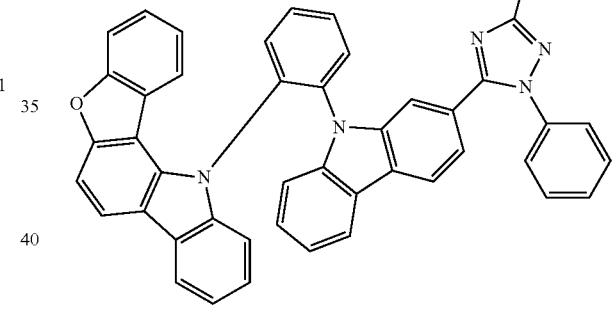
86
117
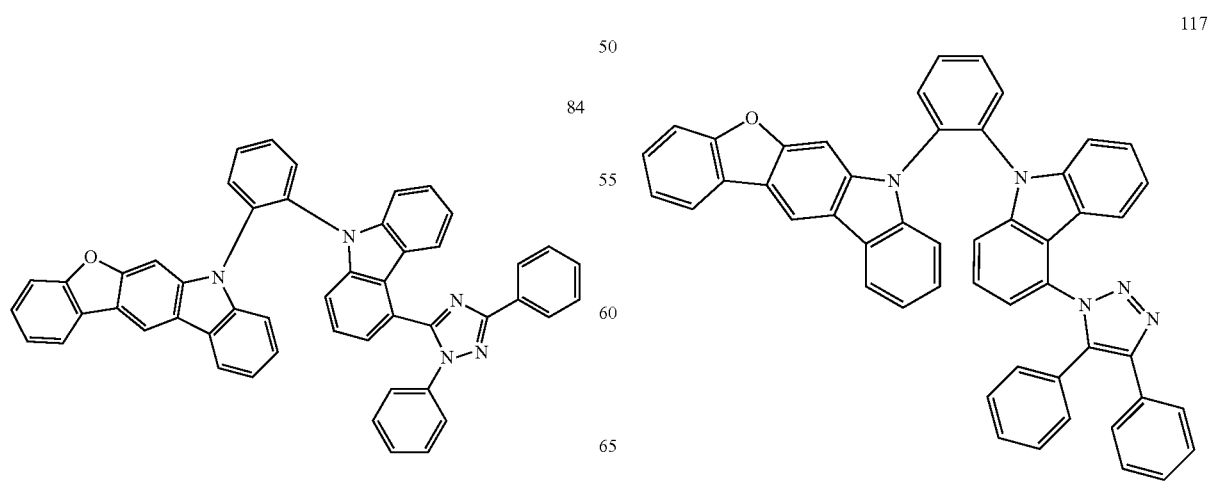

-continued
116
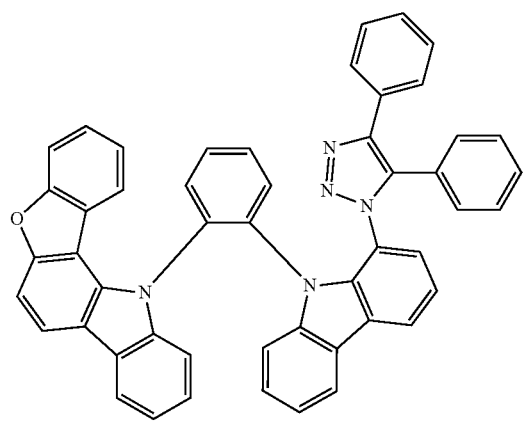
115
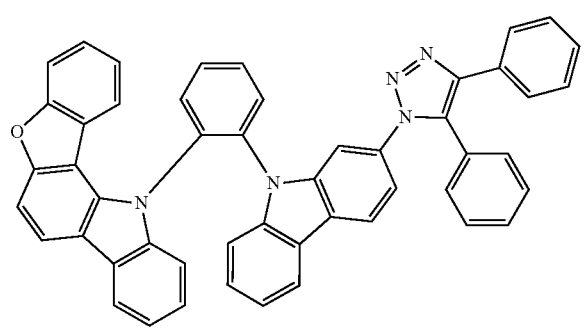
19
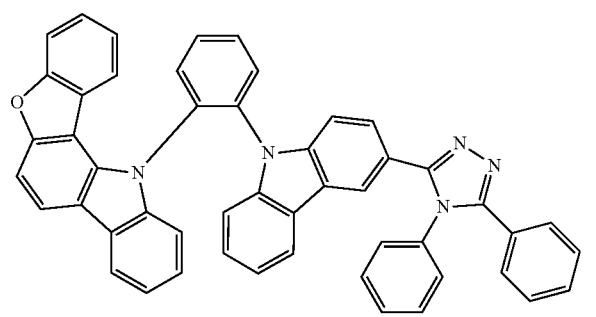
20
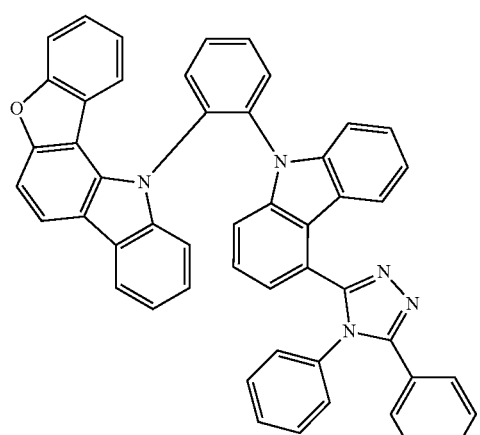
-continued
21
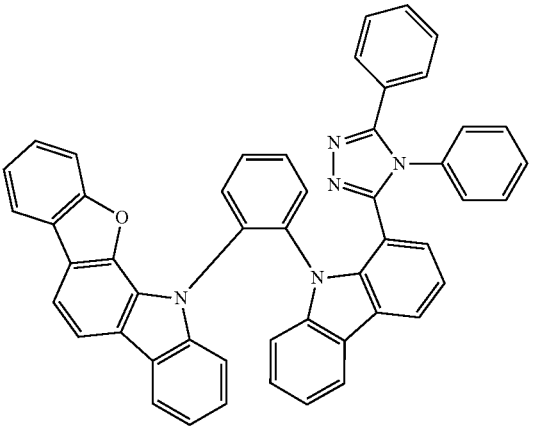
50
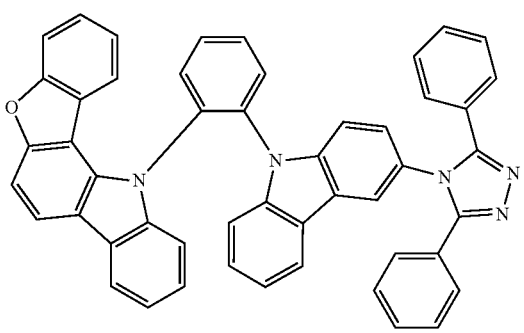
49
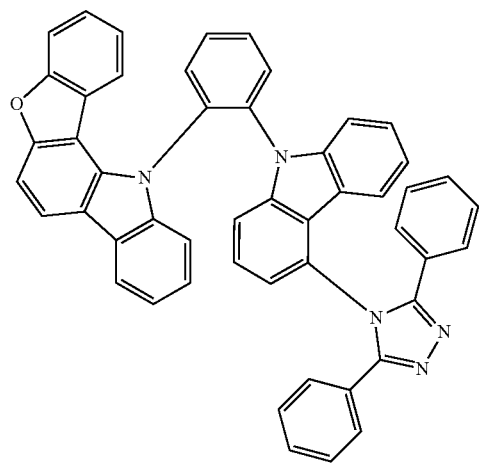
48
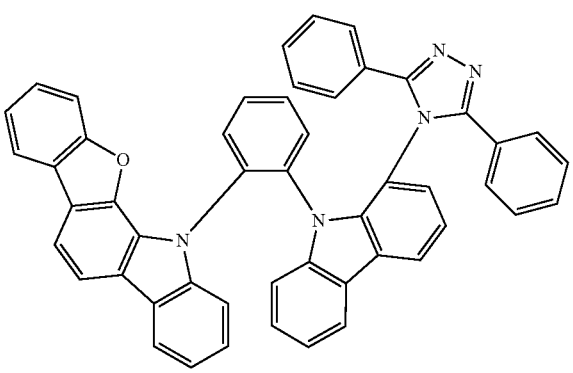

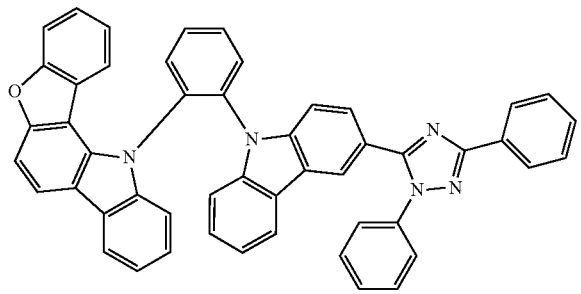
87
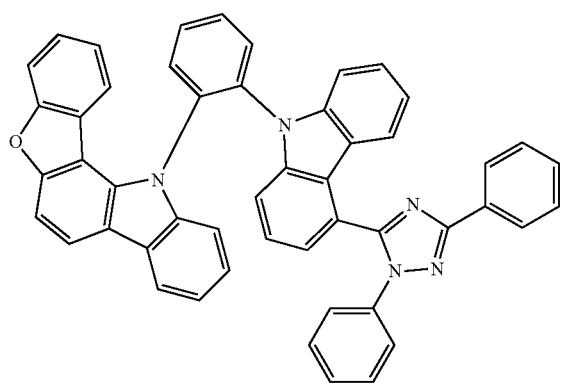
88
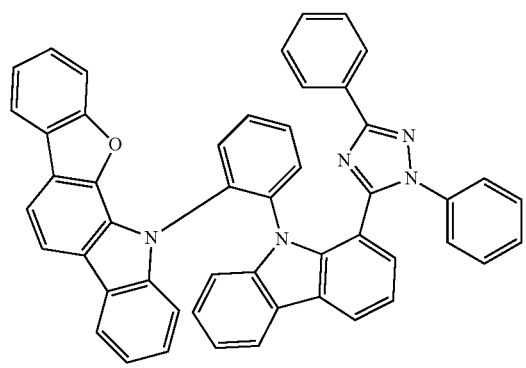
89
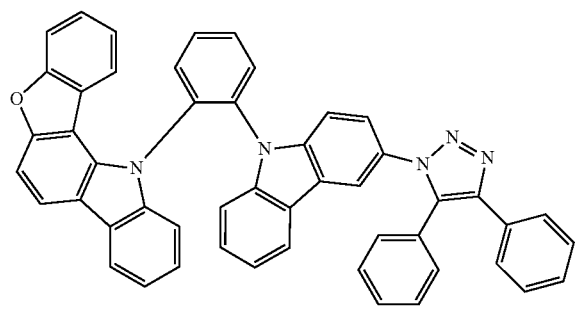
114
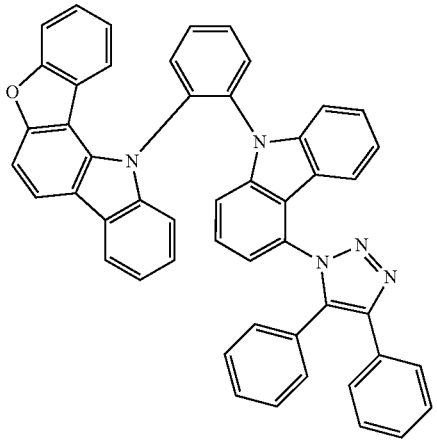
113
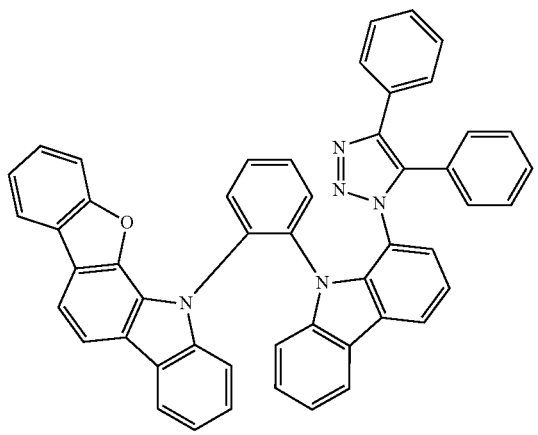
112
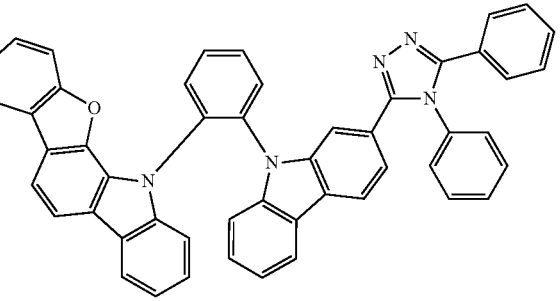
22
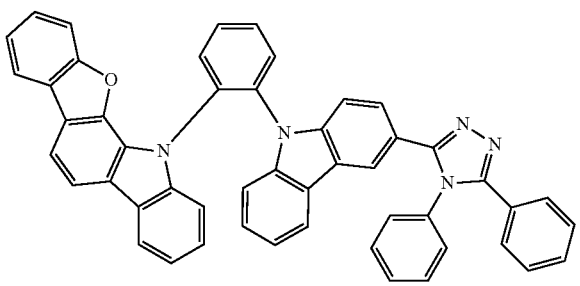
23

24
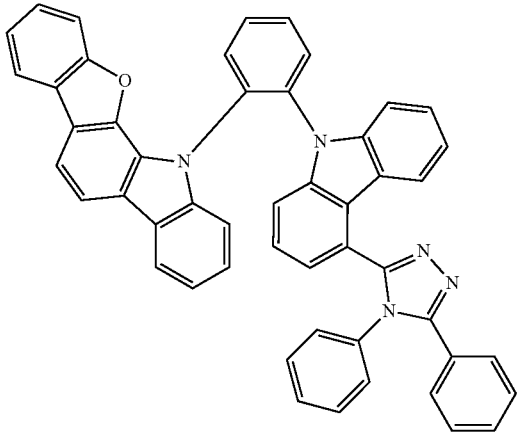
47
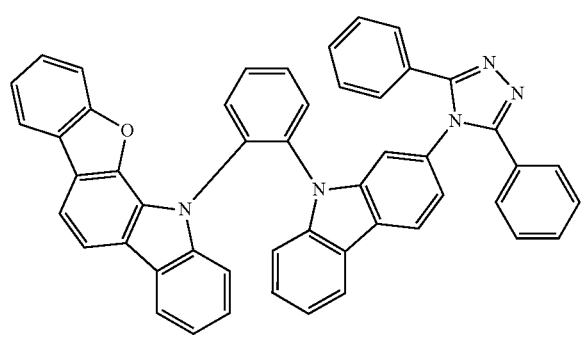
46
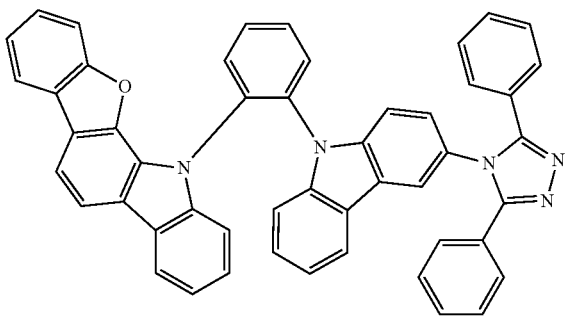
45
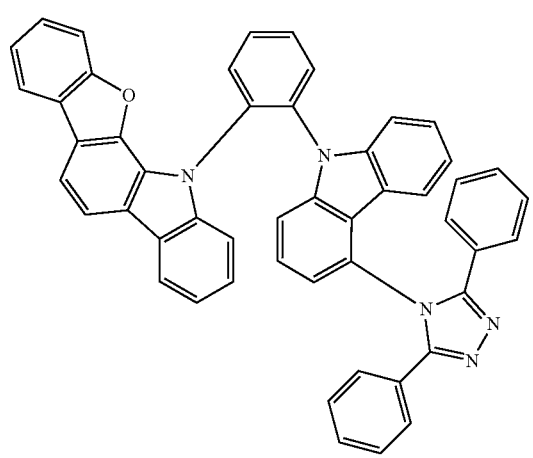
90
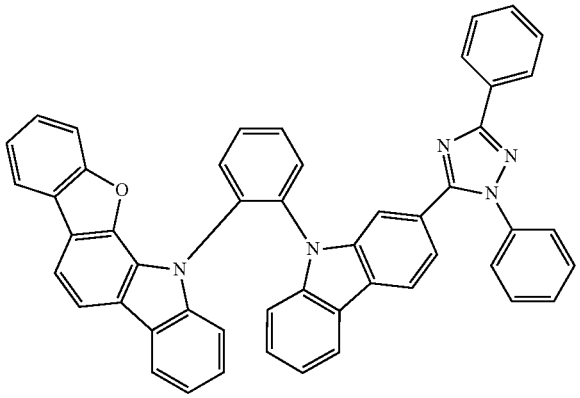
91
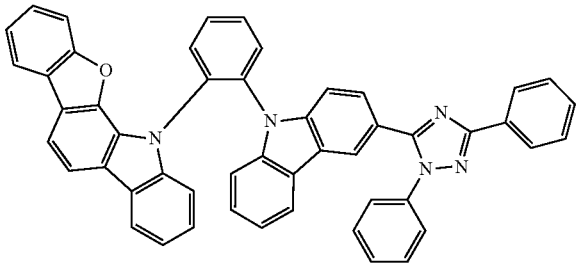
92
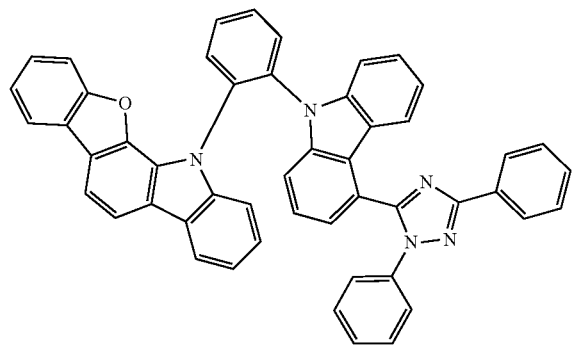
111
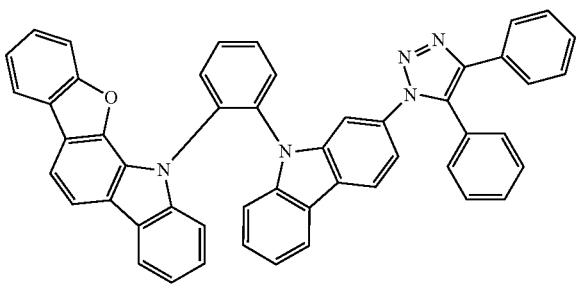

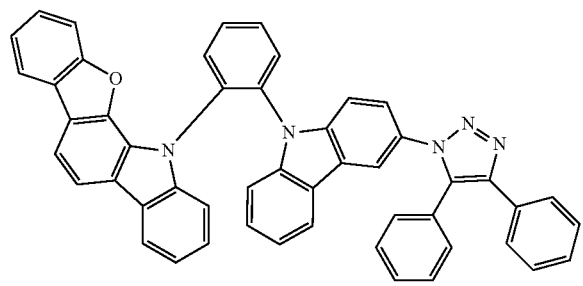
110
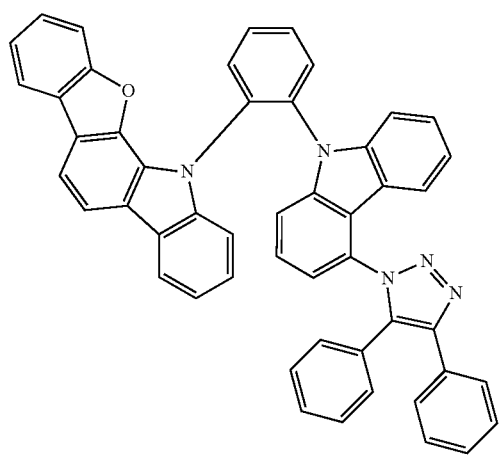
109
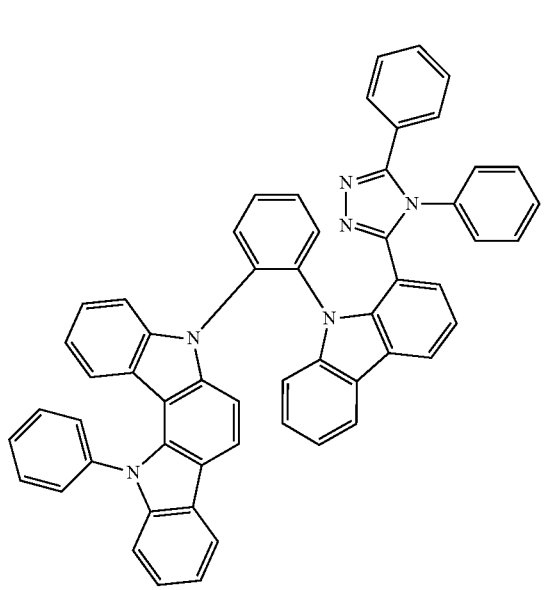
25
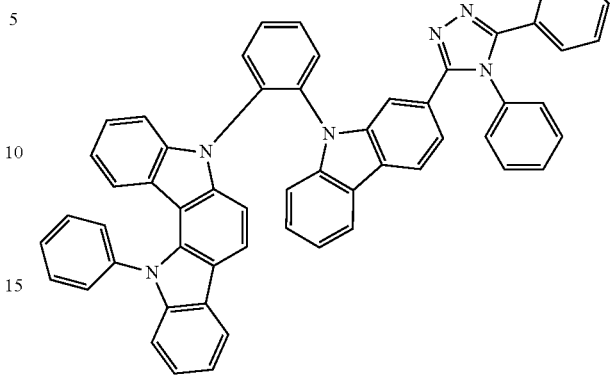
26
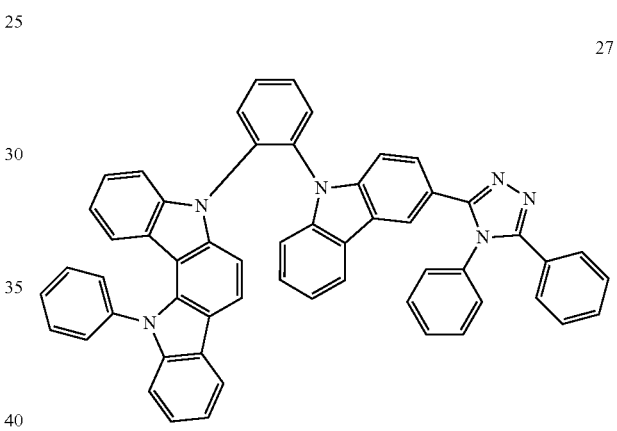
27
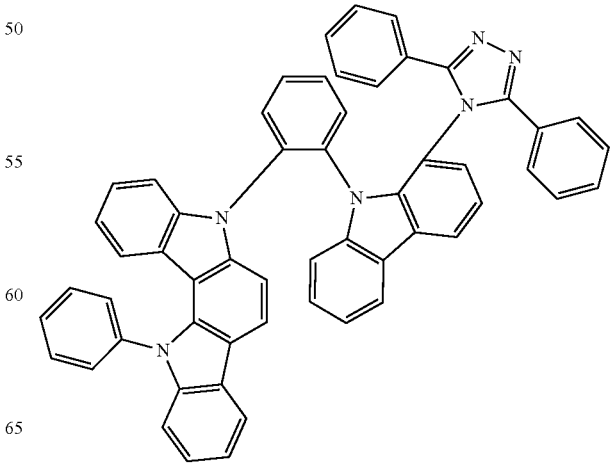
44

43
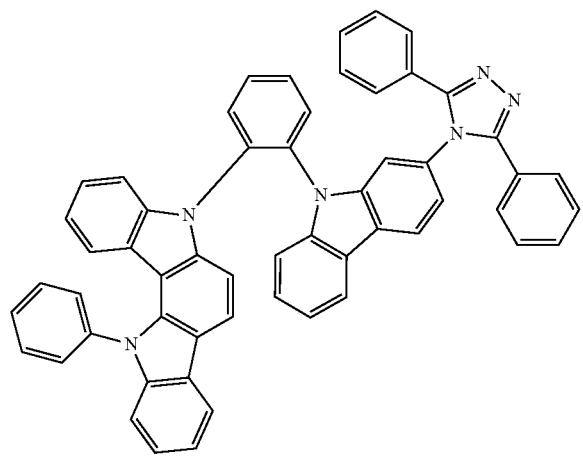
42
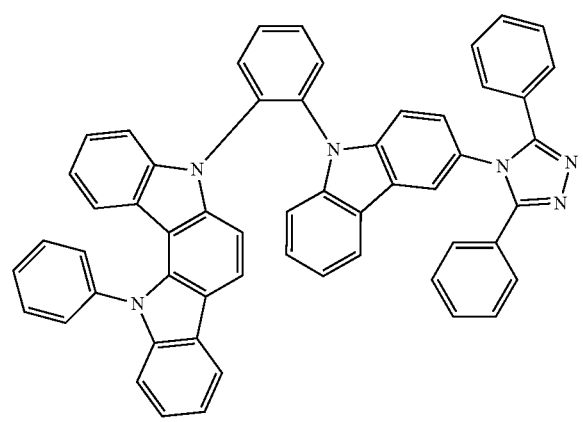
93
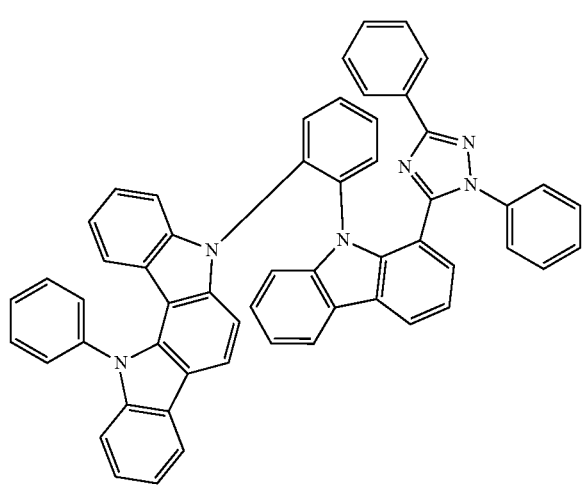
94
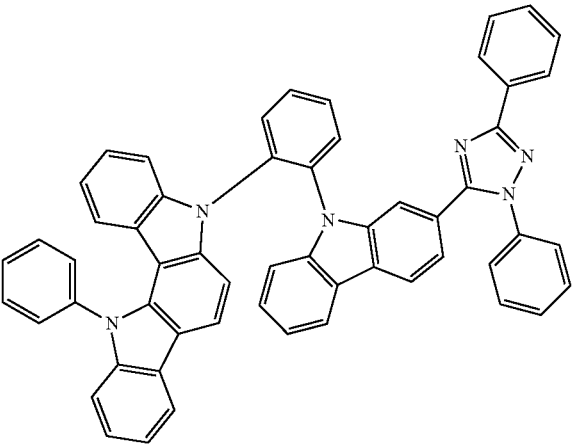
95
108
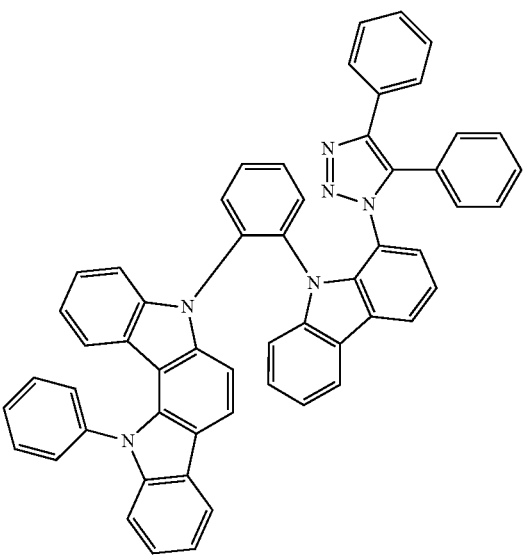

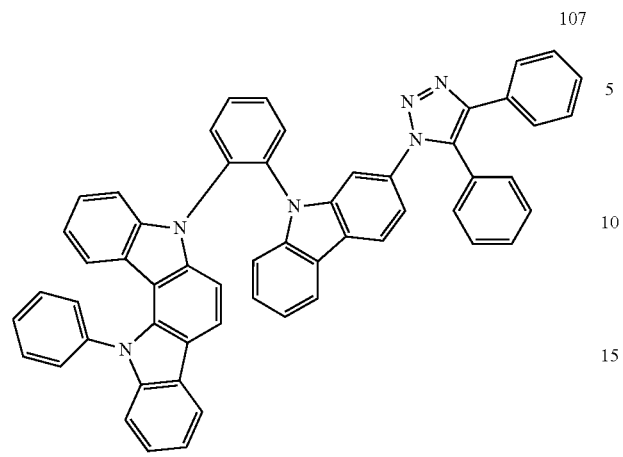
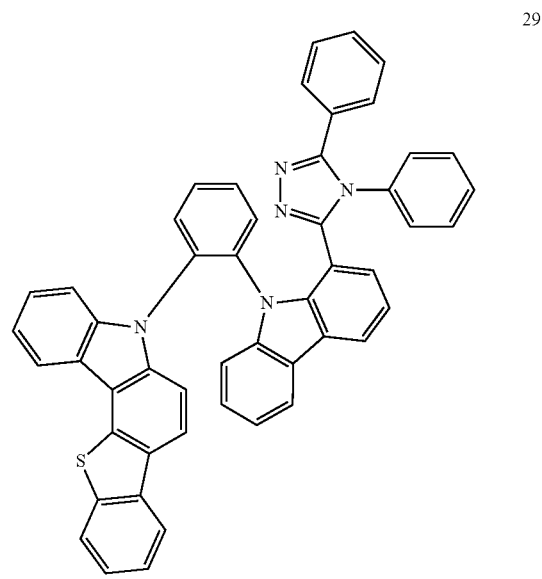
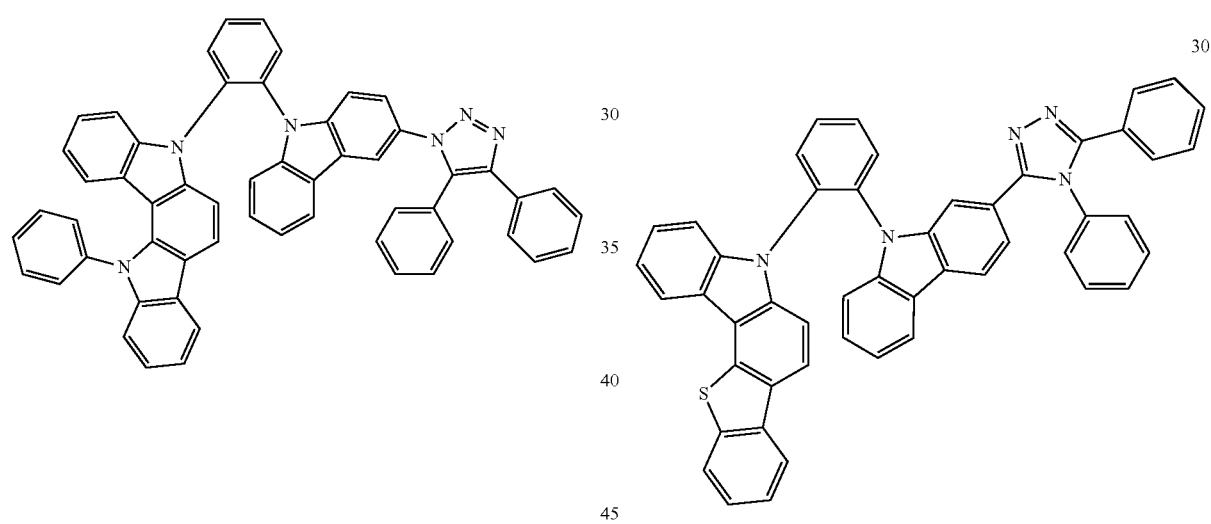
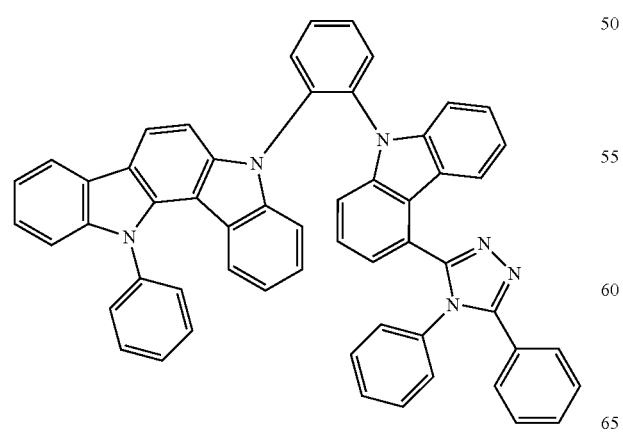
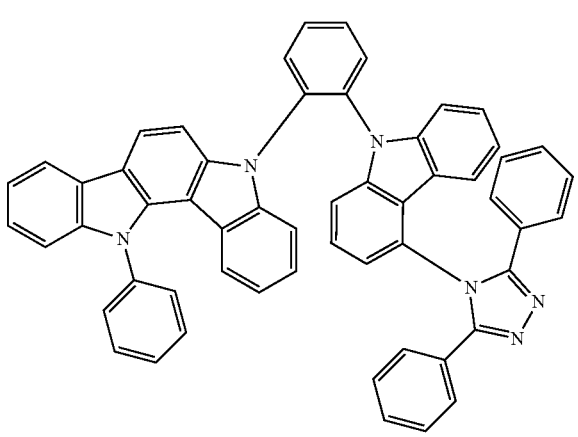

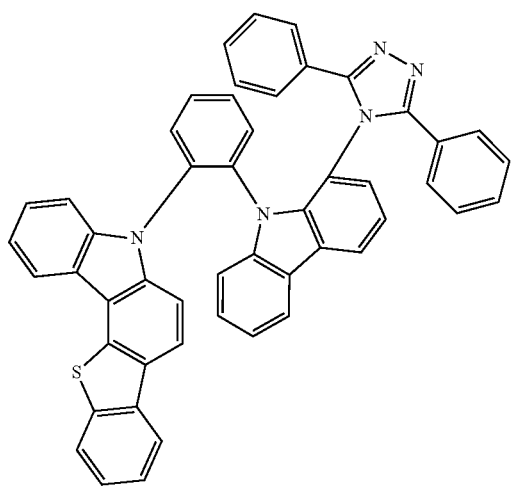
40
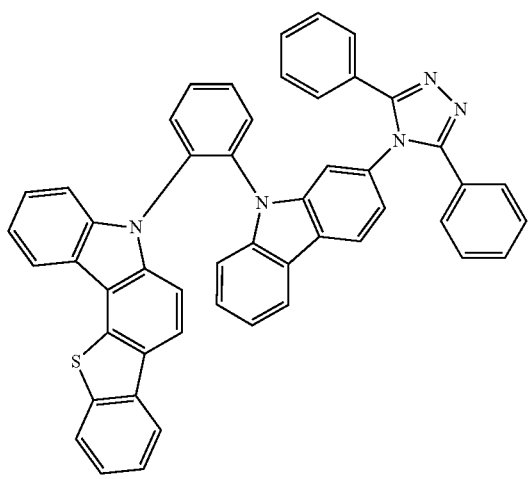
39
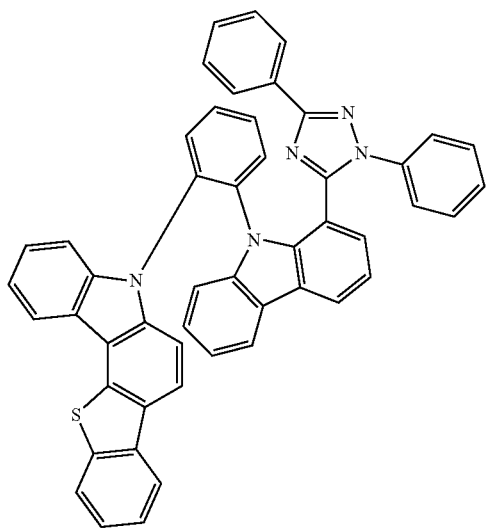
97
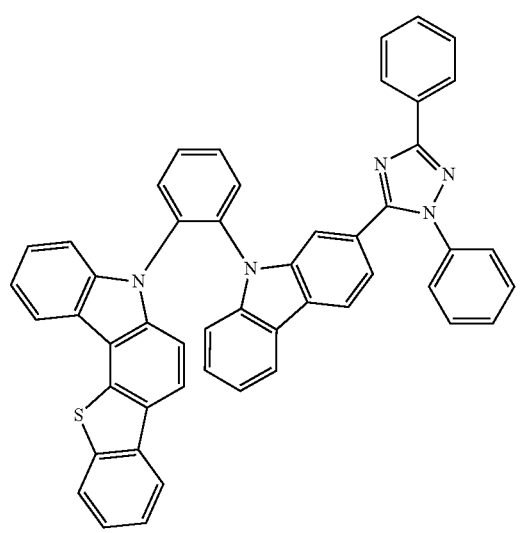
98
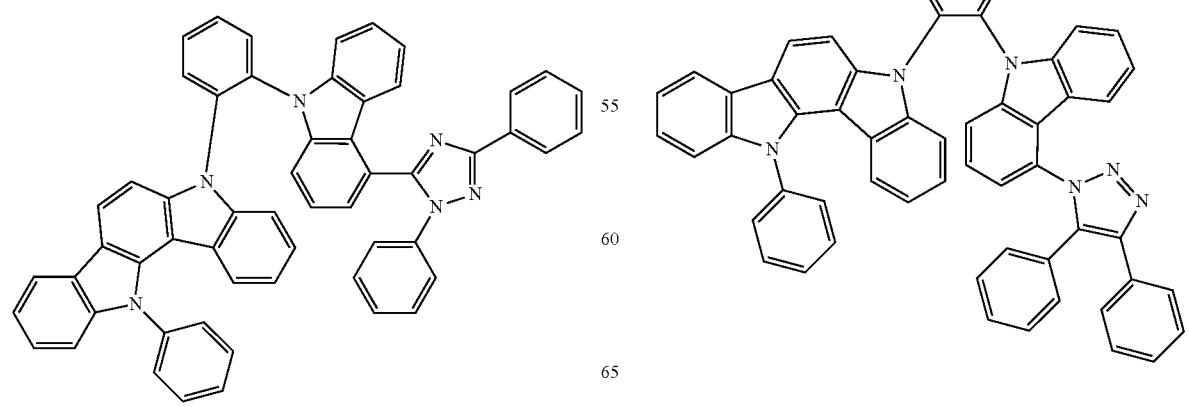
96
105

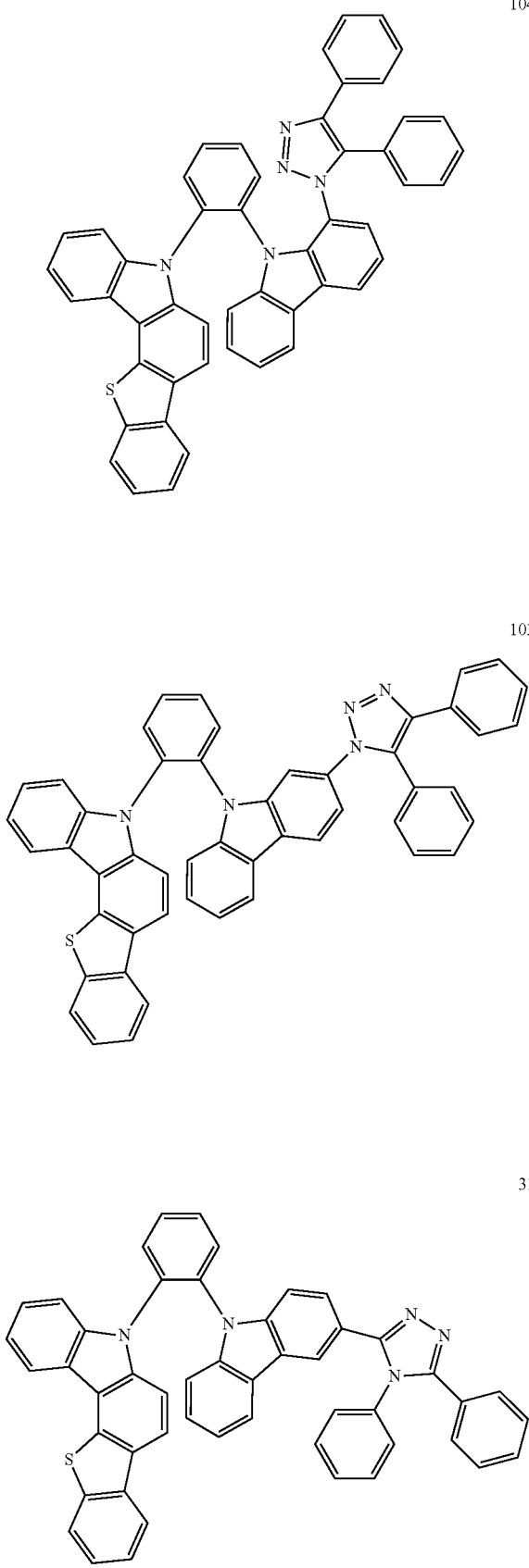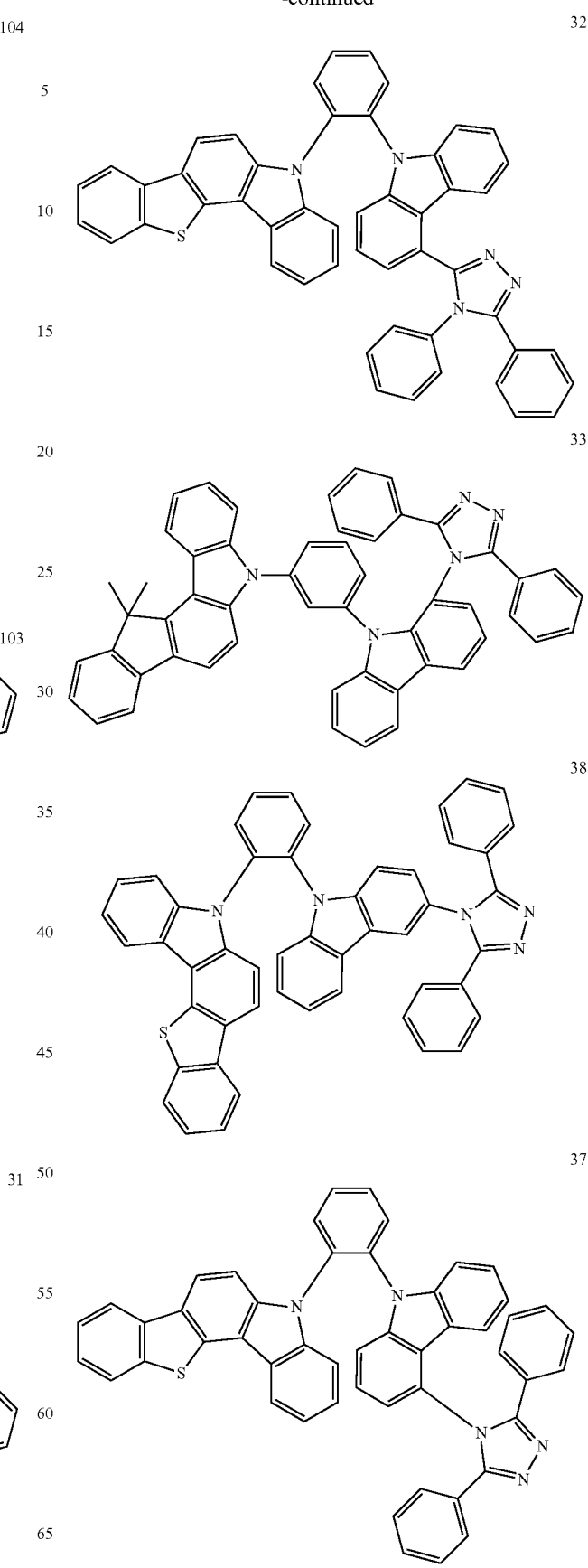

34
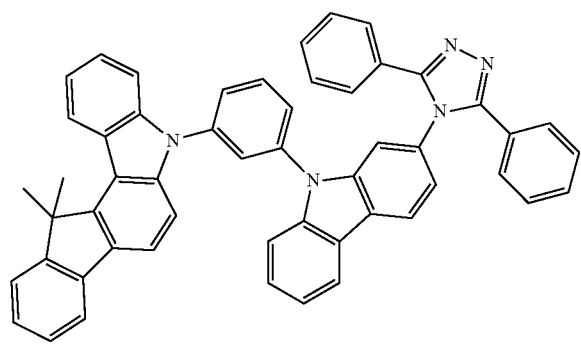
99
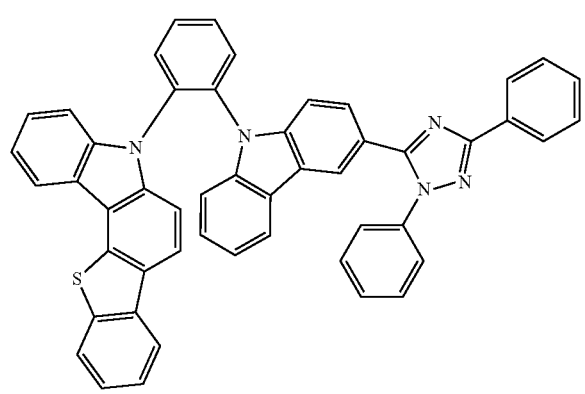
100
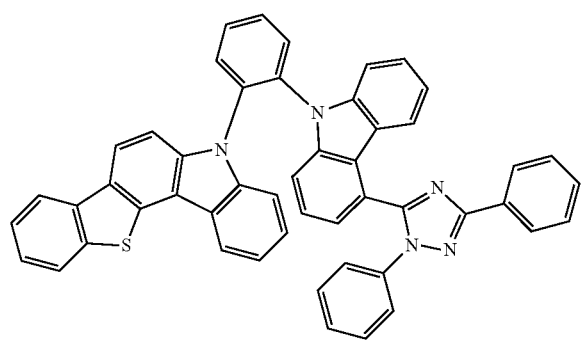
35
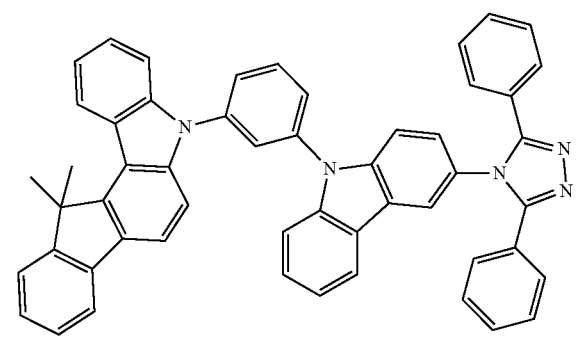
102
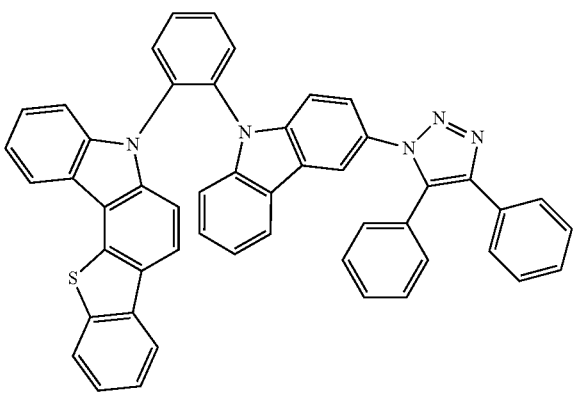
101
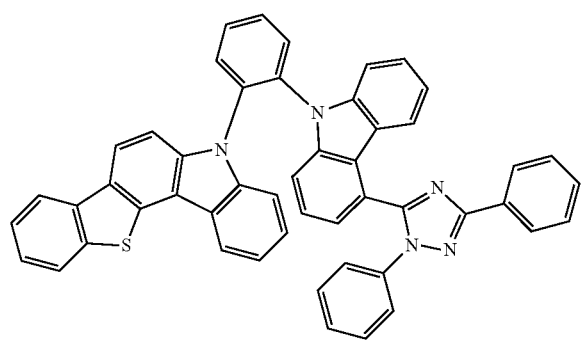
36
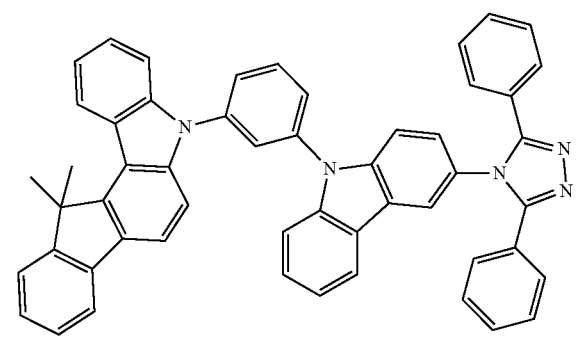

133
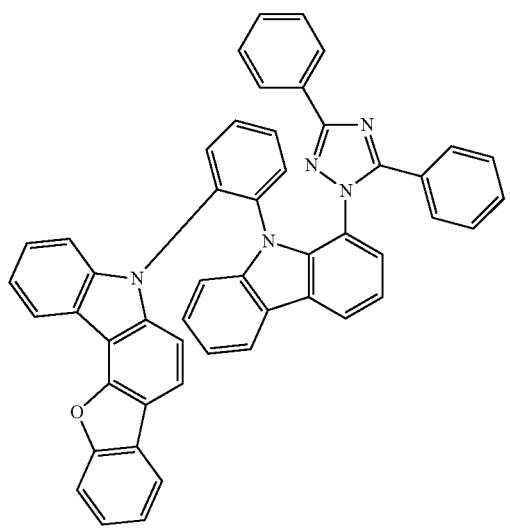
134
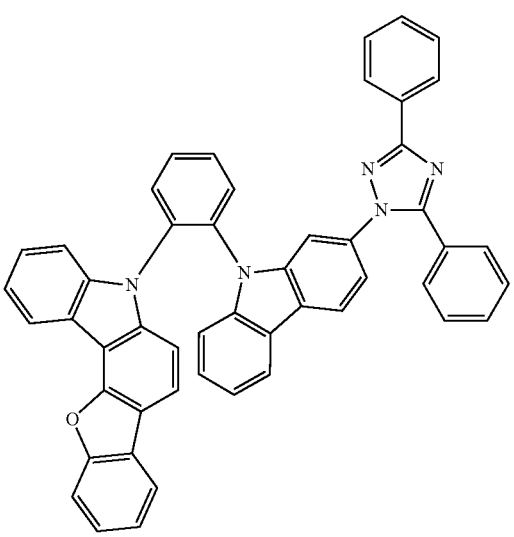
135
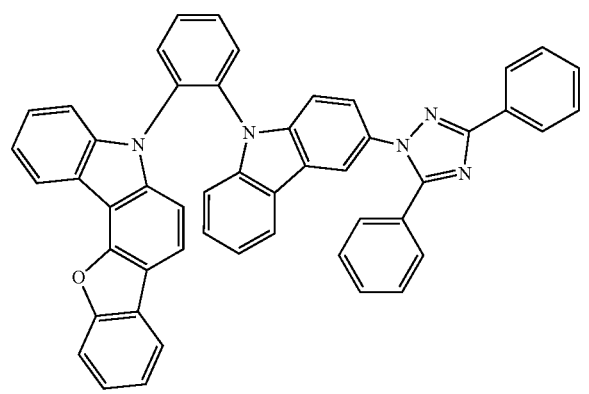
196
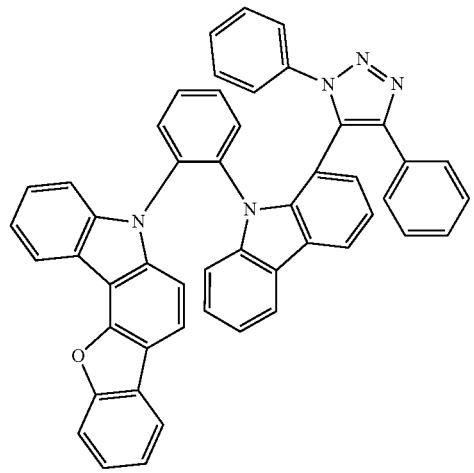
195
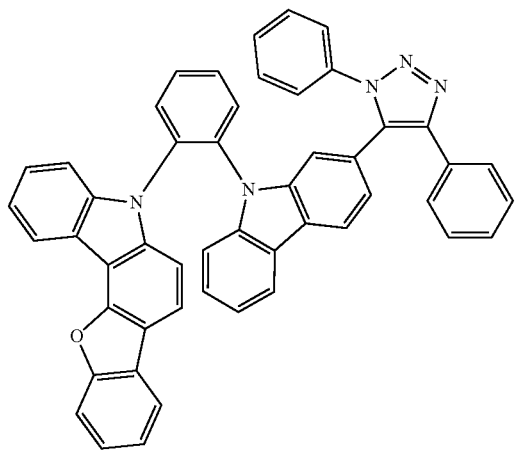
194
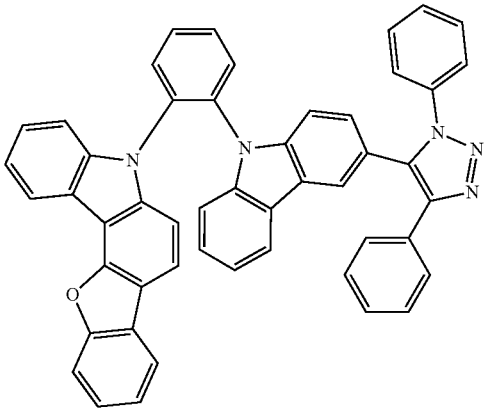

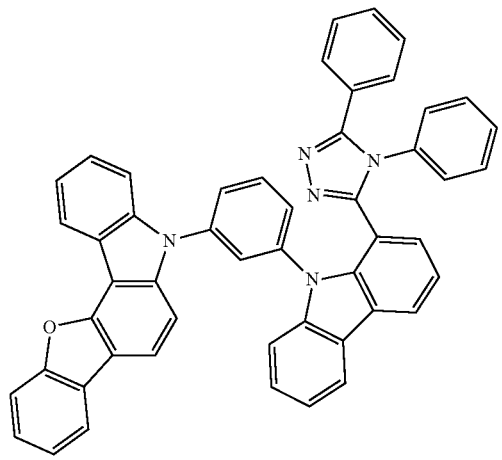
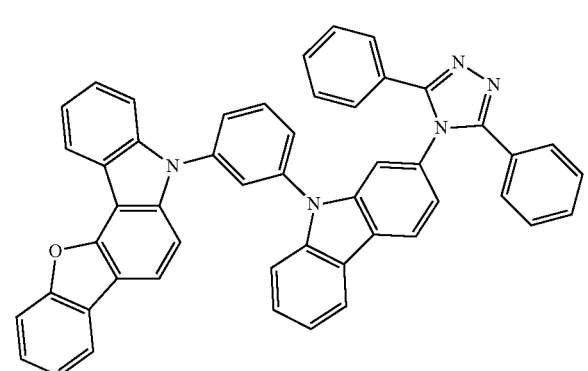
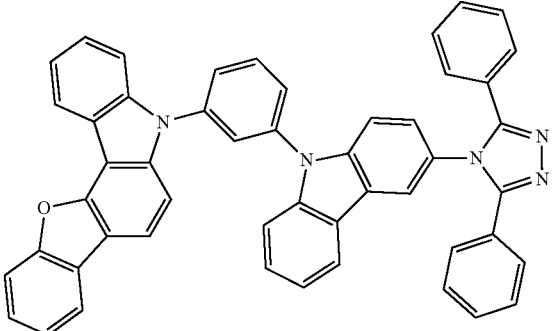
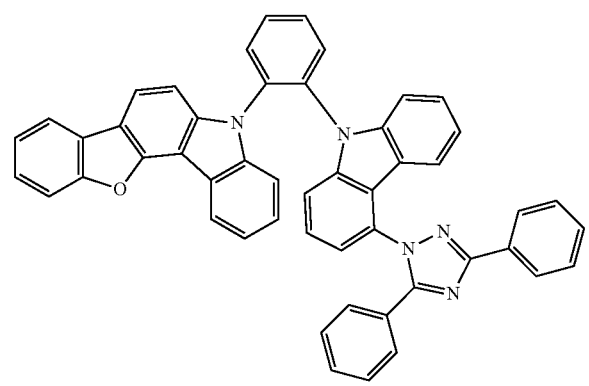
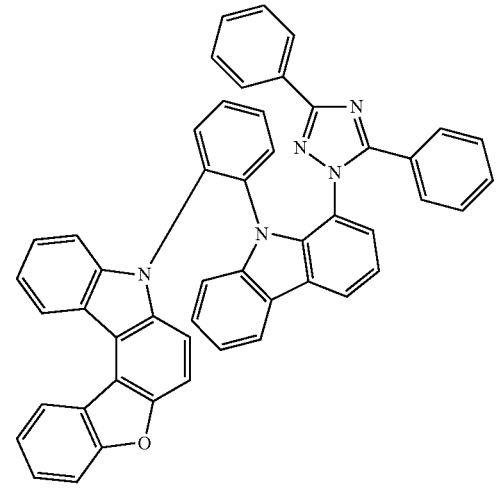

138
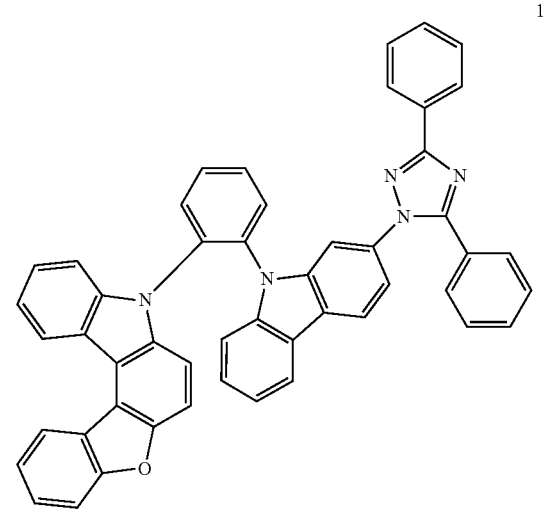
193
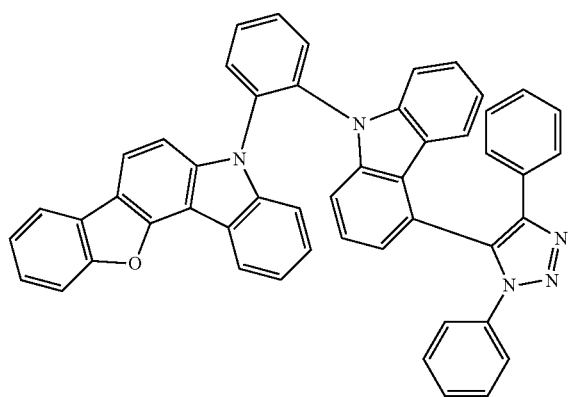
192
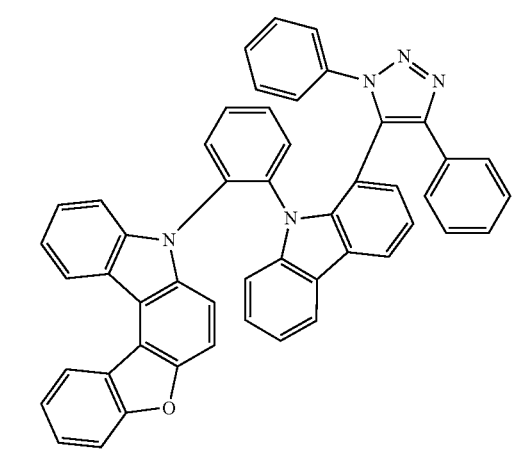
191
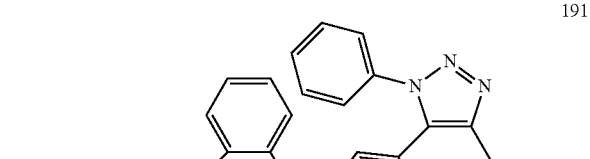
200
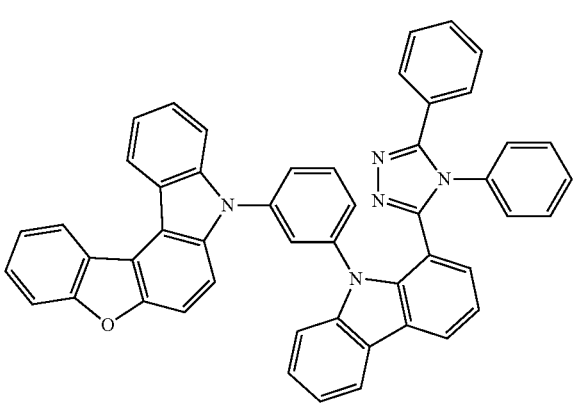
201
202
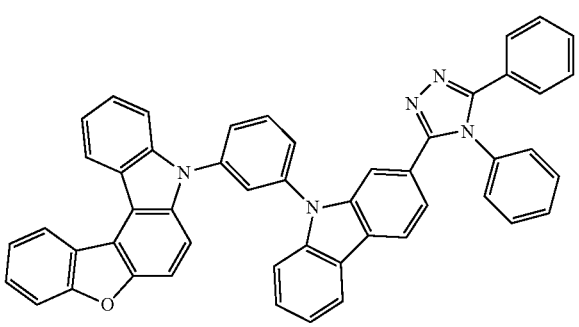

257
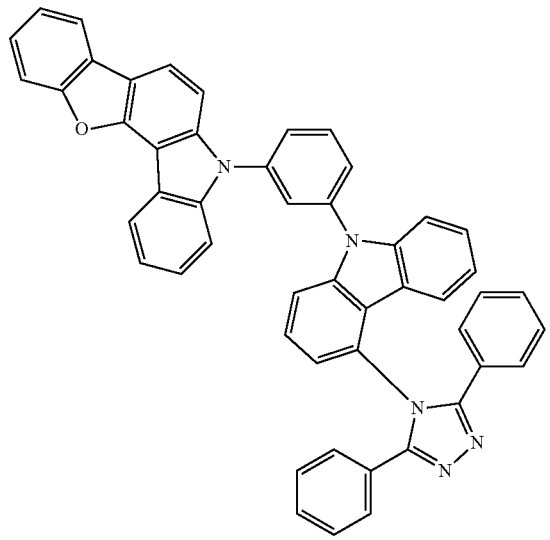
256
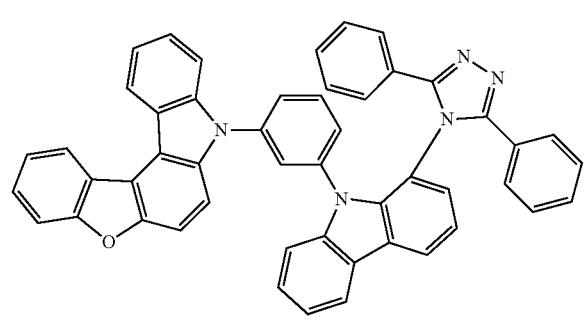
255
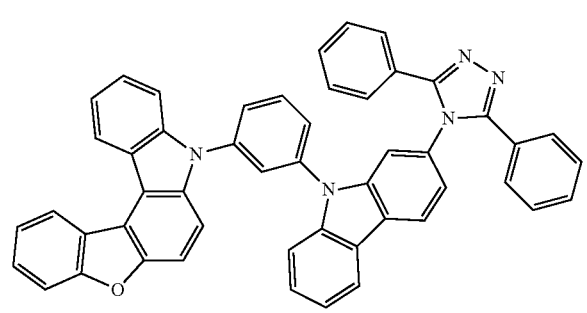
139
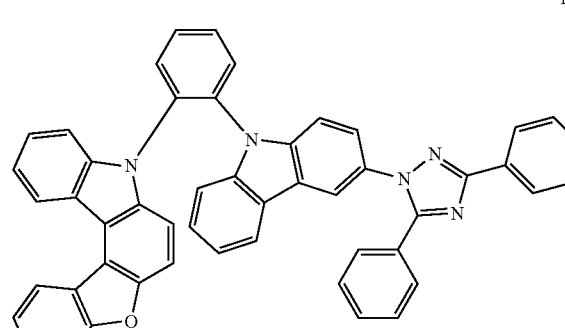
140
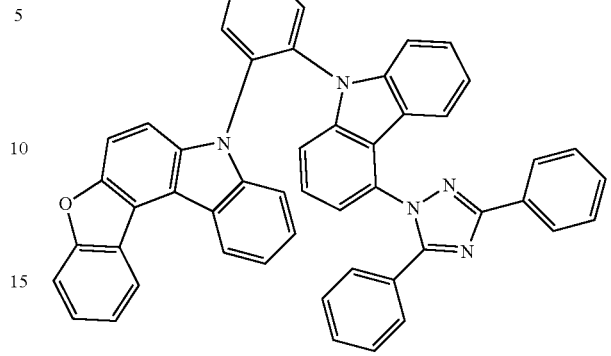
141
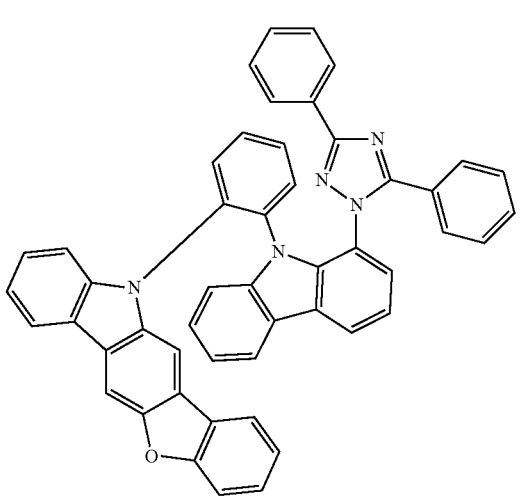
190
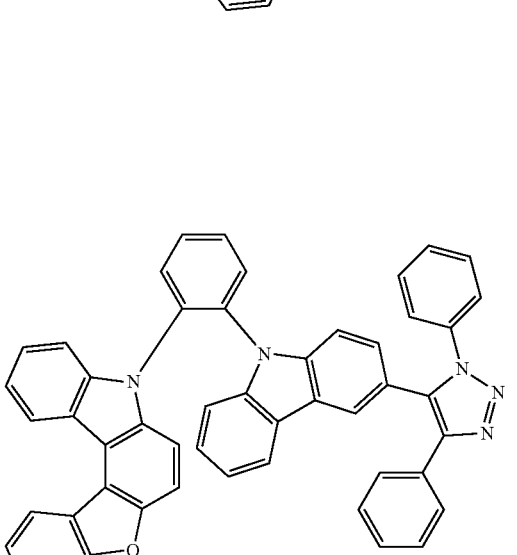

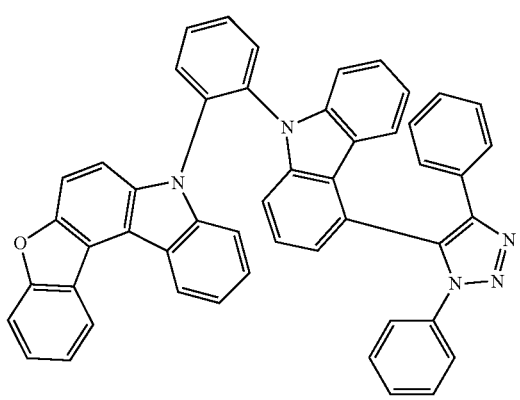
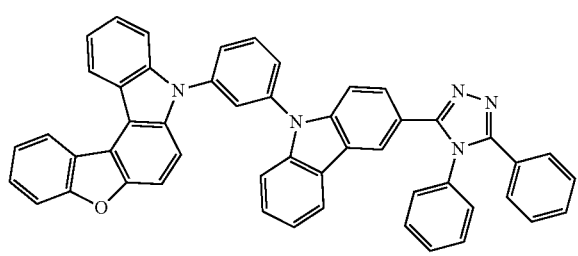
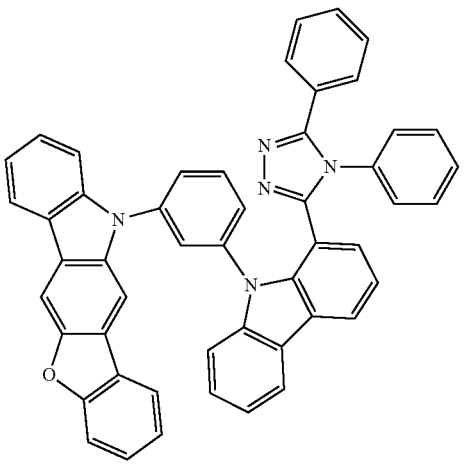
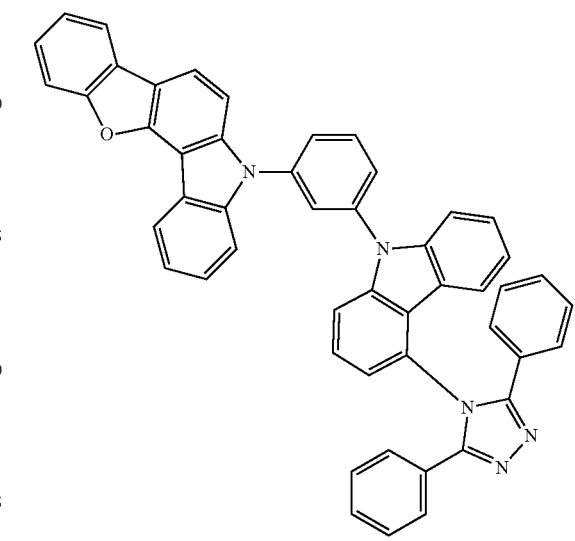

252
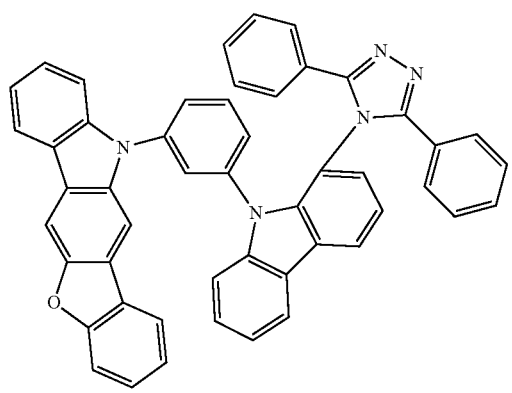
142
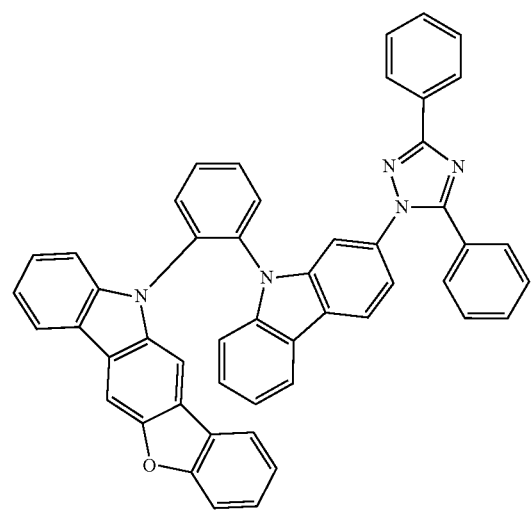
143
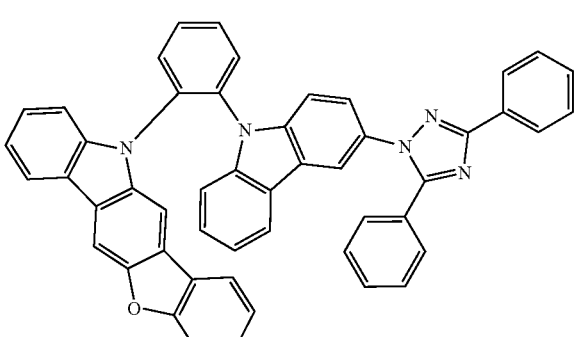
144
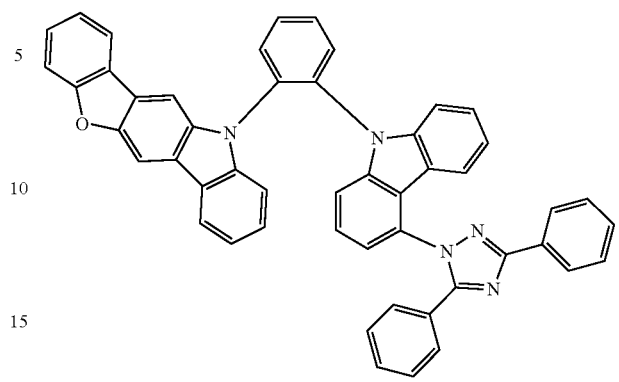
187
186
185
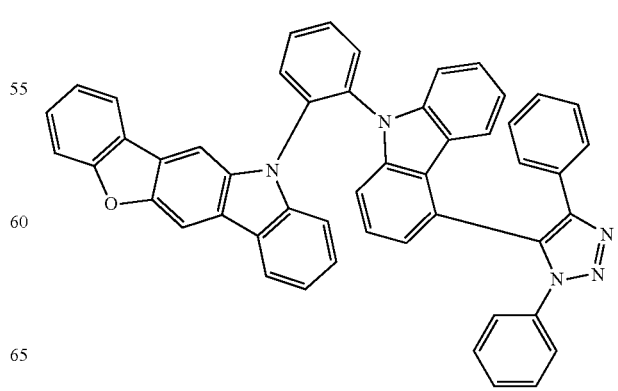

206
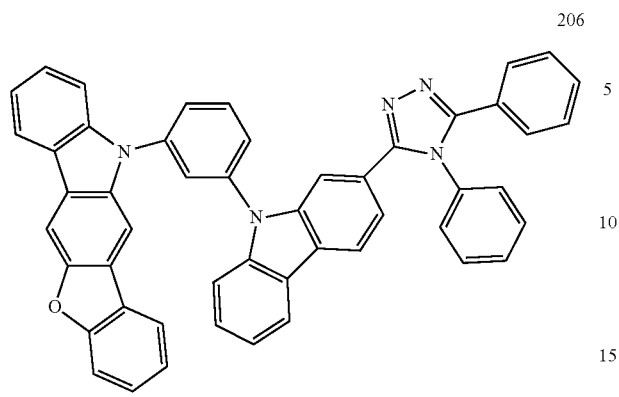
207
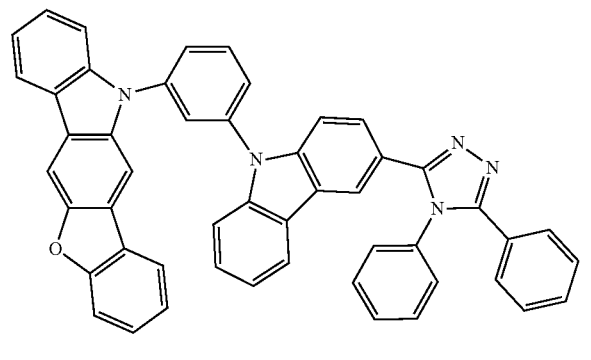
208
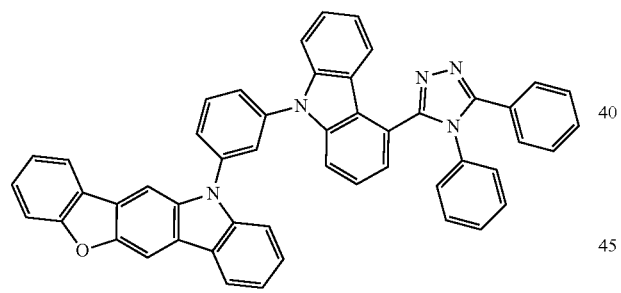
251
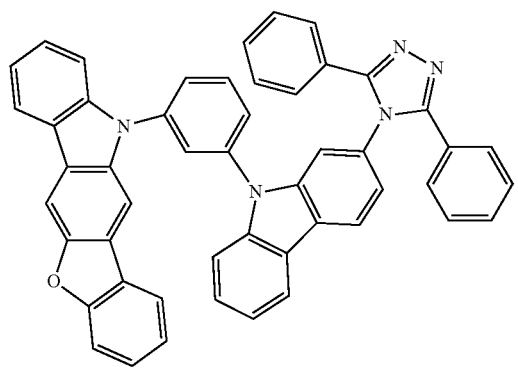
250
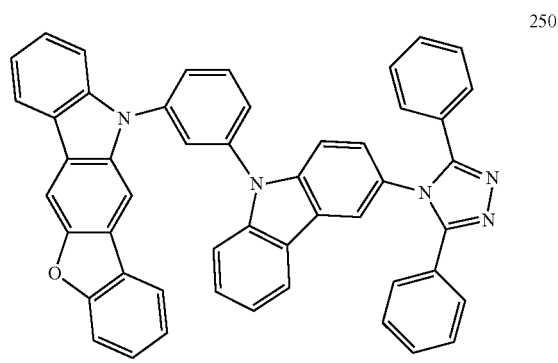
249
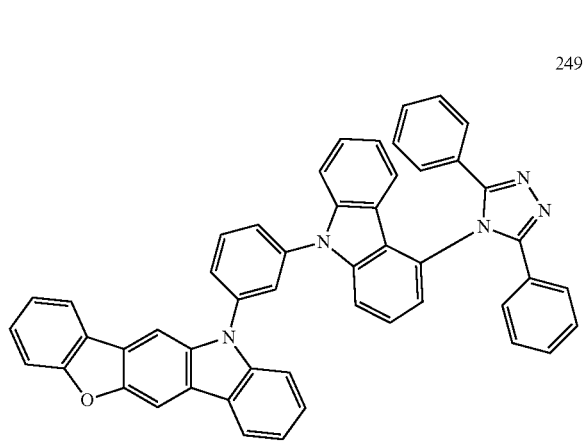
145
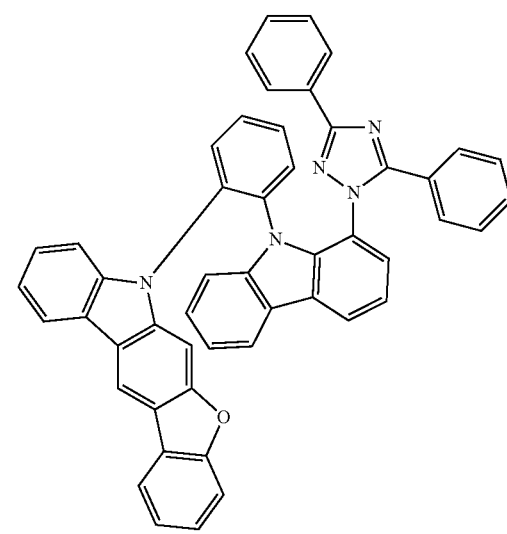

146
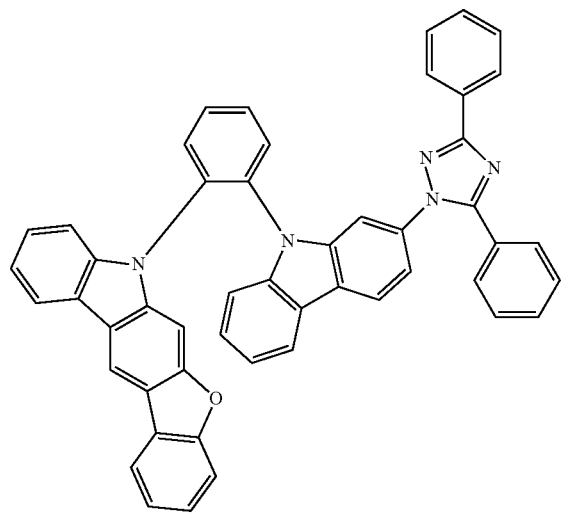
147
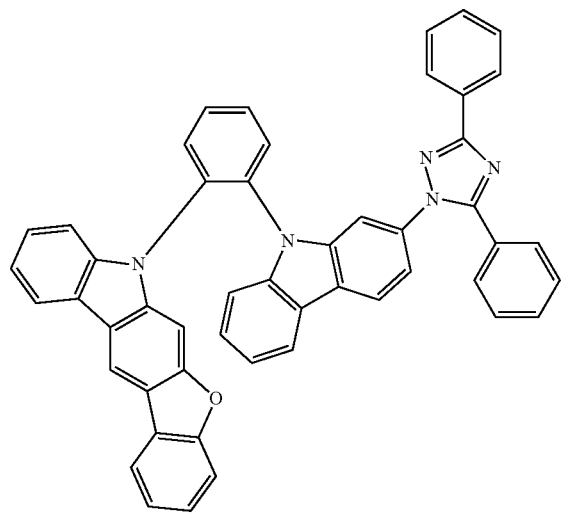
184
183
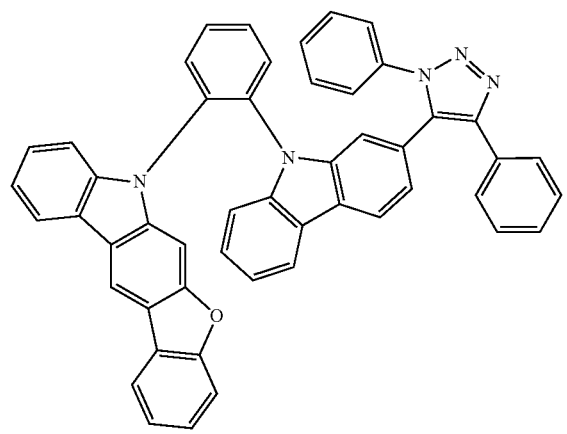
182
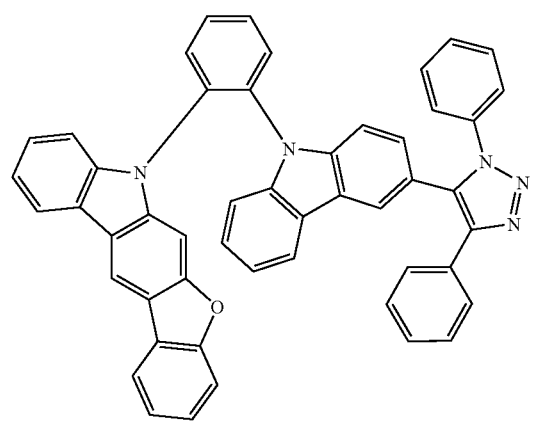
209
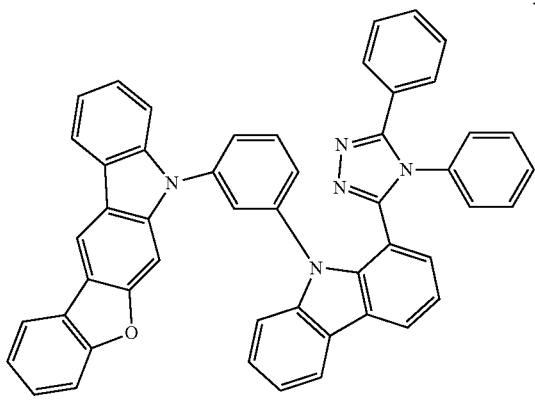
210
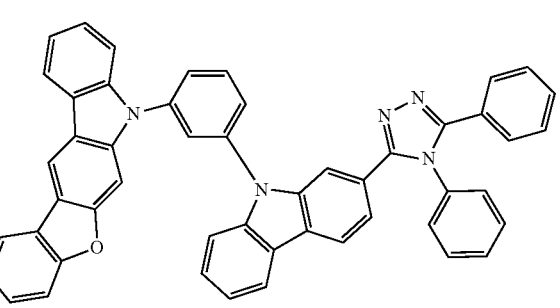

211
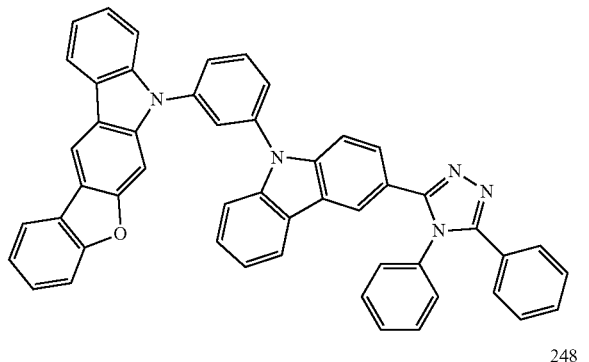
248
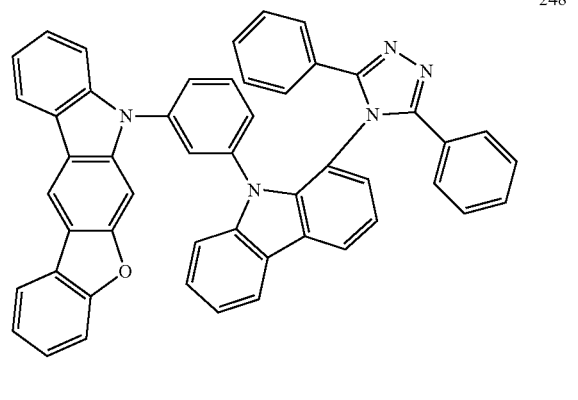
247
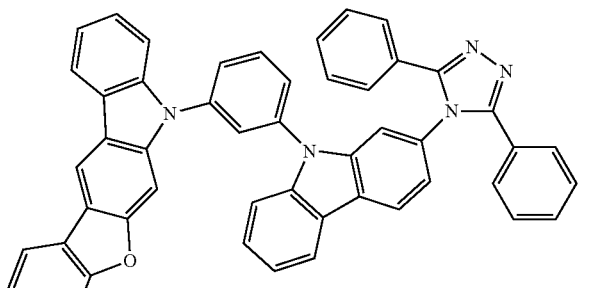
246
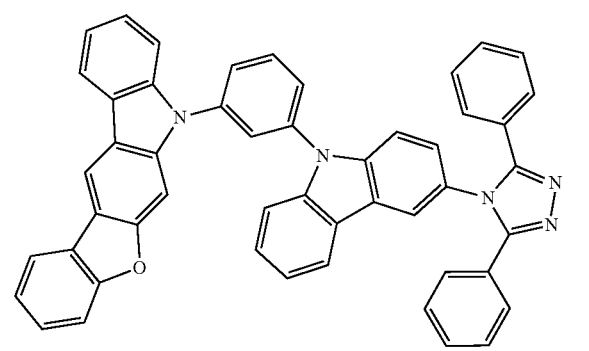
148
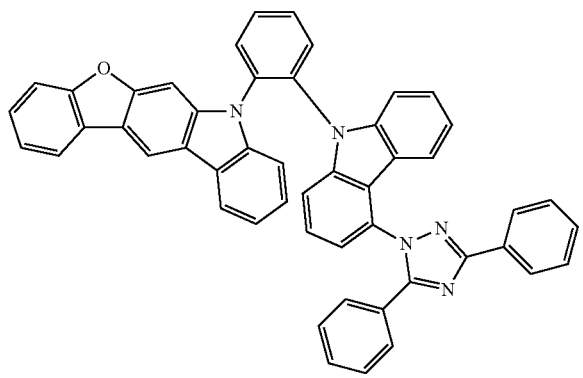
149
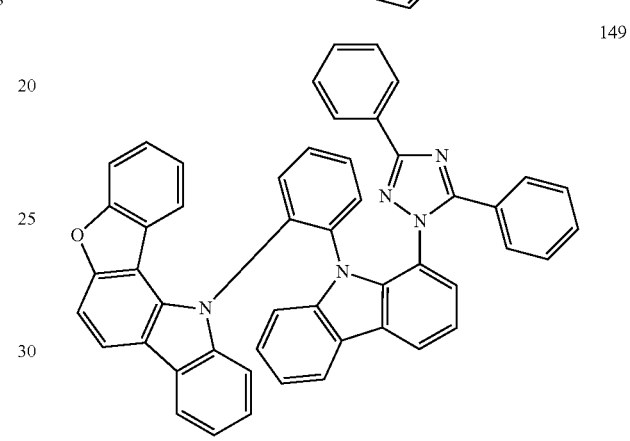
150
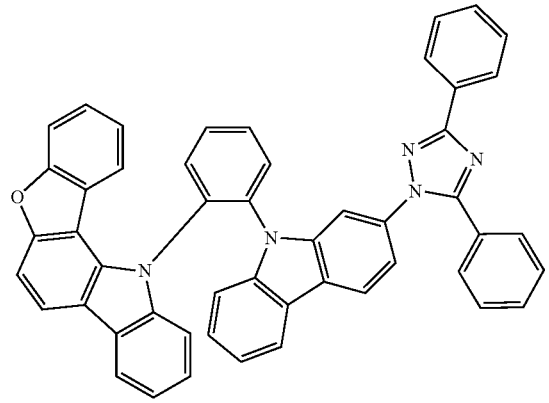
181
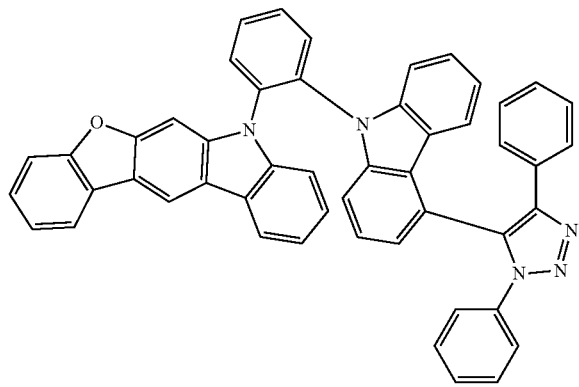

180
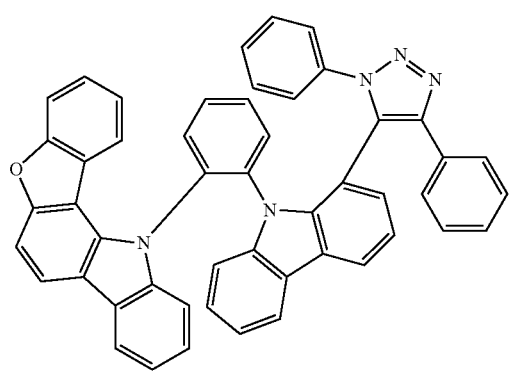
179
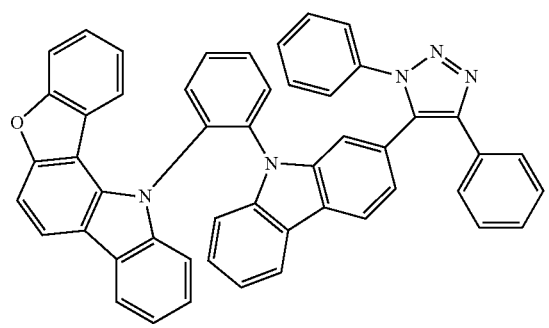
212
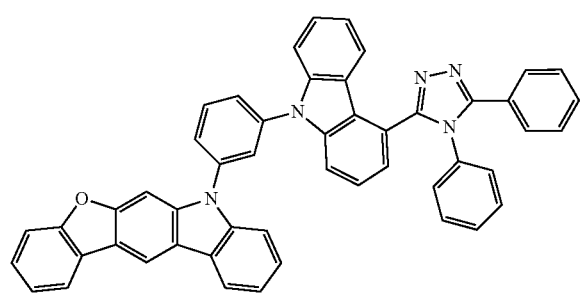
213
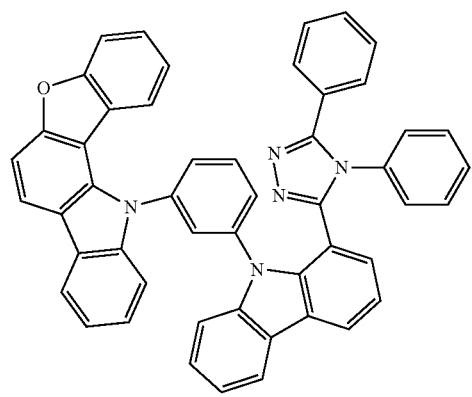
214
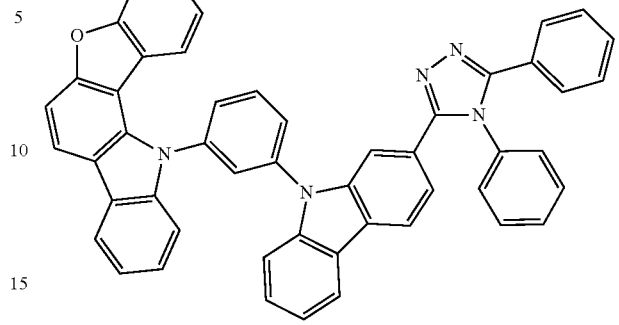
245
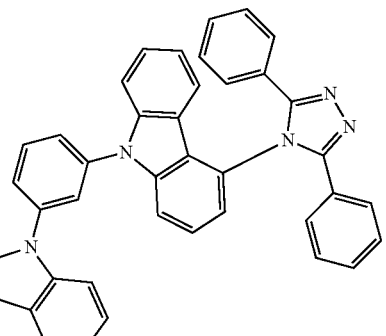
244
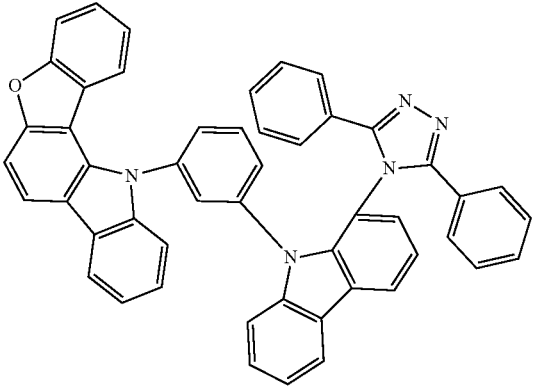
243
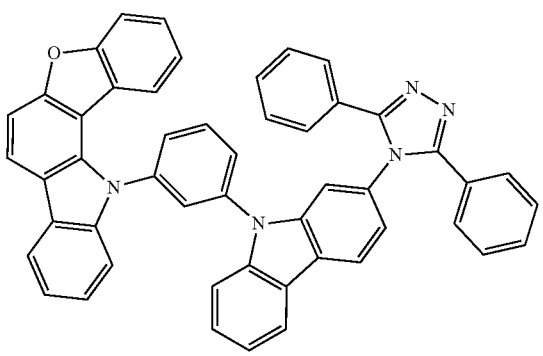

151
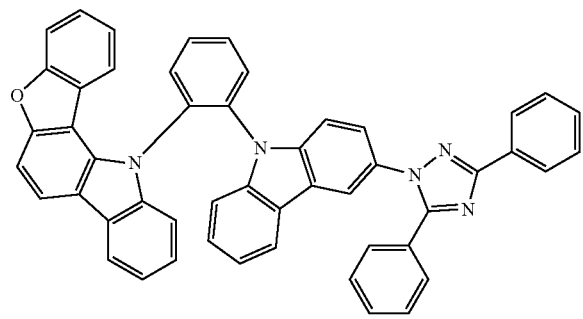
152
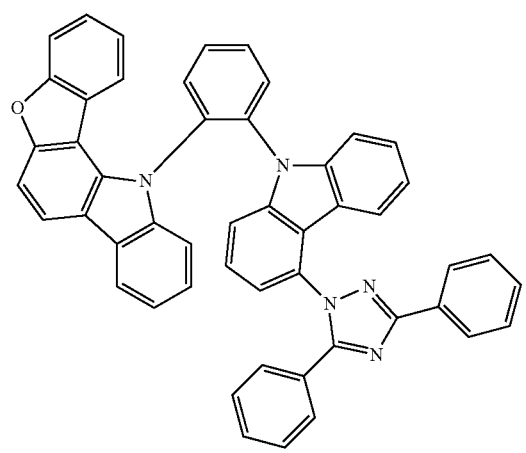
153
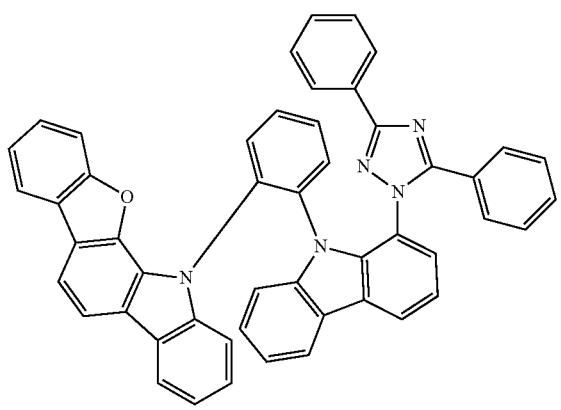
178
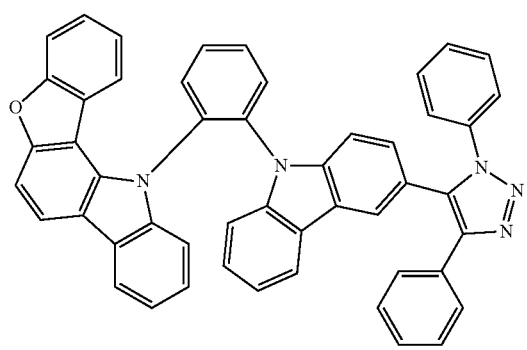
177
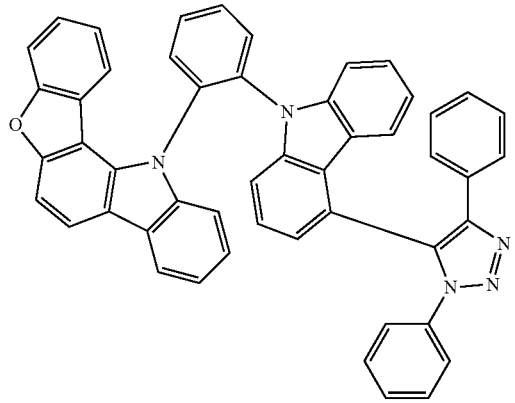
176
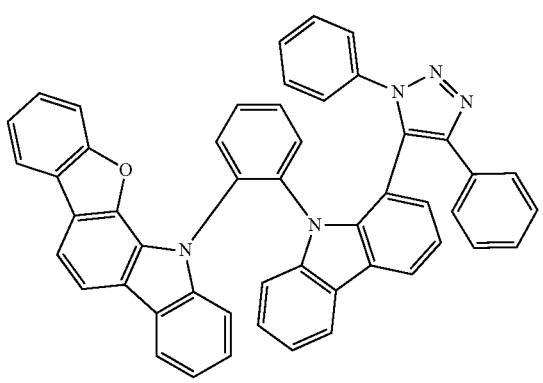
215
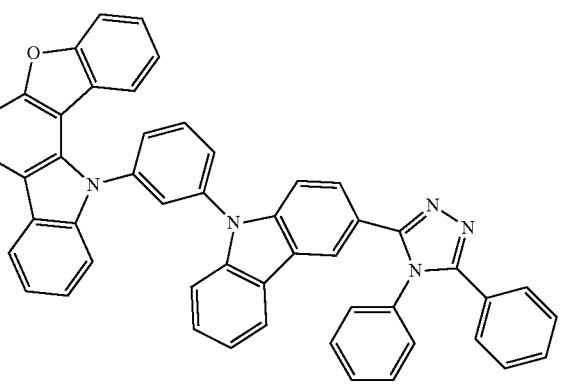

216
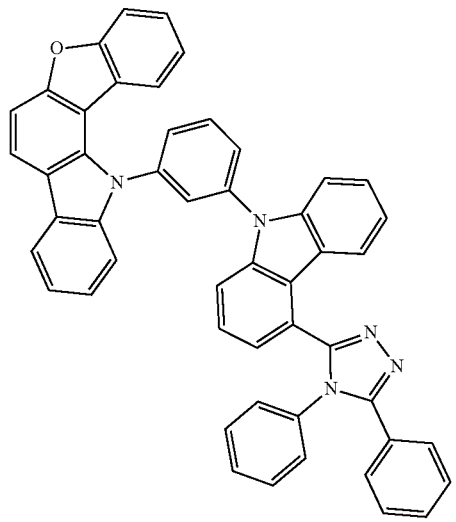
241
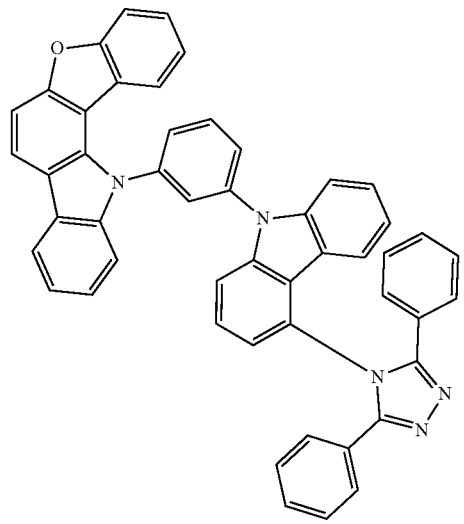
217
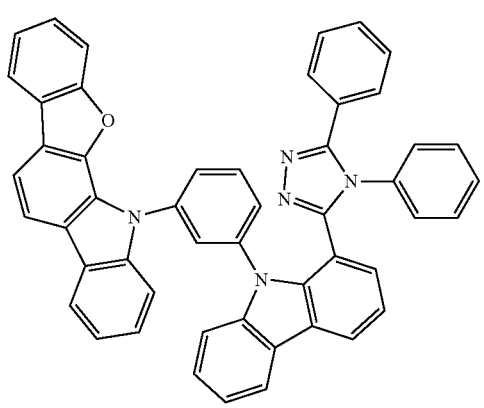
240
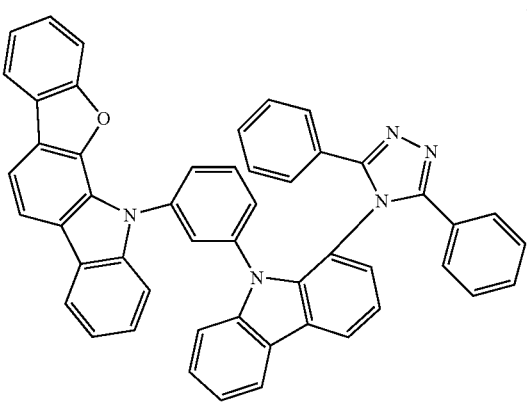
242
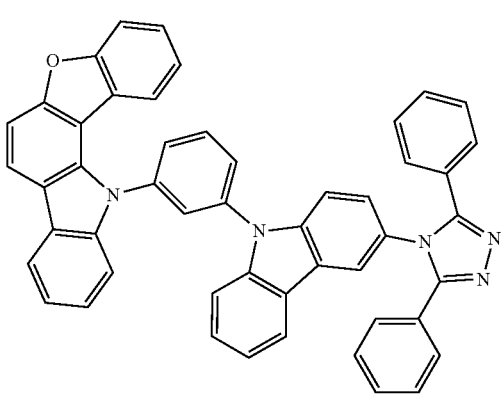
154
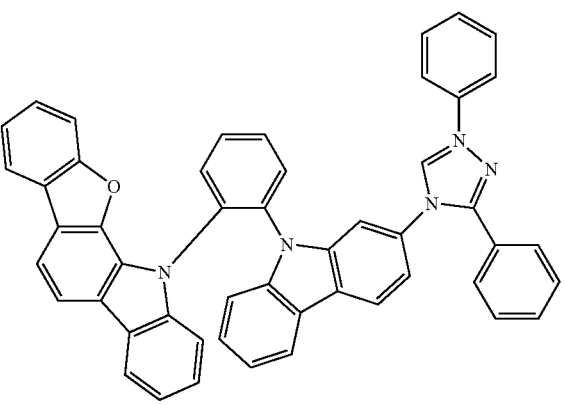

155
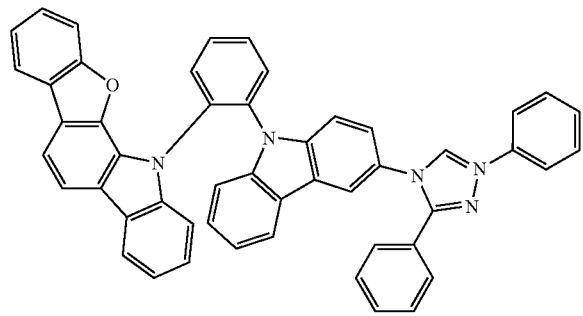
156
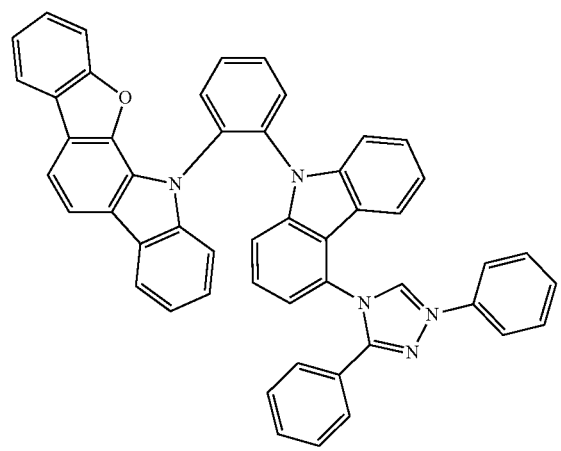
175
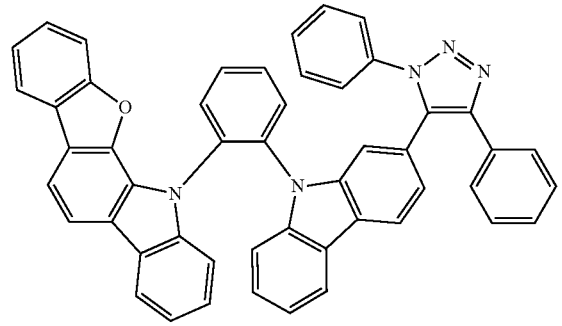
174
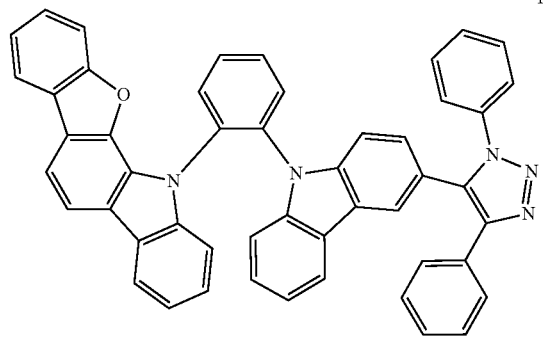
173
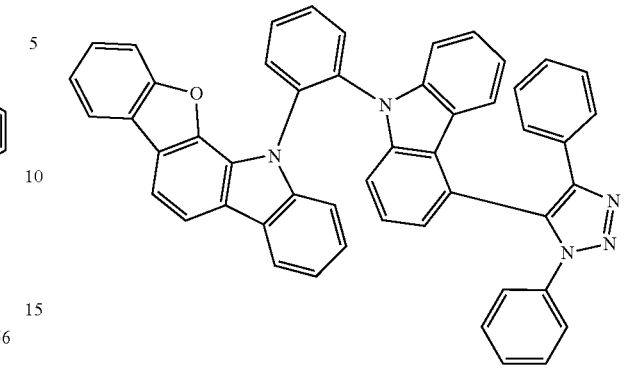
218
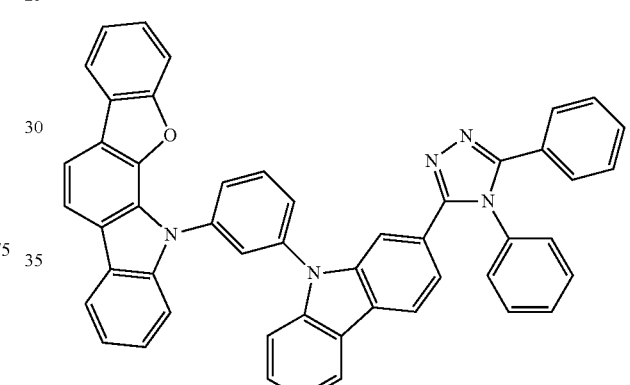
219
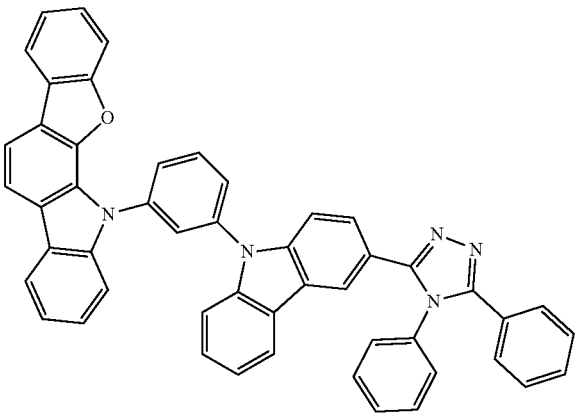

220
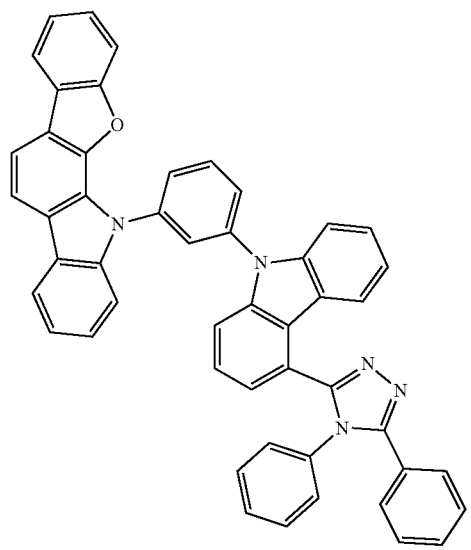
237
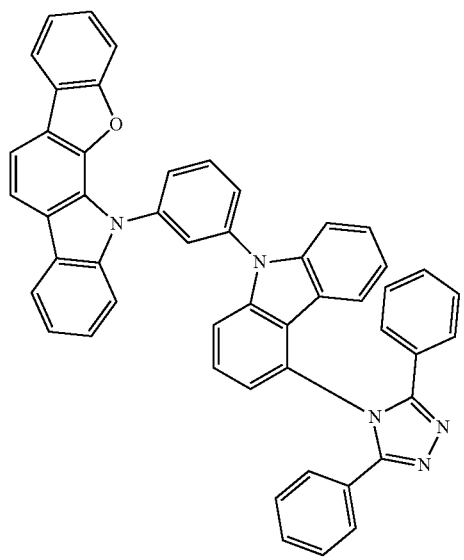
239
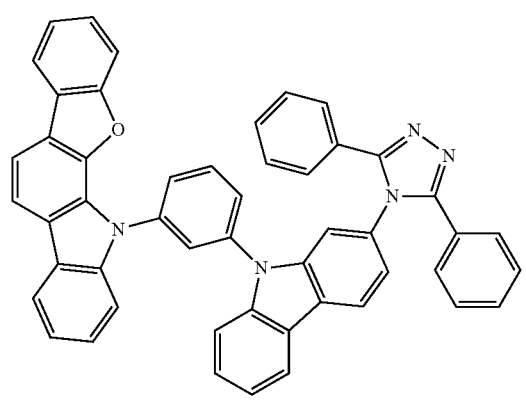
238
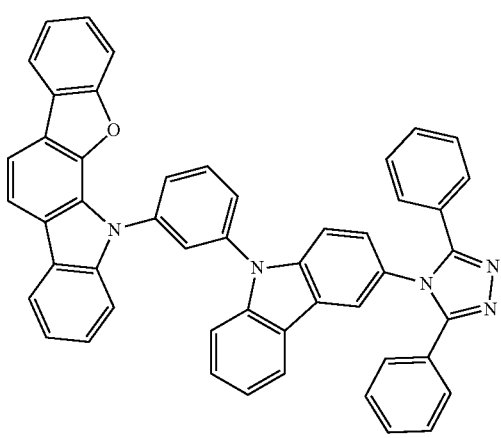
157
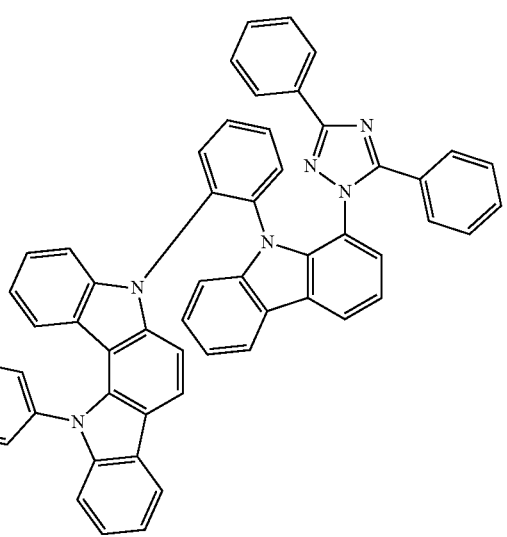

158
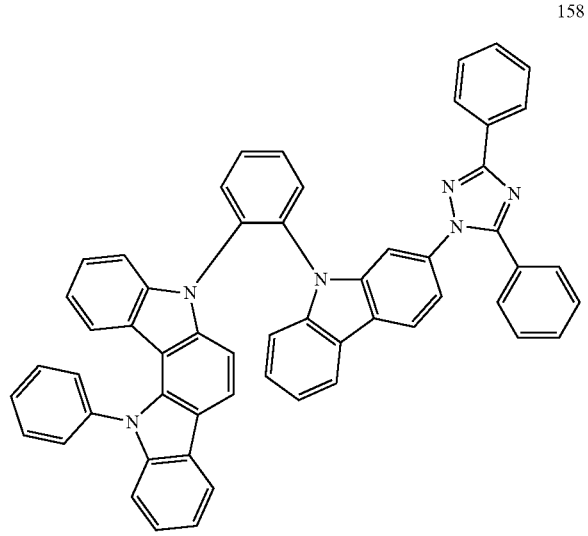
159
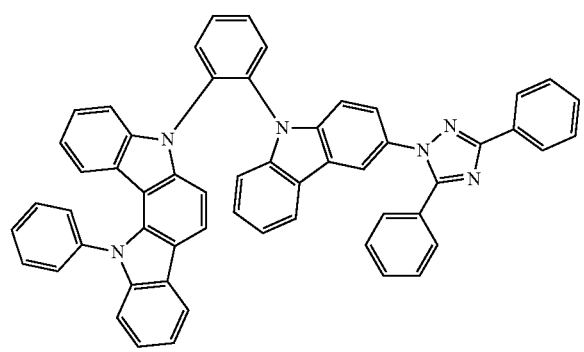
172
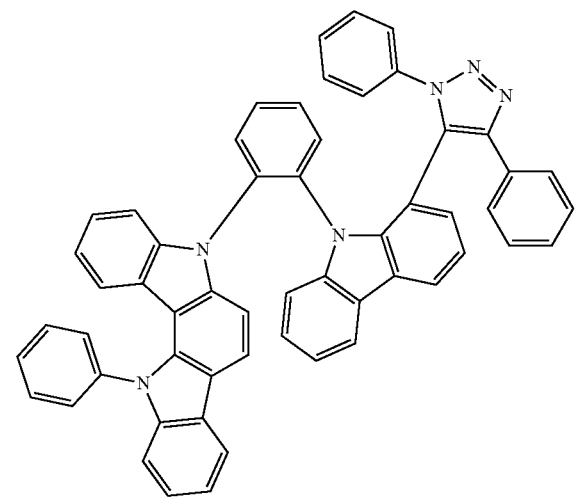
171
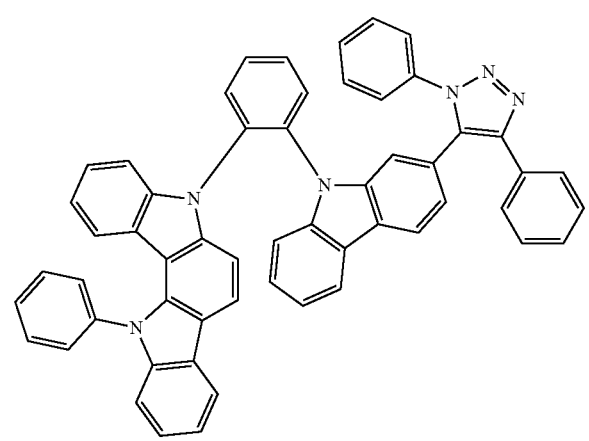
170
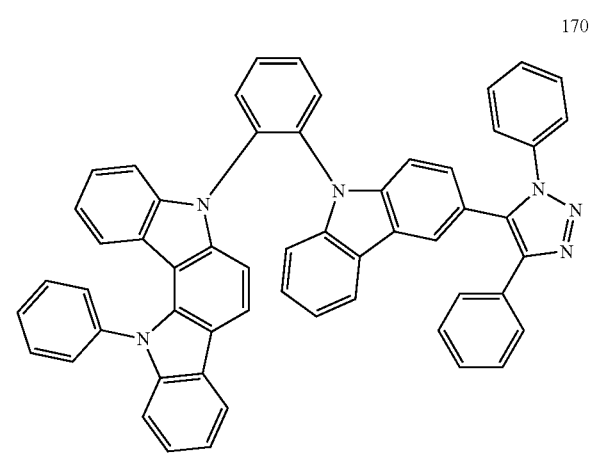
221
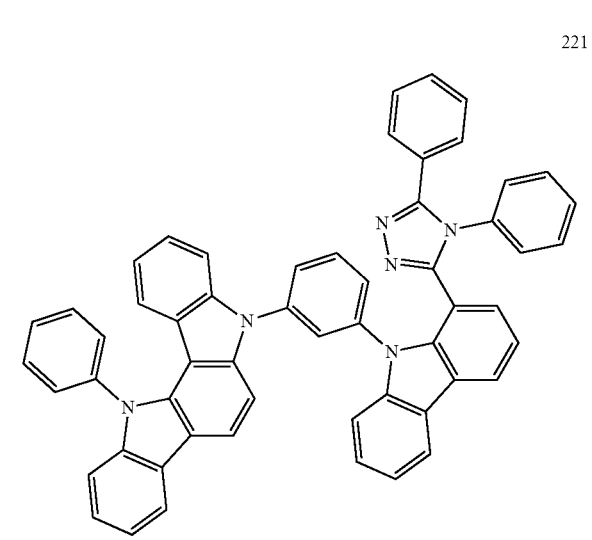

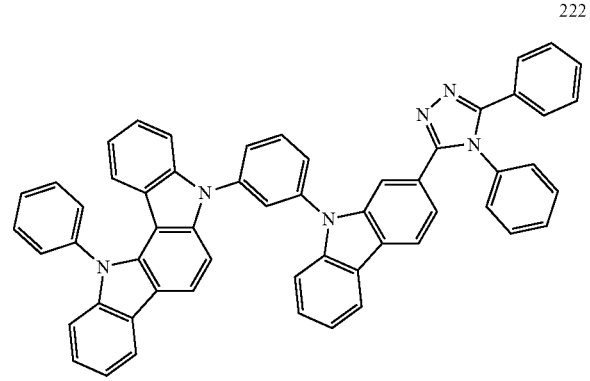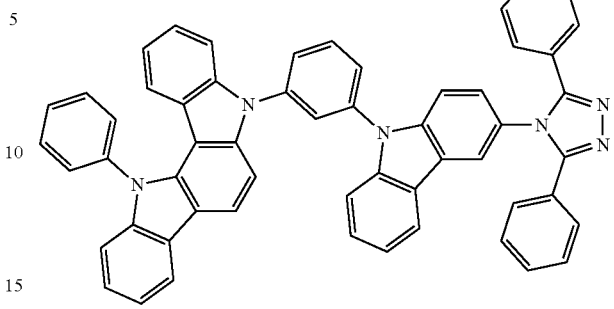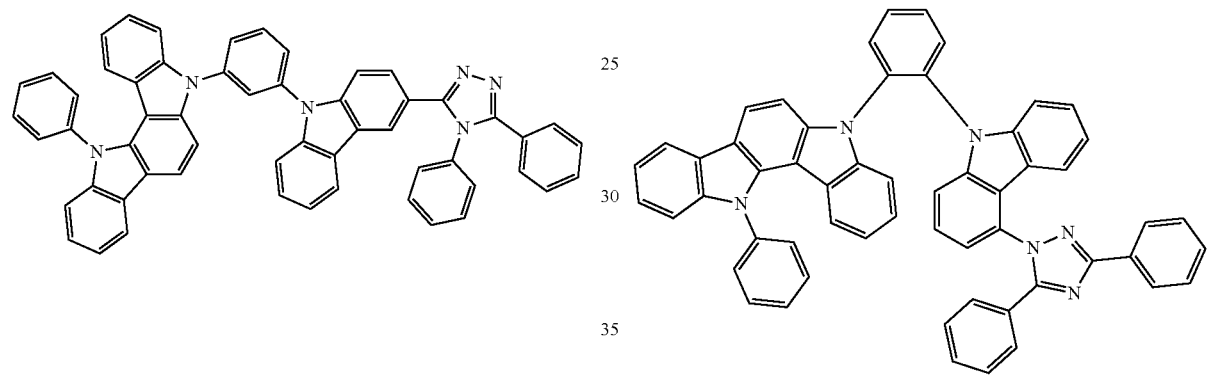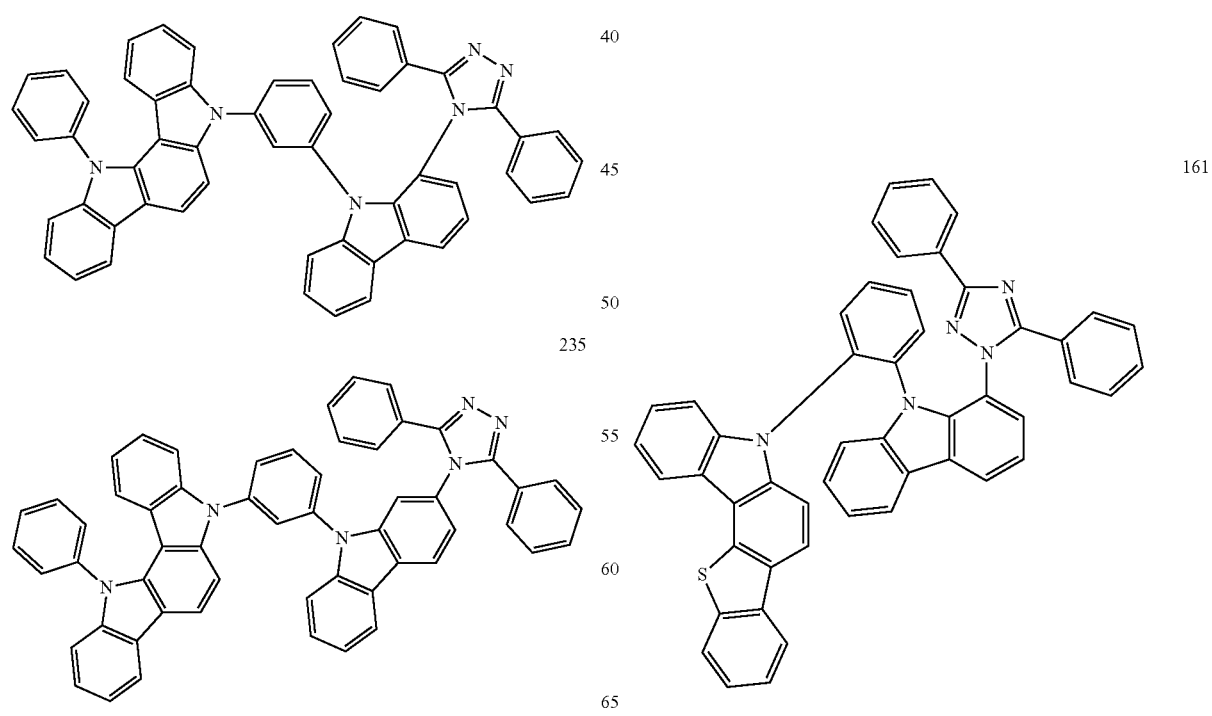

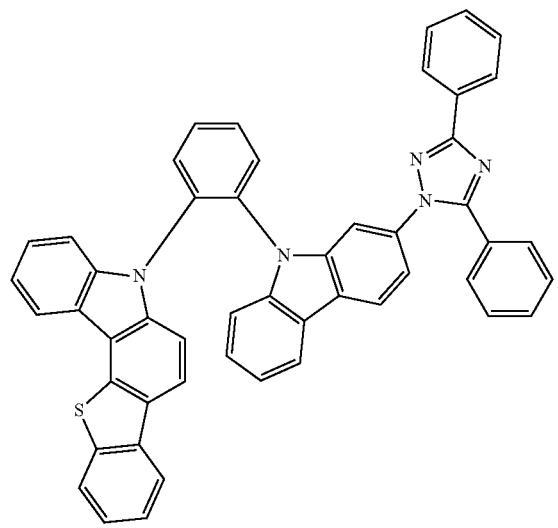
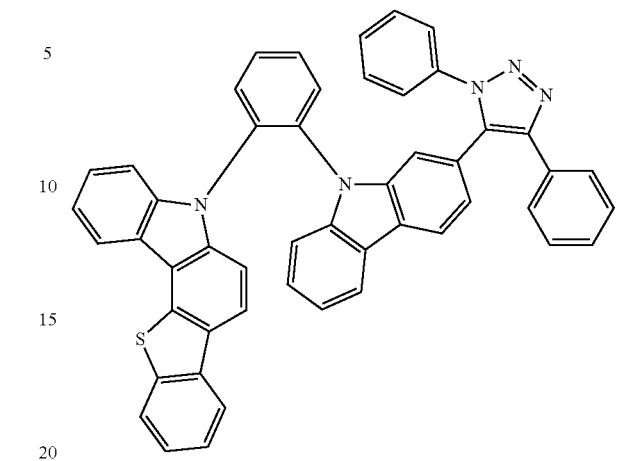
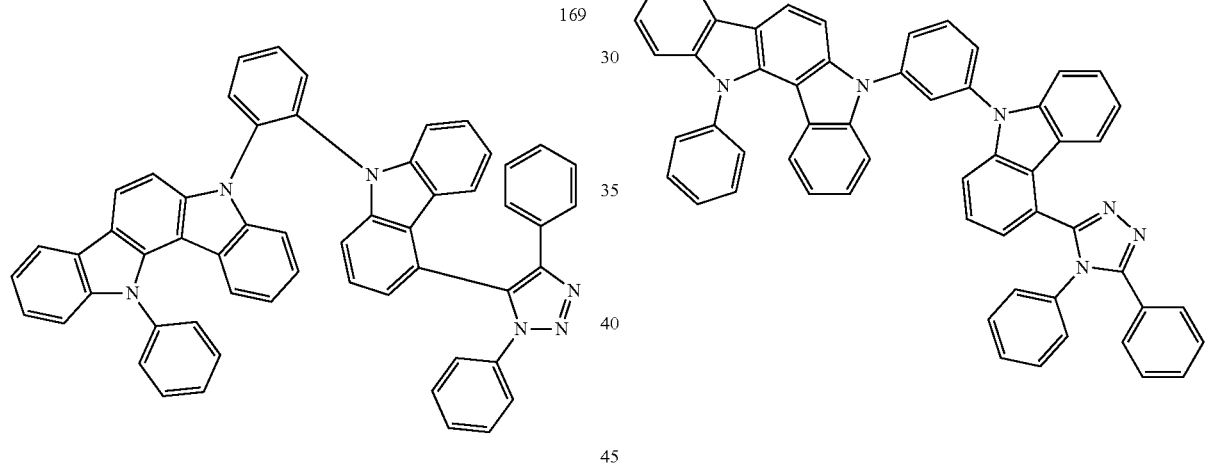
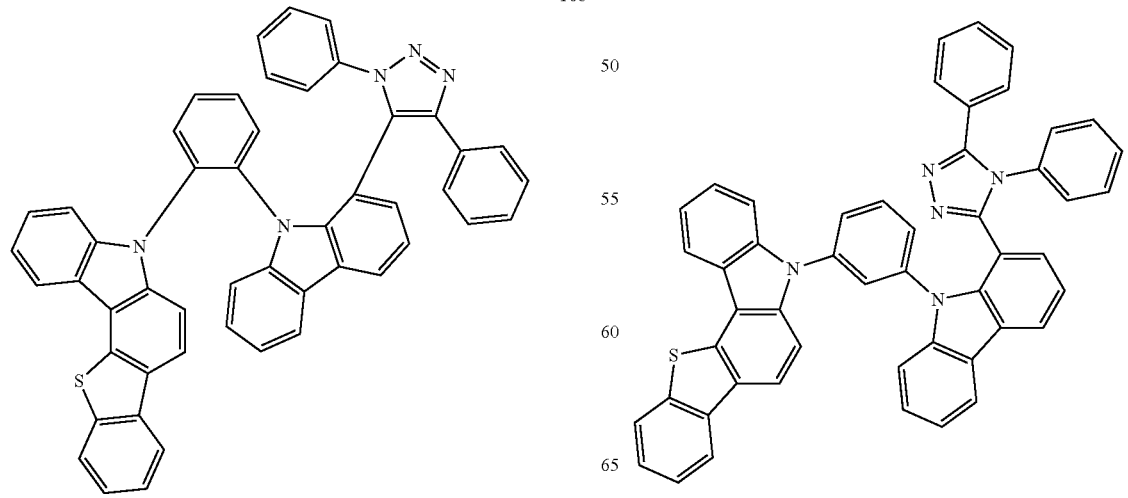

226
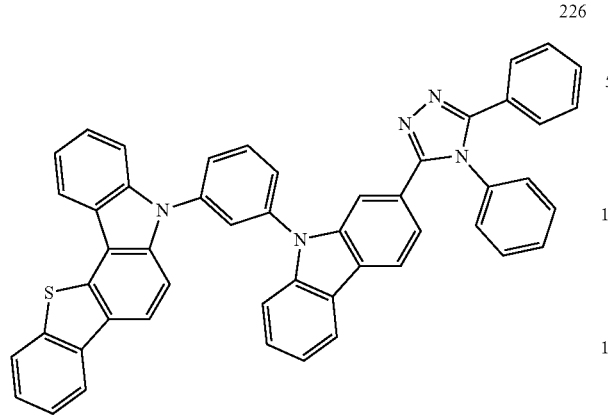
231
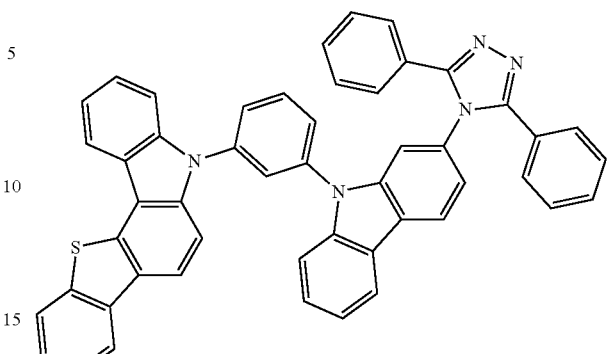
163
233
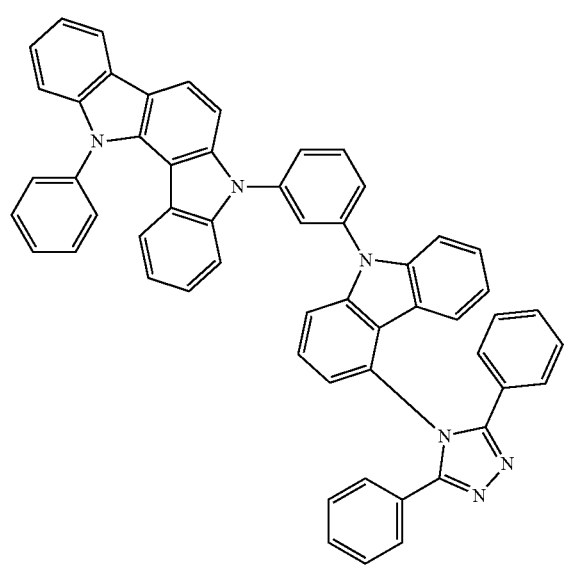
164
232
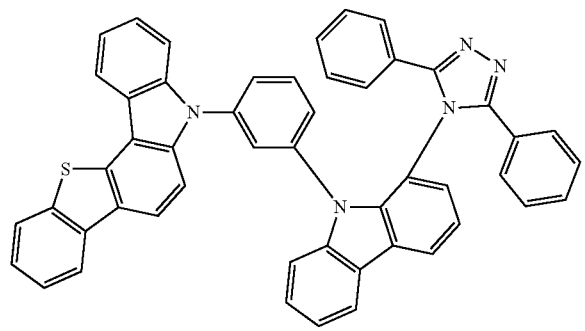
166
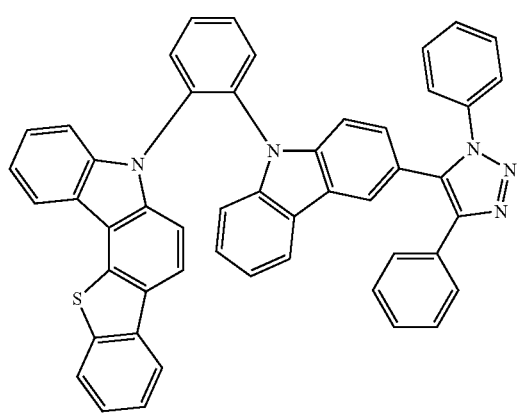

165
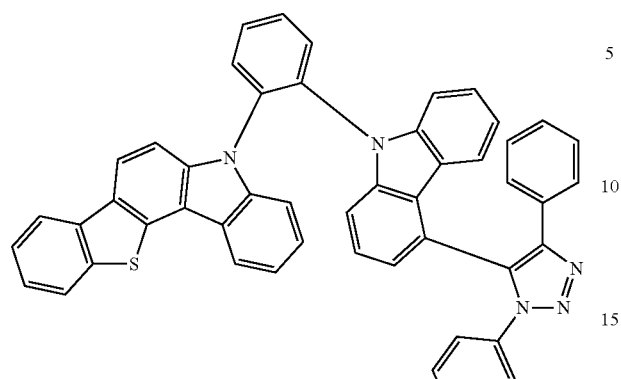
227
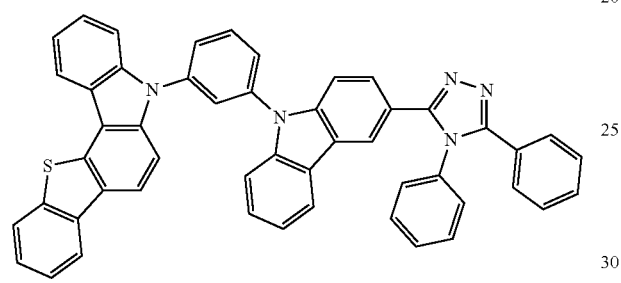
228
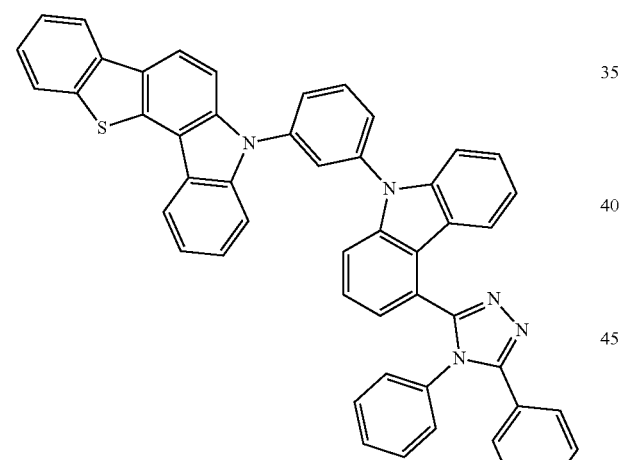
230
229
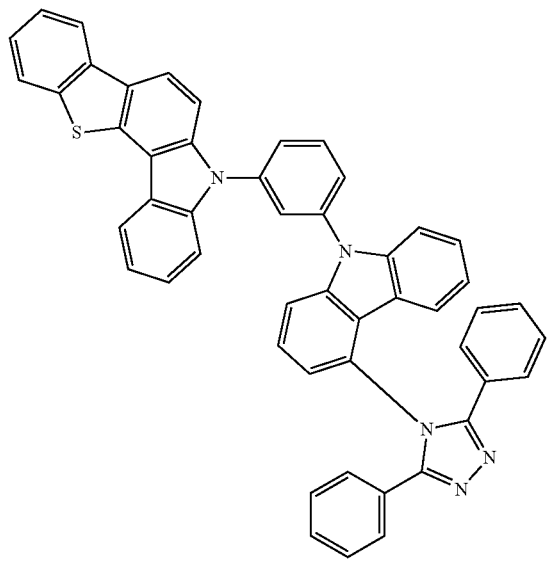
261
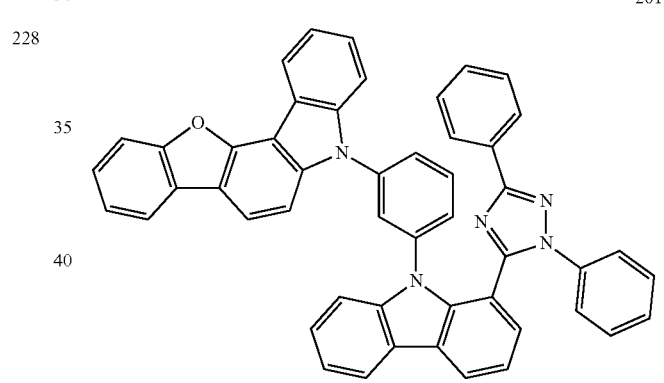
262
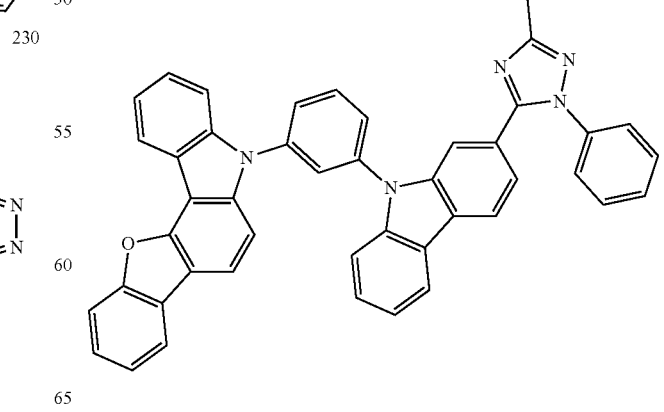

263
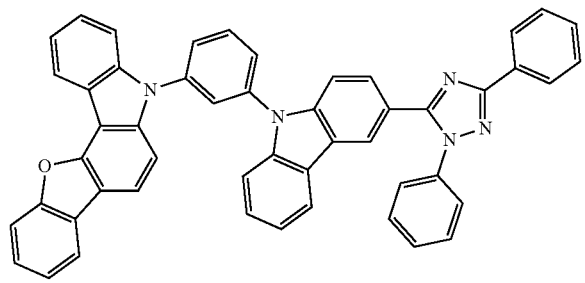
325
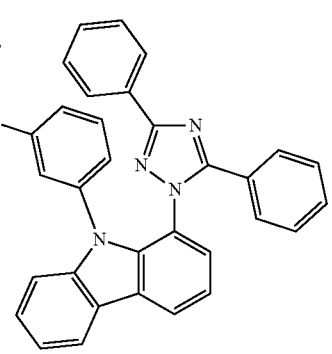
324
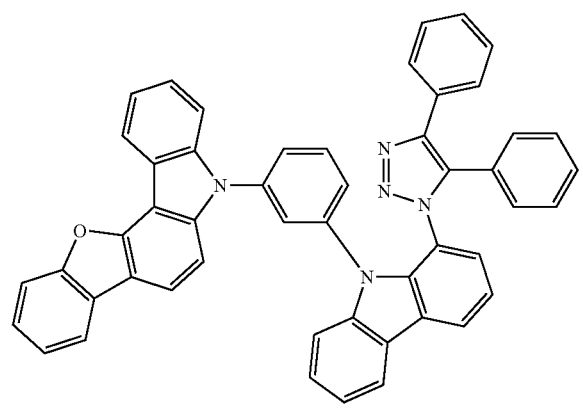
326
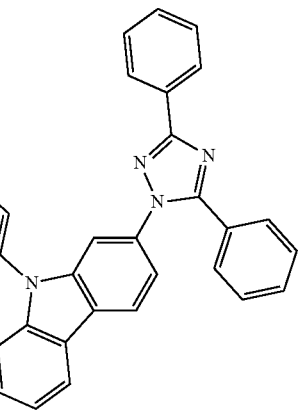
323
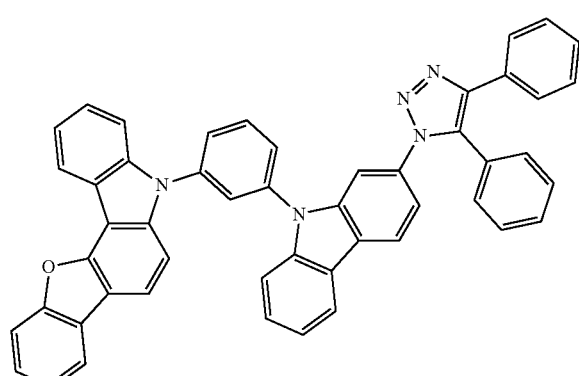
327
322
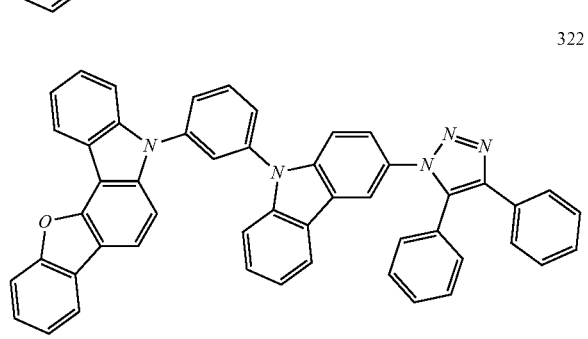
388
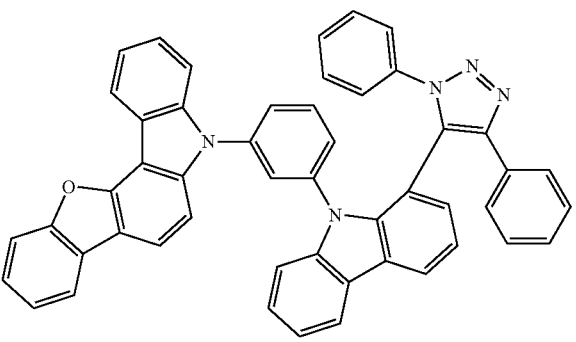

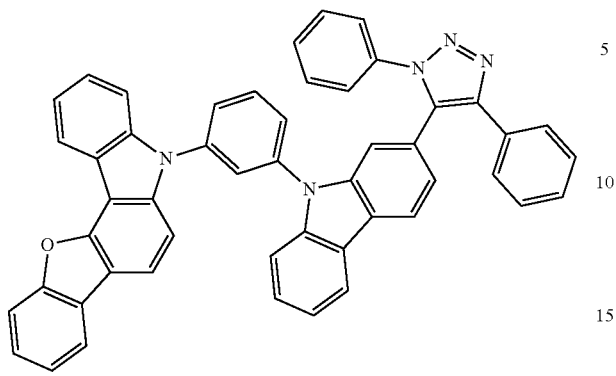
387
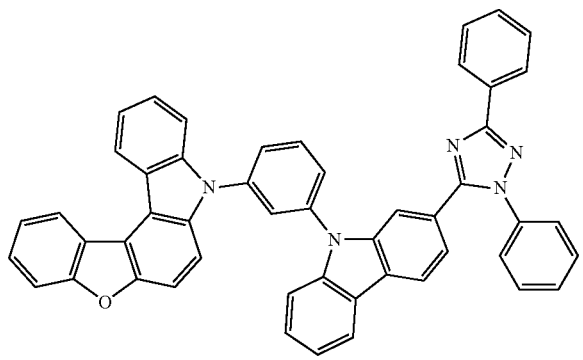
266
386
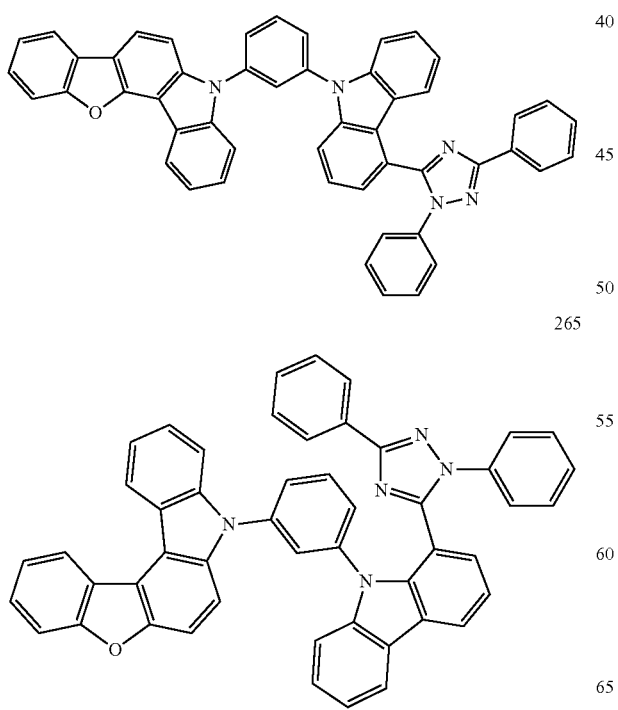
264
265
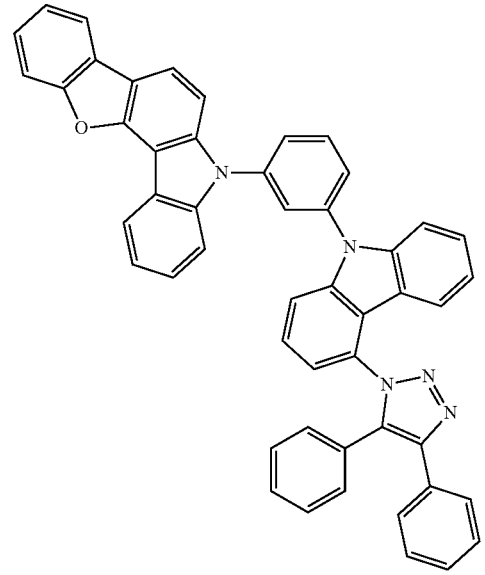
321
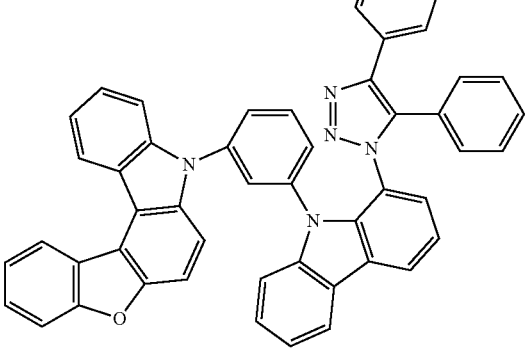
320

101
-continued
319
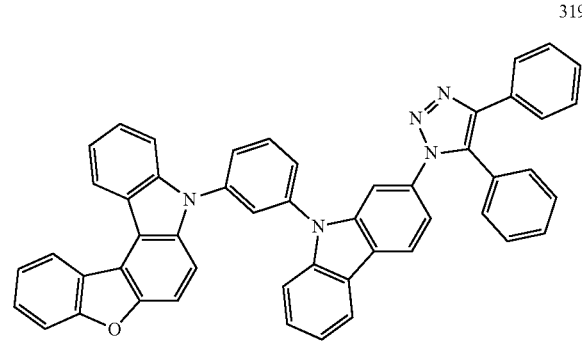
328
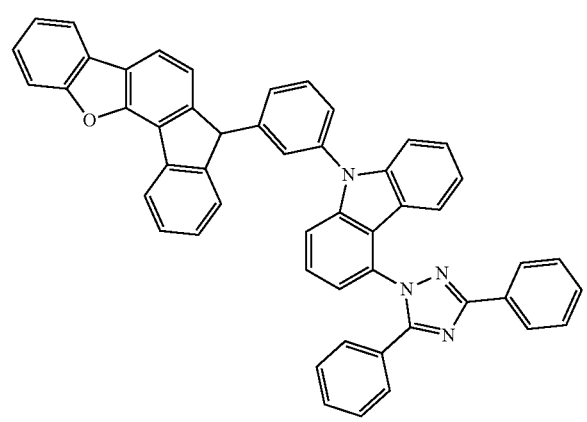
329
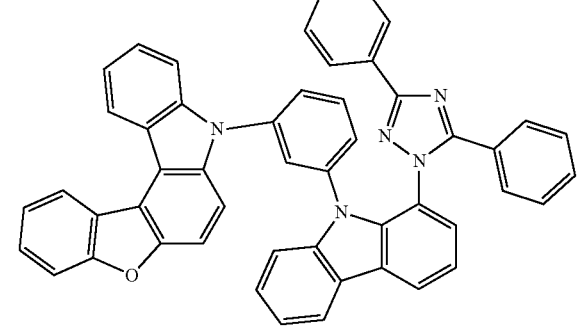
330
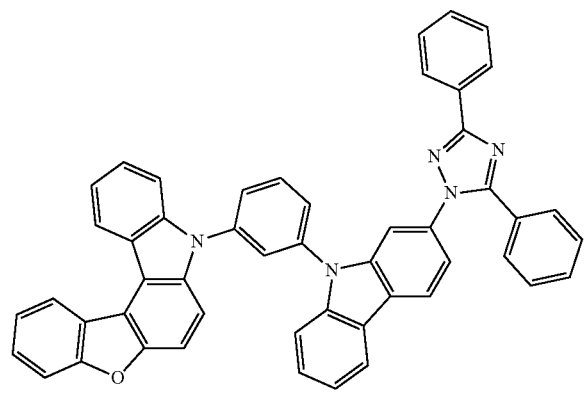
102
-continued
385
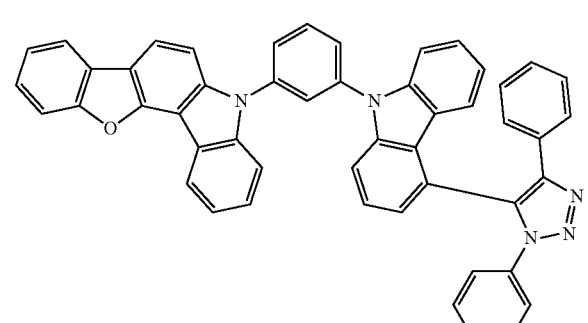
384
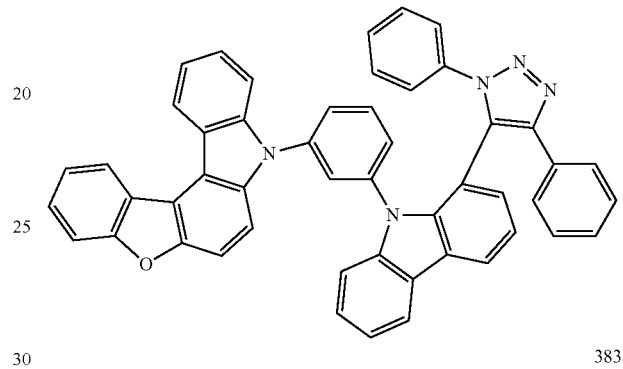
383
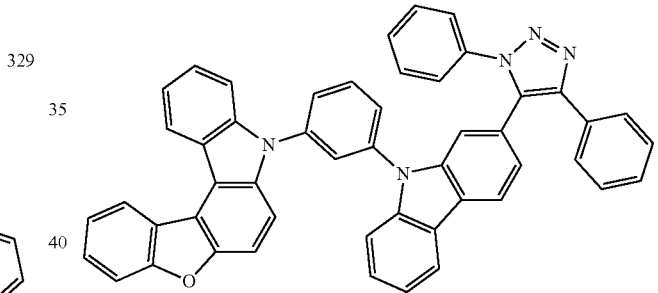
267
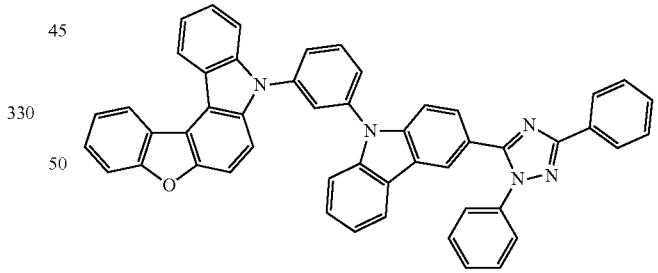
268
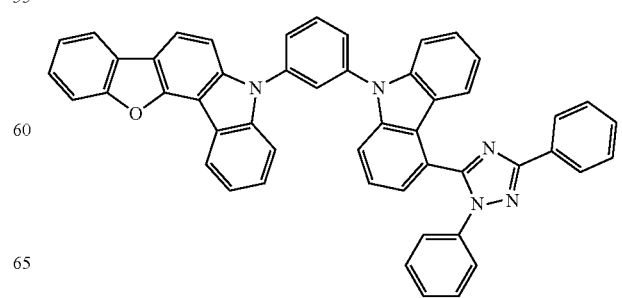

-continued
269
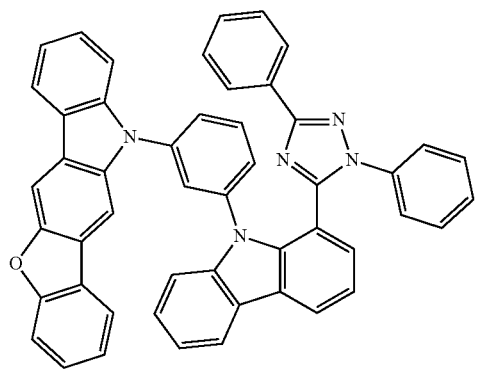
318
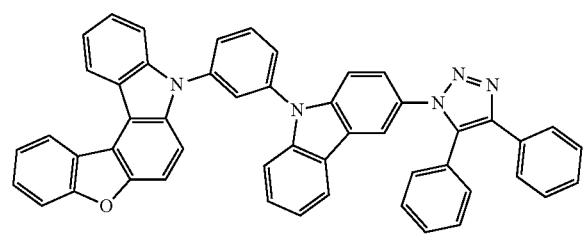
317
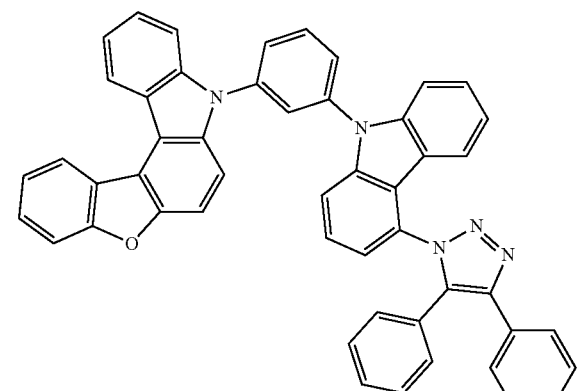
316
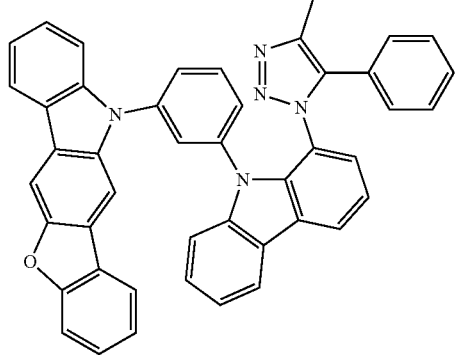
-continued
331
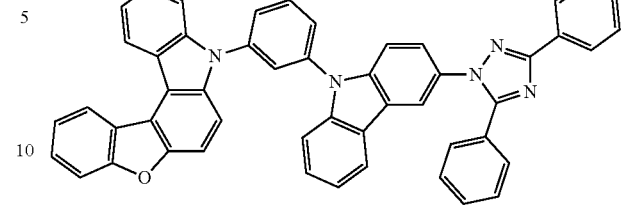
332
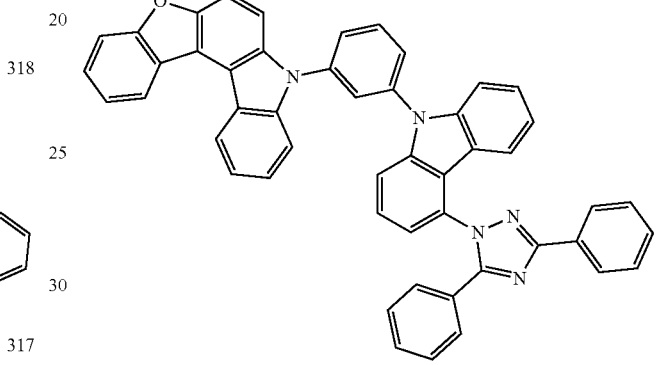
333
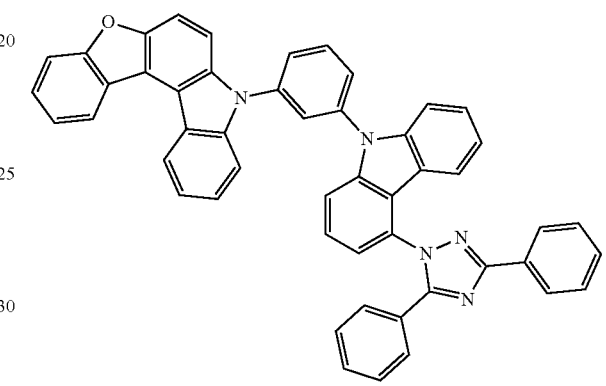
382
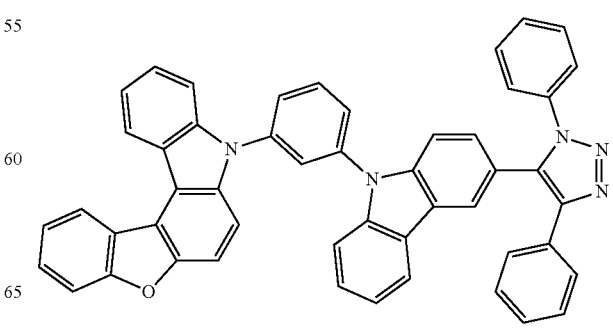

381
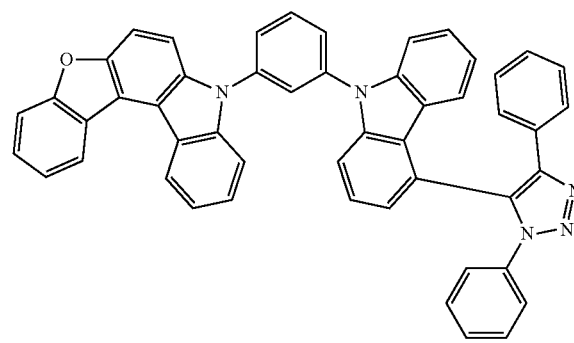
380
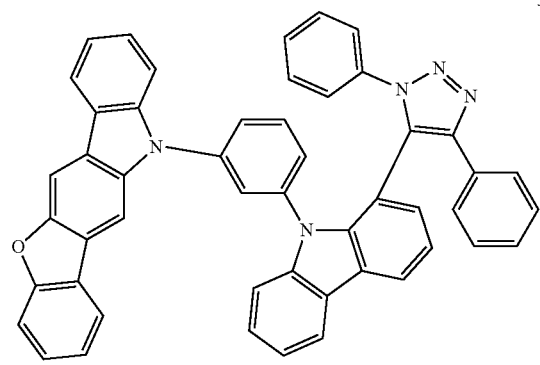
270
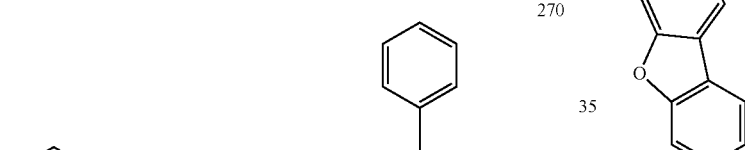
271
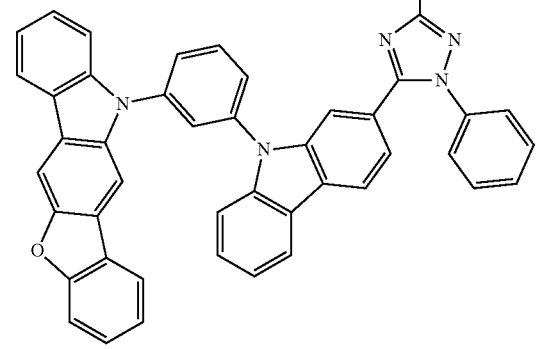
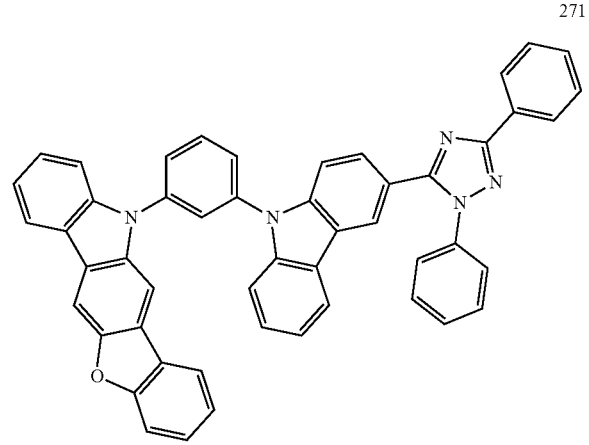
282
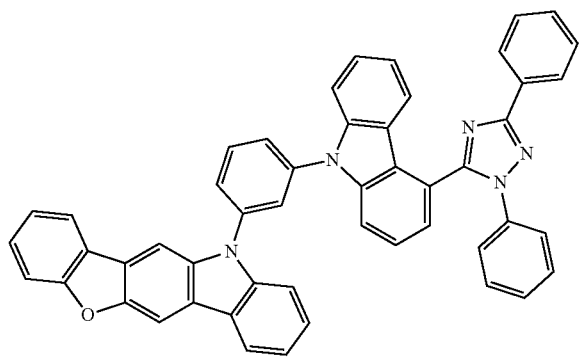
315
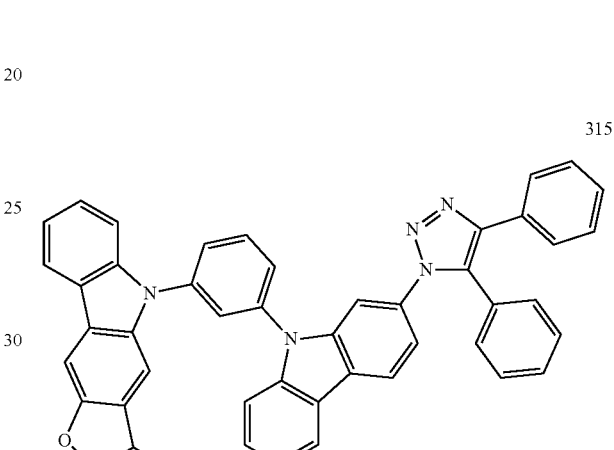
314
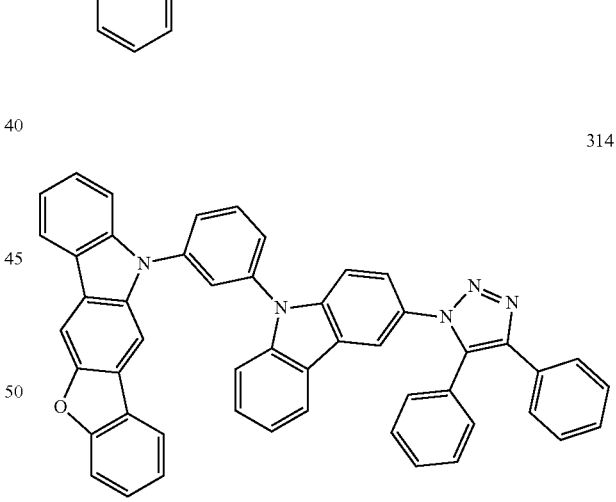
313
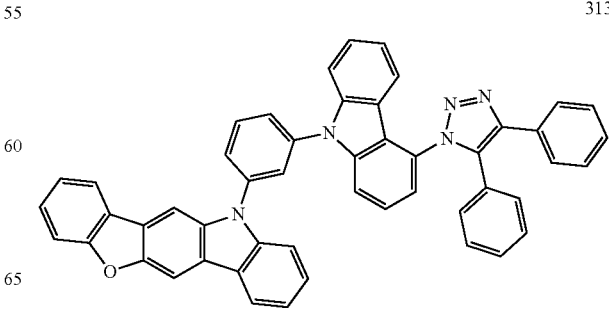

334
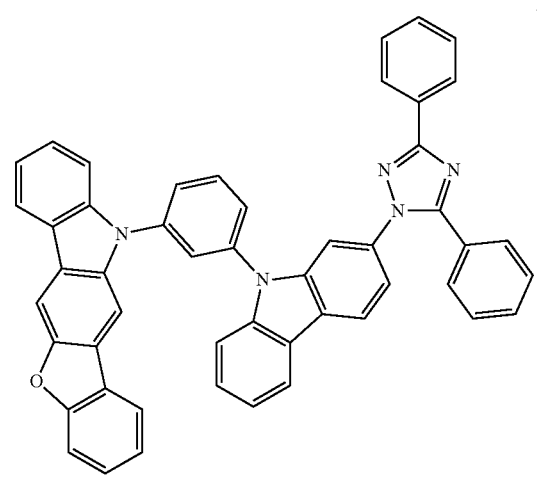
335
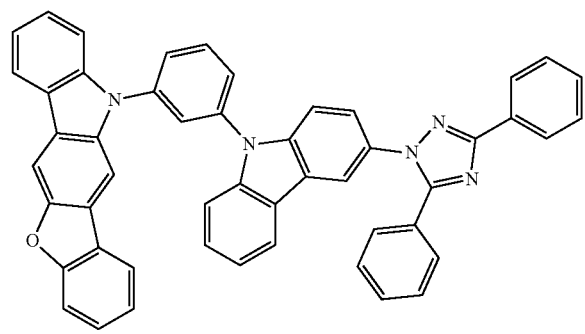
336
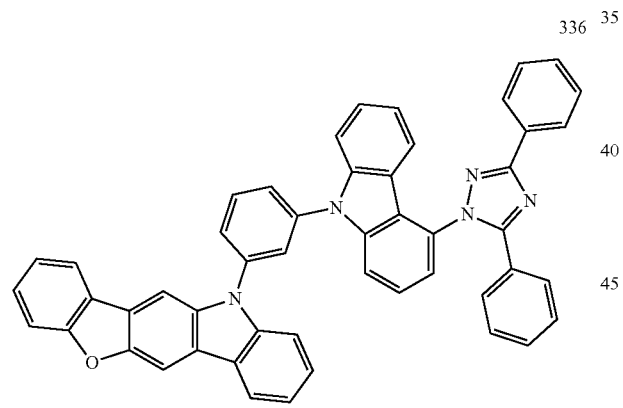
379
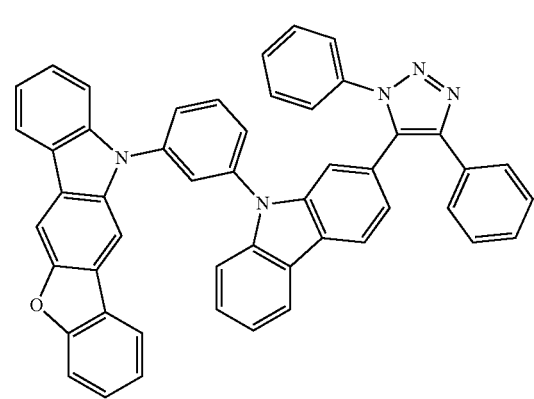
378
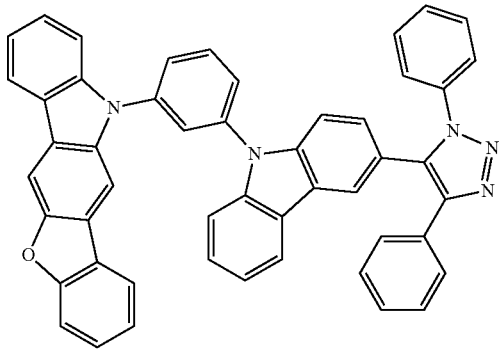
377
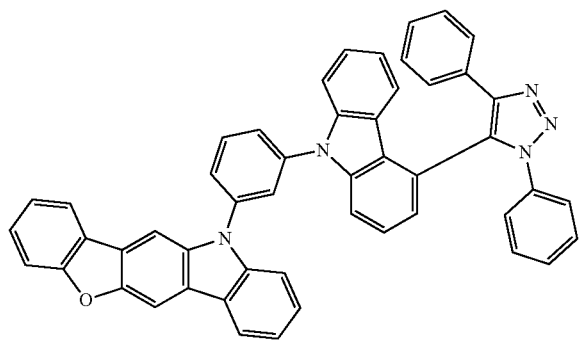
273
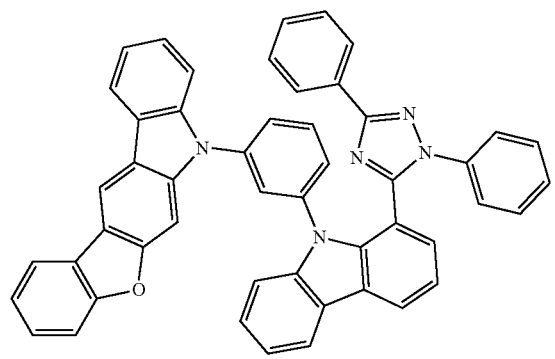
274
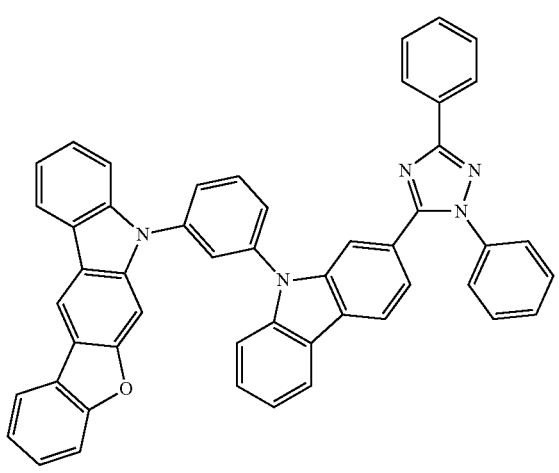

-continued
275
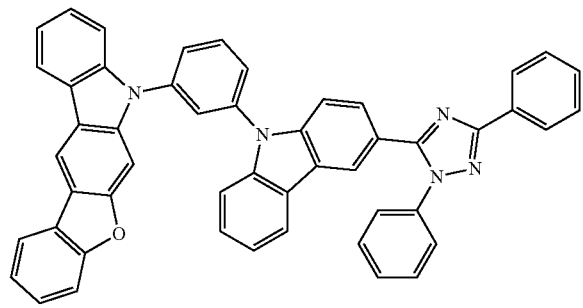
312
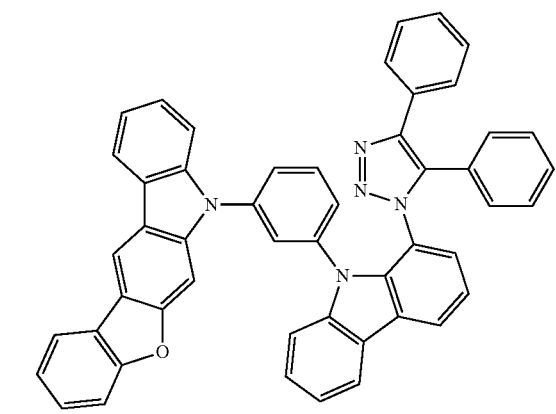
311
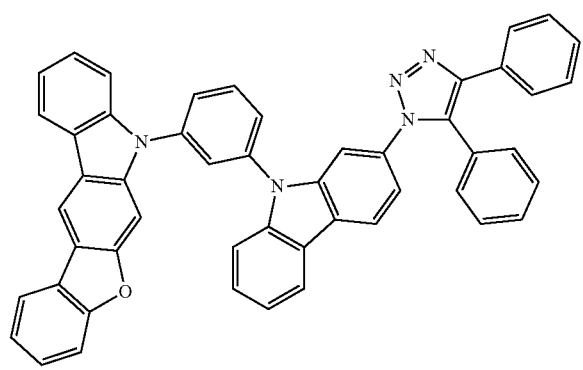
310
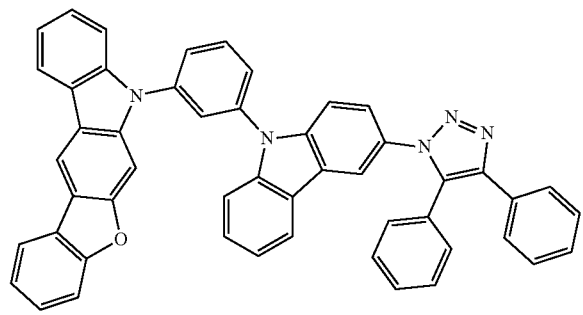
-continued
337
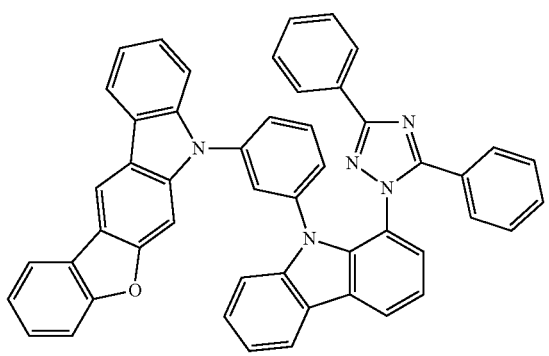
338
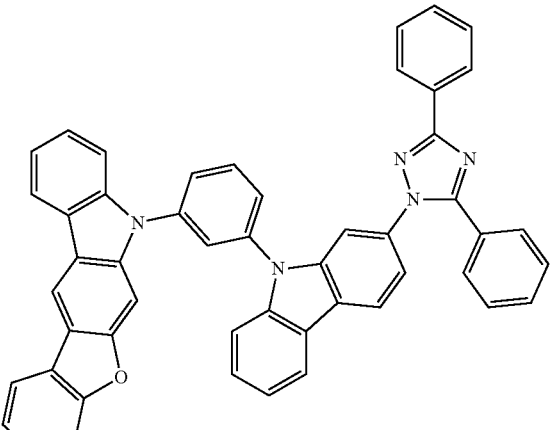
339
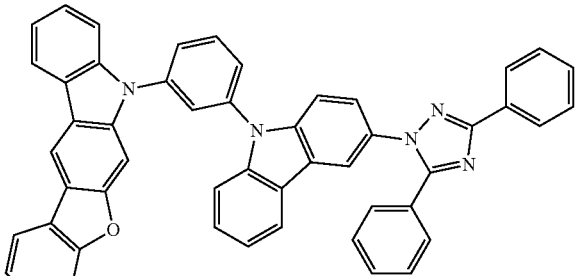
376
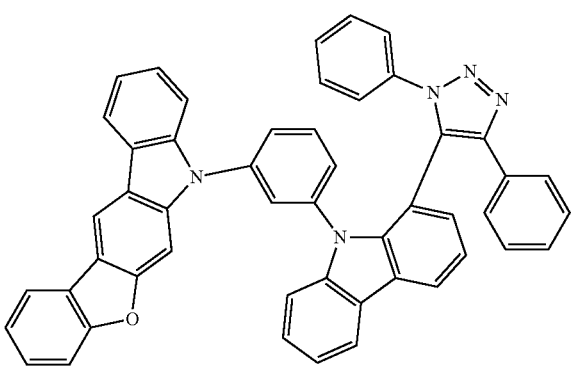

375
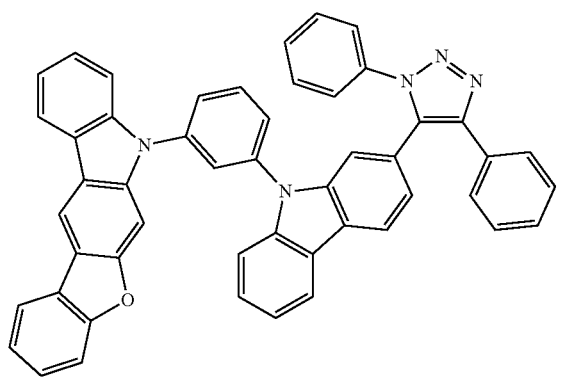
374
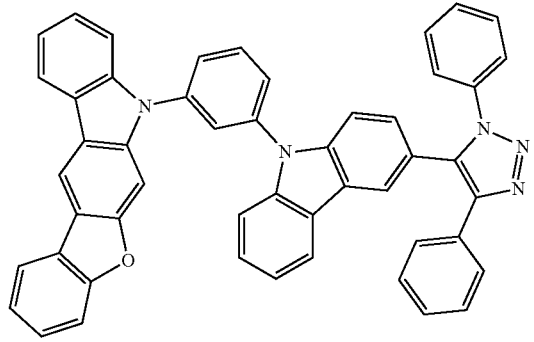
276
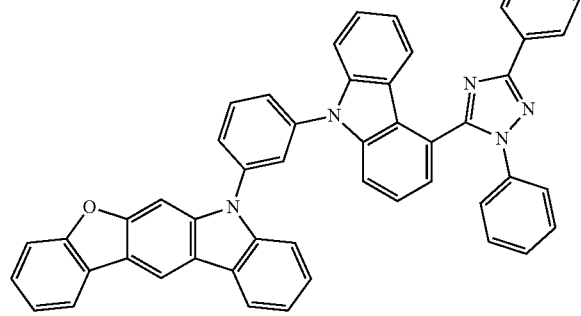
277
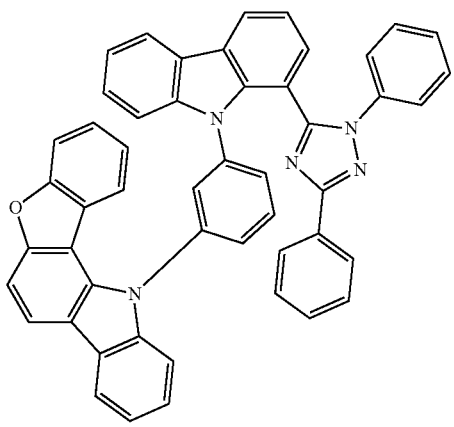
278
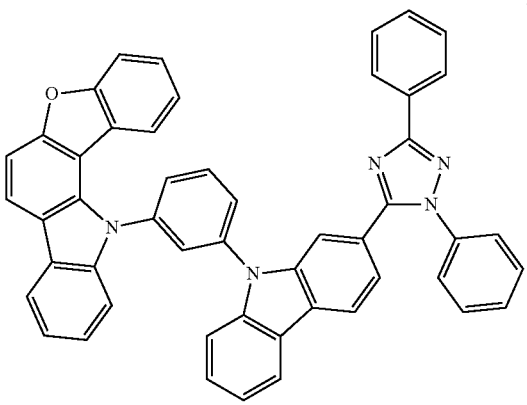
309
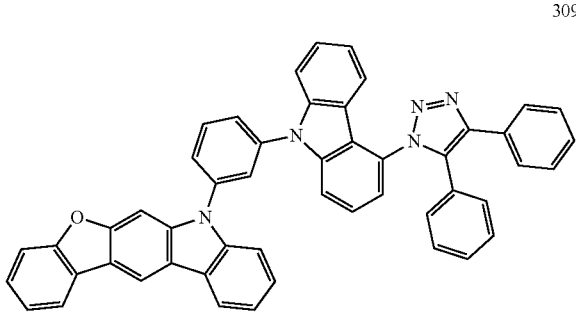
308
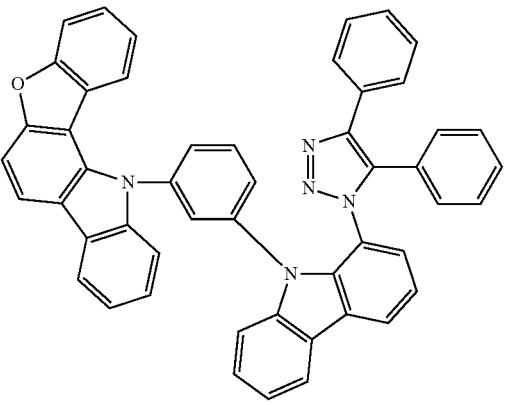
307
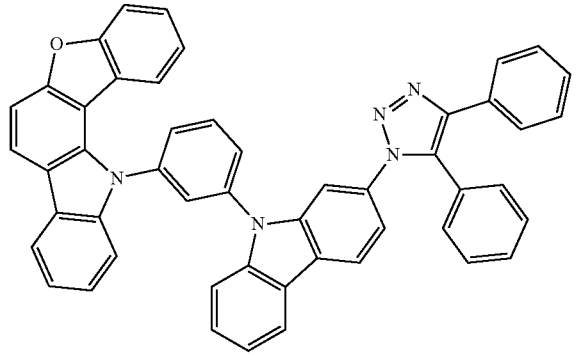

-continued
340
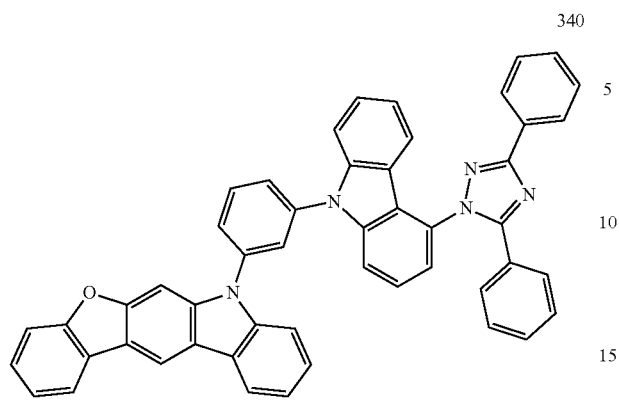
341
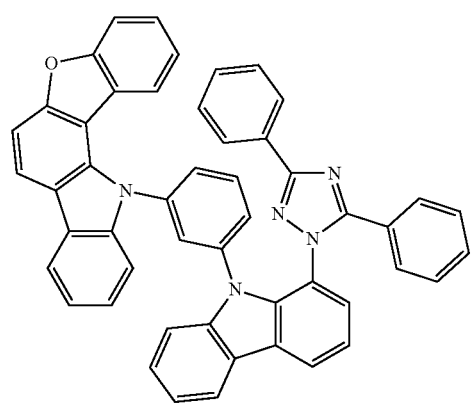
342
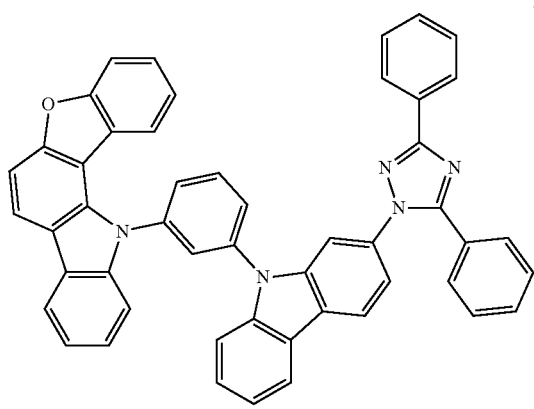
373
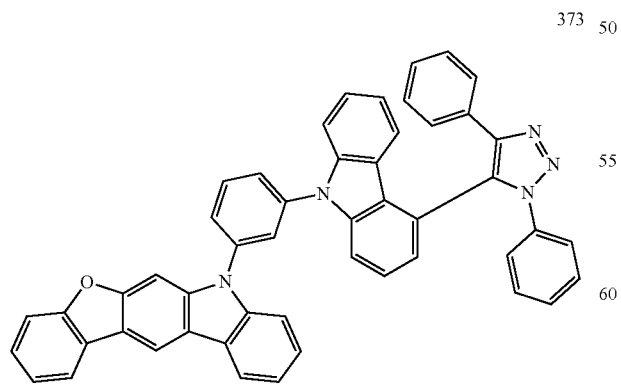
-continued
372
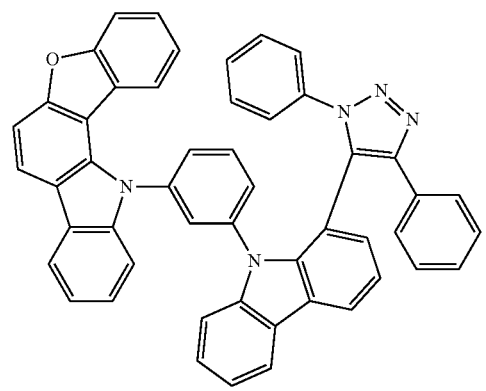
371
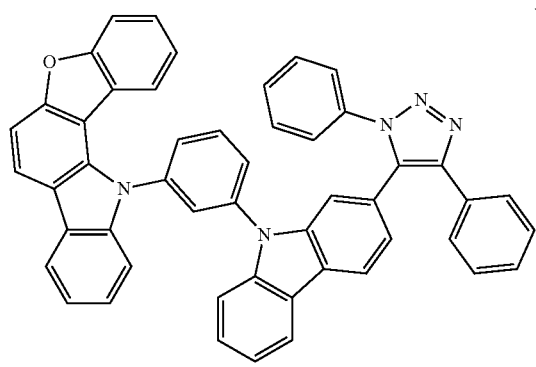
279
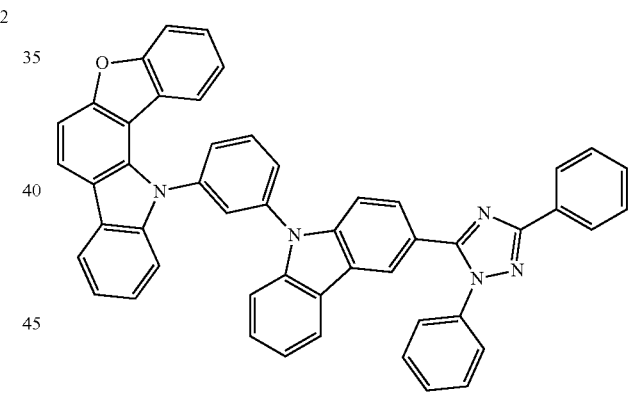
280
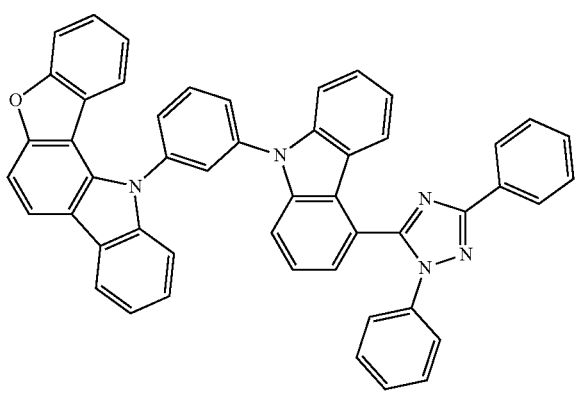

281
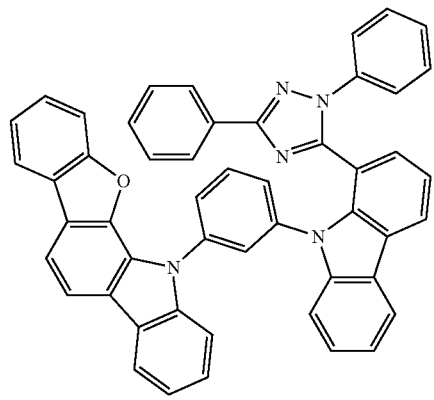
304
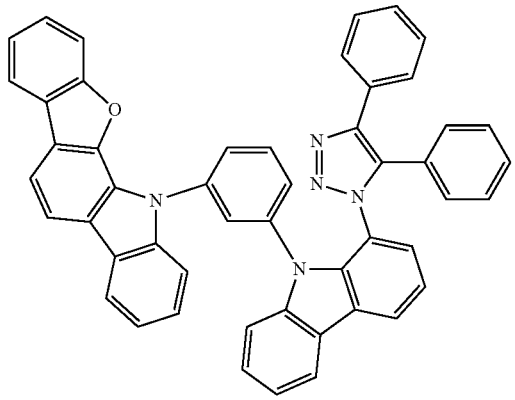
306
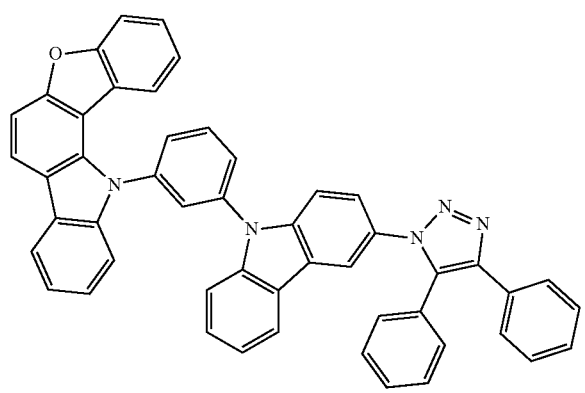
343
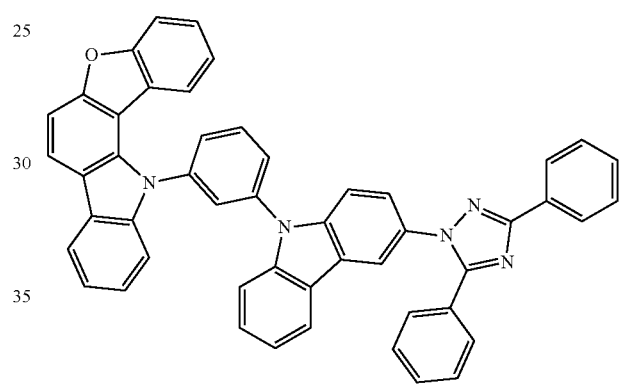
305
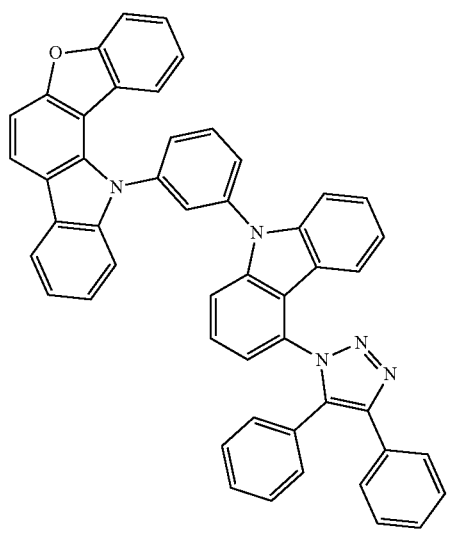
344
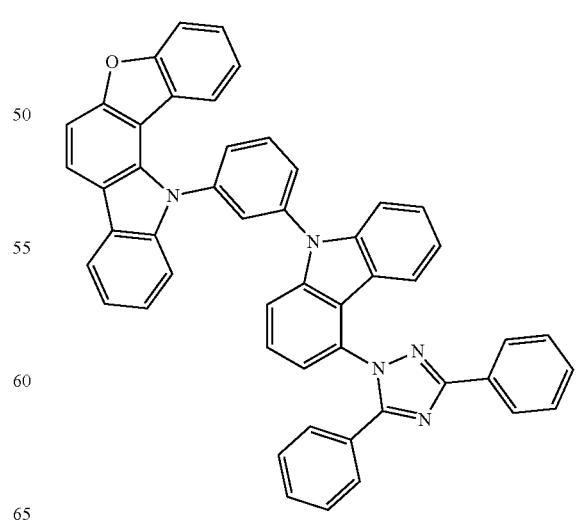

345
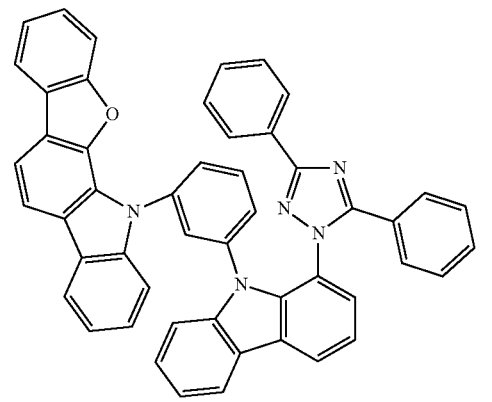
370
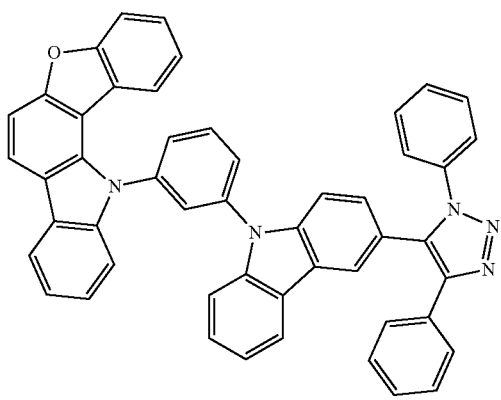
369
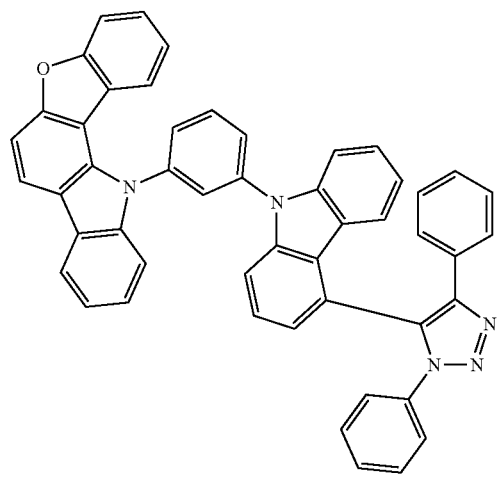
368
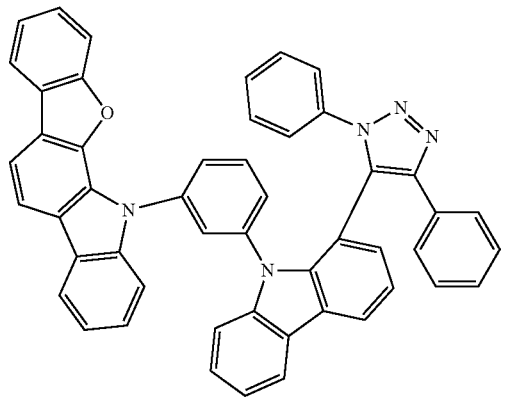
282
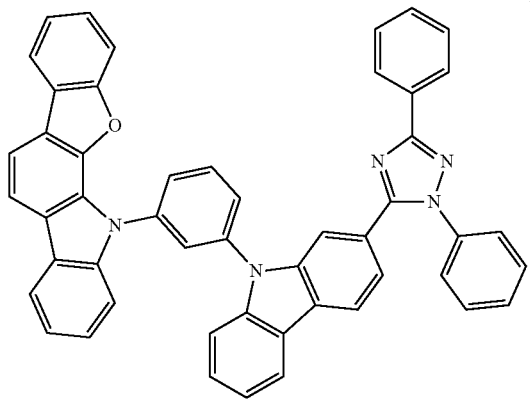
283
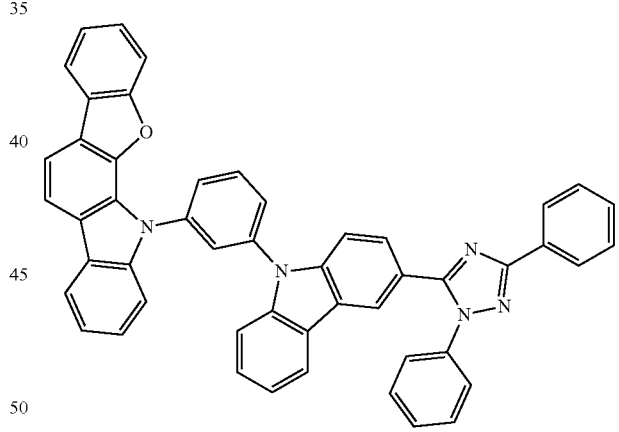
284
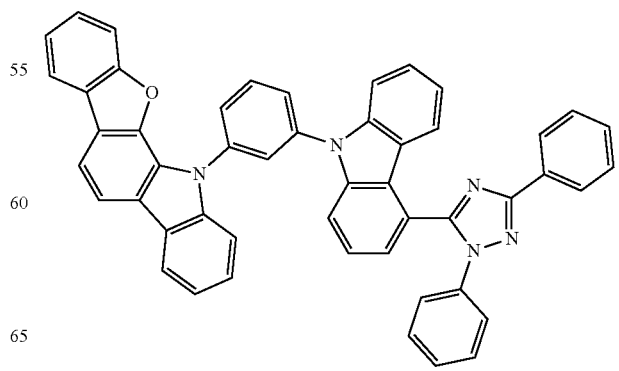

119
-continued
303
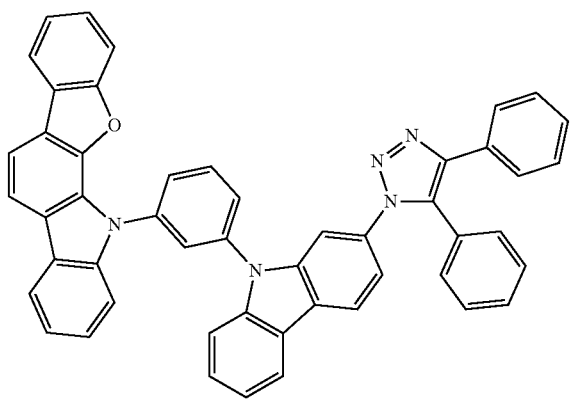
302
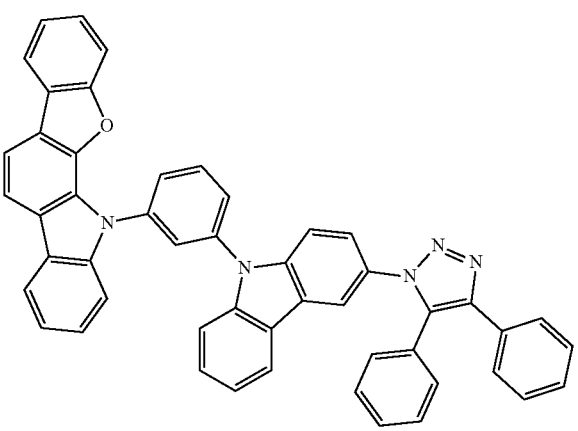
301
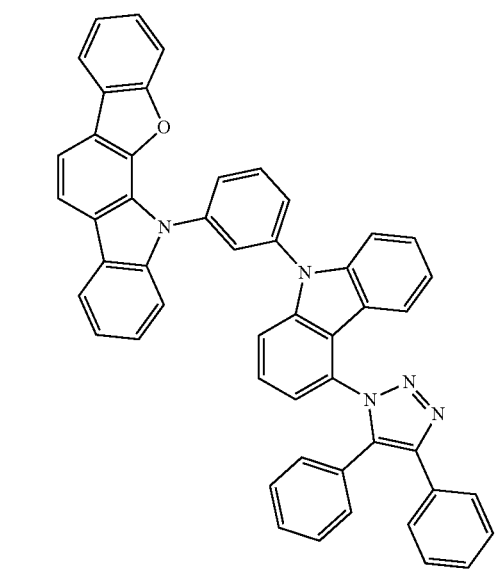
120
-continued
346
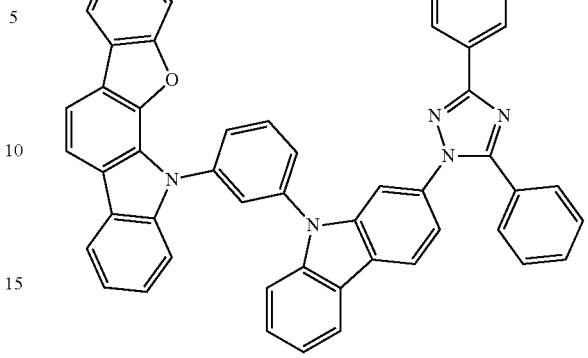
347
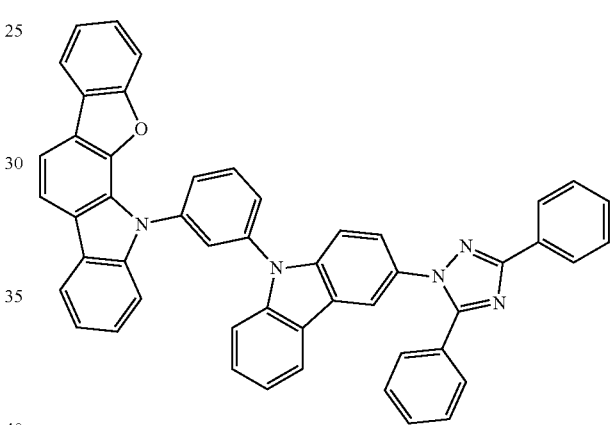
348
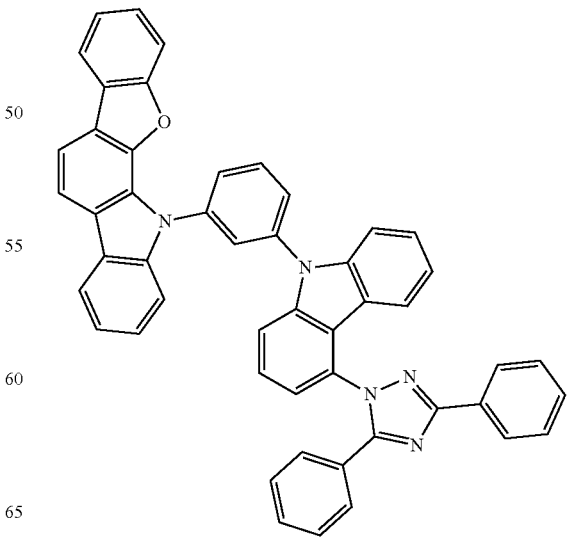

367
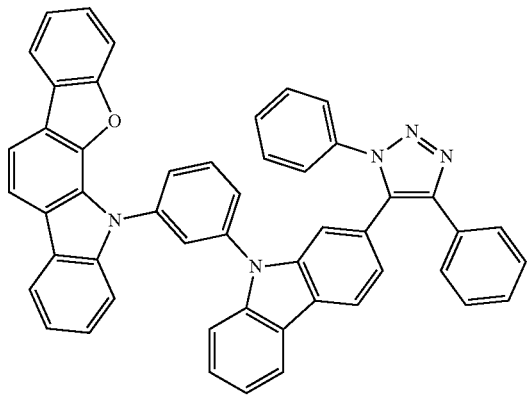
366
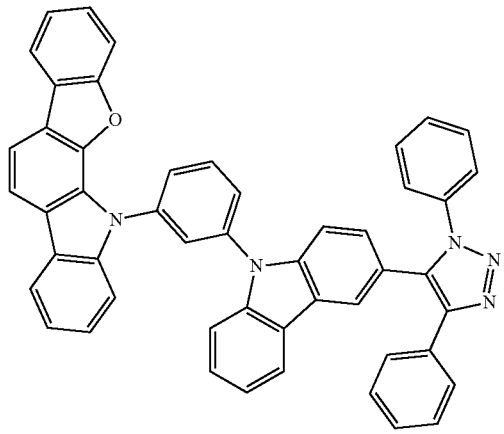
285
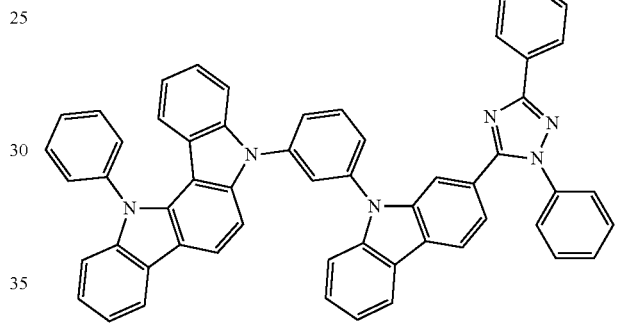
286
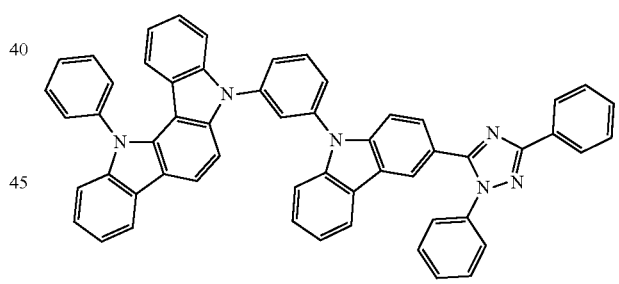
287
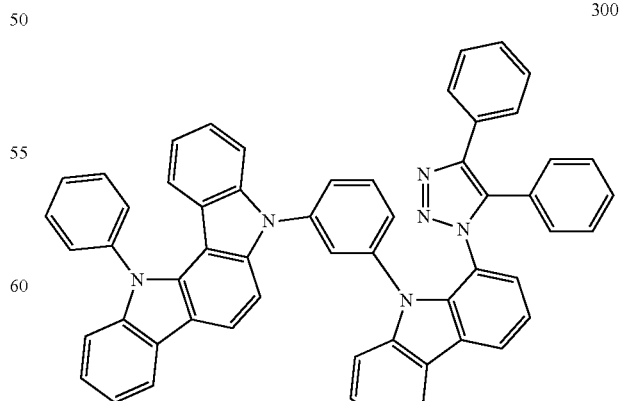
365
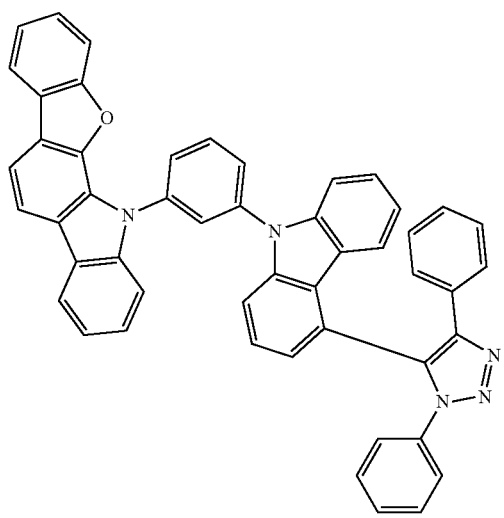
300

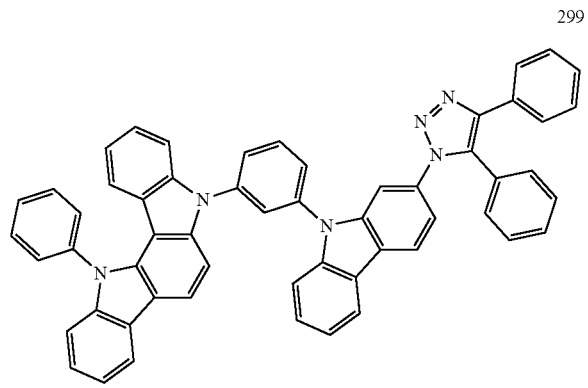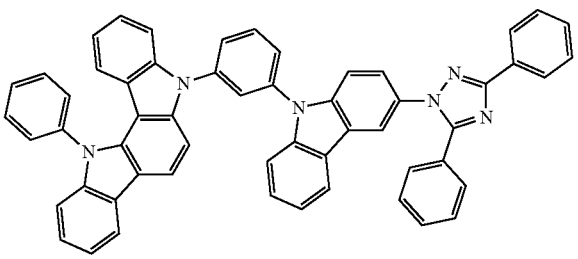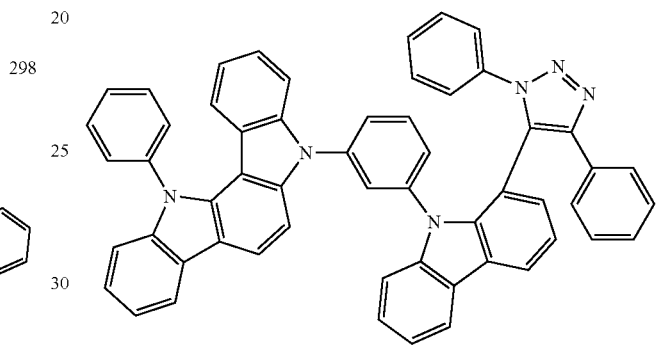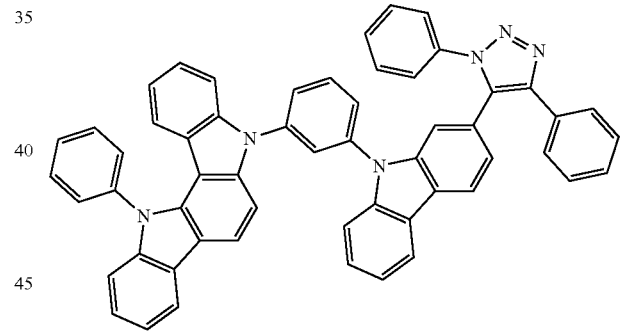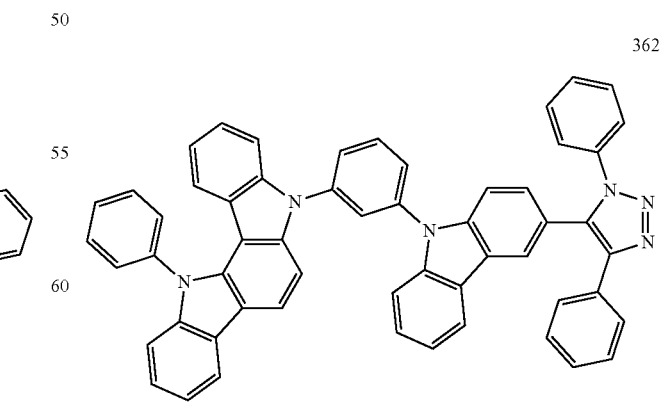

-continued
288
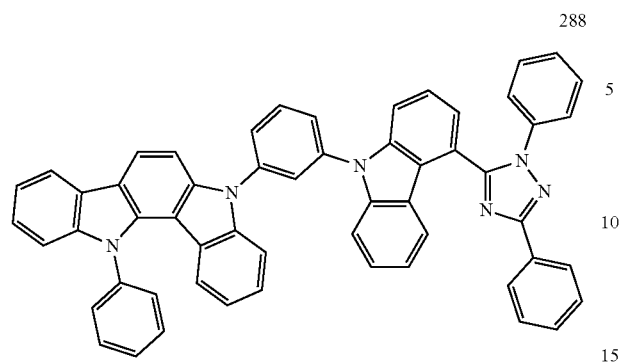
289
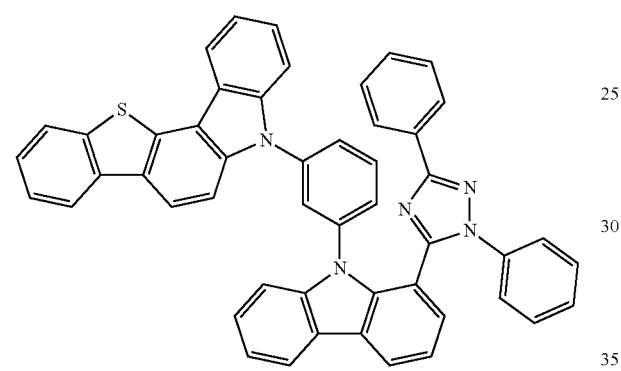
290
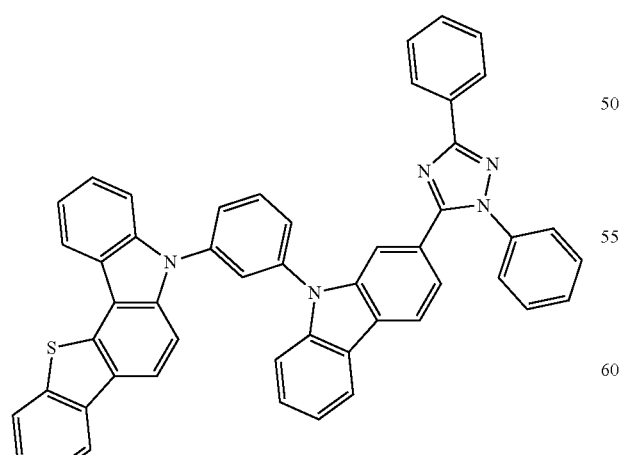
-continued
297
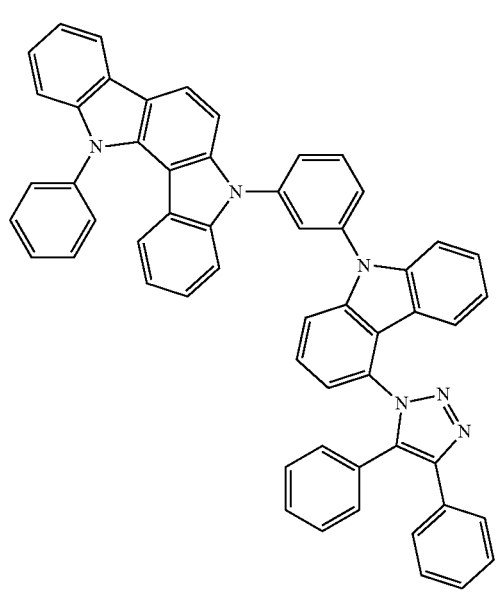
296
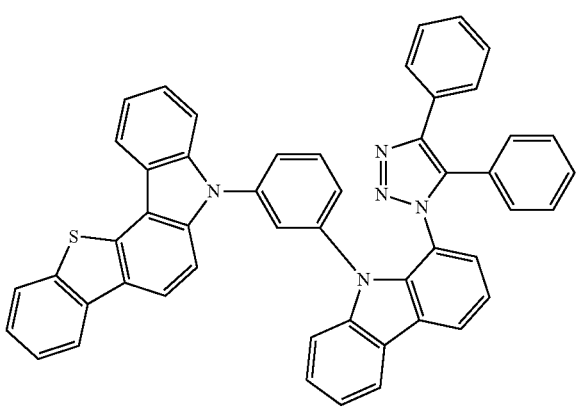
295
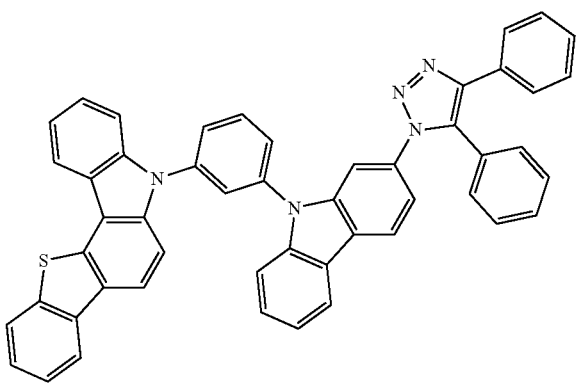

352
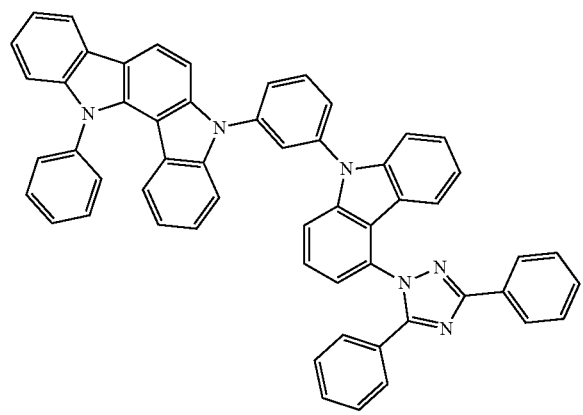
353
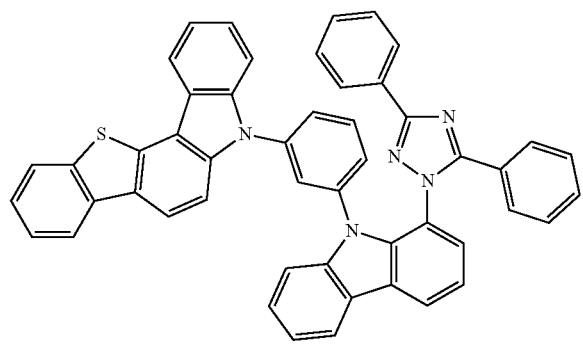
354
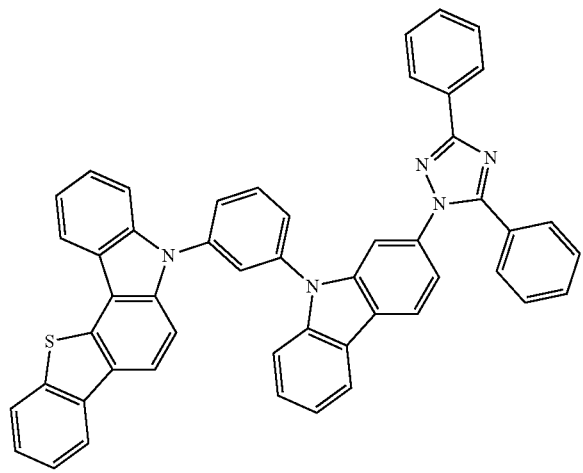
361
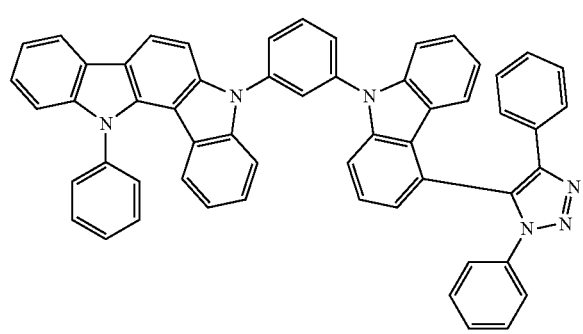
360
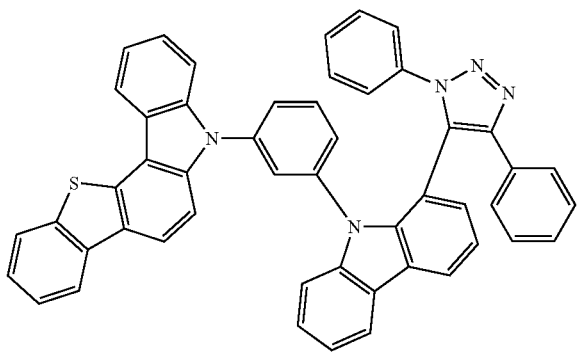
359
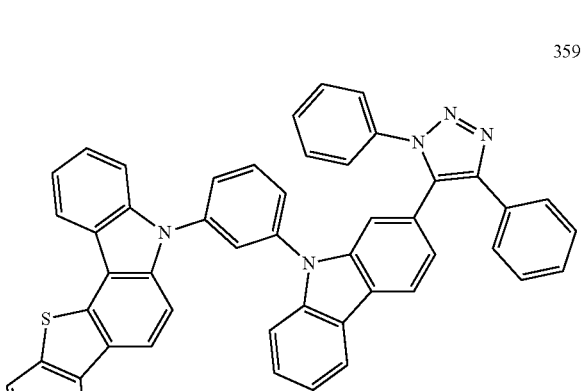
291
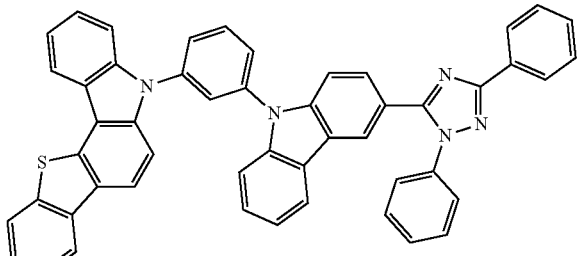
292
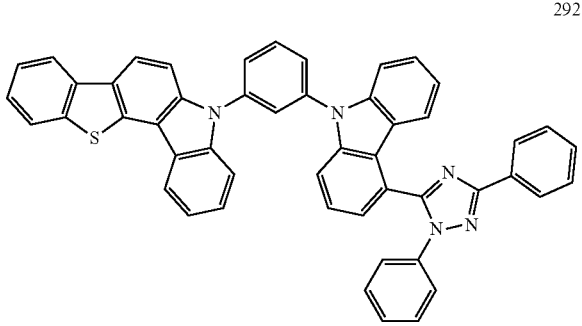

294
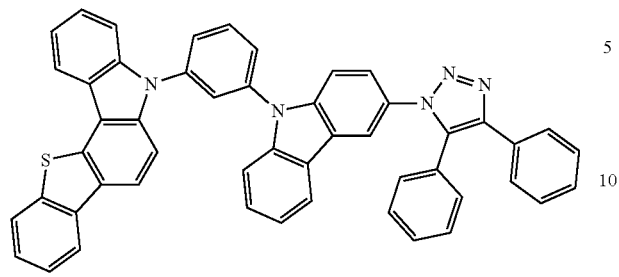
293
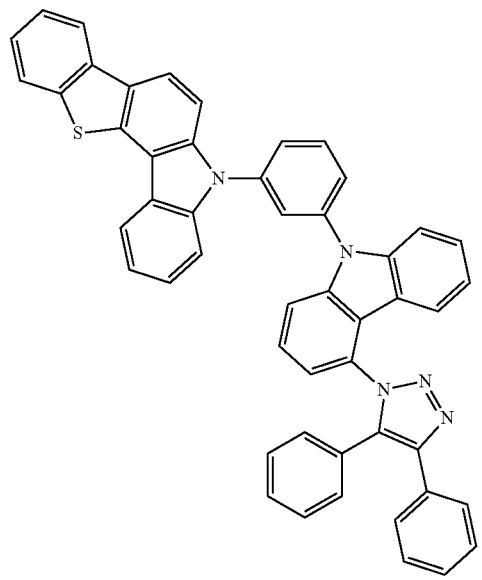
355
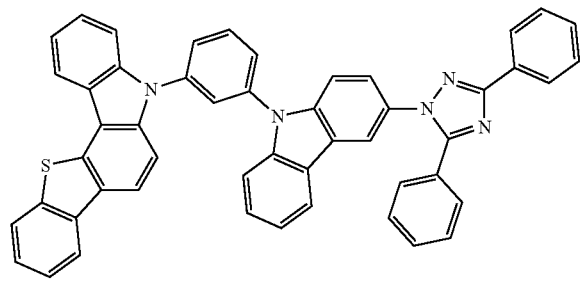
356
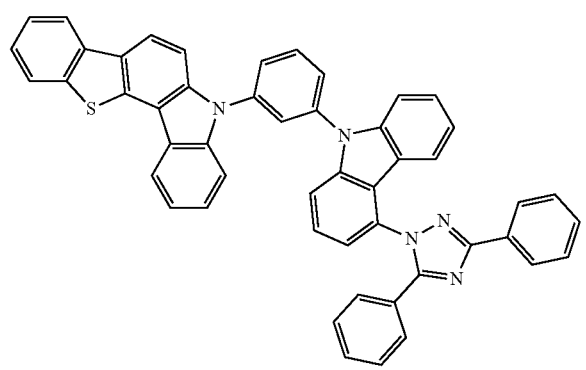
358
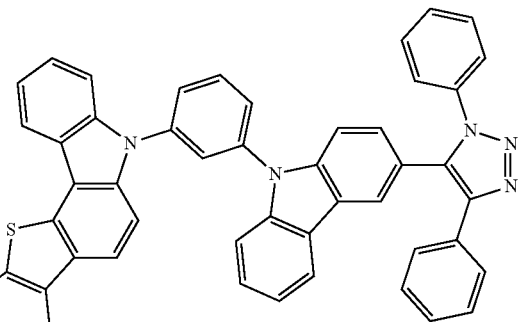
357
389
390
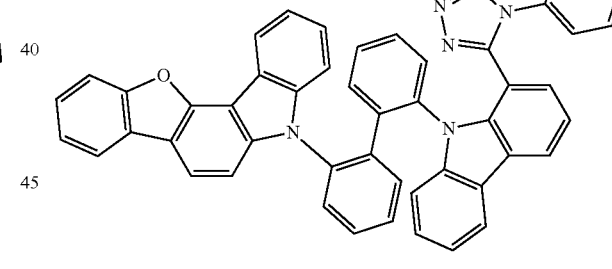

391
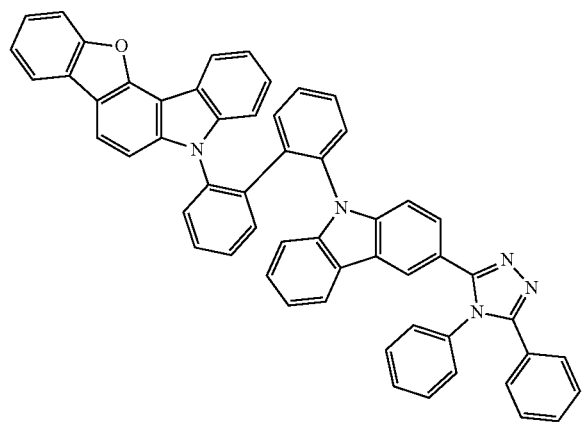
452
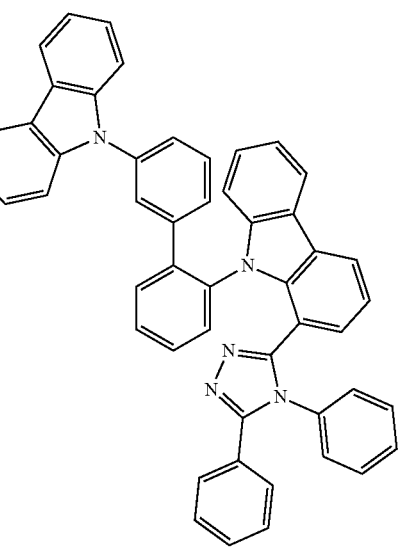
451
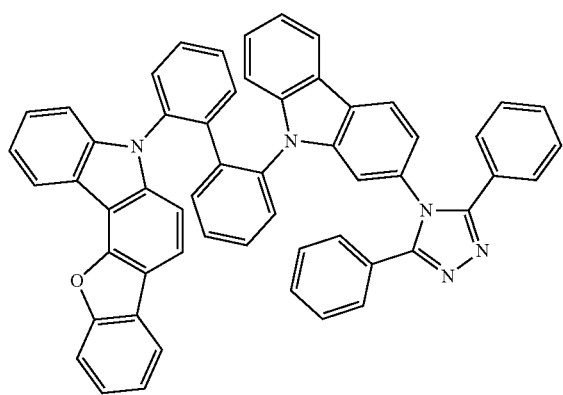
450
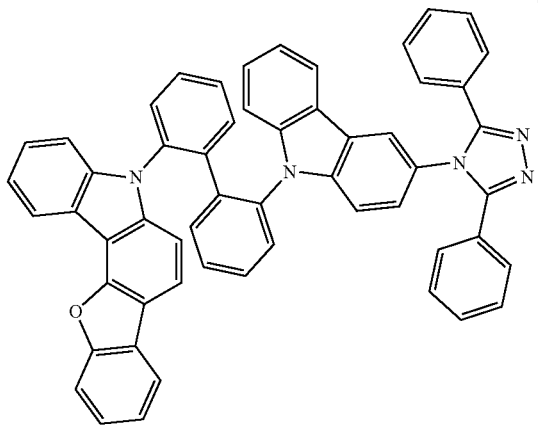
453
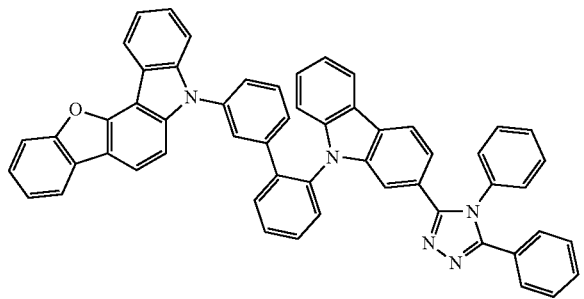
454
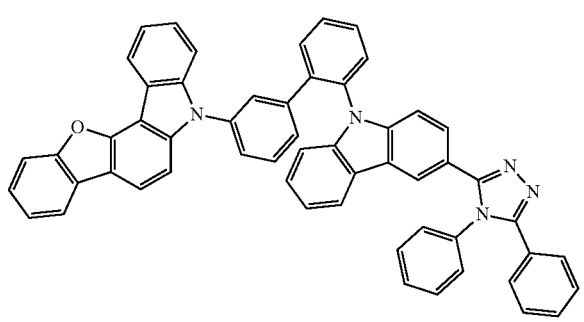
455

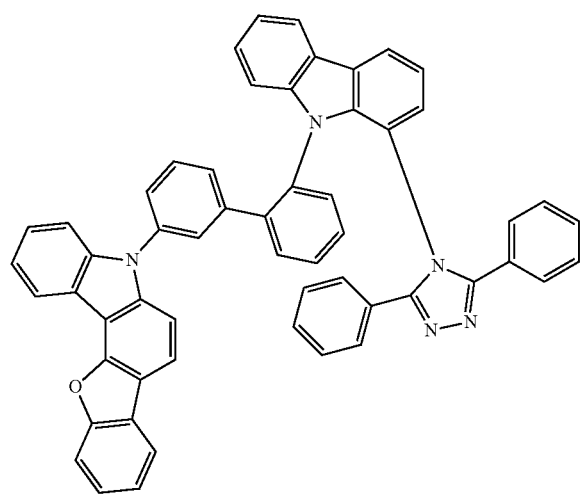
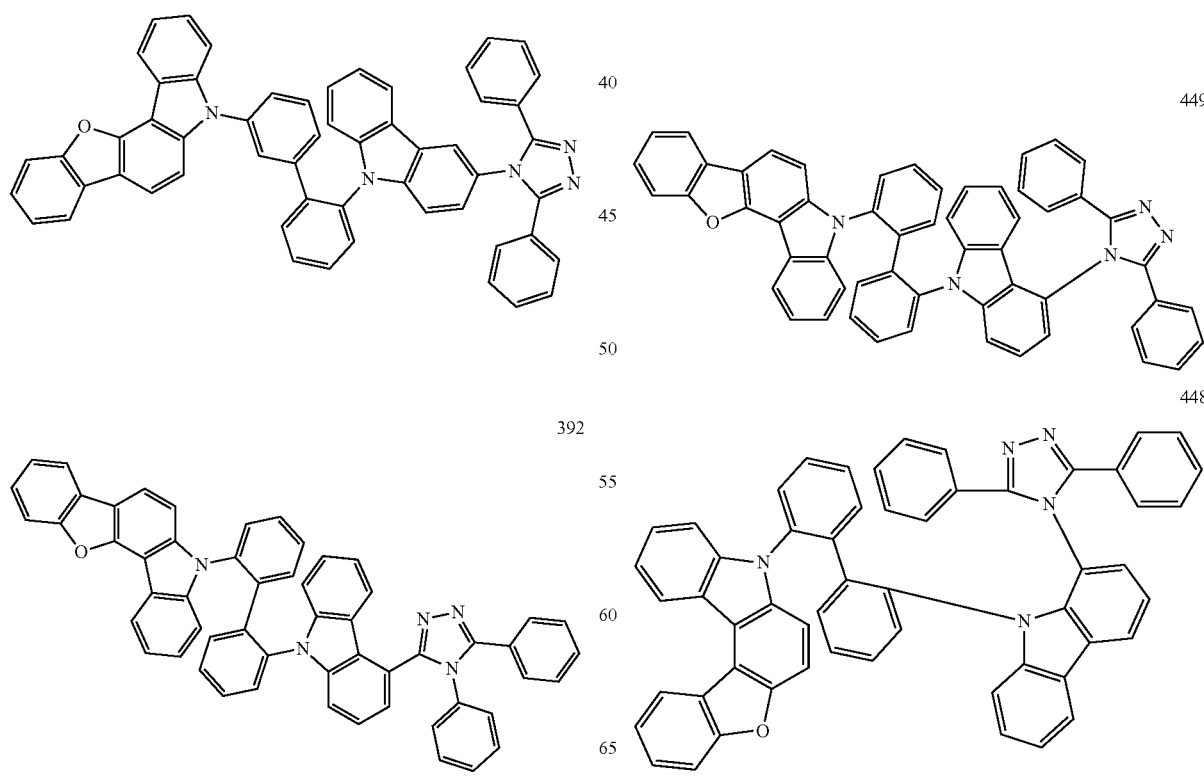
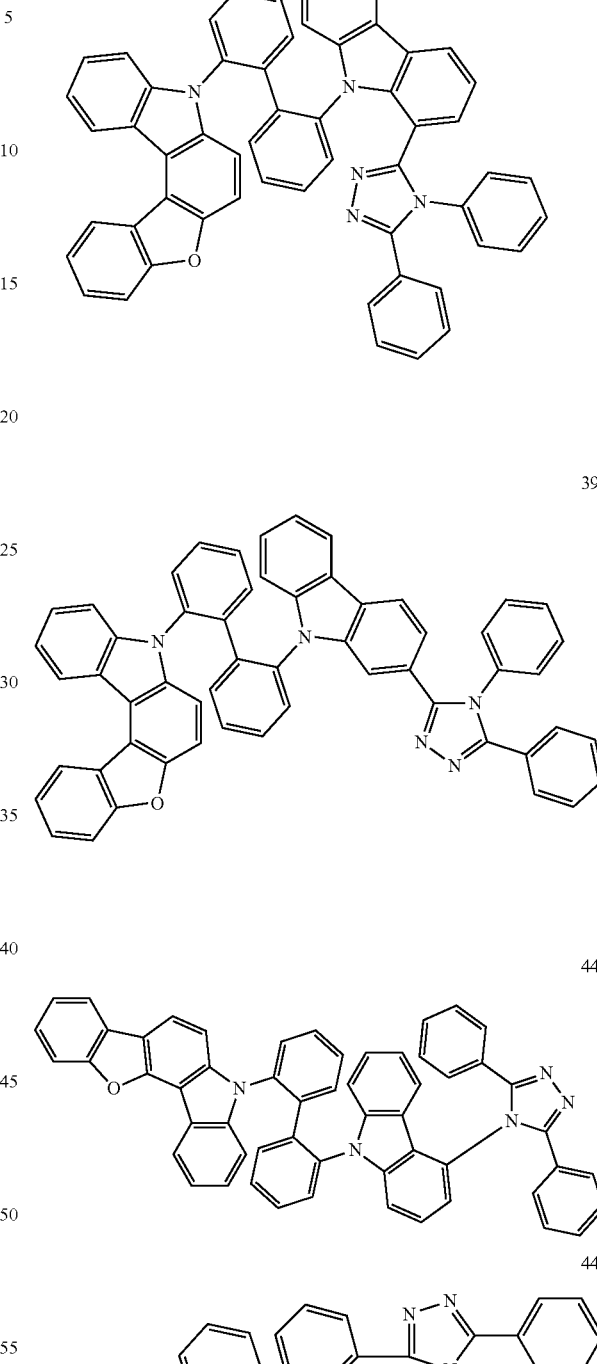

447
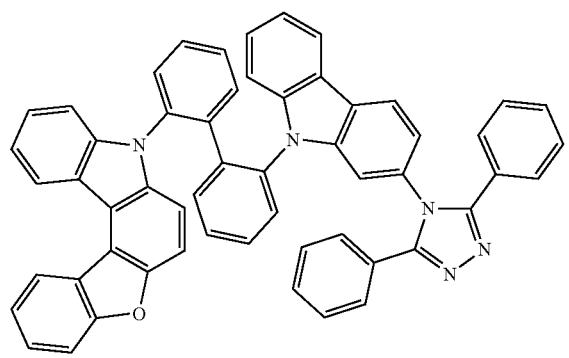
456
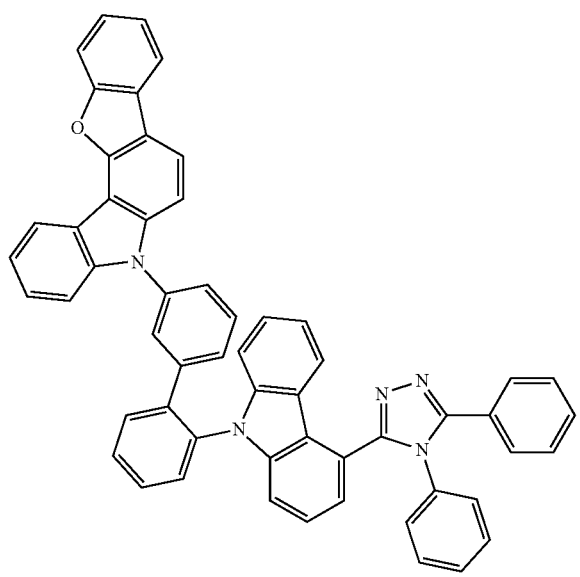
457
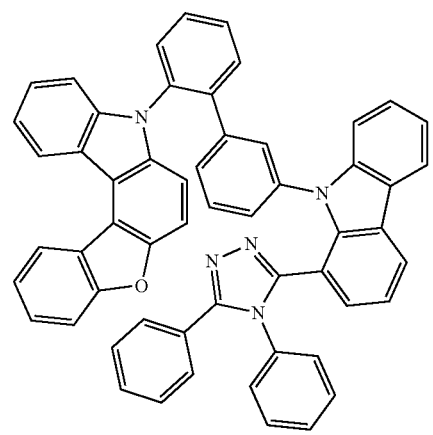
458
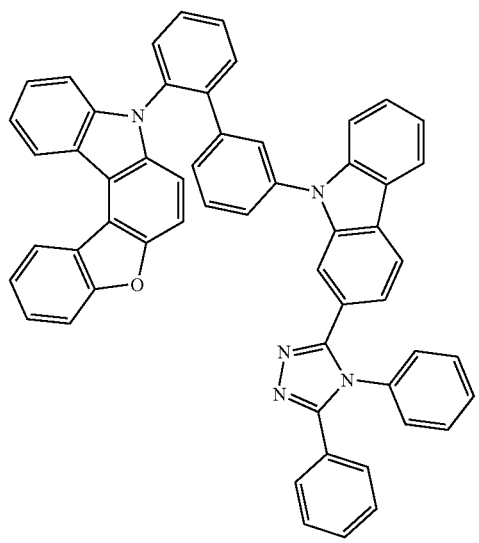
513
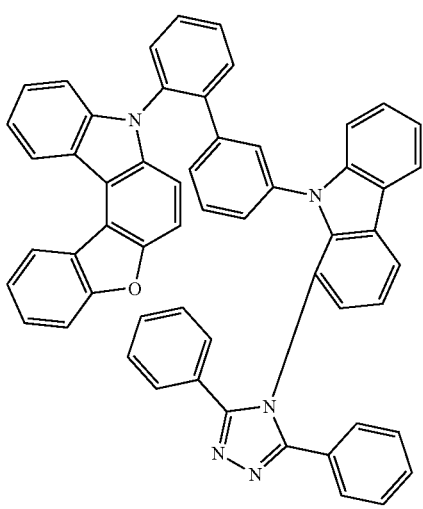
512

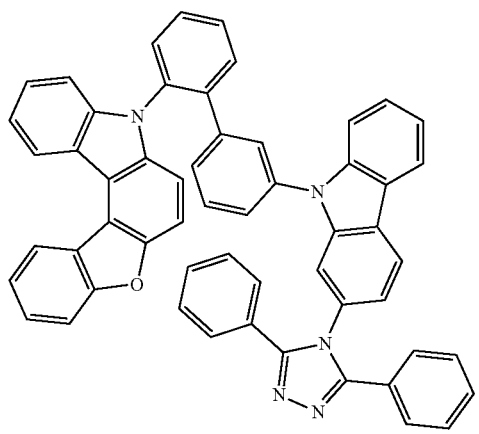
511
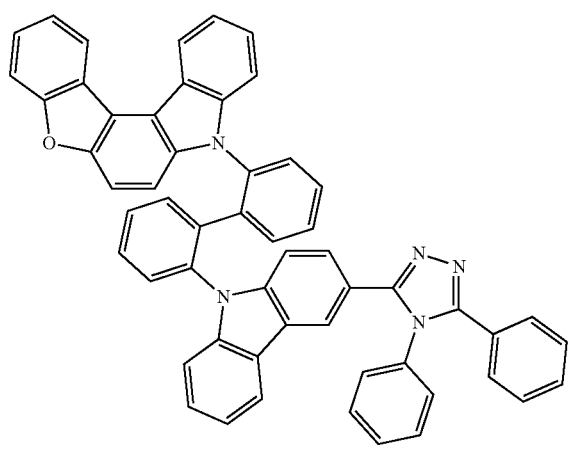
395
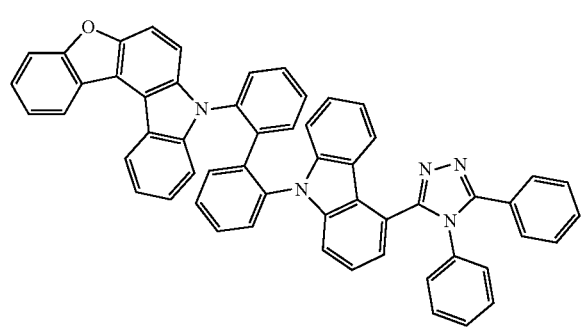
396
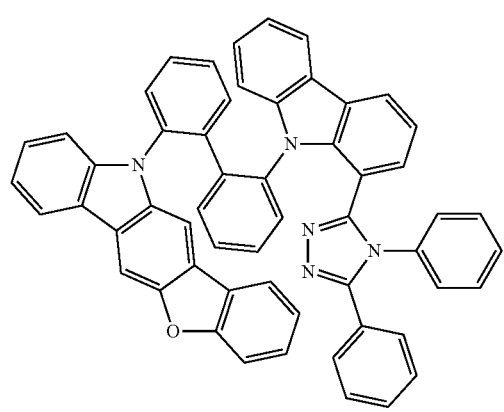
397
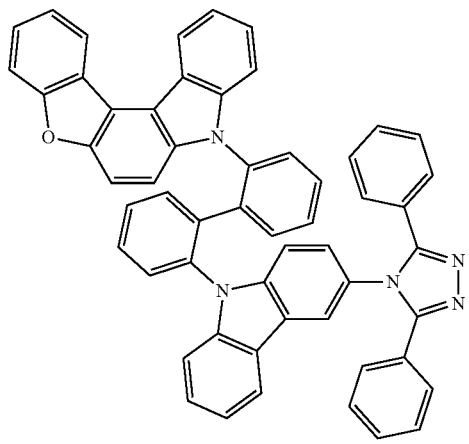
446
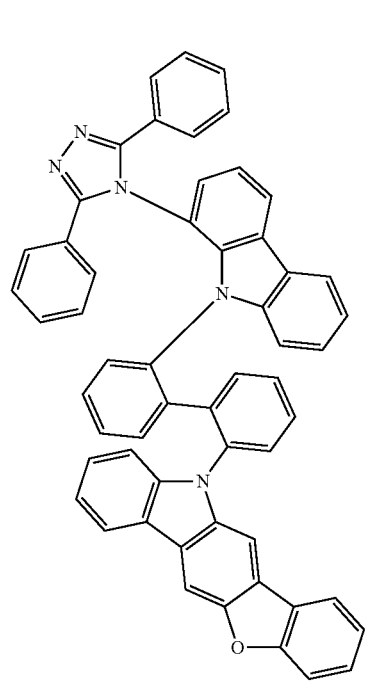
445
444

459
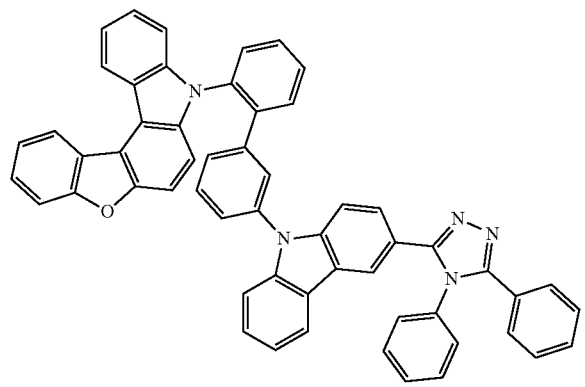
460
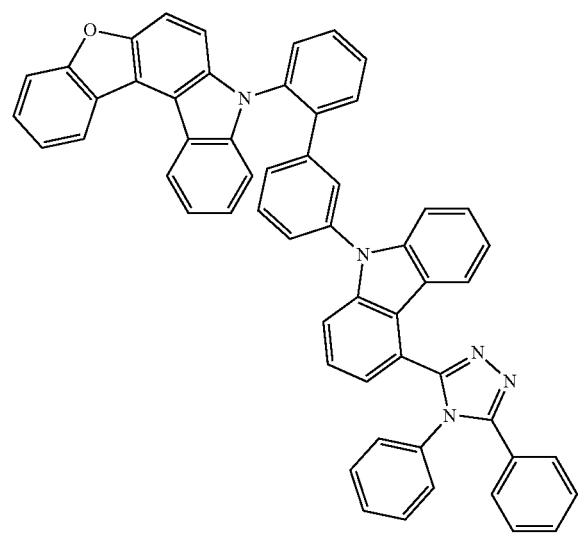
461
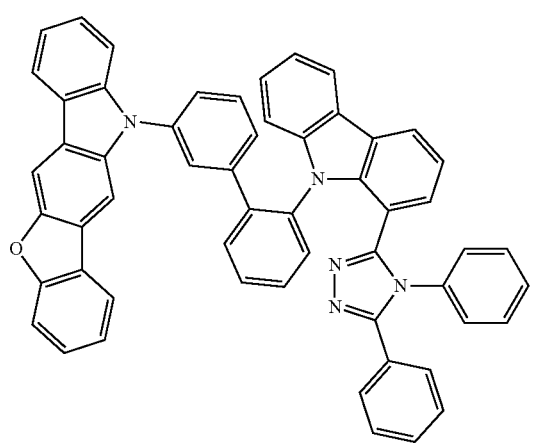
510
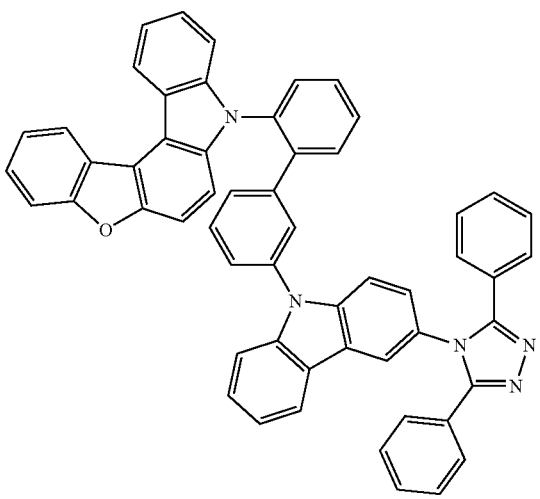
509
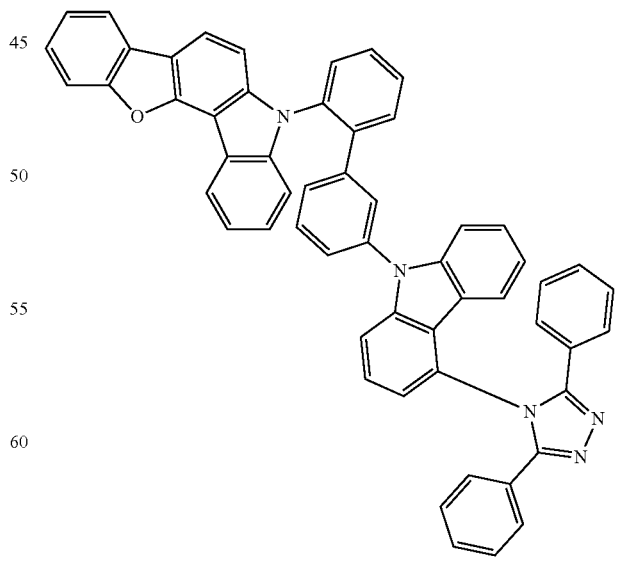

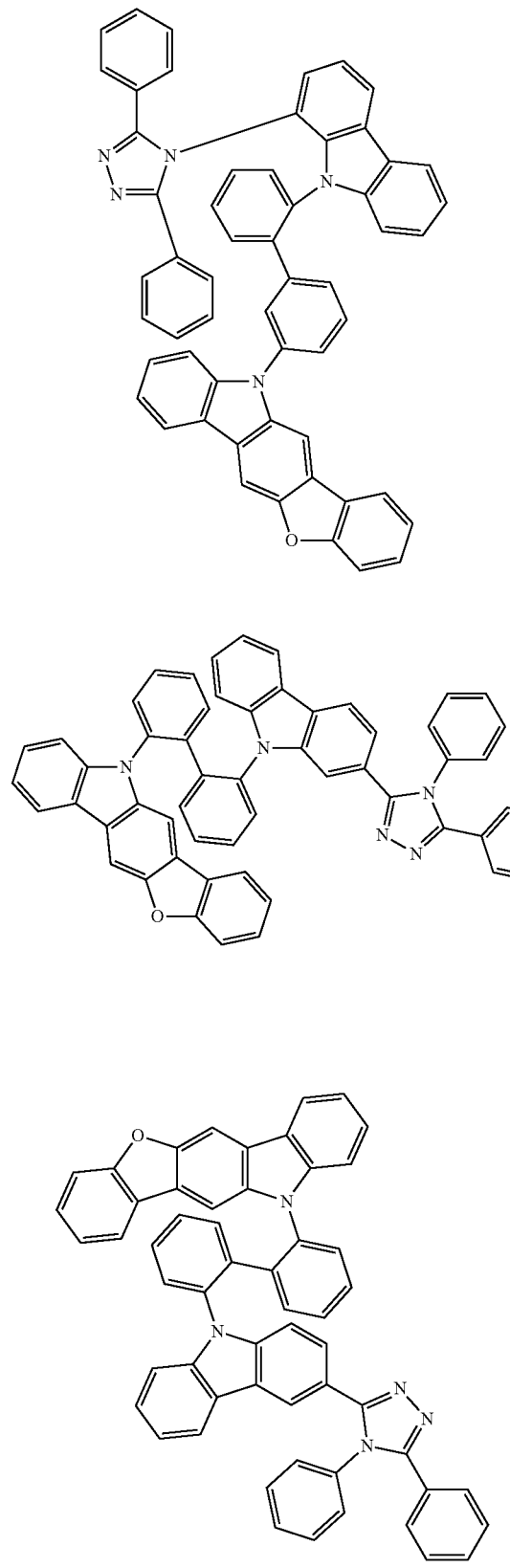
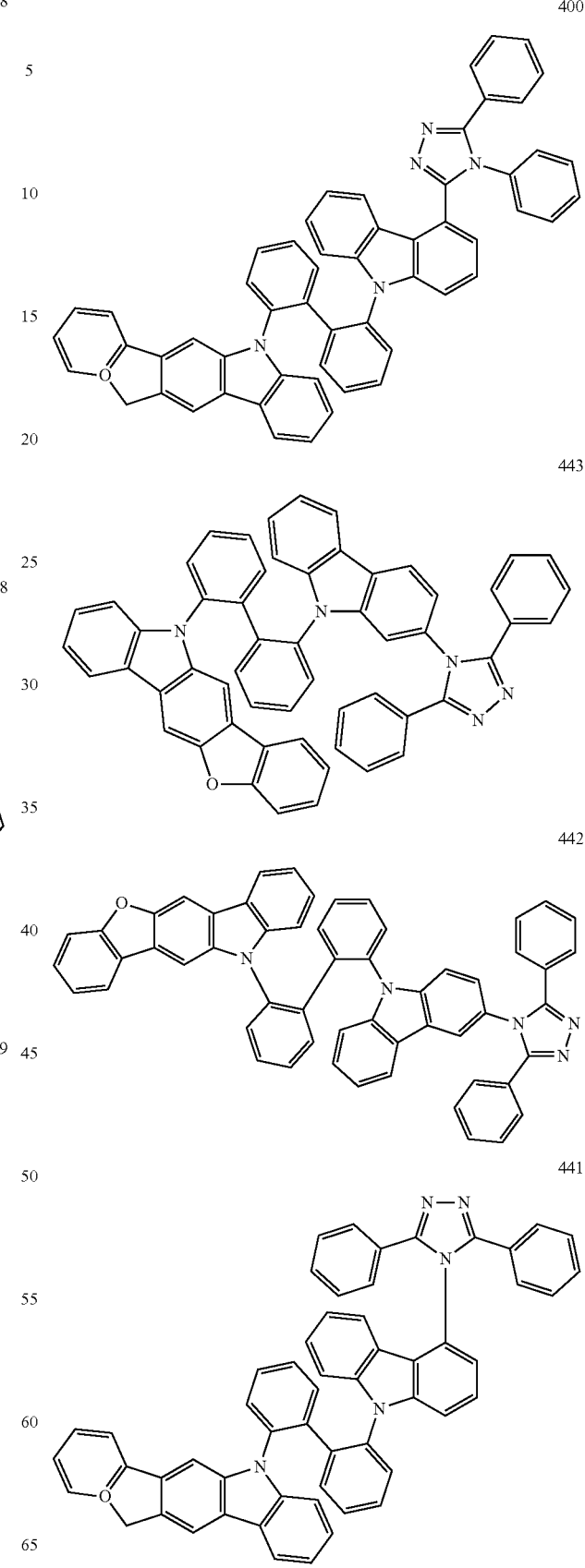

-continued
462
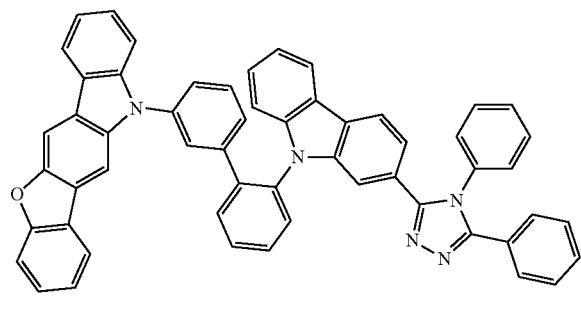
463
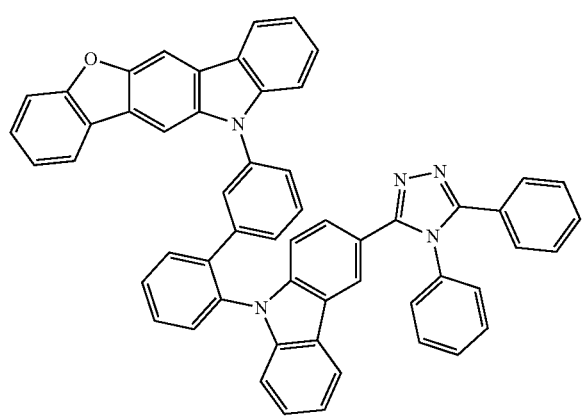
464
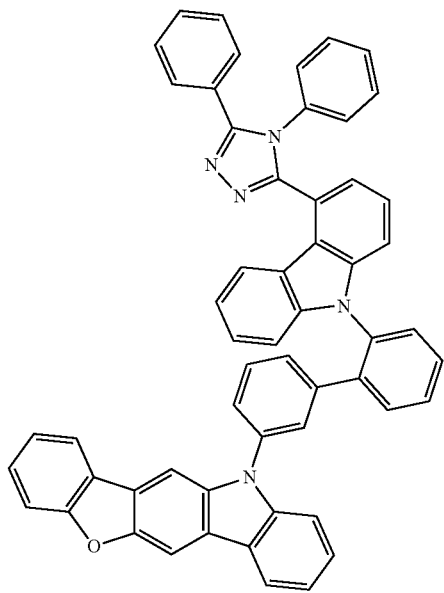
-continued
507
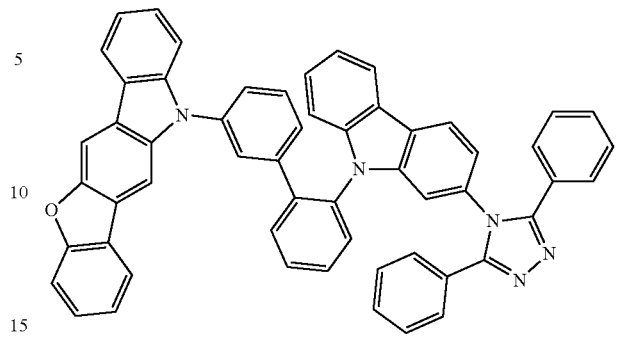
506
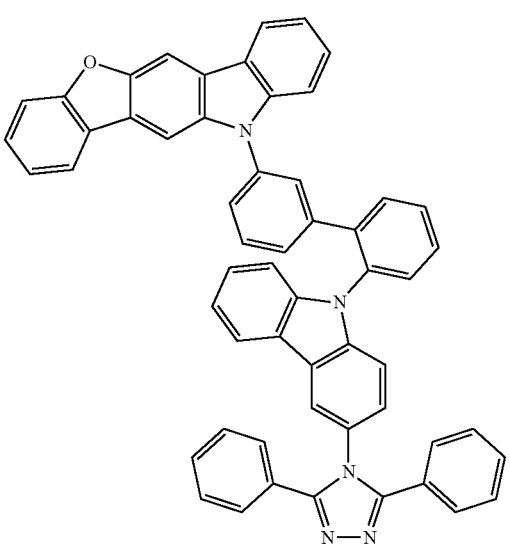
505
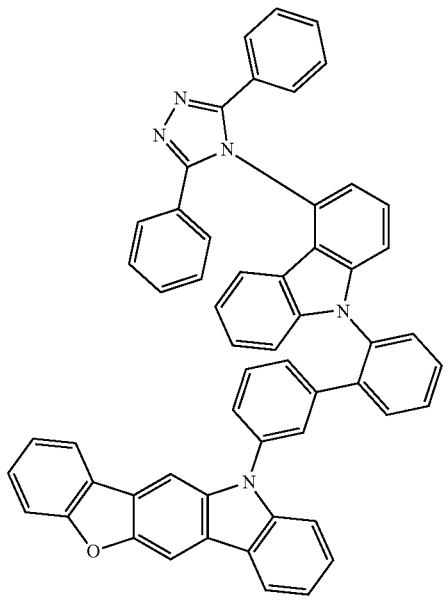

145
146
401
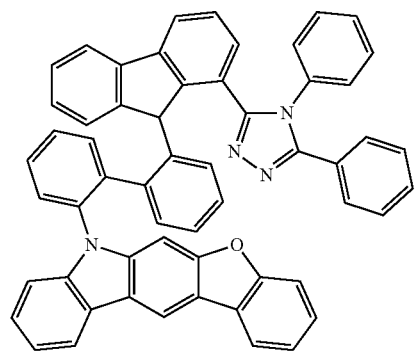
402
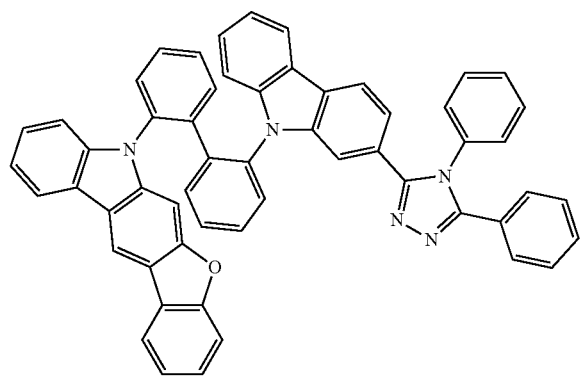
403
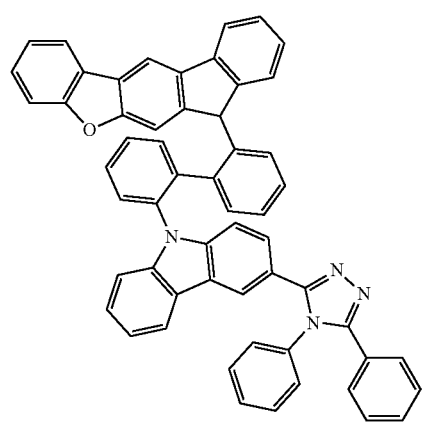
440
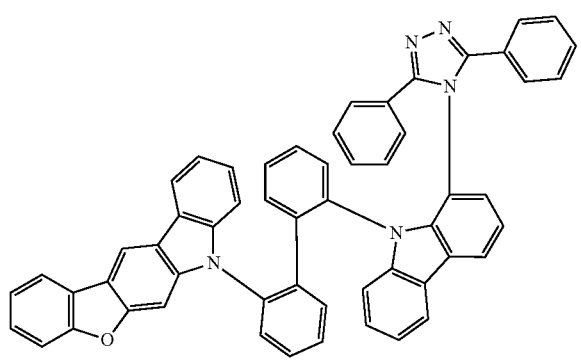
439
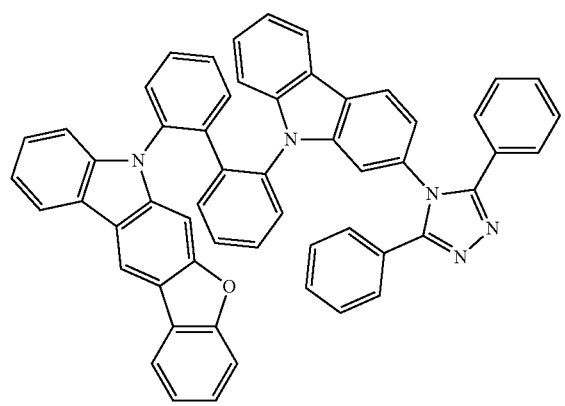
438
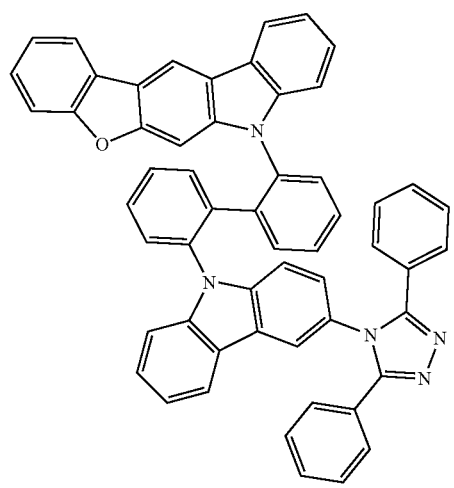

-continued
465
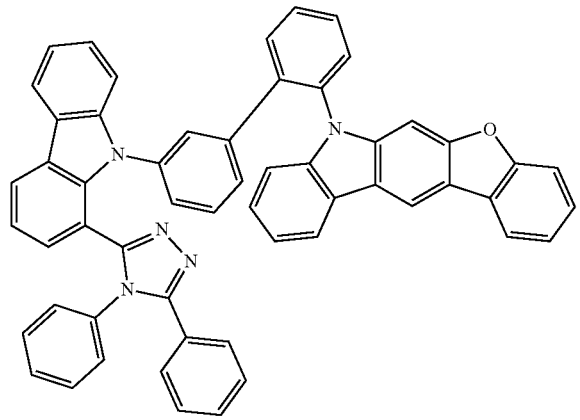
466
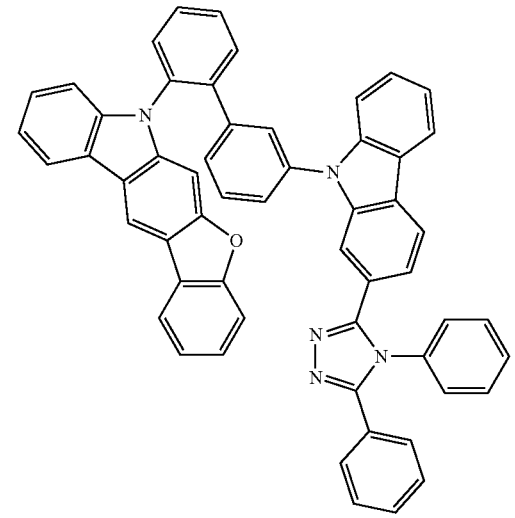
467
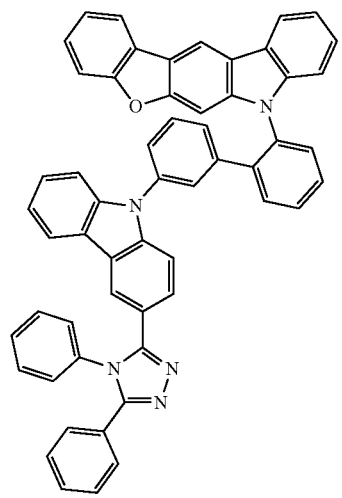
504
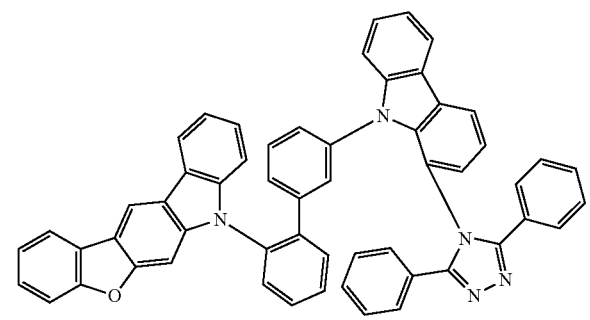
503
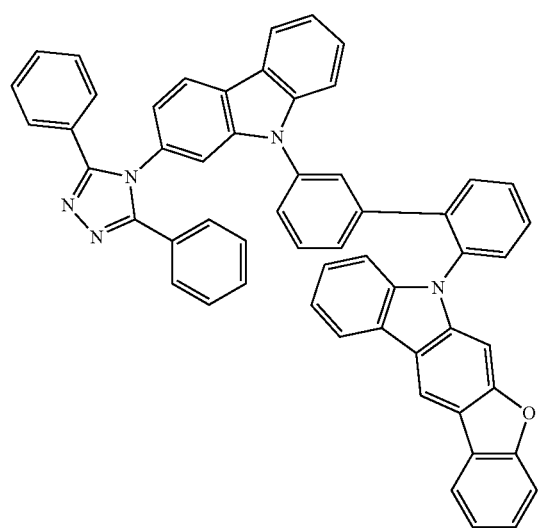
502
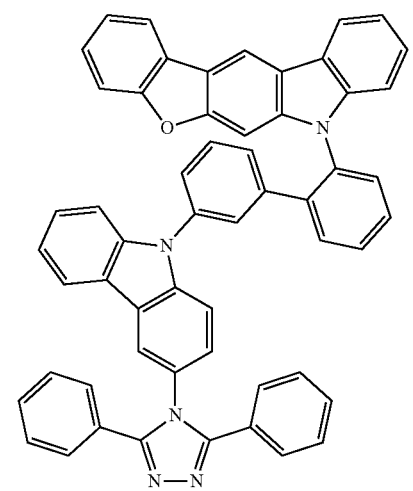

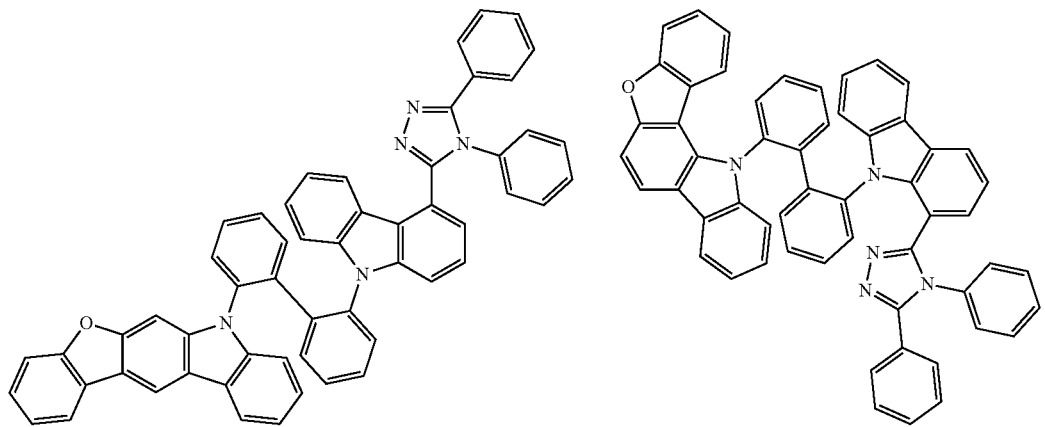
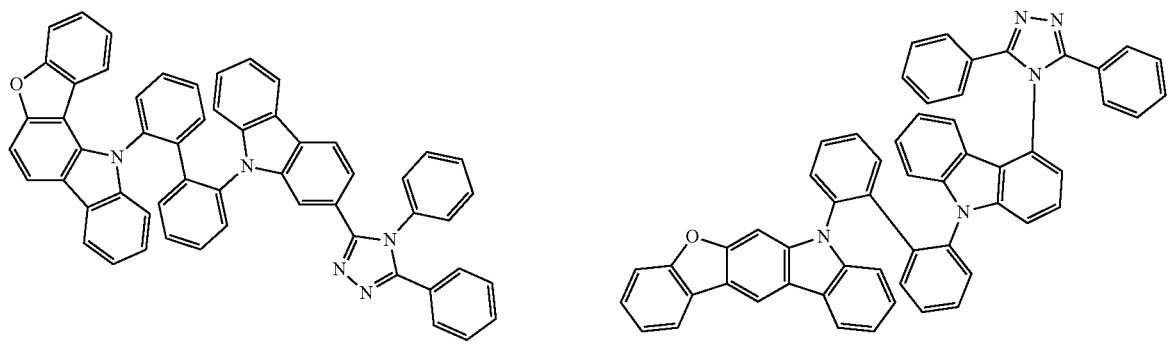
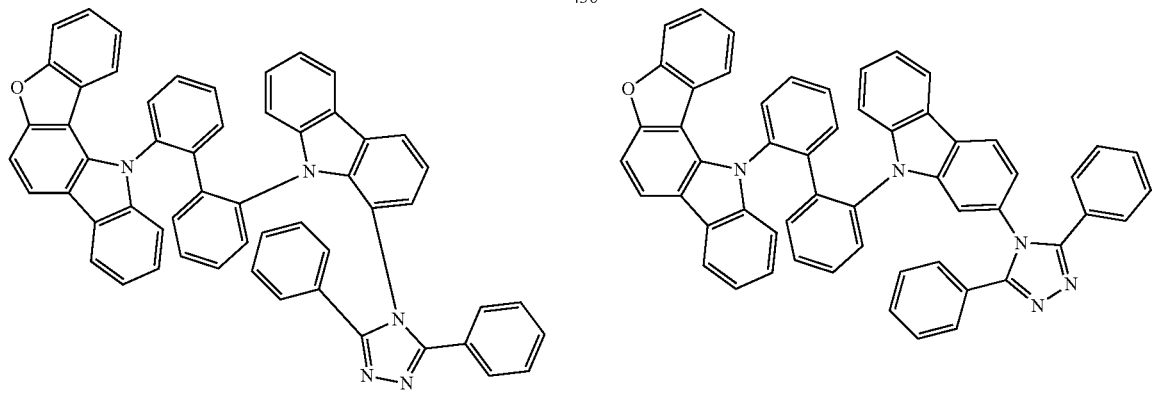
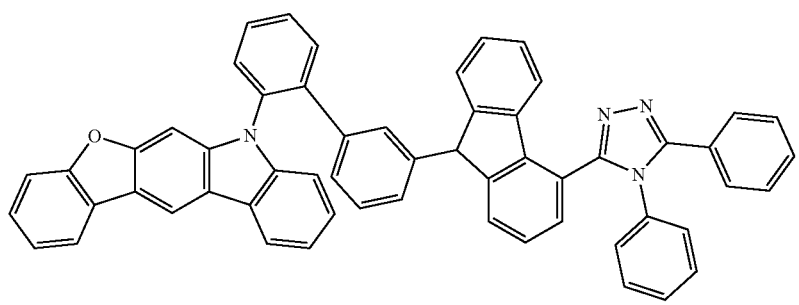

-continued
469
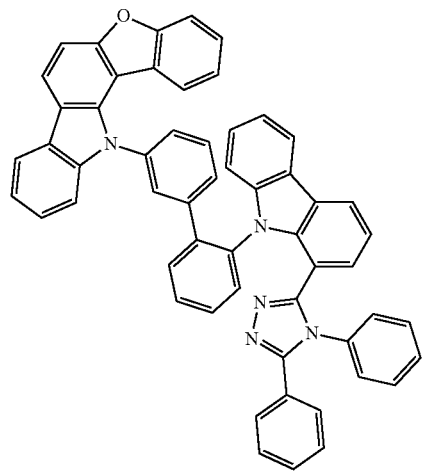
470
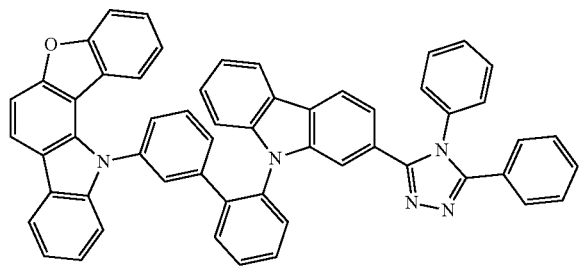
501
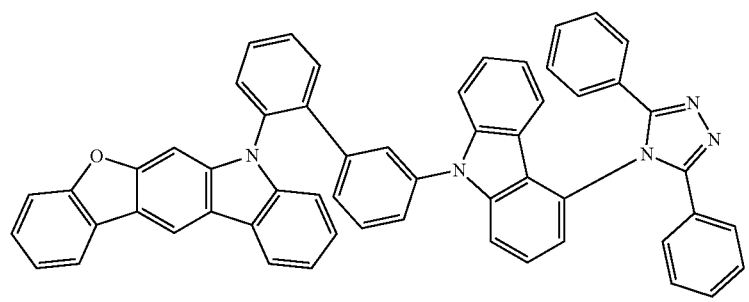
500
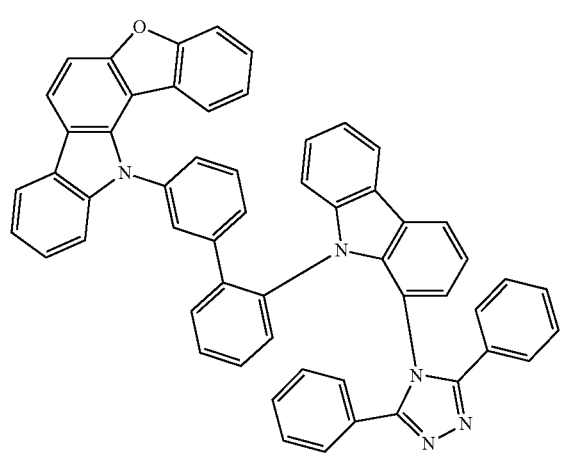
499
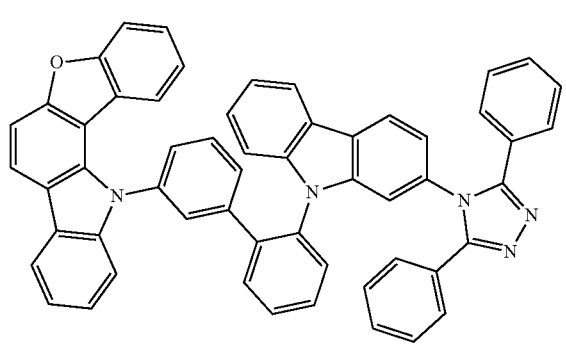

-continued
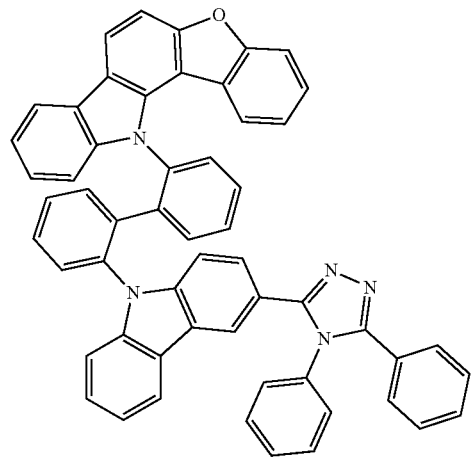
407
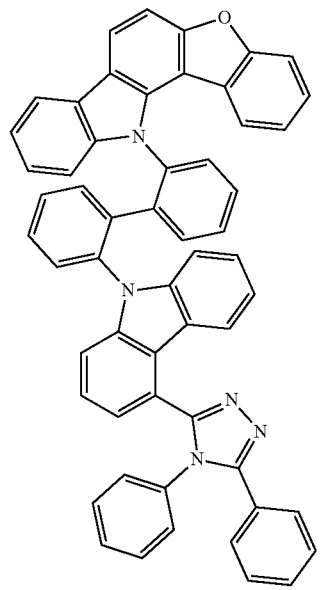
408
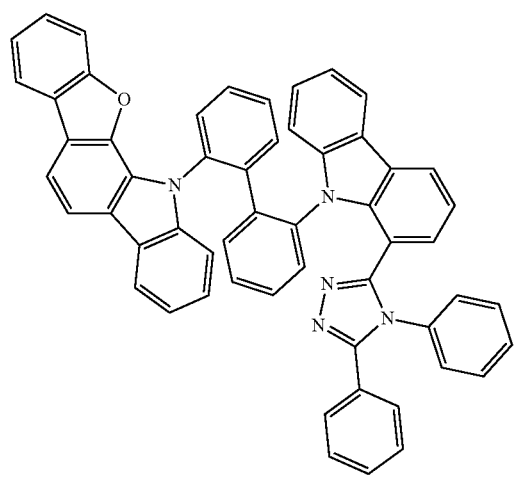
409
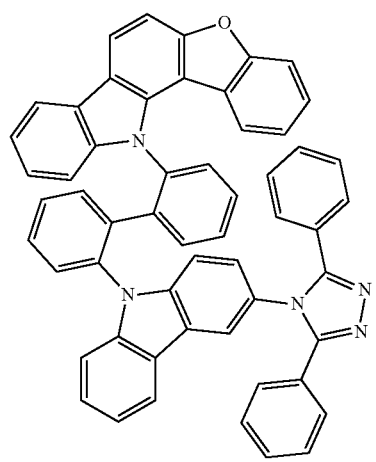
434
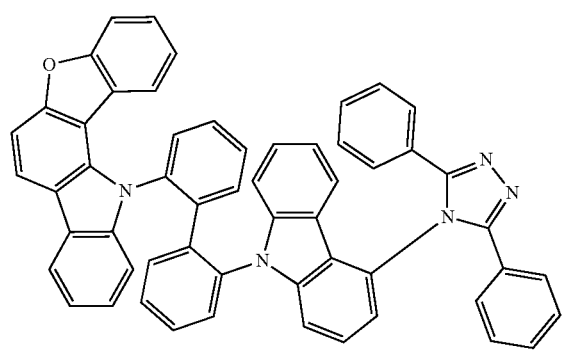
433
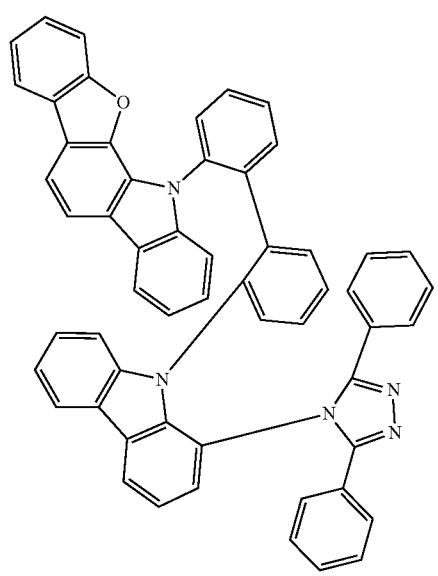
432

-continued
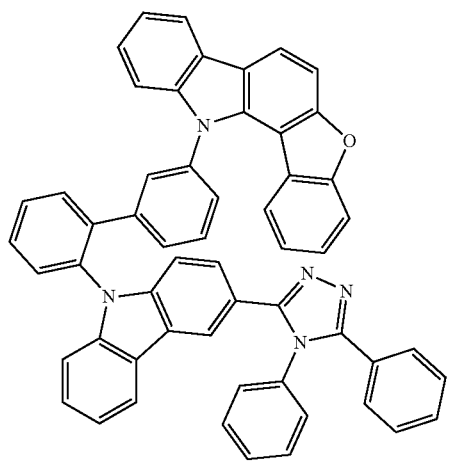
471
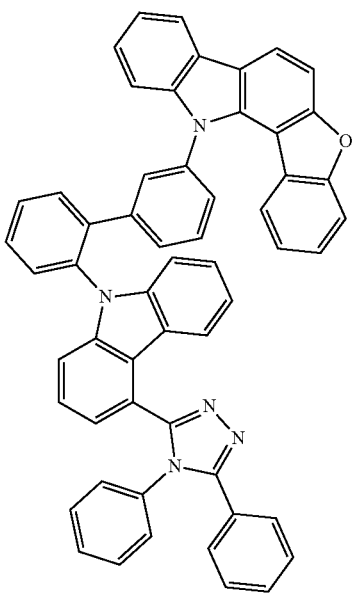
472
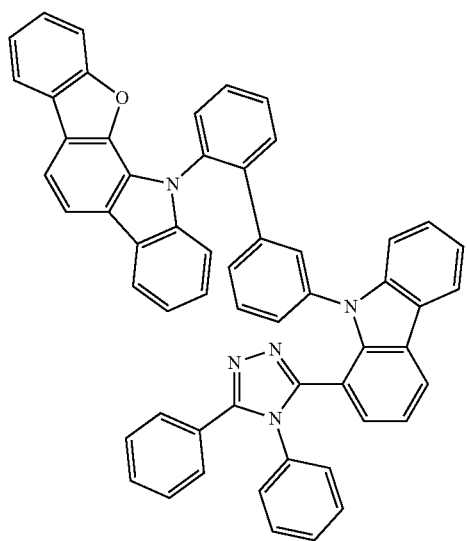
473
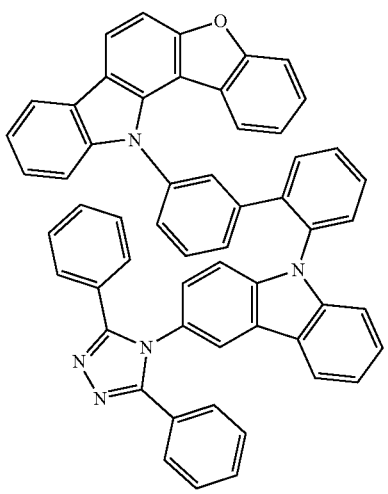
498

-continued
497
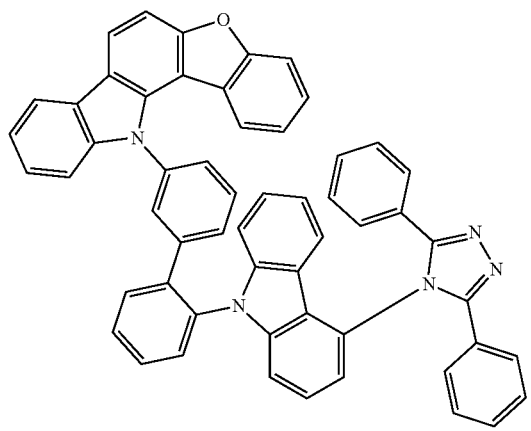
496
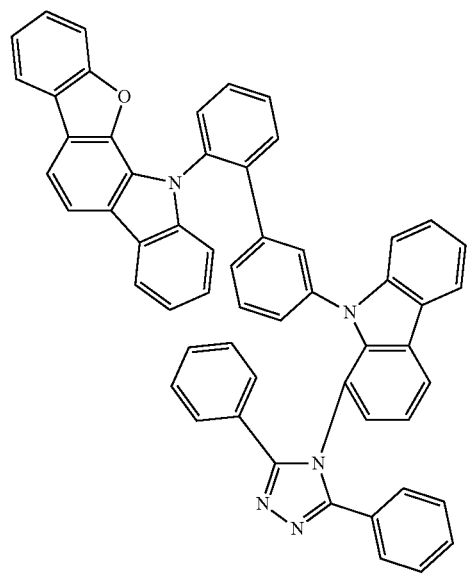
410
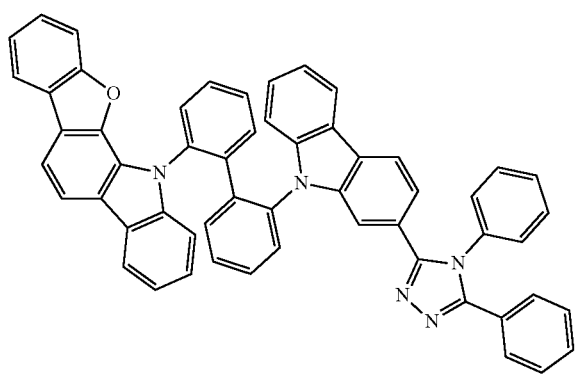
411
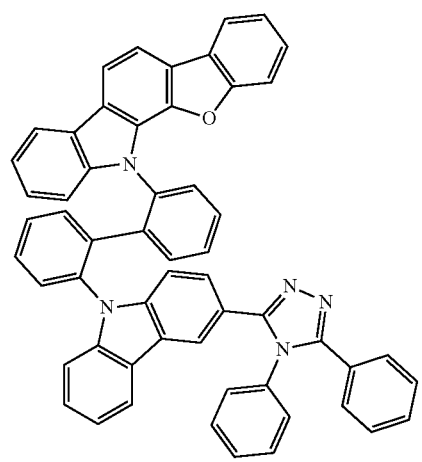
412
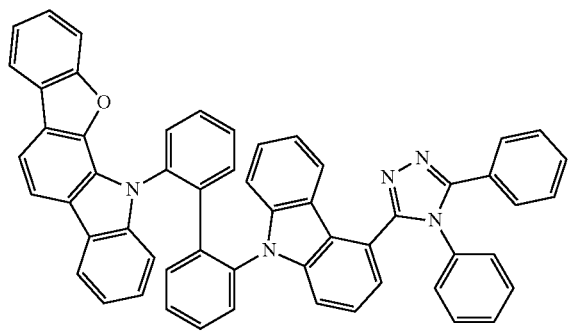
431
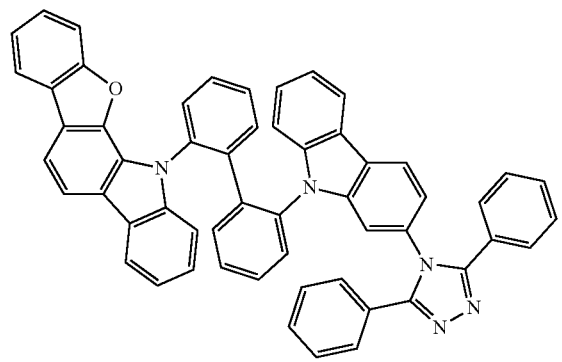

-continued
430
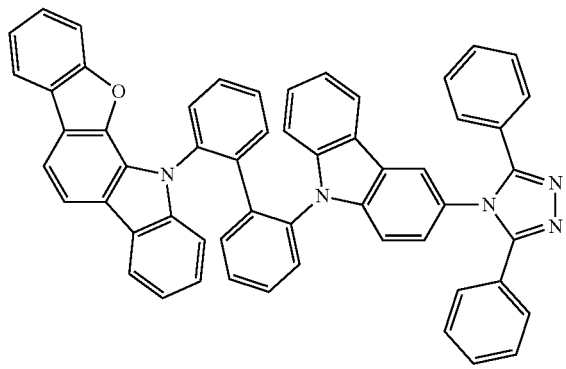
429
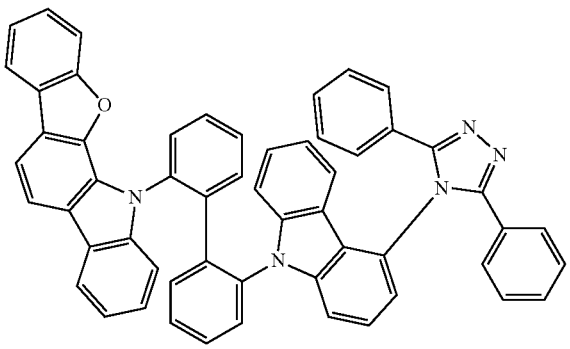
474
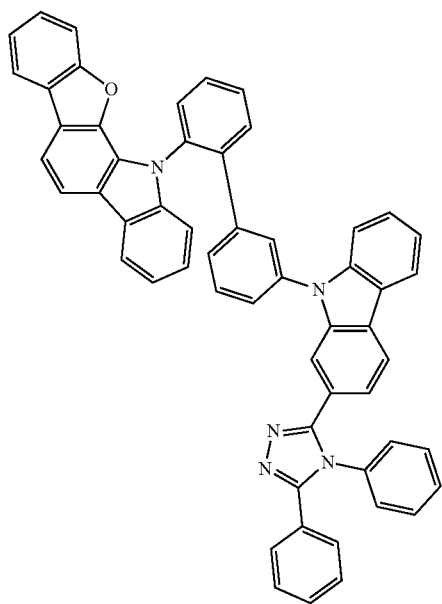
475
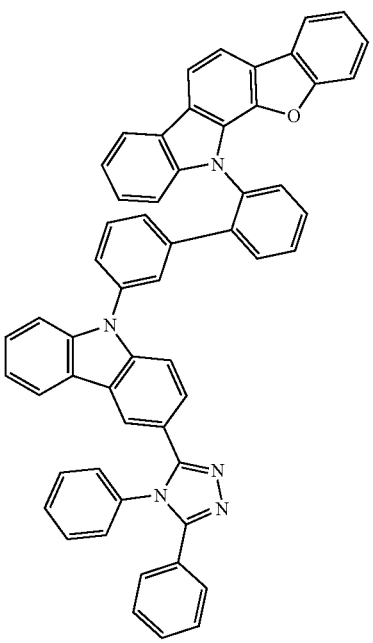
476
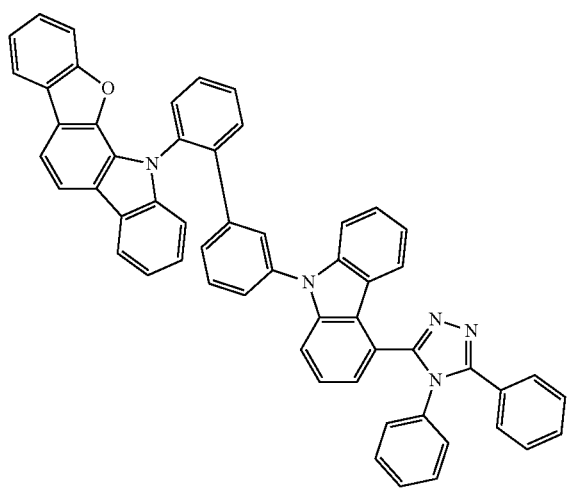
495
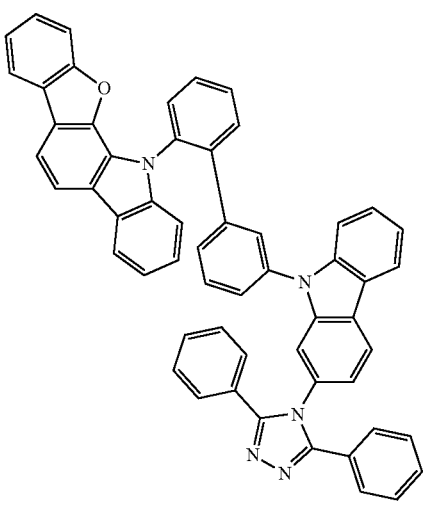

-continued
494
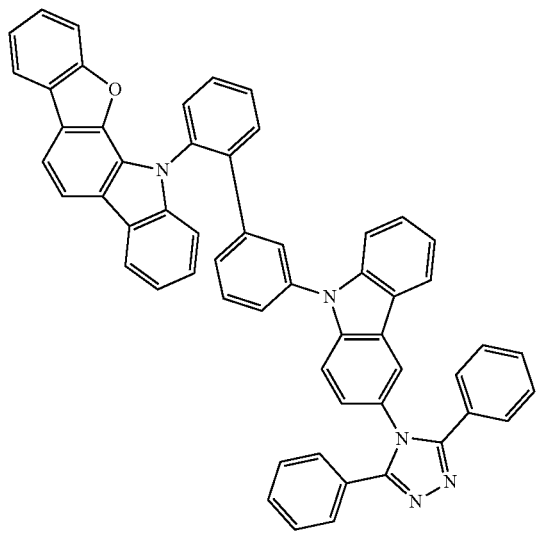
493
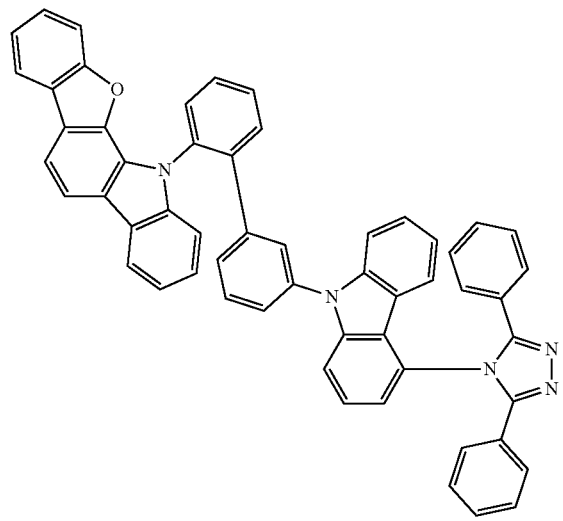
413
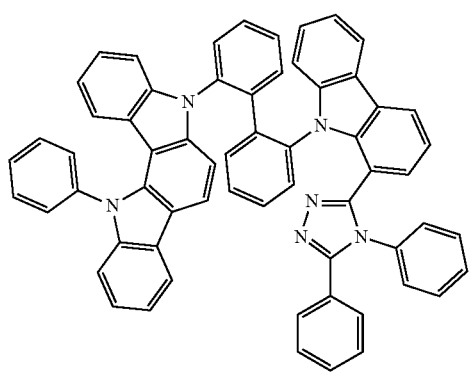
414
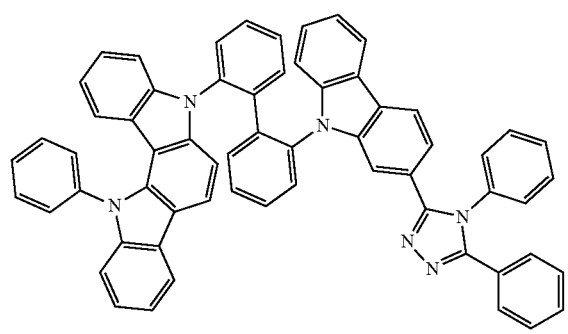
415
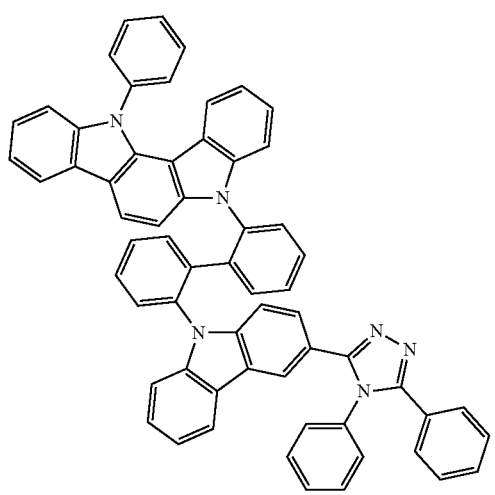
428
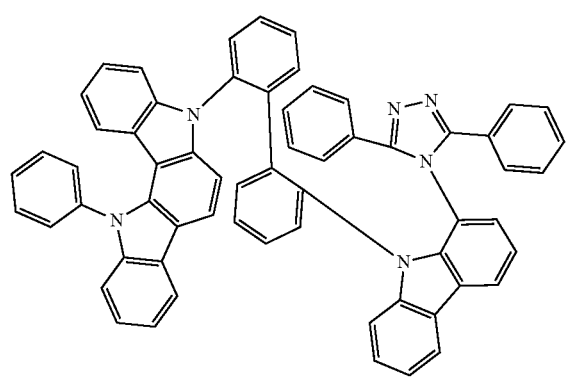

-continued
427
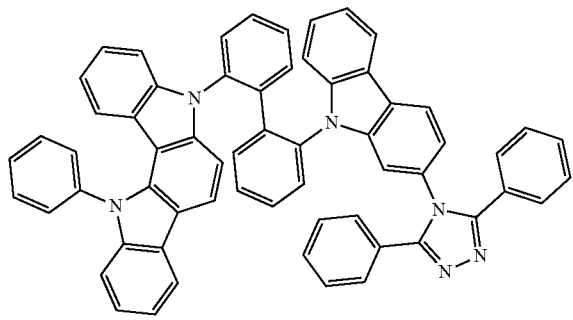
426
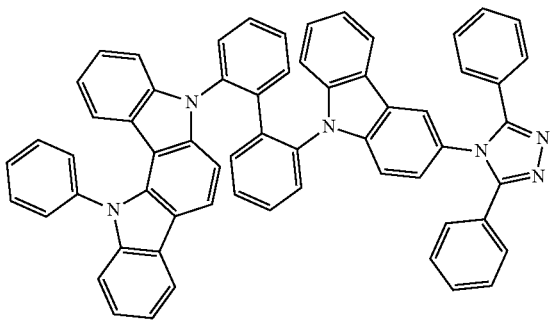
477
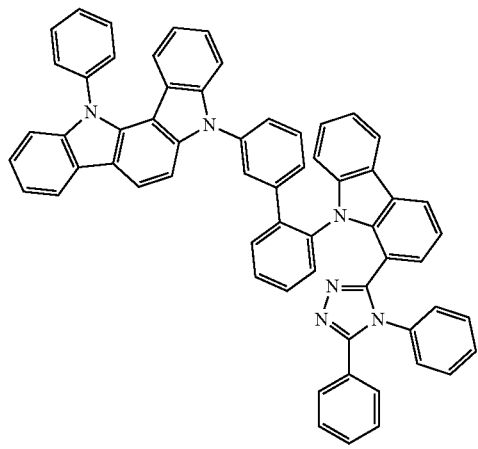
478
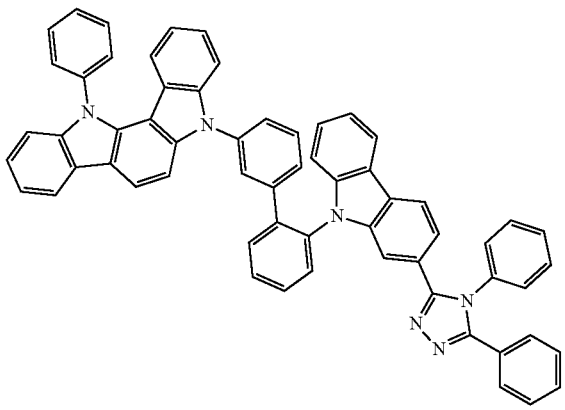
479
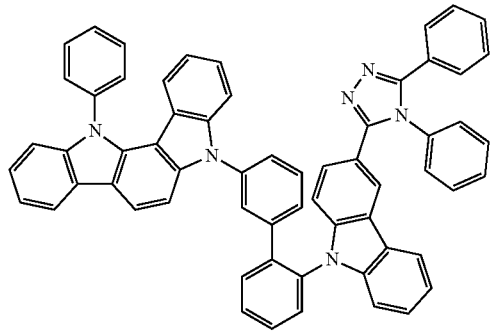
492
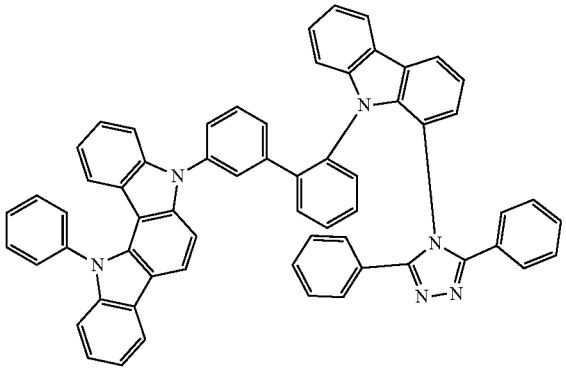
491
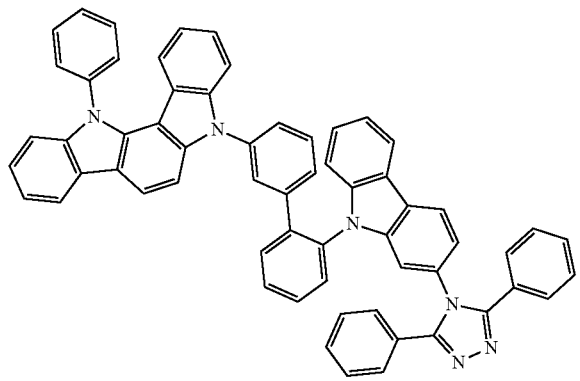
490
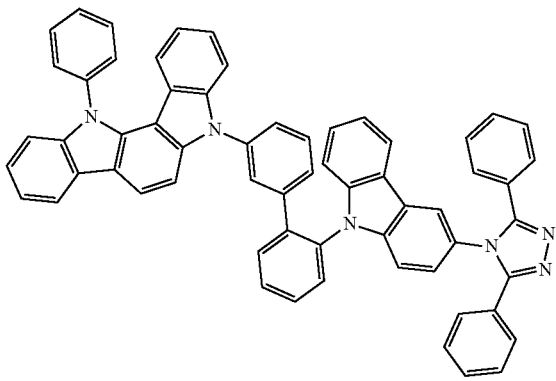

-continued
416
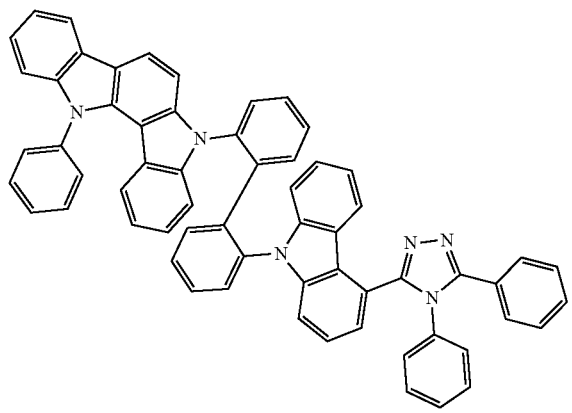
417
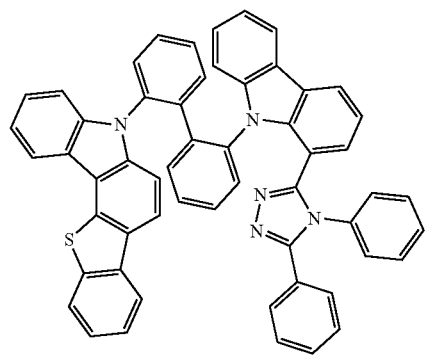
418
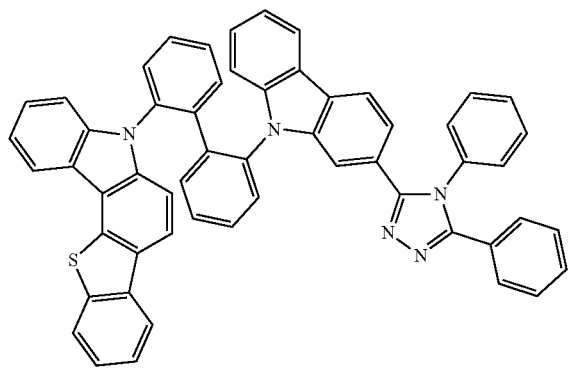
425
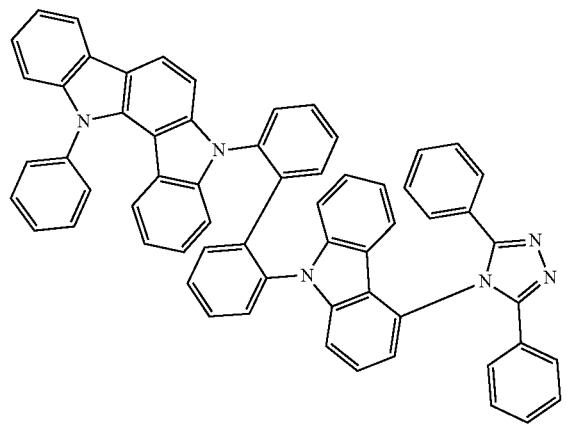
424
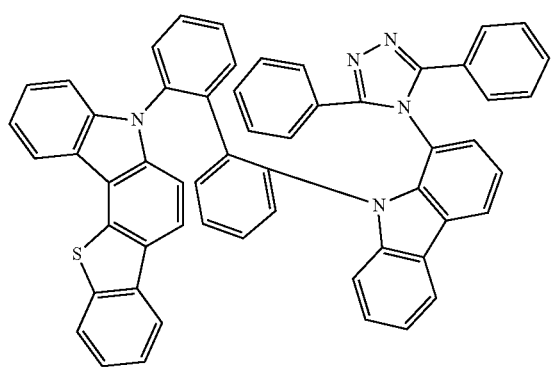
423
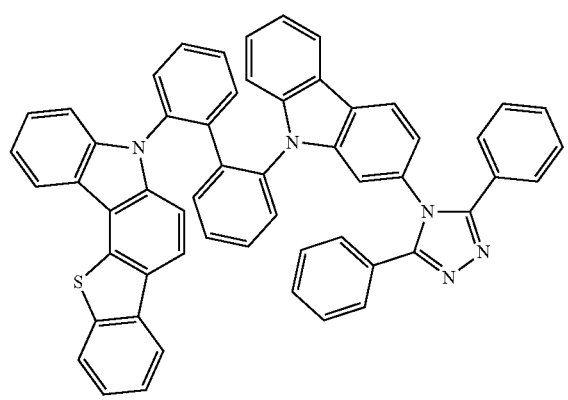

480
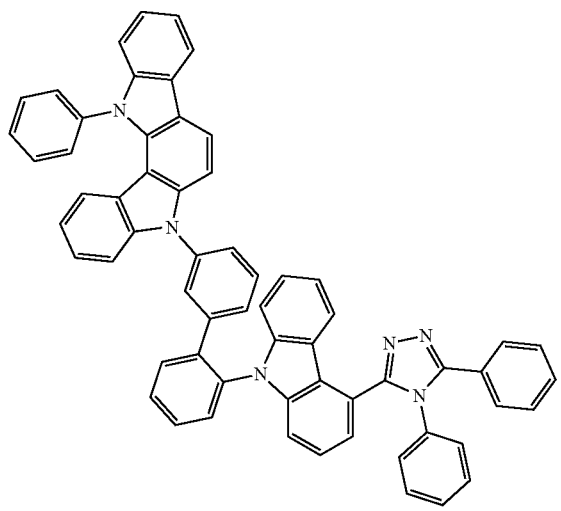
481
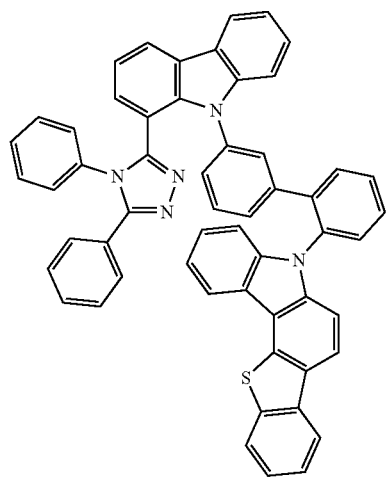
482
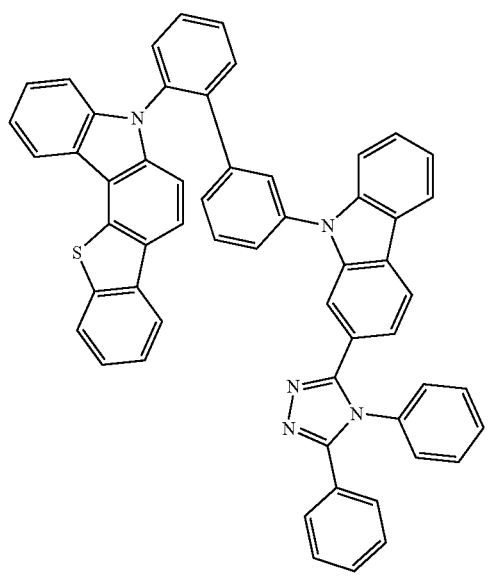
489
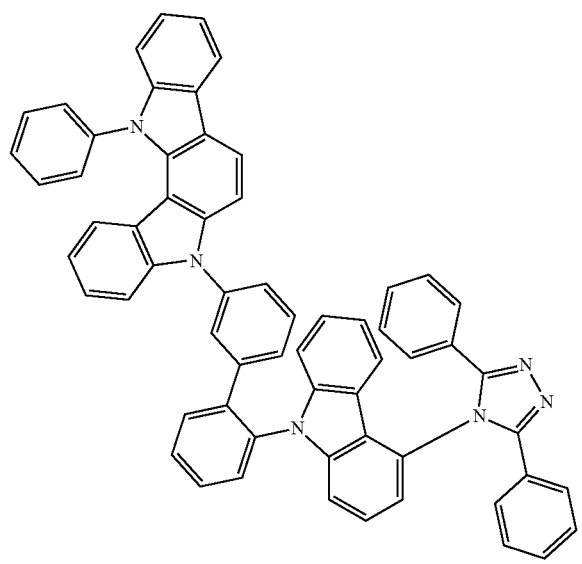

-continued
488
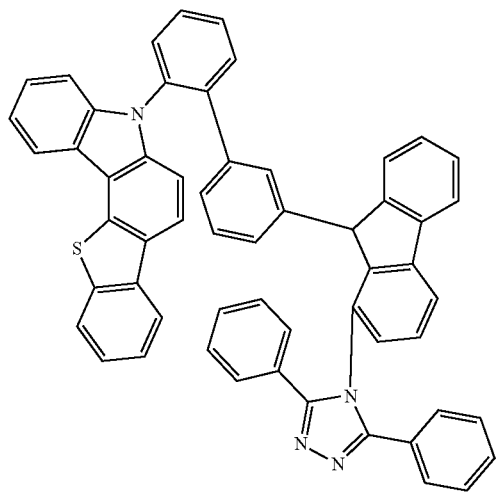
487
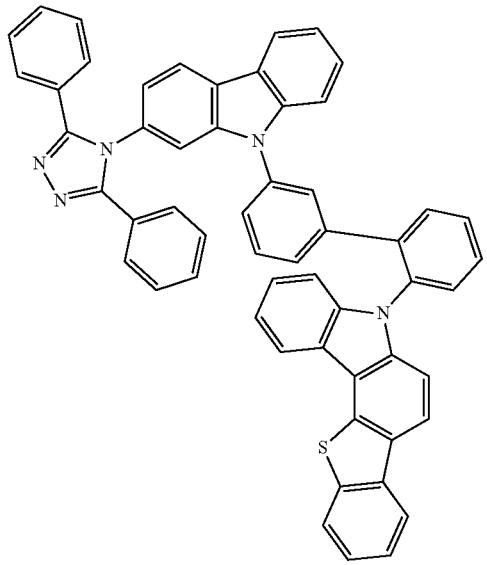
419
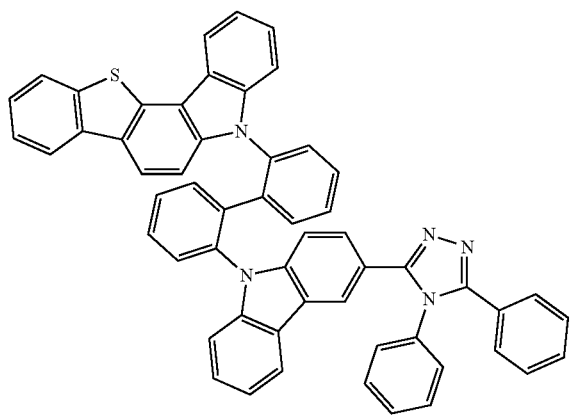
420
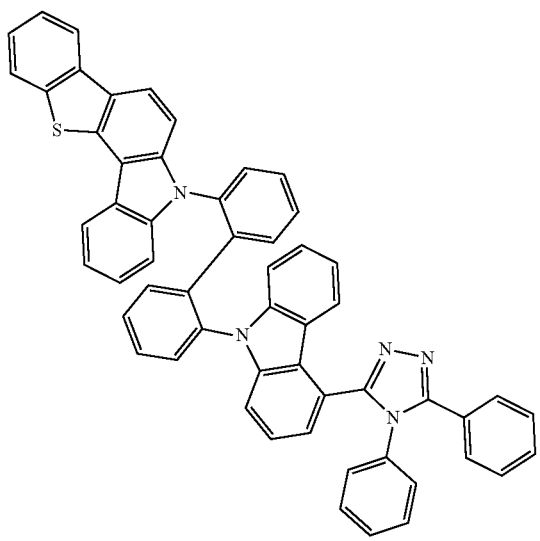
422
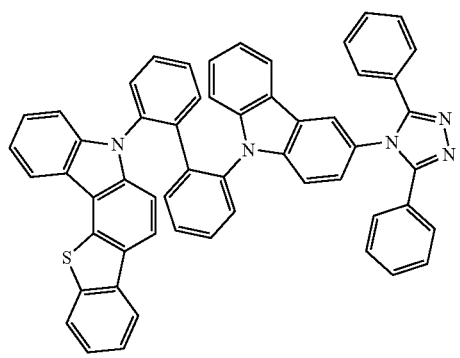
421
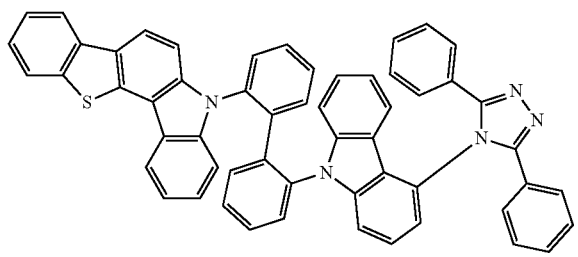

-continued
483
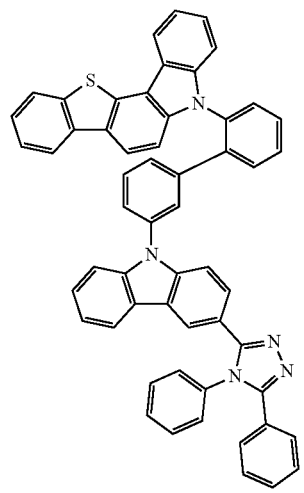
484
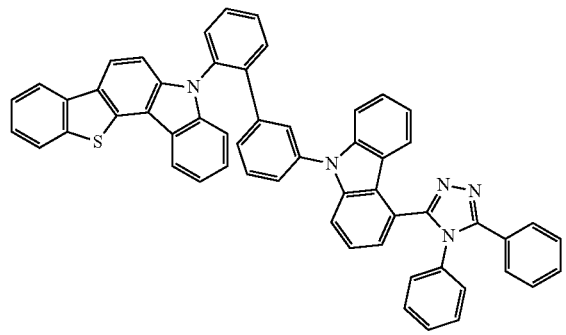
486
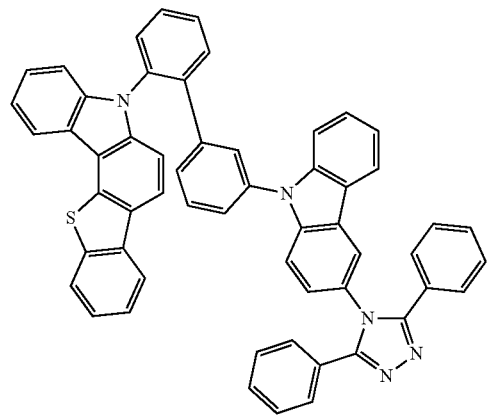
485
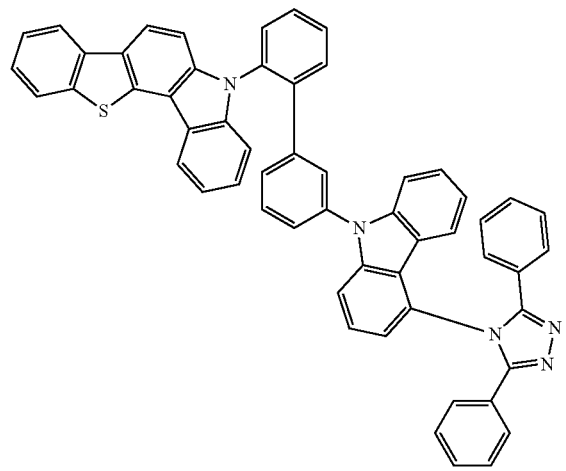
517
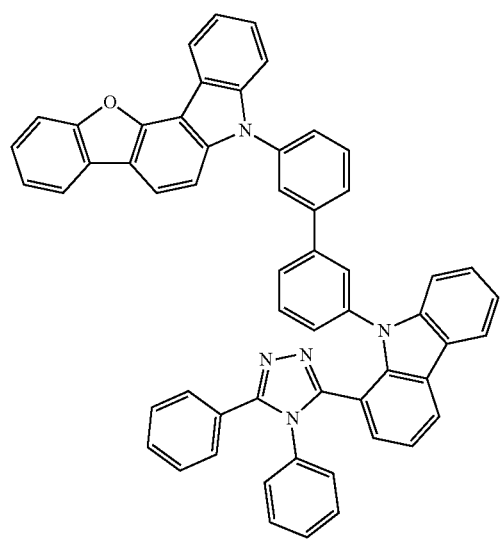
518
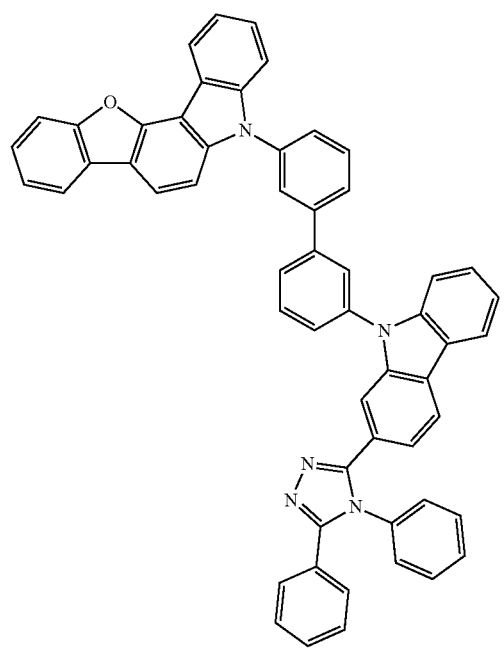

519
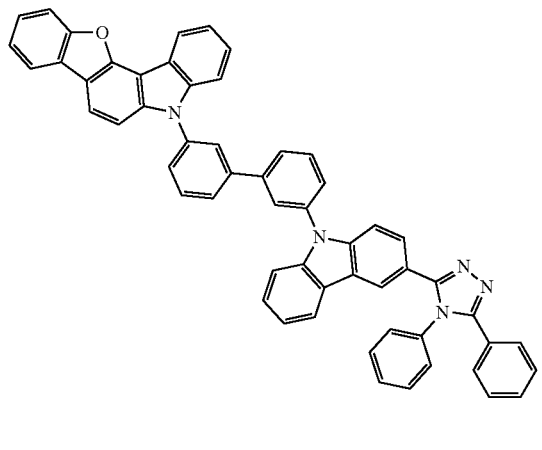
580
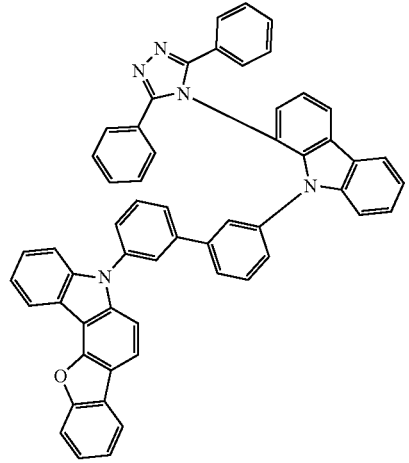
579
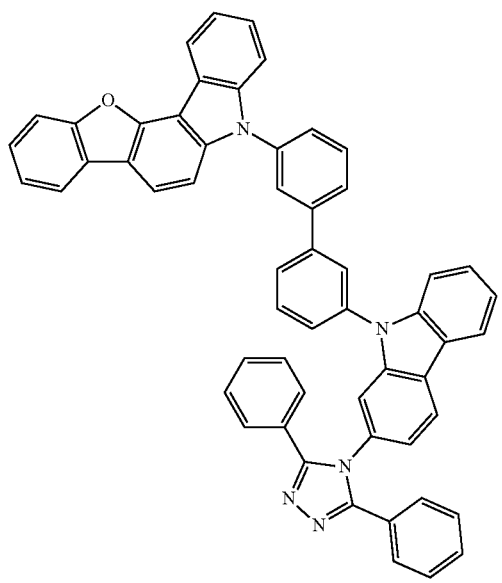
578
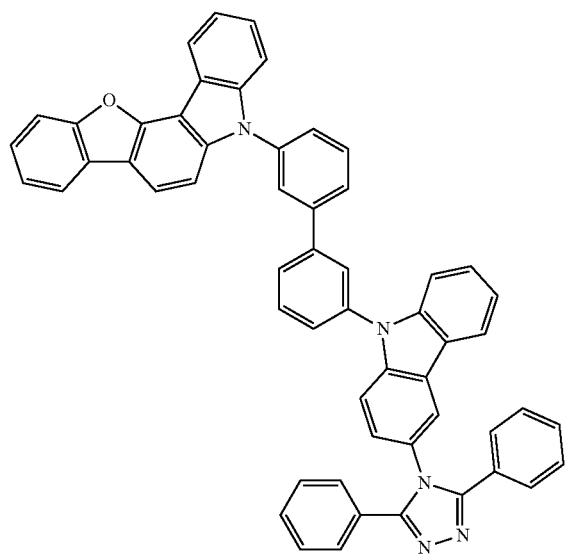

-continued
175
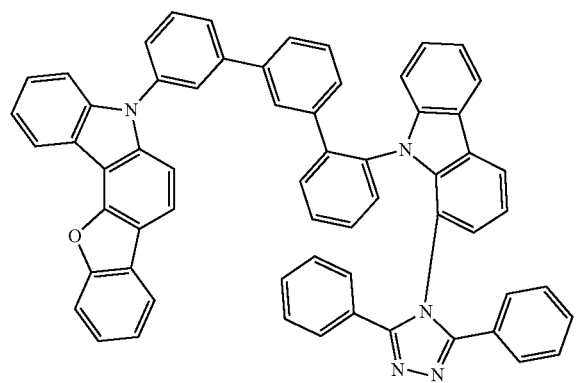
612
176
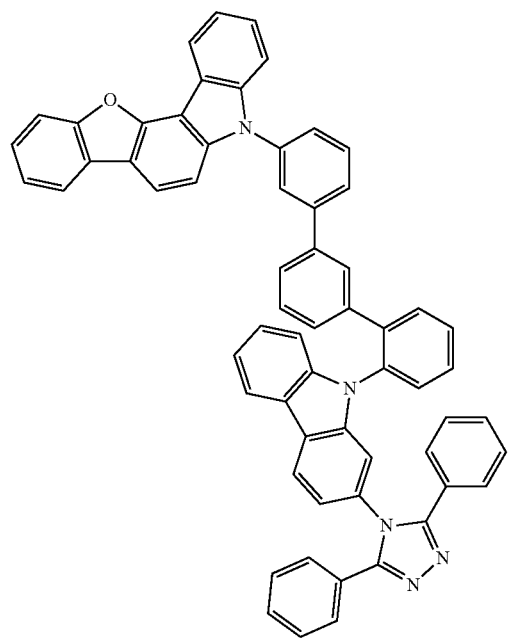
611
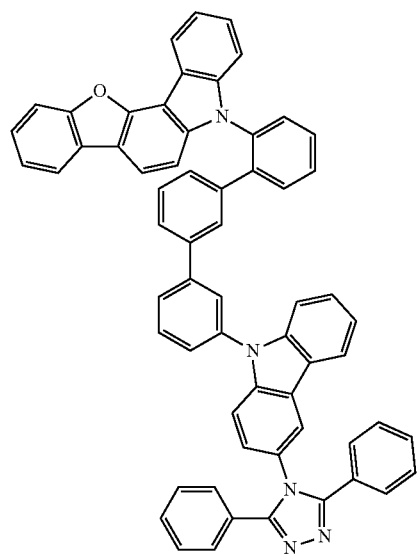
610
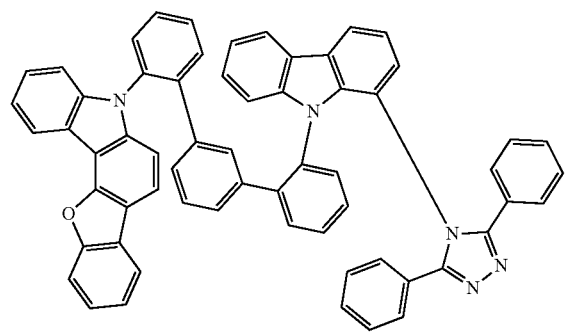
613

-continued
177
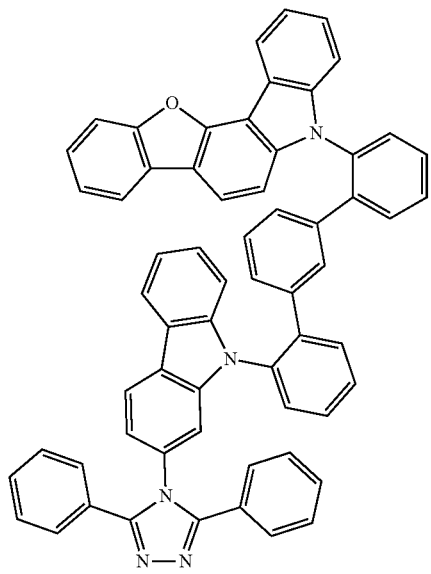
614
178
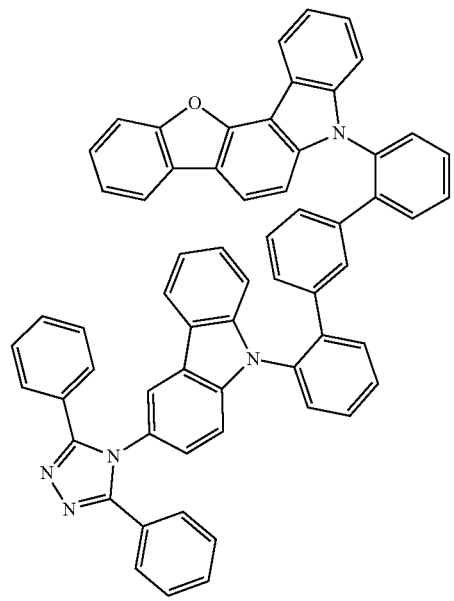
615
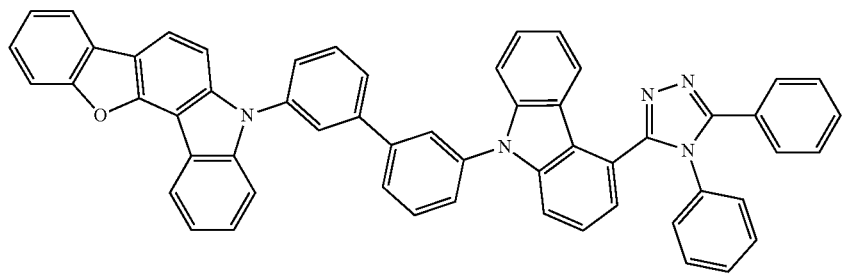
520
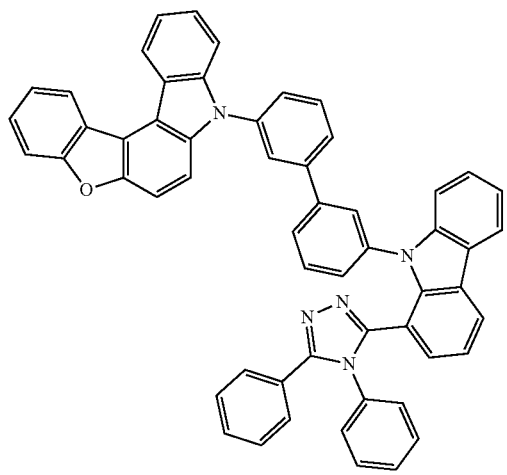
521
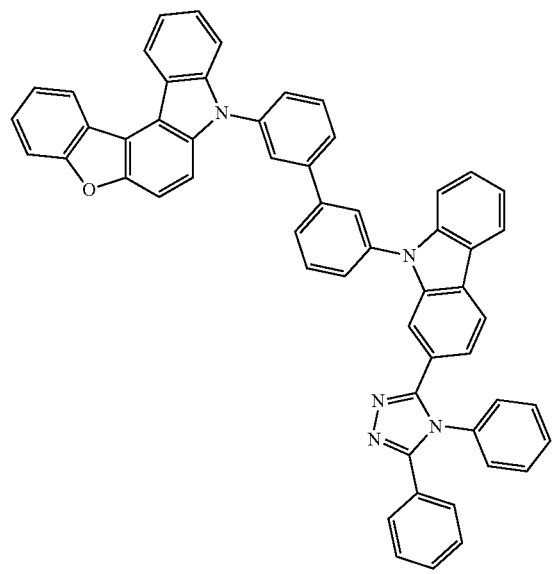
522

-continued
577
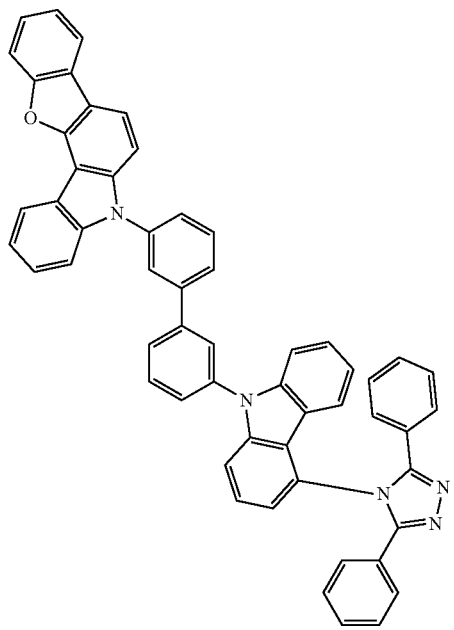
576
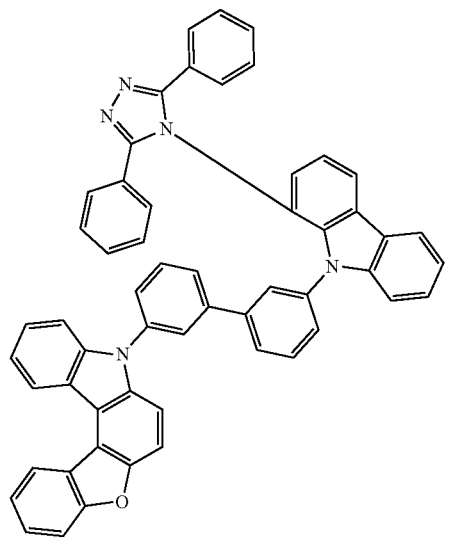
575
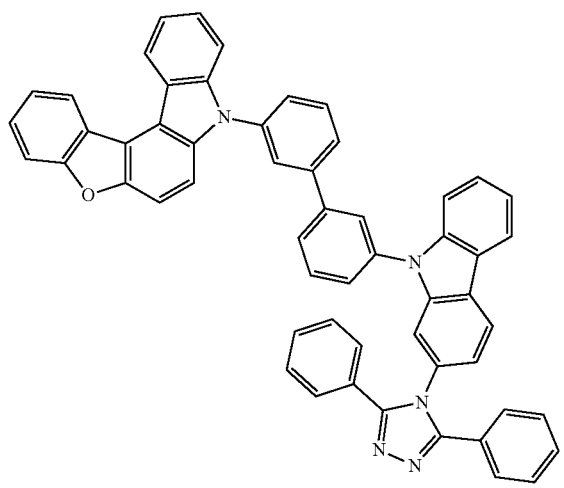
609
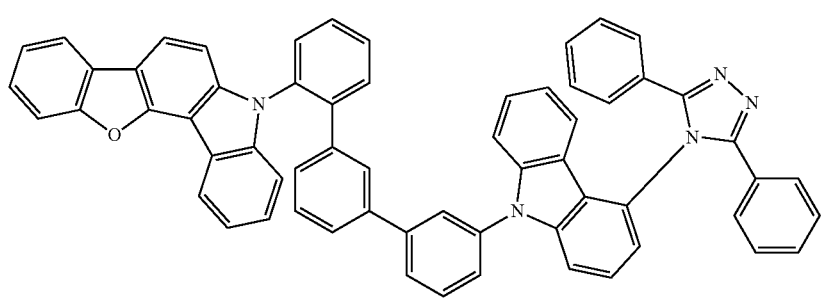

-continued
608
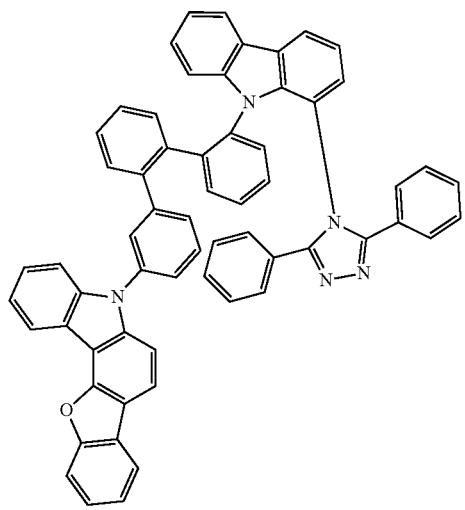
607
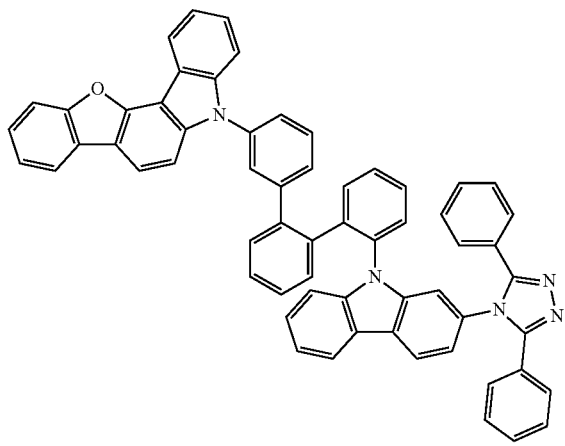
616
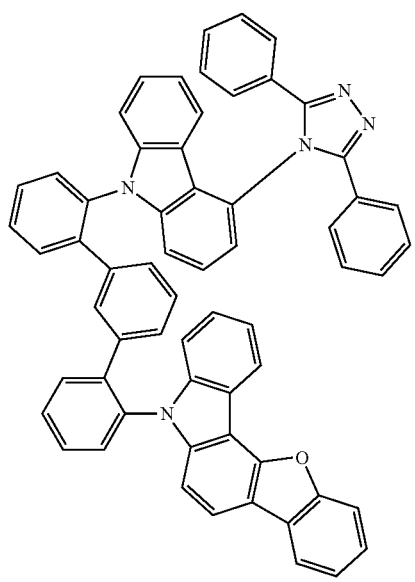
617
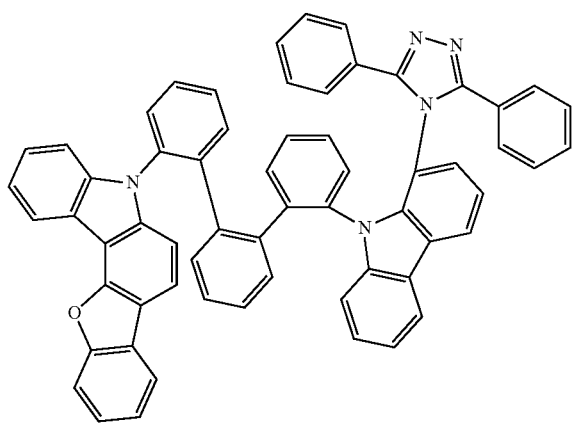
618
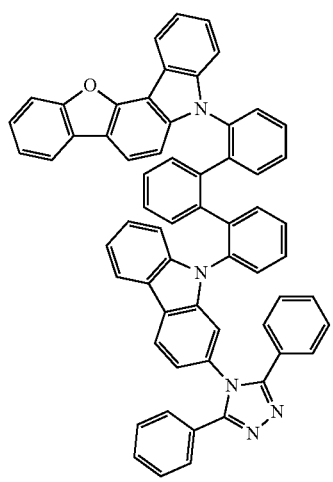
523
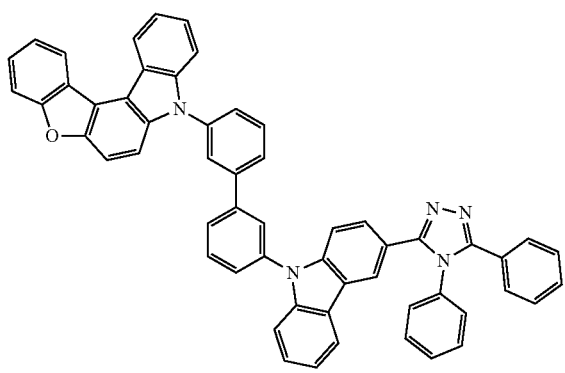

-continued
524
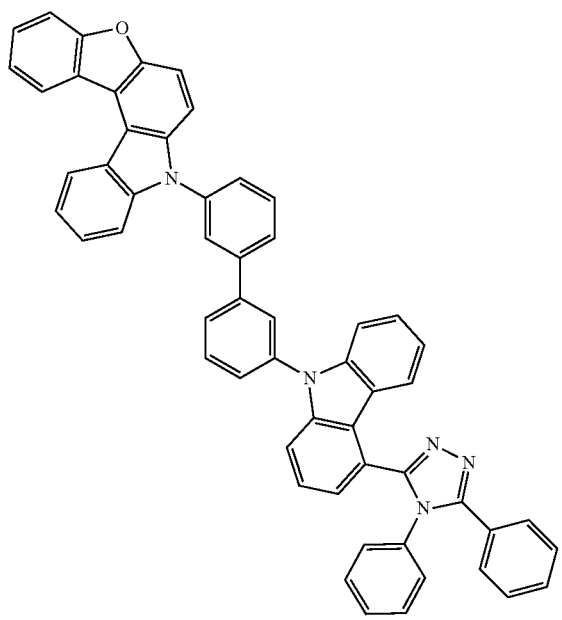
525
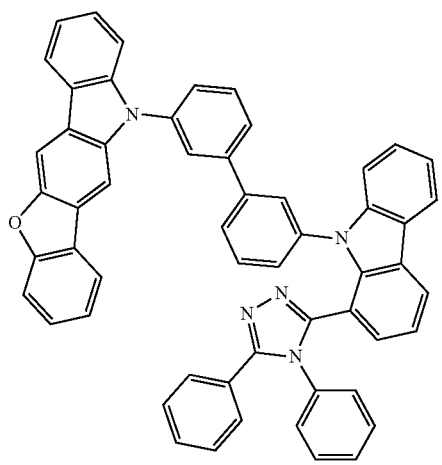
574
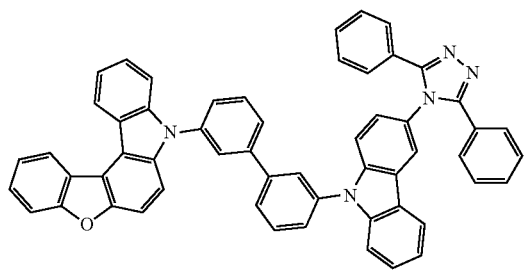
573
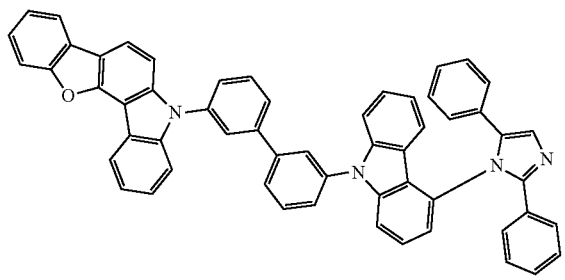
572
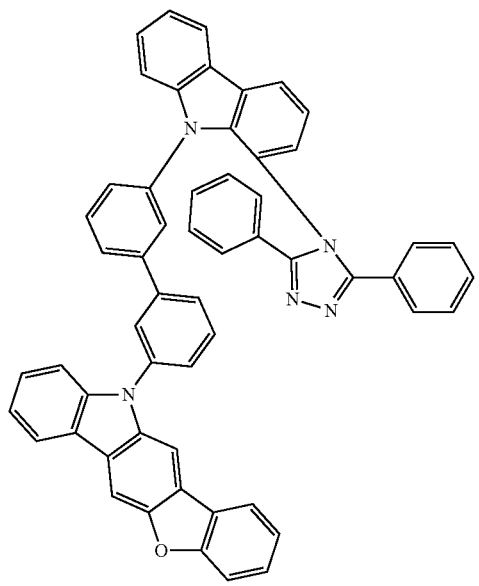
606
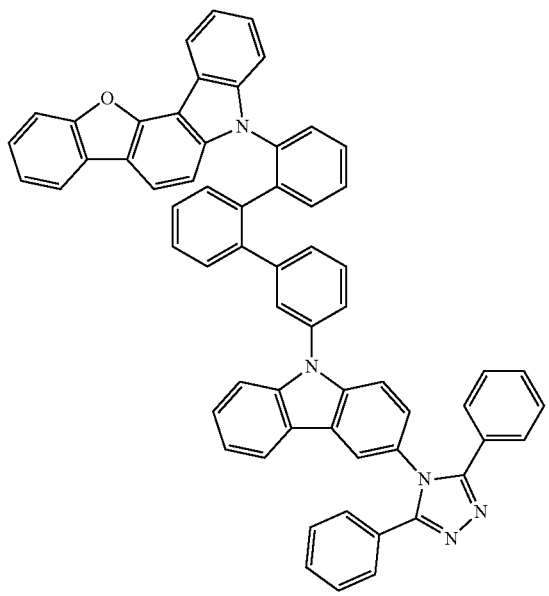

-continued
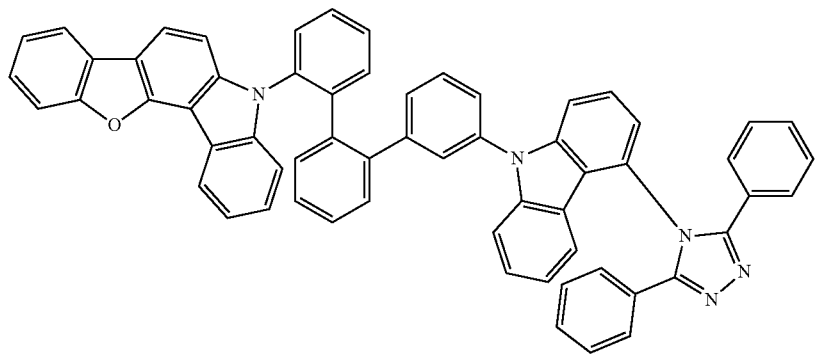
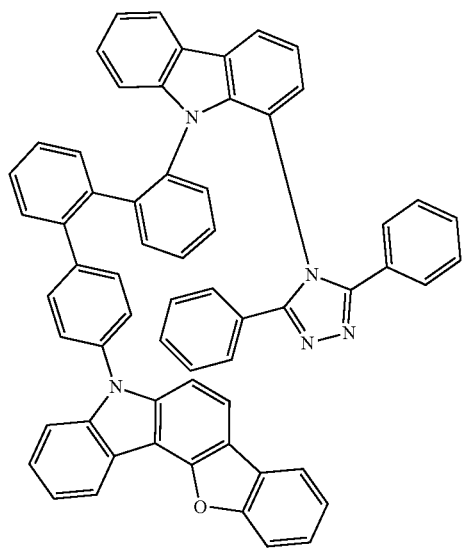
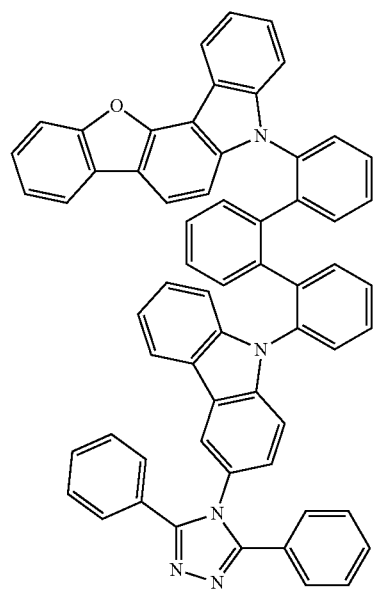
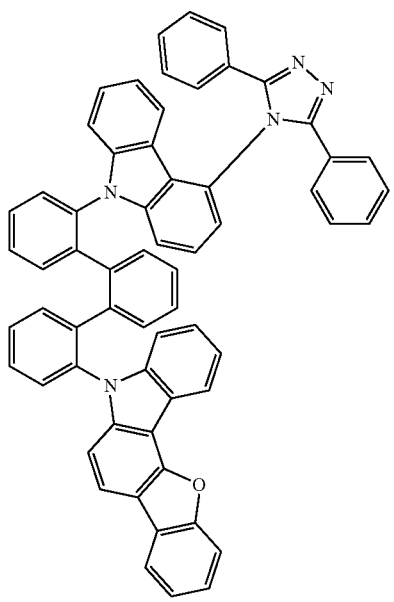
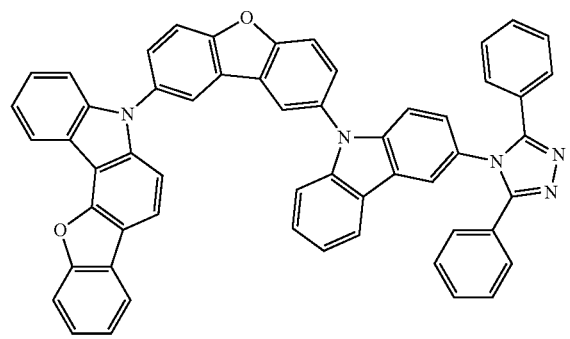

-continued
526
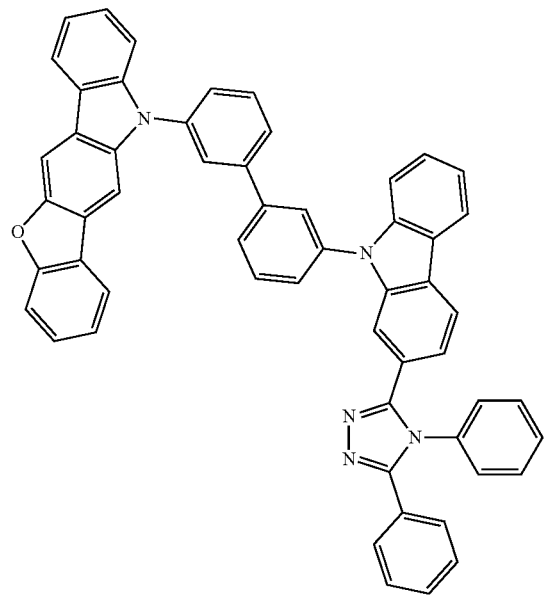
527
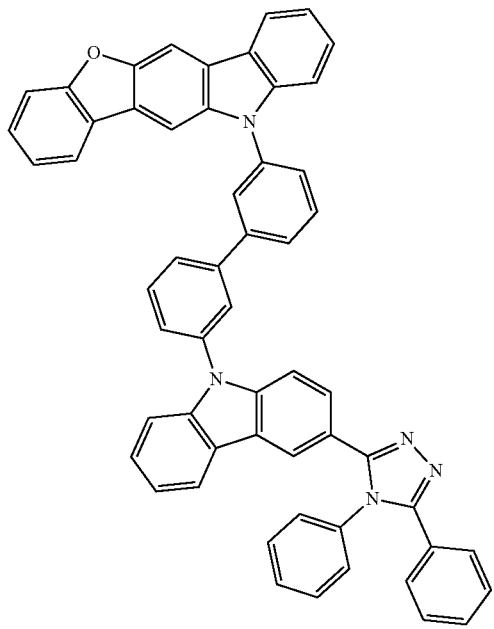
528
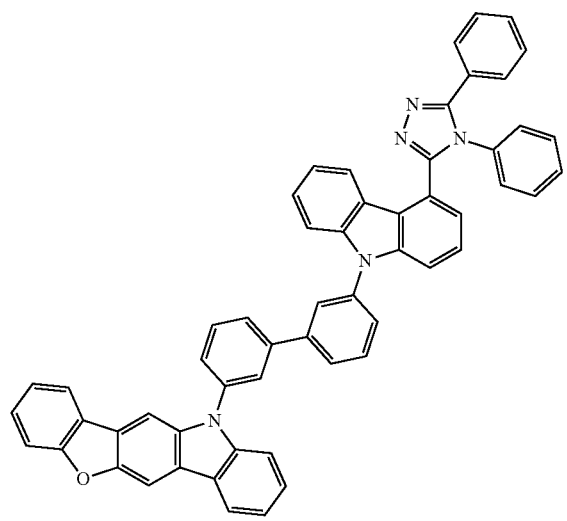
571
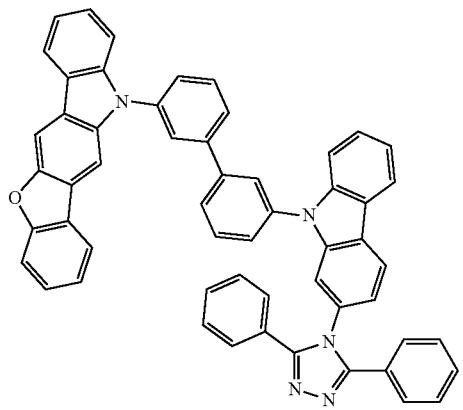
570
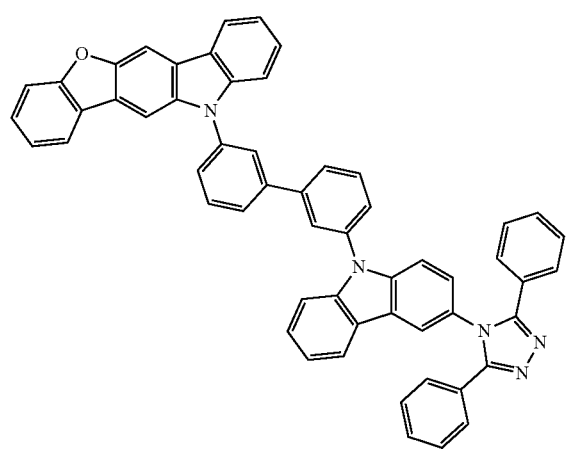
569
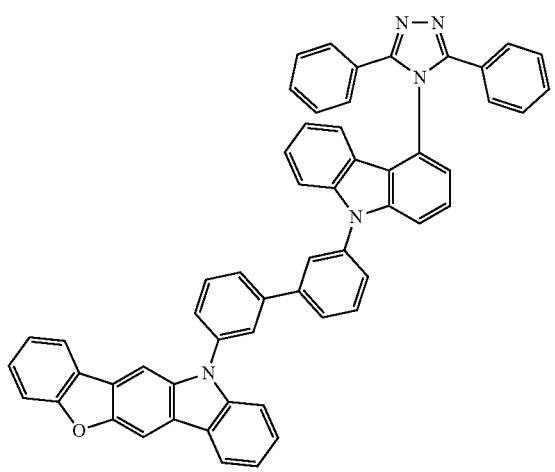

-continued
603
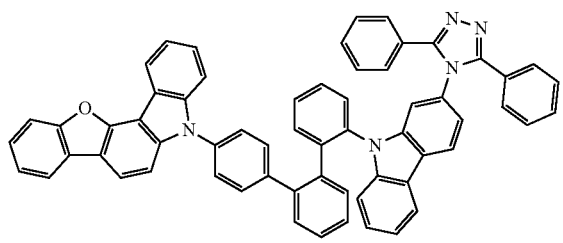
602
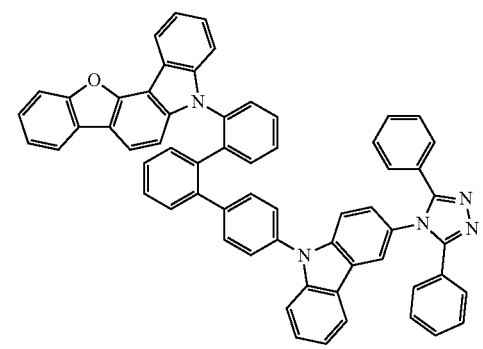
601
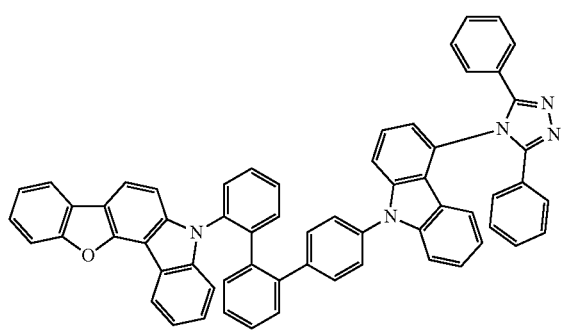
622
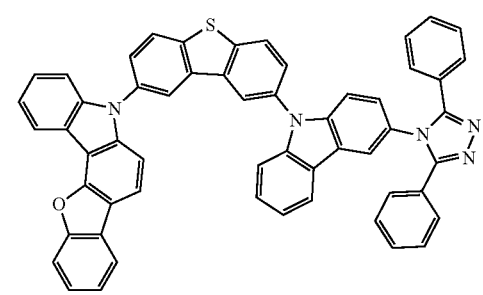
623
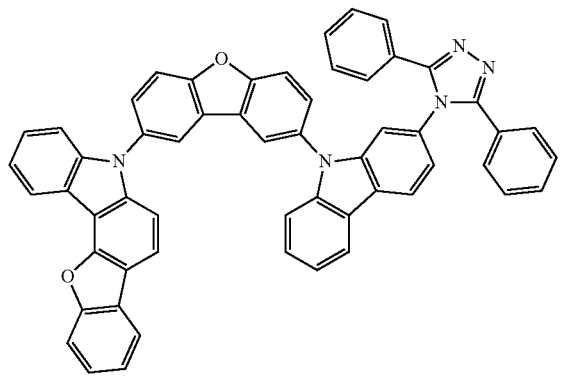
624
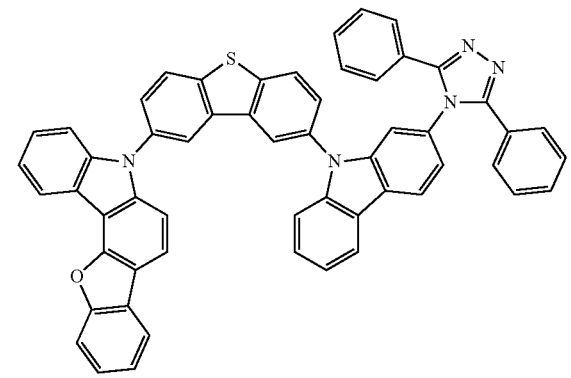
529
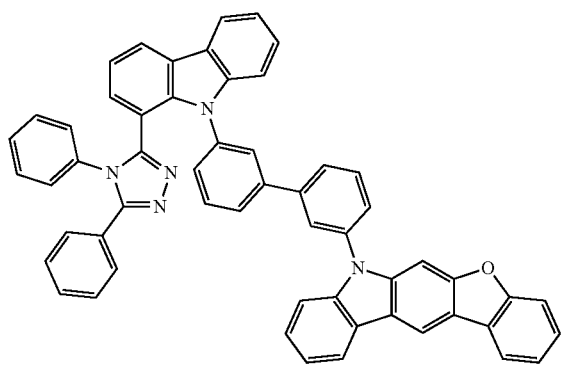
530
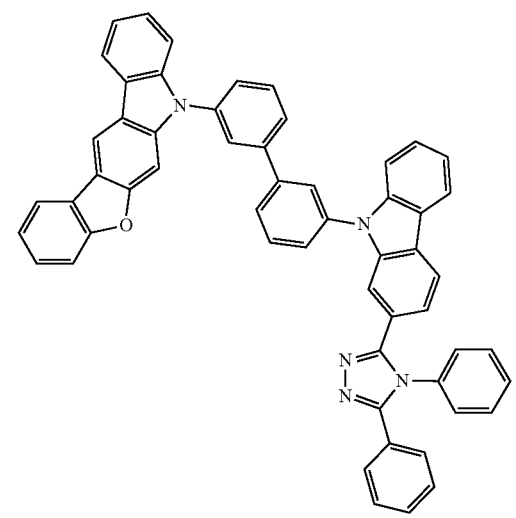

-continued
531
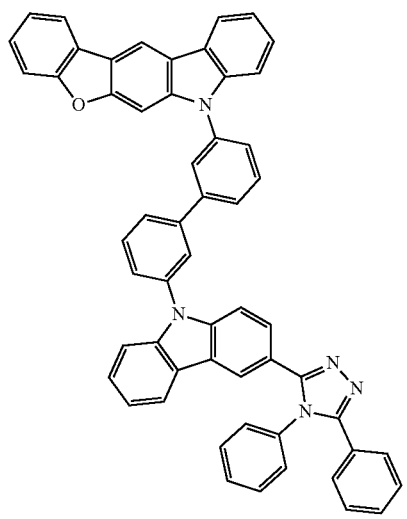
568
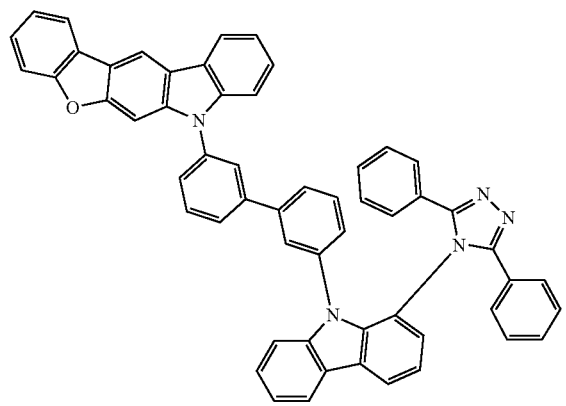
567
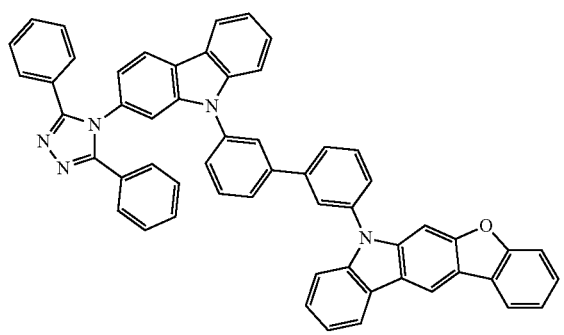
566
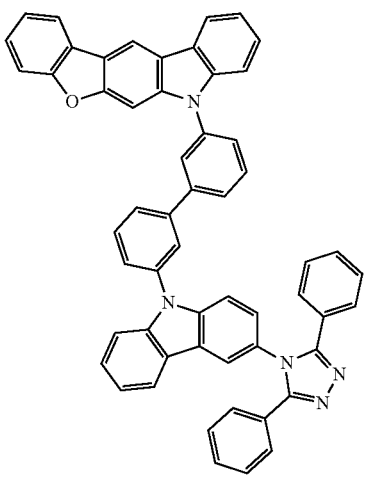
600
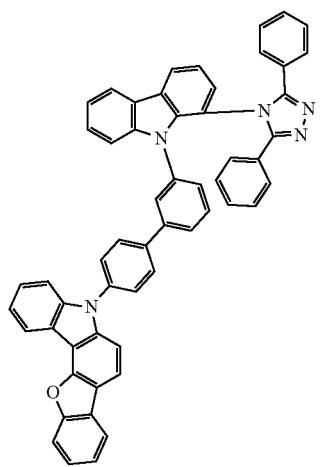
599
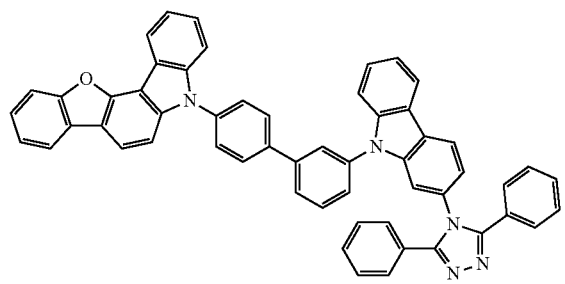

598
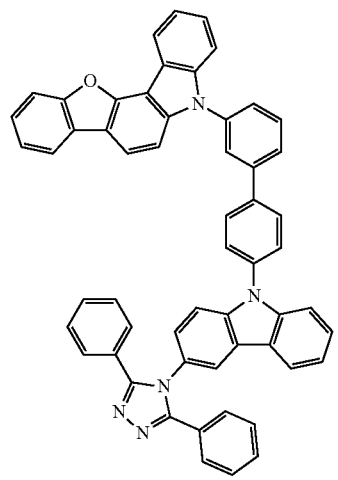
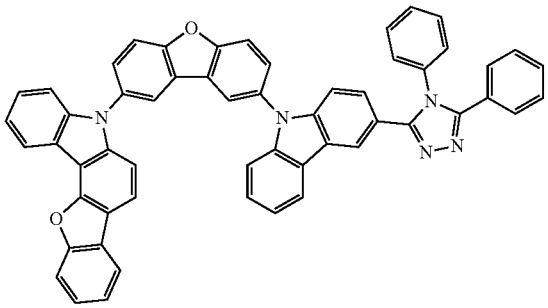
628
627
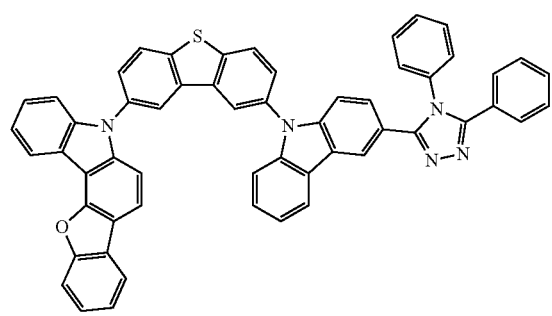
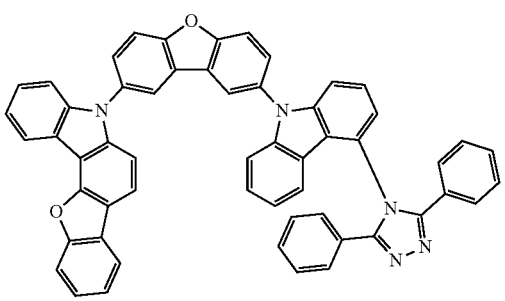
626
532
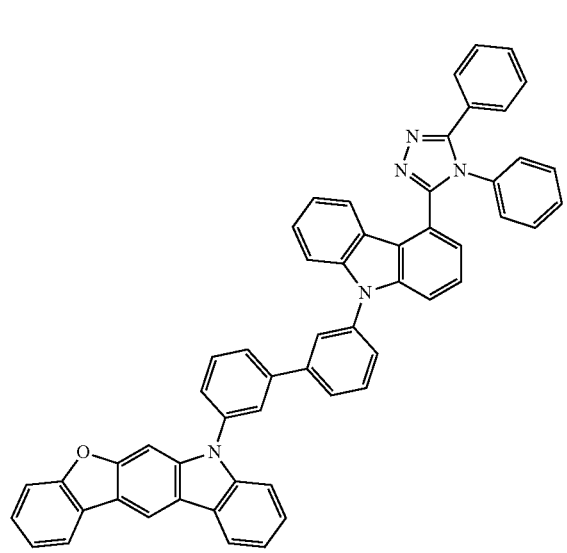
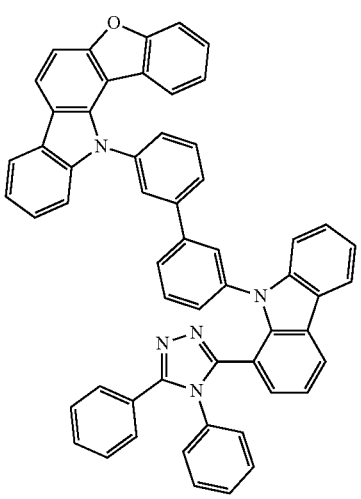
533

-continued
534
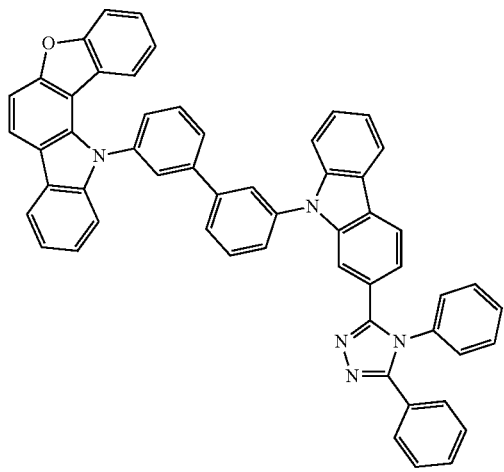
565
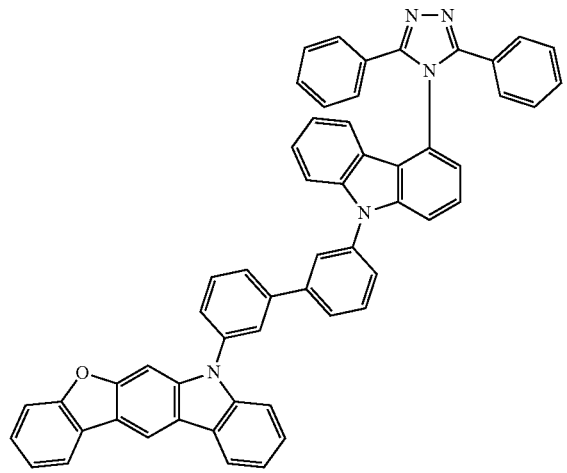
564
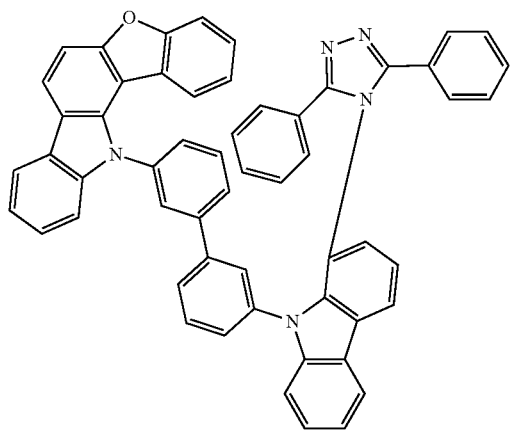
563
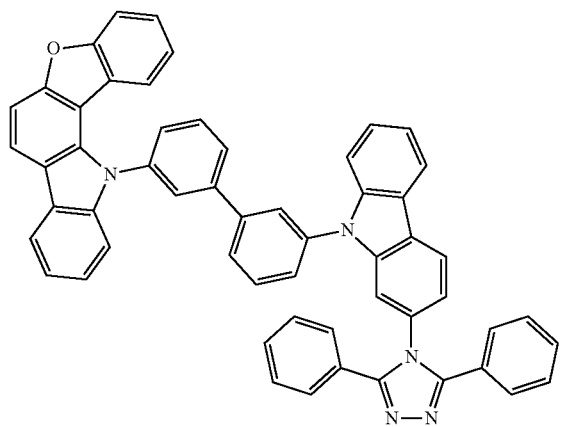
597
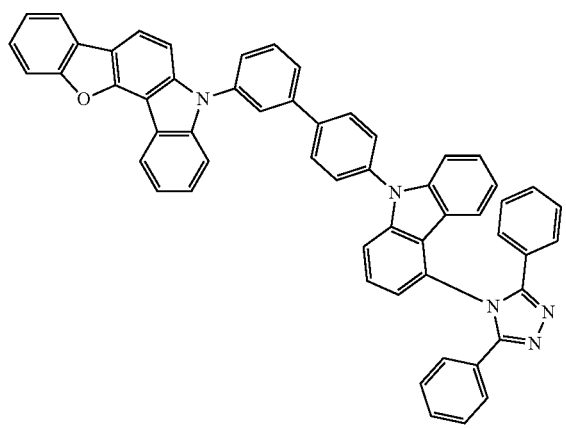
581
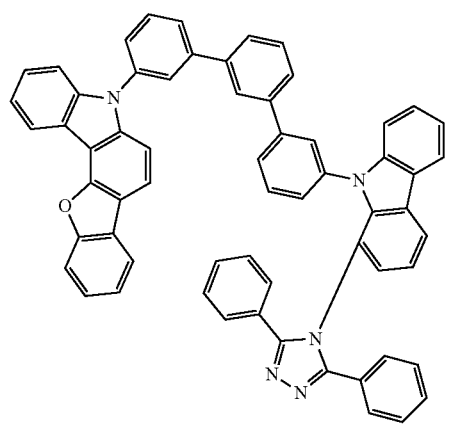

-continued
197
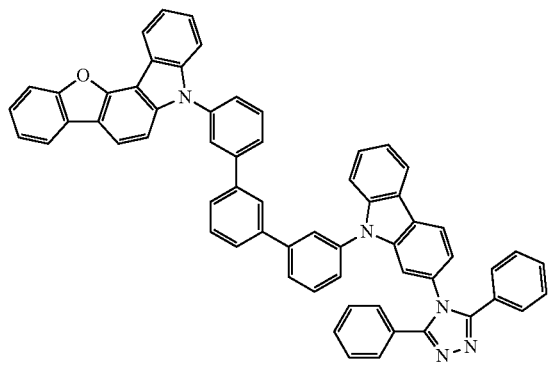
582
198
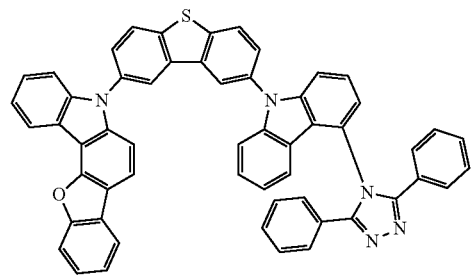
625
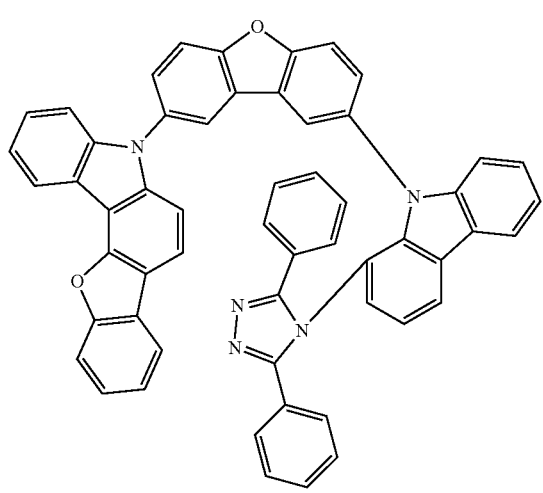
629
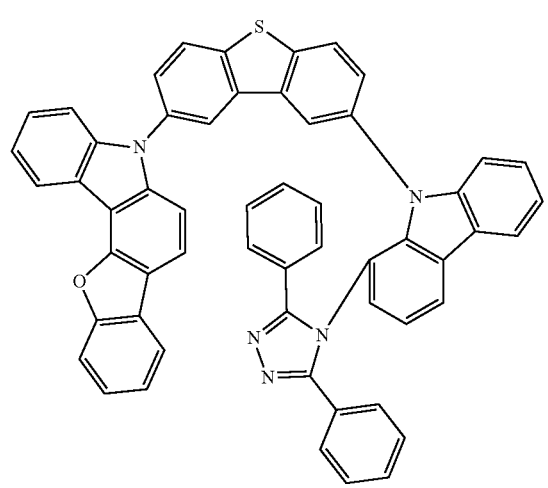
630
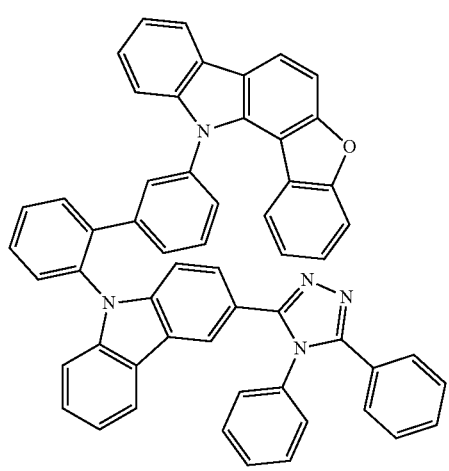
535
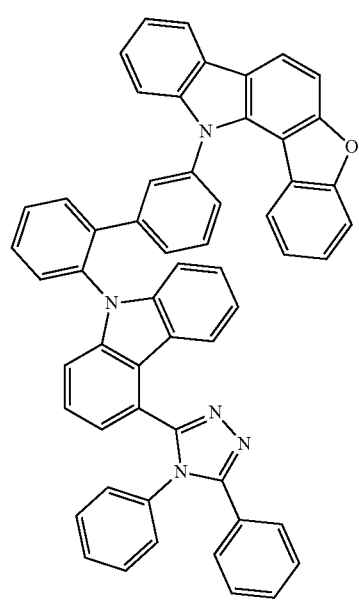
536

-continued
537
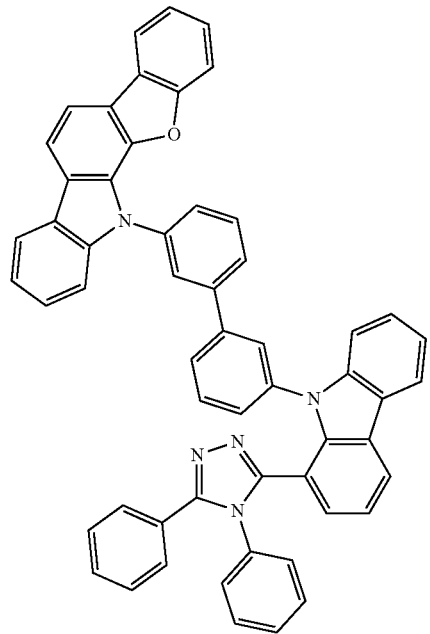
562
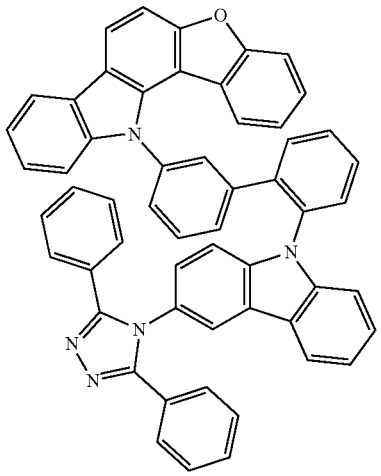
561
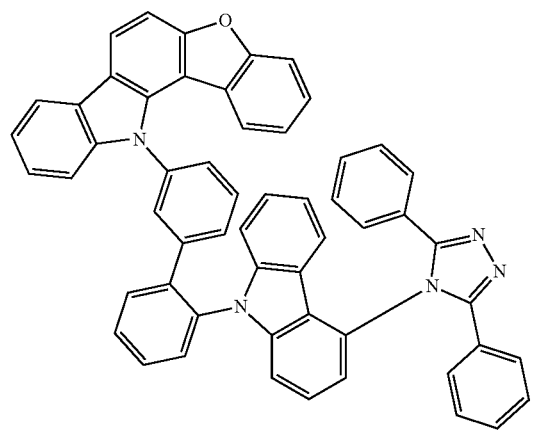
560
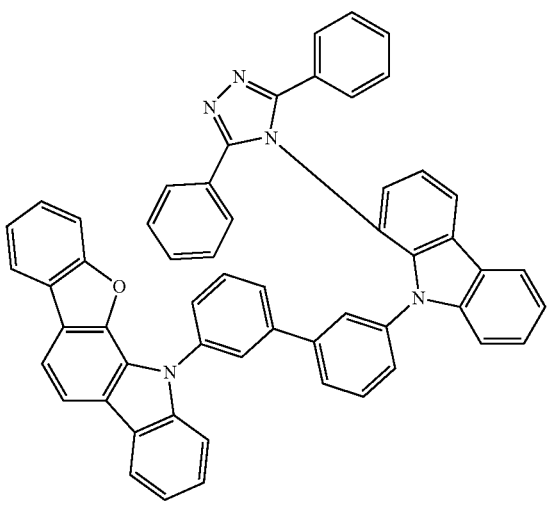
583
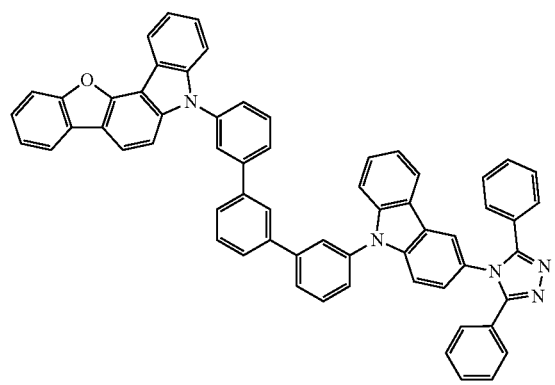
584
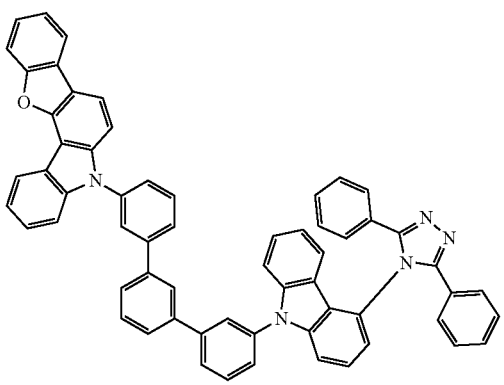

-continued
585
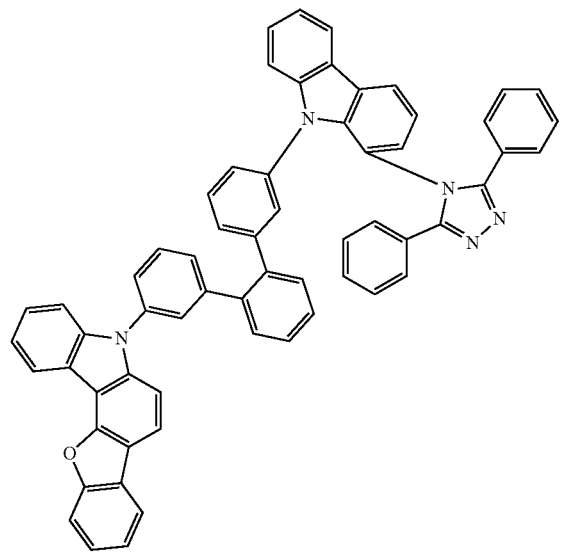
631
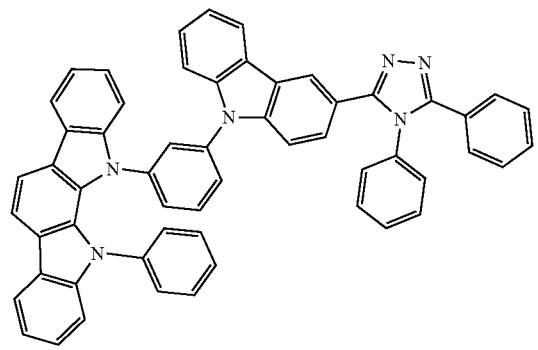
632
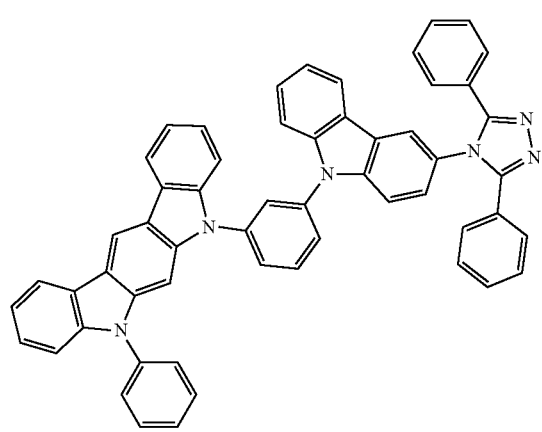
633
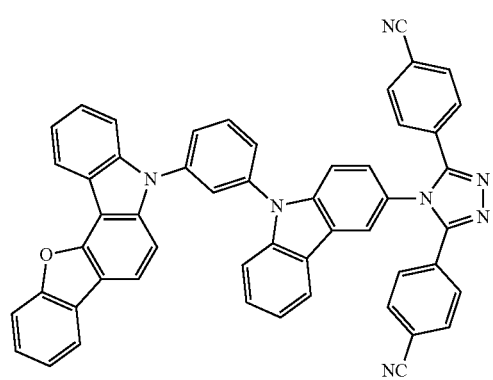
538
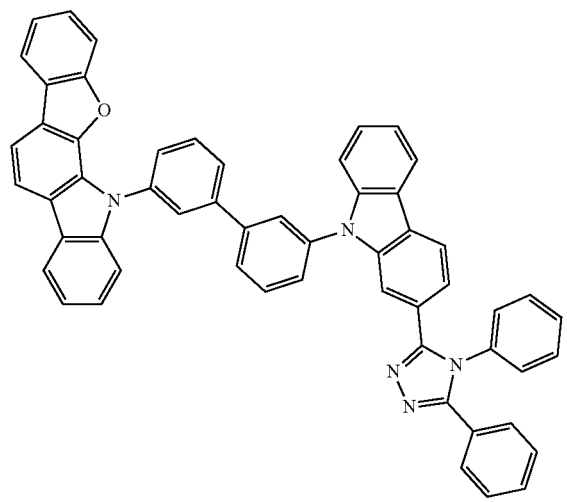
539
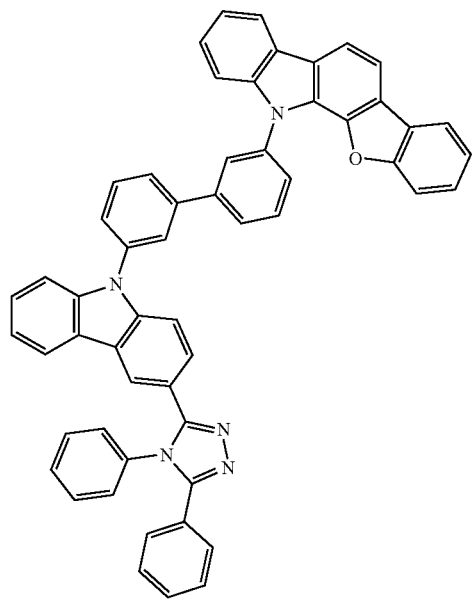

203                                          204
-continued
540
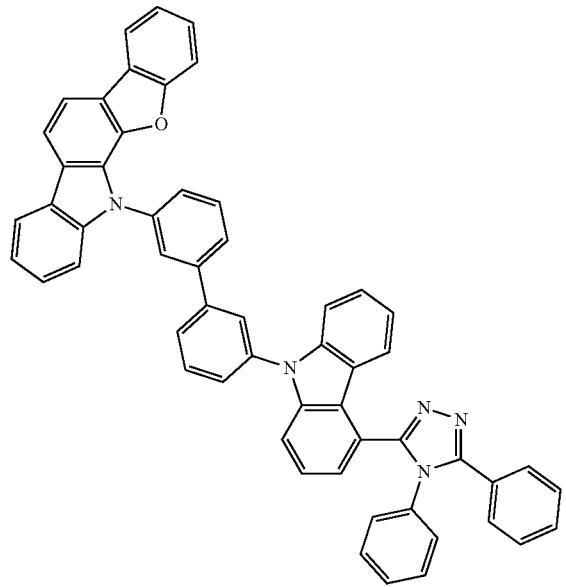
559
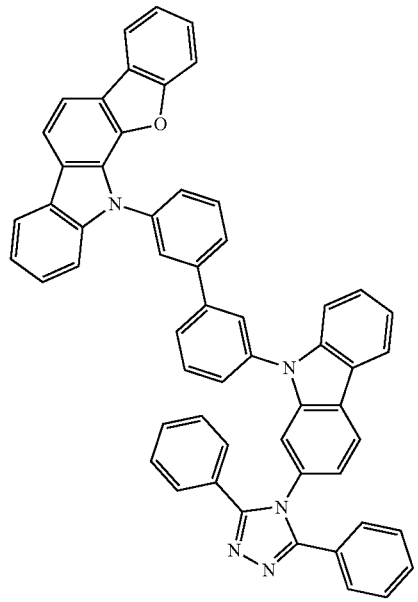
558
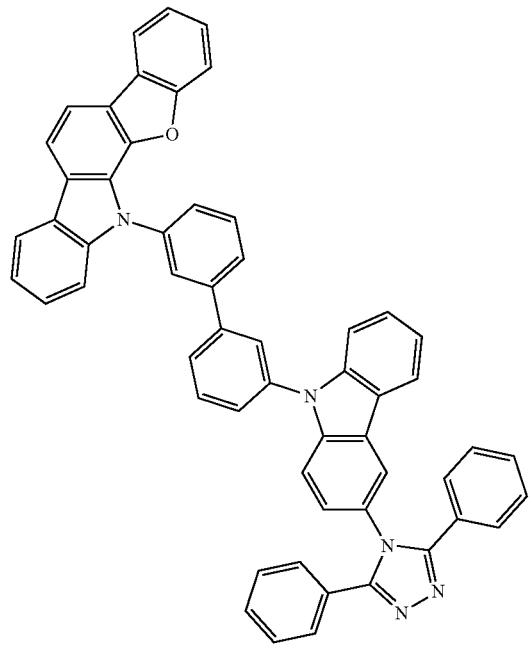
557
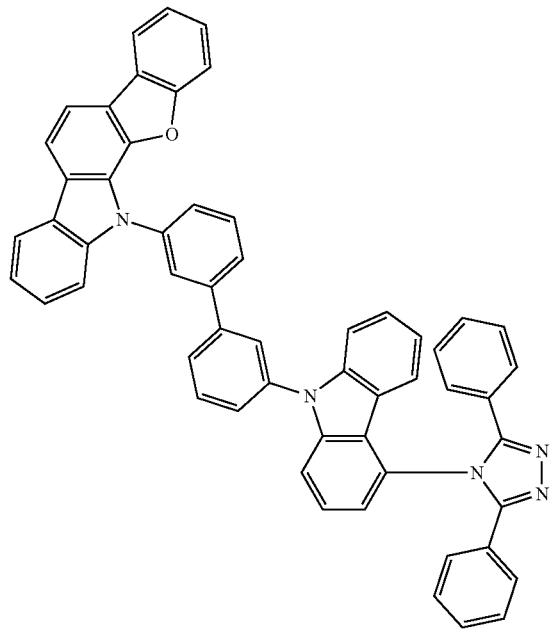

-continued
586
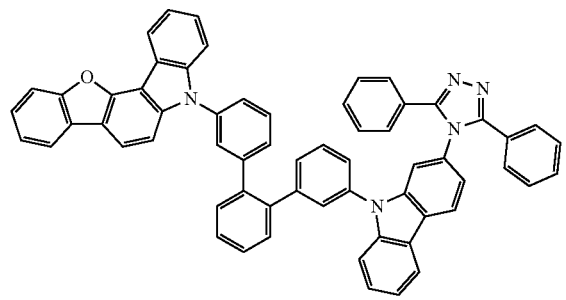
587
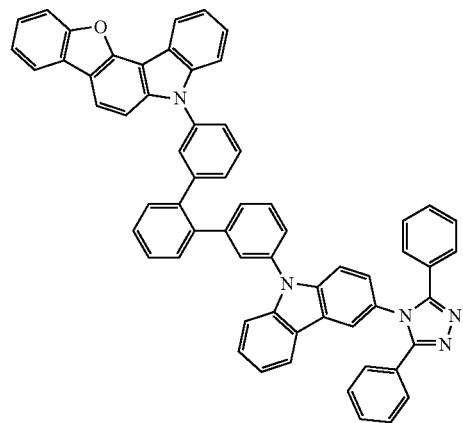
588
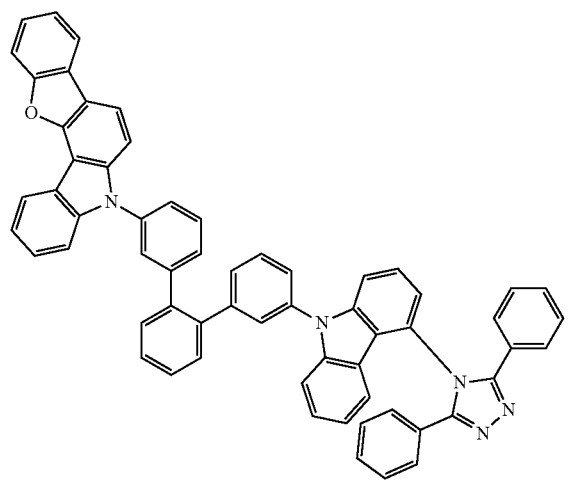
634
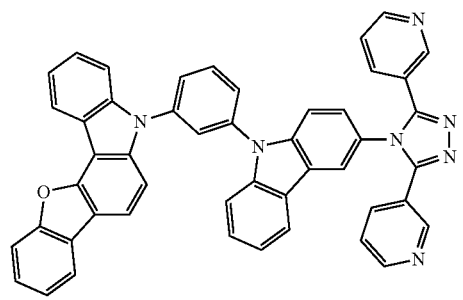
635
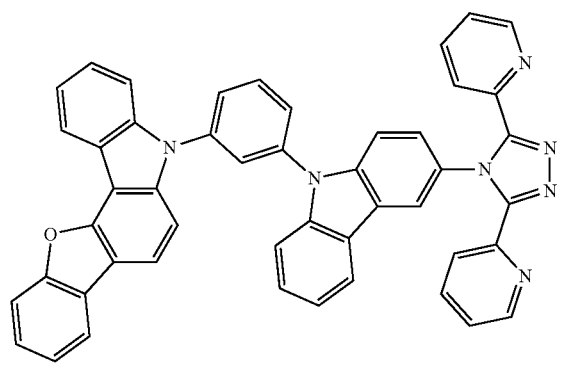
636
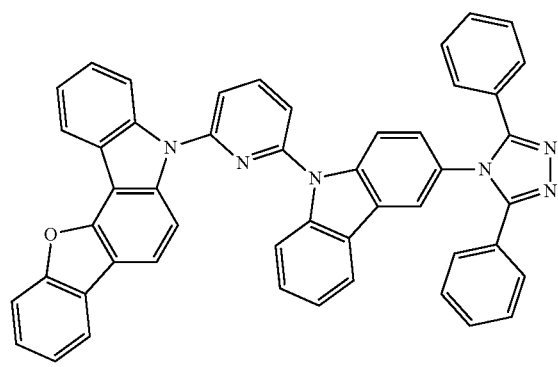

-continued
541
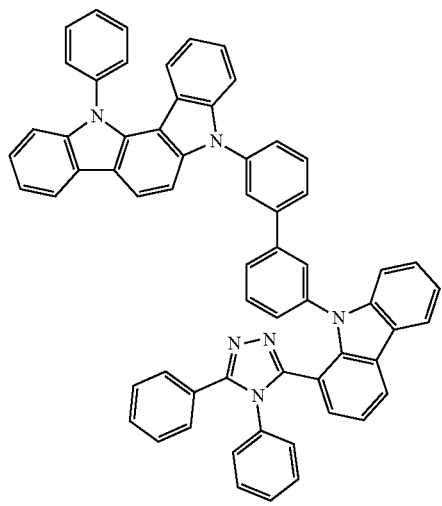
542
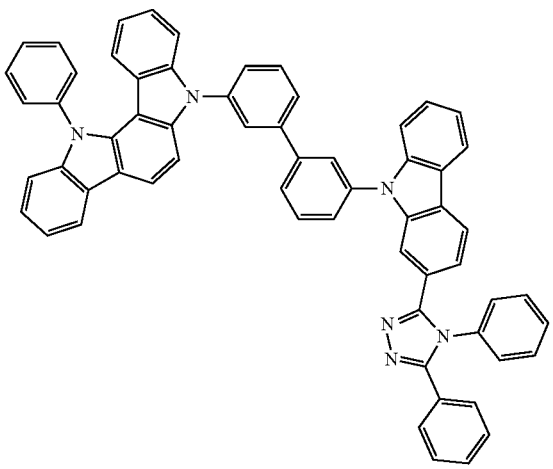
543
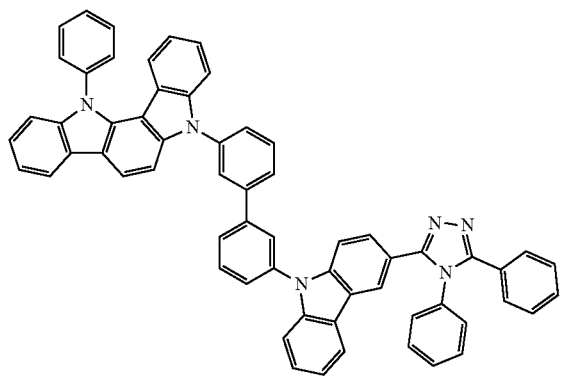
556
555
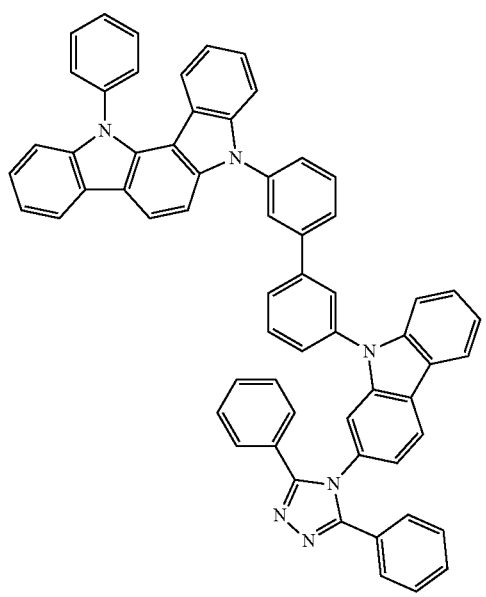
554
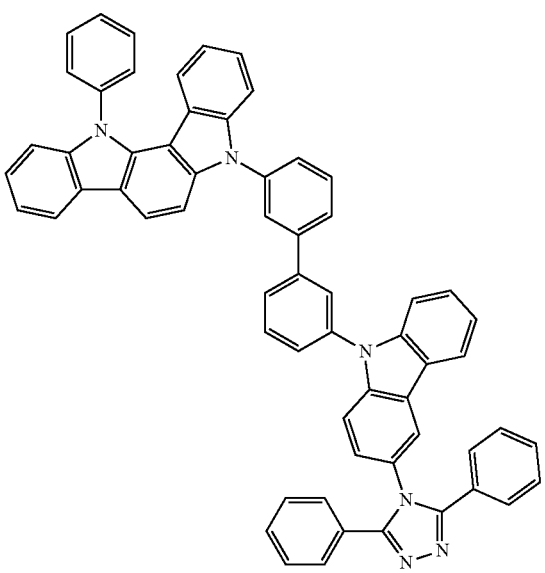

-continued
589
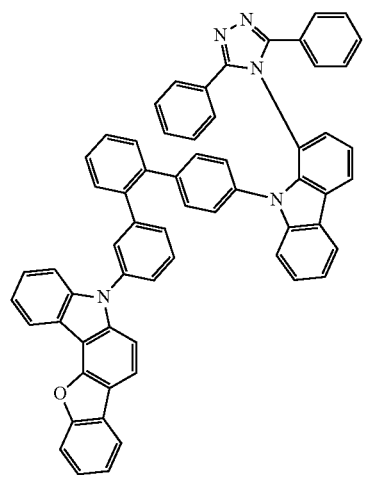
590
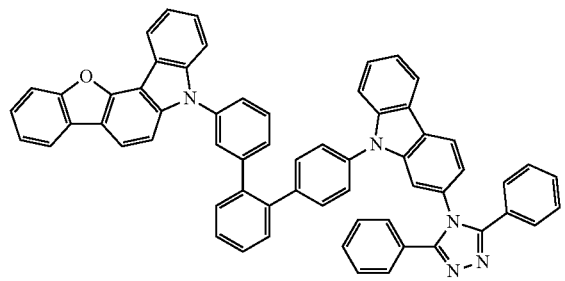
591
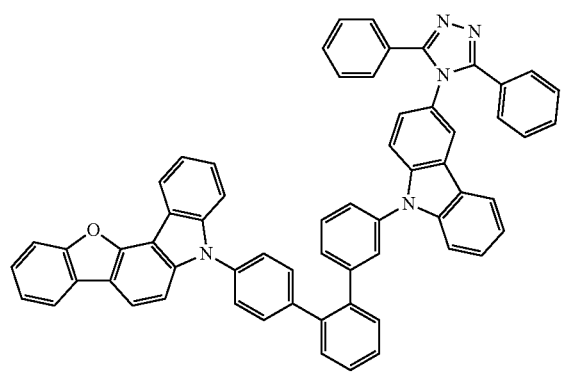
637
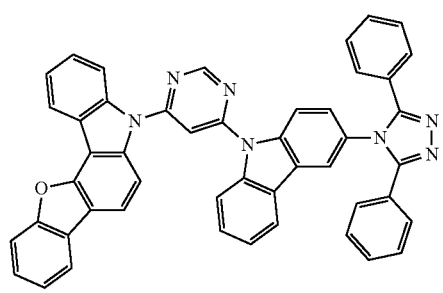
638
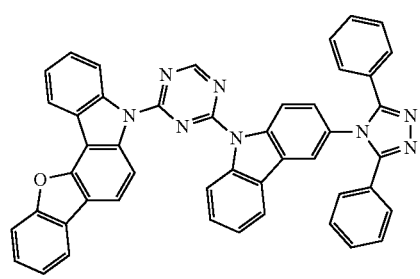
544
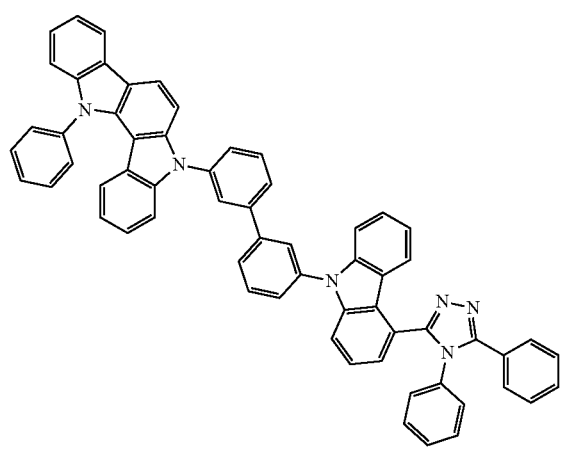

-continued
545
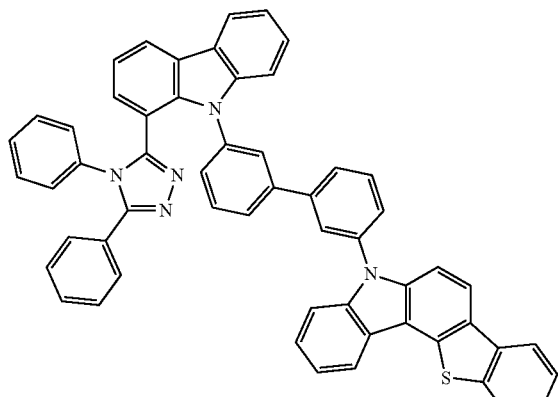
546
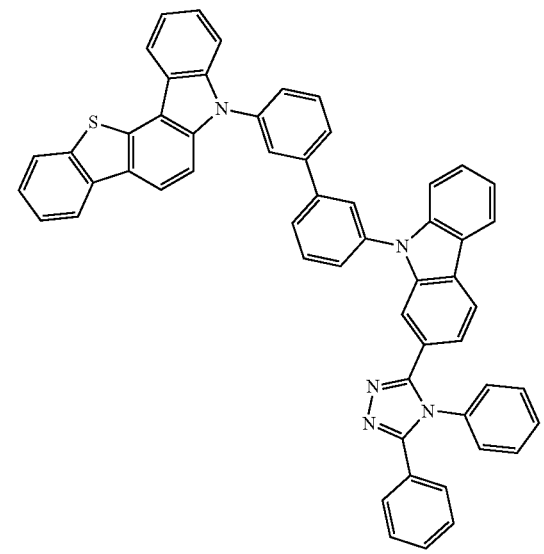
553
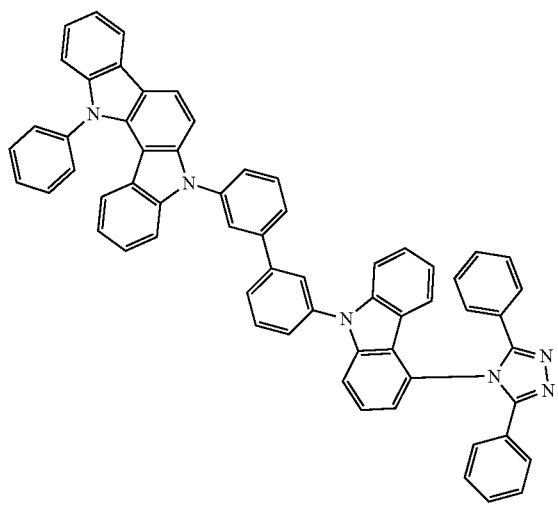
552
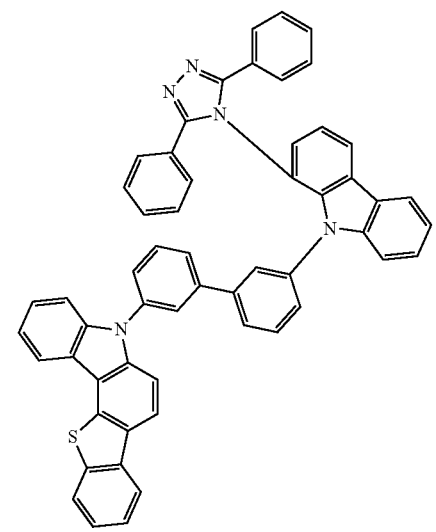
551
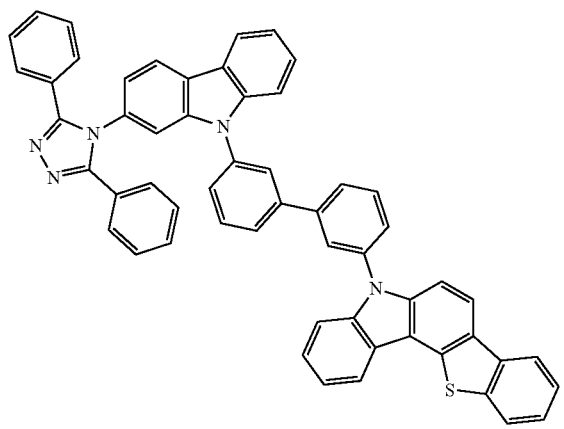
592
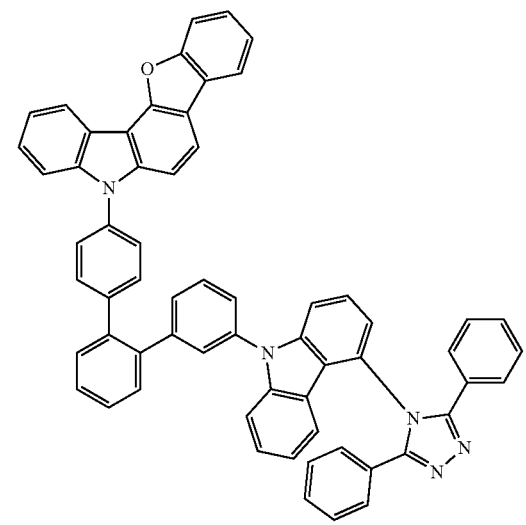

593
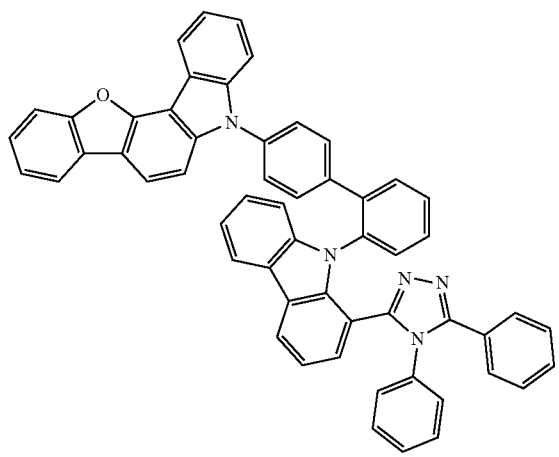
594
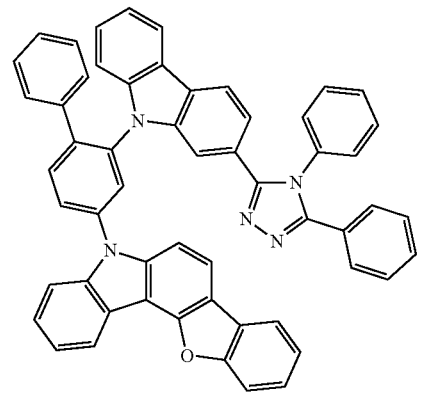
547
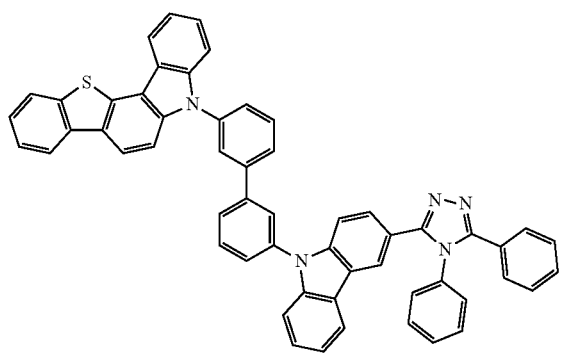
548
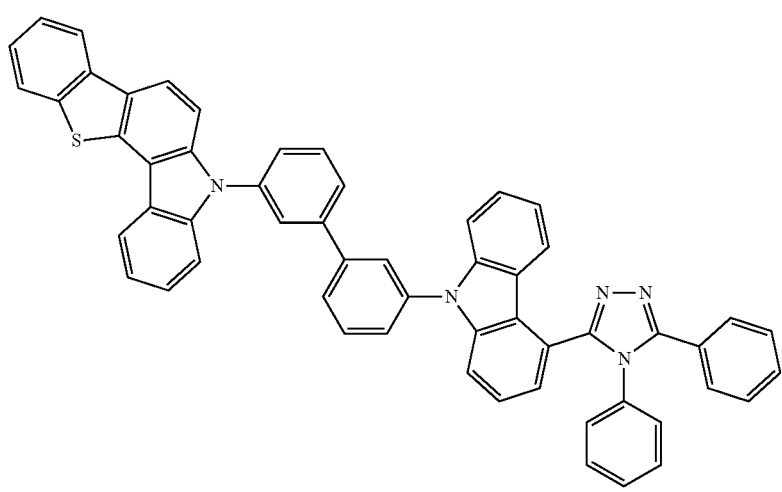

549

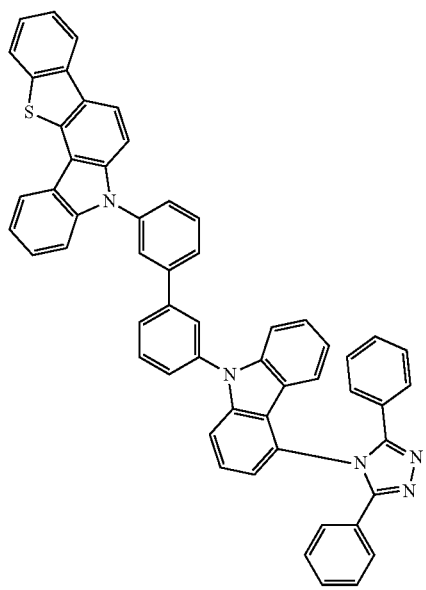

550

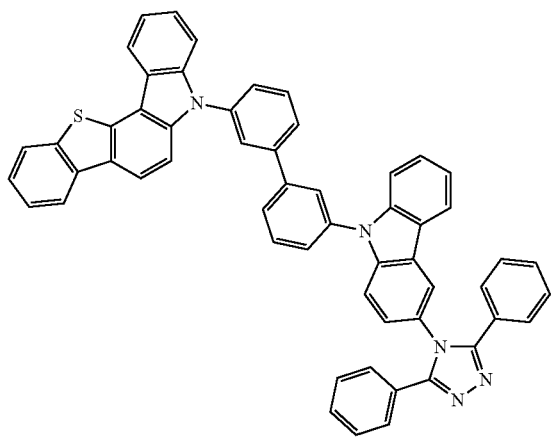

595

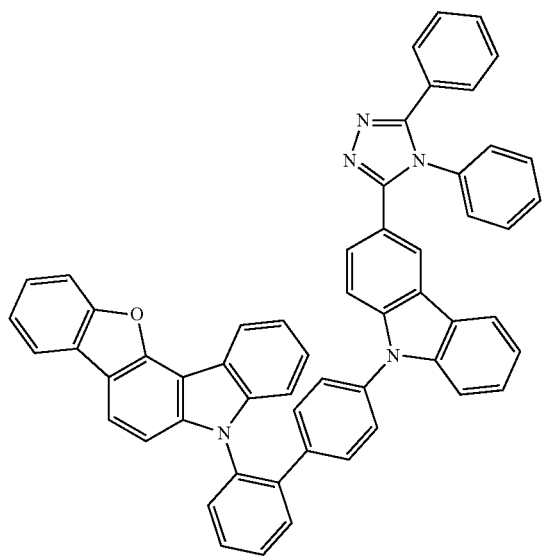

596

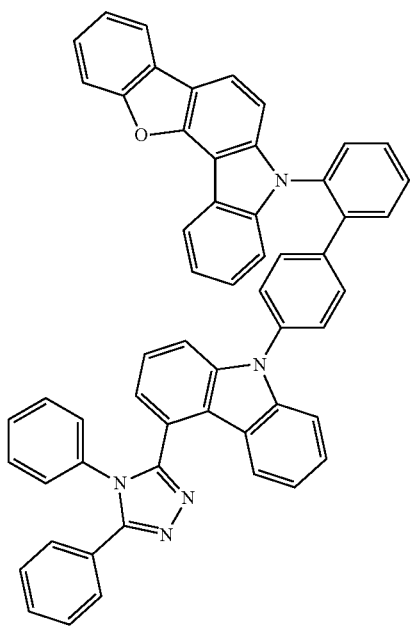

The condensed cyclic compound represented by Formula 1 may have at least one triazole group as a substituent. Therefore, as shown in Formula 1', since the condensed cyclic compound represented by Formula 1 has a "condensed carbazolyl group-$L_1$-carbazolyl group-triazole group" moiety in a conjugate structure as a basic skeleton, the adjustment of the conjugate length is facilitated. In addition, if necessary, the control may be performed such that the conjugate length does not increase. Thus, the condensed cyclic compound represented by Formula 1 may have high triplet energy. Therefore, the efficiency of the organic light-emitting device including the condensed cyclic compound may be improved.

As shown in Formula 1', the conjugate length of the condensed cyclic compound represented by Formula 1 may be adjusted as desired, depending on whether $R_{81}$ and $R_{82}$, which are the substituents of the triazole group, participate in the conjugate structure, and depending on how many members of the aromatic ring $CY_1$ to $CY_3$ include:

Formula 1'

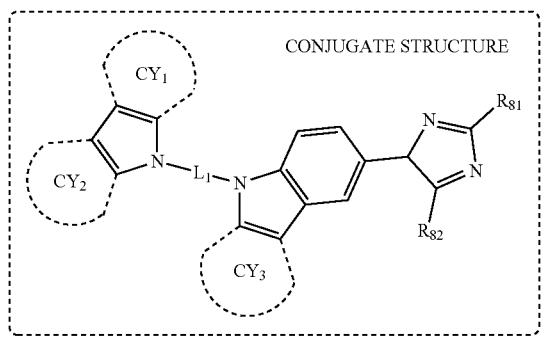

The condensed cyclic compound represented by Formula 1 includes two carbazolyl groups as shown in Formula 1'. Due to substituent characteristics of the carbazolyl group, the condensed cyclic compound represented by Formula 1 may have high thermal stability and high charge mobility.

In addition, as described above, due to characteristics of the molecular structure, the condensed cyclic compound represented by Formula 1 has a high glass transition temperature ($T_g$) and a high thermal decomposition temperature ($T_d$). As such, the condensed cyclic compound represented by Formula 1 may have excellent thermal stability, and the organic light-emitting device including the condensed cyclic compound may have high efficiency and a long lifespan.

The condensed cyclic compound represented by Formula 1, the highest occupied molecular orbital (HOMO), lowest unoccupied molecular orbital (LUMO), T1, and S1 energy levels of Compounds 199, 258, 631, 632, 66, 38, 227, 250, 223, 238, 235, 67, 263, 386, 322, and 327 and Compound A were evaluated by a DFT method of Gaussian (structurally optimized at a level of B3LYP, 6-31G(d,p)), and results thereof are shown in Table 1.

TABLE 1

| Compound | HOMO (eV) | LUMO (eV) | $T_1$ (eV) | $S_1$ (eV) |
|---|---|---|---|---|
| 199 | −5.344 | −1.056 | 3.006 | 3.777 |
| 258 | −5.484 | −1.319 | 3.005 | 3.767 |
| 631 | −5.282 | −1.026 | 2.901 | 3.684 |
| 632 | −5.206 | −1.290 | 2.830 | 3.589 |
| 66 | −5.486 | −1.225 | 3.000 | 3.724 |
| 38 | −5.533 | −1.235 | 2.960 | 3.751 |
| 227 | −5.39 | −1.064 | 2.969 | 3.786 |
| 250 | −5.529 | −1.420 | 2.782 | 3.569 |
| 223 | −5.096 | −1.008 | 2.960 | 3.647 |
| 238 | −5.628 | −1.261 | 2.954 | 3.802 |
| 235 | −5.132 | −1.297 | 2.956 | 3.500 |
| 67 | −5.355 | −1.242 | 3.003 | 3.627 |
| 263 | −5.380 | −1.136 | 2.976 | 3.772 |

TABLE 1-continued

| Compound | HOMO (eV) | LUMO (eV) | $T_1$ (eV) | $S_1$ (eV) |
|---|---|---|---|---|
| 386 | −5.429 | −1.131 | 3.006 | 3.779 |
| 322 | −5.393 | −1.109 | 3.006 | 3.783 |
| 327 | −5.406 | −1.156 | 3.006 | 3.778 |
| A | −5.638 | −1.288 | 3.145 | 3.280 |

Referring to Table 1, it is confirmed that the condensed cyclic compound represented by Formula 1 has excellent electric characteristics, for example, a high $T_1$ energy level.

Synthesis methods of the condensed cyclic compound represented by Formula 1 may be understood by one of ordinary skill in the art by referring to Synthesis Examples provided below.

Accordingly, another aspect of embodiments provides an organic light-emitting device that includes:
a first electrode;
a second electrode; and
an organic layer that is disposed between the first electrode and the second electrode,
wherein the organic layer includes an emission layer, and
wherein the organic layer includes at least one of the condensed cyclic compound represented by Formula 1.

The condensed cyclic compound represented by Formula 1 may be used in the organic layer of the organic light-emitting device. For example, the condensed cyclic compound represented by Formula 1 may be used as a host in the emission layer of the organic layer. However, embodiments of the present disclosure are not limited thereto.

The organic light-emitting device may have, due to the inclusion of an organic layer including the condensed cyclic compound represented by Formula 1, low driving voltage, high efficiency, high brightness, and long lifespan.

The condensed cyclic compound represented by Formula 1 is suitable for use in an organic layer of an organic light-emitting device, for example, for use as a material for forming a hole transport layer, a material for forming an electron blocking material, and/or a host in an emission layer of the organic layer. Thus, another aspect provides an organic light-emitting device that includes: a first electrode; a second electrode; and an organic layer that is disposed between the first electrode and the second electrode, wherein the organic layer includes an emission layer, and wherein the organic layer includes at least one condensed cyclic compound represented by Formula 1.

The organic light-emitting device may have, due to the inclusion of an organic layer including the condensed cyclic compound represented by Formula 1, low driving voltage, high efficiency, high brightness, high quantum emission efficiency, and a long lifespan.

For example, the condensed cyclic compound represented by Formula 1 may be included in the emission layer.

In an embodiment, the emission layer may include the condensed cyclic compound represented by Formula 1, wherein the condensed cyclic compound represented by Formula 1 may be a delayed fluorescent material.

In another embodiment, the emission layer may include a host and a dopant (wherein an amount of the host is greater than that of the dopant), and the host may include the condensed cyclic compound represented by Formula 1. The condensed cyclic compound which serves as the host may deliver energy to the dopant according to the delayed fluorescence emission mechanism. The dopant may include at least one selected from a fluorescent dopant and a phosphorescent dopant. The dopant may be selected from any known dopants. The host may further include any host selected from known hosts.

In one or more embodiment, the emission layer may include a host and a dopant (wherein an amount of the host is greater than that of the dopant), and the dopant may include the condensed cyclic compound represented by Formula 1. The condensed cyclic compound which serves as the dopant may emit delayed fluorescence according to the delayed fluorescence emission mechanism. The host may be selected from any known dopants.

The emission layer may emit red light, green light, or blue light.

In an embodiment, the emission layer may be a blue light emission layer including a phosphorescent dopant.

In one or more embodiments, the condensed cyclic compound represented by Formula 1 may be included in the hole transport region.

For example, the hole transport region of the organic light-emitting device may include at least one selected from a hole transport layer and an electron blocking layer, and at least one selected from the hole transport layer and the electron blocking layer may include the condensed cyclic compound represented by Formula 1.

For example, the hole transport region of the organic light-emitting device may include the hole transport layer, wherein the hole transport layer includes the condensed cyclic compound represented by Formula 1.

For example, the hole transport region of the organic light-emitting device may include the electron blocking layer, wherein the electron blocking layer includes the condensed cyclic compound represented by Formula 1. The electron blocking layer may directly contact the emission layer.

In an embodiment, the condensed cyclic compound represented by Formula 1 may be included in the electron transport region.

For example, the electron transport region of the organic light-emitting device may include the electron transport layer, wherein the electron transport layer includes the condensed cyclic compound represented by Formula 1.

For example, the electron transport region of the organic light-emitting device may include the hole blocking layer, wherein the hole blocking layer includes the condensed cyclic compound represented by Formula 1. The hole blocking layer may directly contact the emission layer.

The term "organic layer" as used herein refers to a single layer and/or a plurality of layers between the first electrode and the second electrode of the organic light-emitting device. The "organic layer" may include, in addition to an organic compound, an organometallic complex including metal.

The FIGURE is a schematic view of an organic light-emitting device 10 according to an embodiment. Hereinafter, the structure of an organic light-emitting device according to an embodiment and a method of manufacturing an organic light-emitting device according to an embodiment will be described in connection with the FIGURE. The organic light-emitting device 10 includes a first electrode 11, an organic layer 15, and a second electrode 19, which are sequentially stacked.

A substrate may be additionally disposed under the first electrode 11 or above the second electrode 19. For use as the substrate, any substrate that is used in general organic light-emitting devices may be used, and the substrate may be a glass substrate or a transparent plastic substrate, each having excellent mechanical strength, thermal stability, transparency, surface smoothness, ease of handling, and water resistance.

In one or more embodiments, the first electrode 11 may be formed by depositing or sputtering a material for forming the first electrode 11 on the substrate. The first electrode 11 may be an anode. The material for forming the first electrode 11 may be selected from materials with a high work function to facilitate hole injection. The first electrode 11 may be a reflective electrode, a semi-transmissive electrode, or a transmissive electrode. The material for forming the first electrode 11 may be indium tin oxide (ITO), indium zinc oxide (IZO), tin oxide ($SnO_2$), or zinc oxide (ZnO). In one or more embodiments, the material for forming the first electrode 11 may be metal, such as magnesium (Mg), aluminum (Al), aluminum-lithium (Al—Li), calcium (Ca), magnesium-indium (Mg—In), or magnesium-silver (Mg—Ag).

The first electrode 11 may have a single-layered structure or a multi-layered structure including two or more layers. For example, the first electrode 11 may have a three-layered structure of ITO/Ag/ITO, but the structure of the first electrode 110 is hot limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In one or more embodiments, the hole transport region may have a hole injection layer/hole transport layer structure or a hole injection layer/hole transport layer/electron blocking layer structure, which are sequentially stacked in this stated order from the first electrode 11.

When the hole transport region includes a hole injection layer (HIL), the hole injection layer may be formed on the first electrode 11 by using one or more suitable methods, for example, vacuum deposition, spin coating, casting, and/or Langmuir-Blodgett (LB) deposition.

When a hole injection layer is formed by vacuum deposition, the deposition conditions may vary according to a material that is used to form the hole injection layer, and the structure and thermal characteristics of the hole injection layer. For example, the deposition conditions may include a deposition temperature of about 100° C. to about 500° C., a vacuum pressure of about $10^{-8}$ torr to about $10^{-3}$ torr, and a deposition rate of about 0 Angstroms per second (A/sec) to about 100 Å/sec. However, the deposition conditions are not limited thereto.

When the hole injection layer is formed using spin coating, coating conditions may vary according to the material used to form the hole injection layer, and the structure and thermal properties of the hole injection layer. For example, a coating speed may be from about 2,000 revolutions per minute (rpm) to about 5,000 rpm, and a temperature at which a heat treatment is performed to remove a solvent after coating may be from about 80° C. to about 200° C. However, the coating conditions are not limited thereto.

Conditions for forming a hole transport layer and an electron blocking layer may be understood by referring to conditions for forming the hole injection layer.

The hole transport region may include at least one selected from m-MTDATA, TDATA, 2-TNATA, NPB, β-NPB, TPD, Spiro-TPD, Spiro-NPB, methylated-NPB, TAPC, HMTPD, 4,4',4''-tris(N-carbazolyl)triphenylamine (TCTA), polyaniline/dodecylbenzene sulfonic acid (PANI/DBSA), poly(3,4-ethylenedioxythiophene)/poly(4-styrenesulfonate) (PEDOT/PSS), polyaniline/camphor sulfonic acid (PAN I/CSA), polyaniline/poly(4-styrene sulfonate) (PAN I/PSS), a compound represented by Formula 201 below, and a compound represented by Formula 202 below:

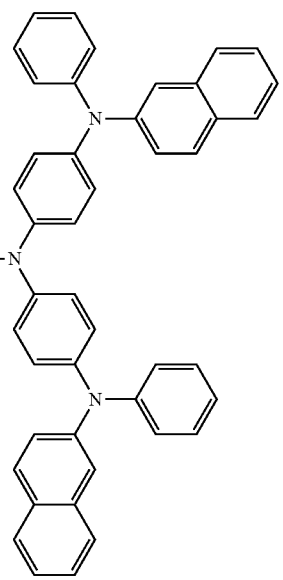

2-TNATA

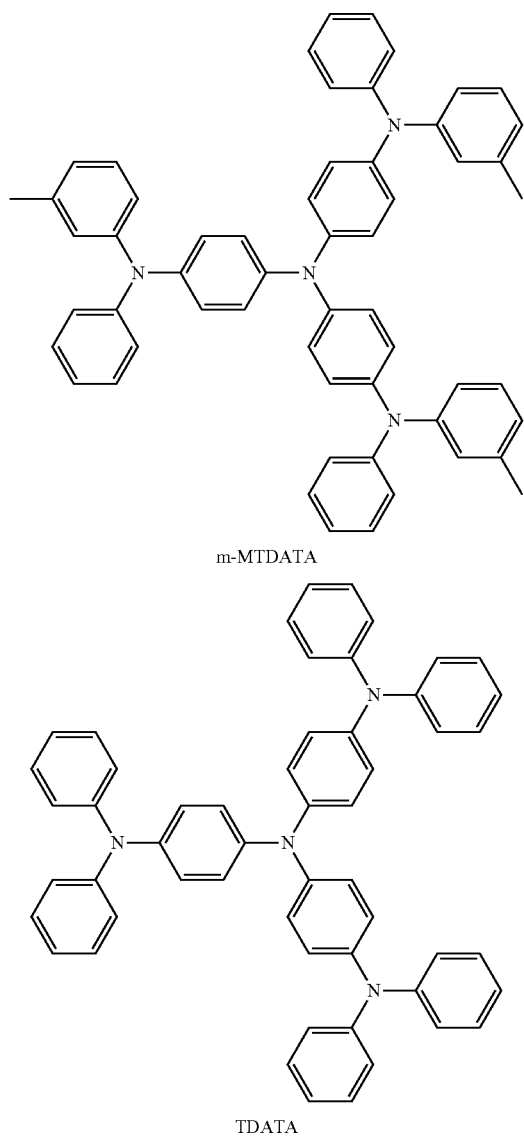

m-MTDATA

TDATA

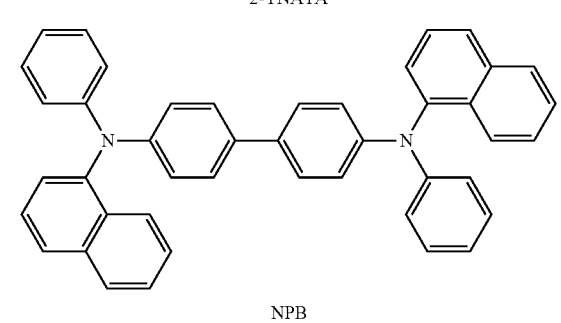

NPB

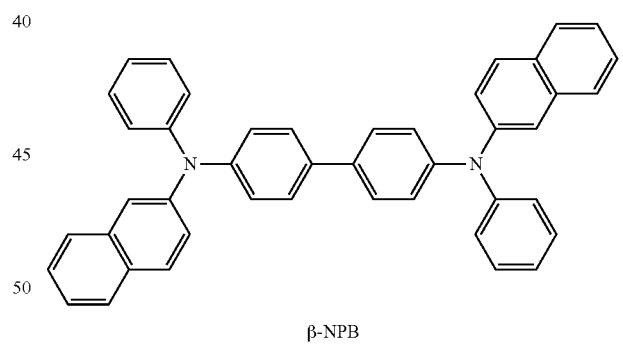

β-NPB

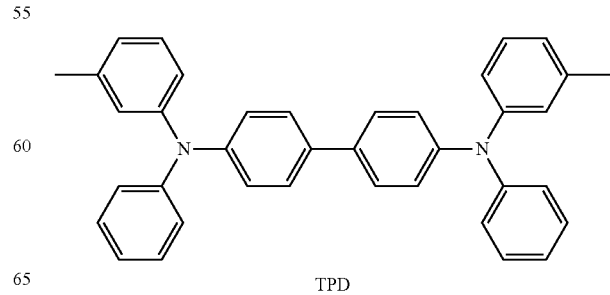

TPD

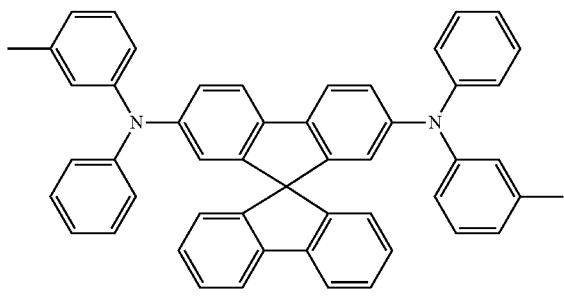
Spiro-TPD

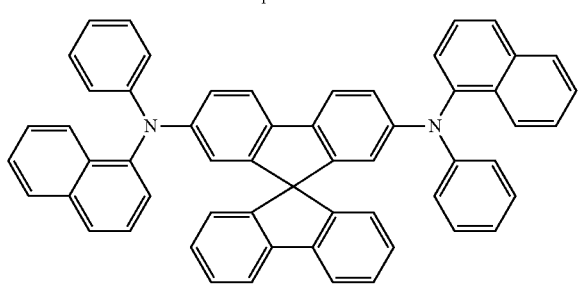
Spiro-NPB

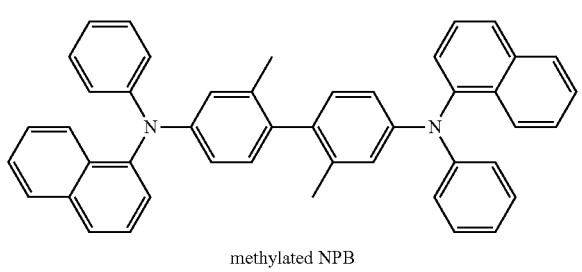
methylated NPB

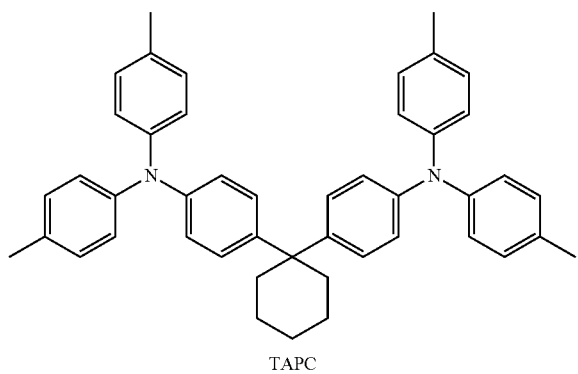
TAPC

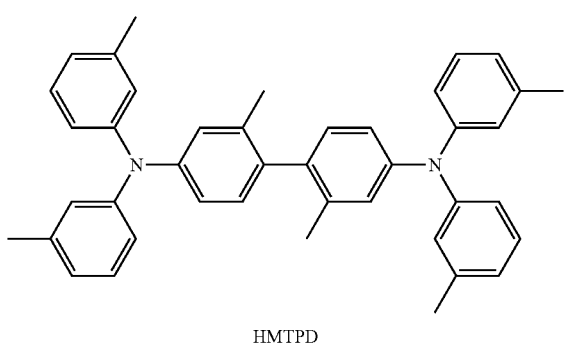
HMTPD

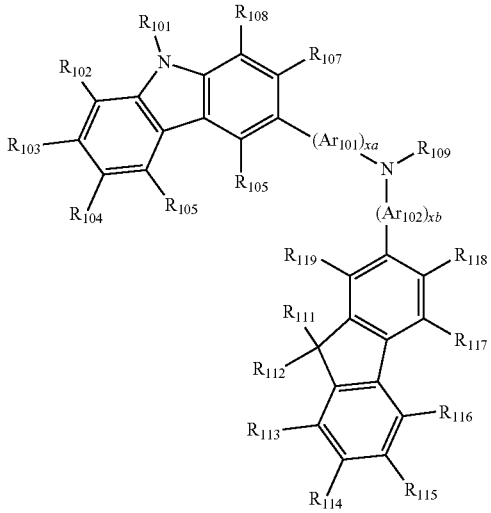
Formula 201

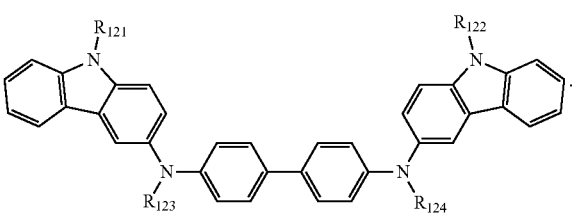
Formula 202

In Formula 201, $Ar_{101}$ and $Ar_{102}$ may each independently be selected from:

a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from deuterium, —F, —Cl, —Br, —I, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may each independently be an integer of 0 to 5, or 0, 1 or 2. For example, xa may be 1 and xb may be 0, but xa and xb are not limited thereto.

In Formulae 201 and 202, $R_{101}$ to $R_{108}$, $R_{111}$ to $R_{119}$, and $R_{121}$ to $R_{124}$ may each independently be selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (for example, a methyl group, an ethyl group, a propyl group, a butyl group, a pentyl group, and a hexyl group), and a $C_1$-$C_{10}$ alkoxy group (for example, a methoxy group, an ethoxy group, a propoxy group, a butoxy group, and a pentoxy group);

a $C_1$-$C_{10}$ alkyl group and a $C_1$-$C_{10}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, or a pyrenyl group; or a phenyl group, a naphthyl group, an anthracenyl group, a fluorenyl group, and a pyrenyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but embodiments of the present disclosure are not limited thereto.

In Formula 201, $R_{109}$ may be selected from:

a phenyl group, a naphthyl group, an anthracenyl group, and a pyridinyl group; and a phenyl group, a naphthyl group, an anthracenyl group, and a pyridinyl group, each substituted with at least one selected from=deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an anthracenyl group, and a pyridinyl group.

According to an embodiment, the compound represented by Formula 201 may be represented by Formula 201A below, but embodiments of the present disclosure are not limited thereto:

Formula 201A

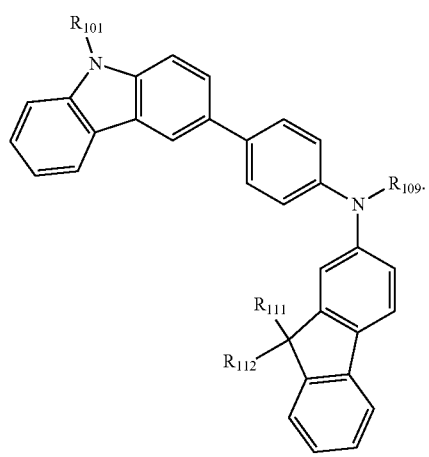

In Formula 201A, $R_{101}$, $R_{111}$, $R_{112}$, and $R_{109}$ may respectively be the same as described above.

For example, the compound represented by Formula 201, and the compound represented by Formula 202 may include compounds HT1 to HT20 illustrated below, but are not limited thereto:

HT1

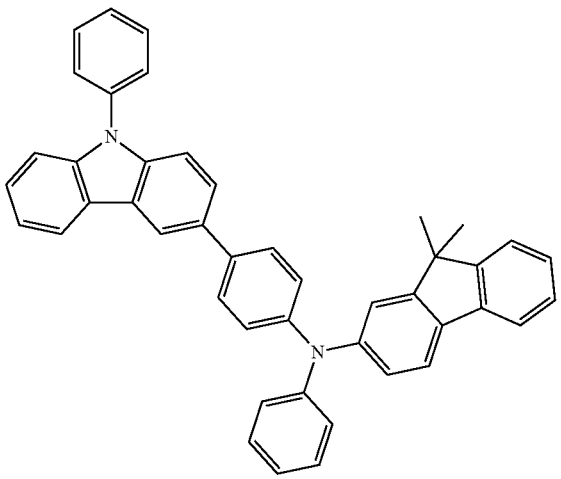

HT2

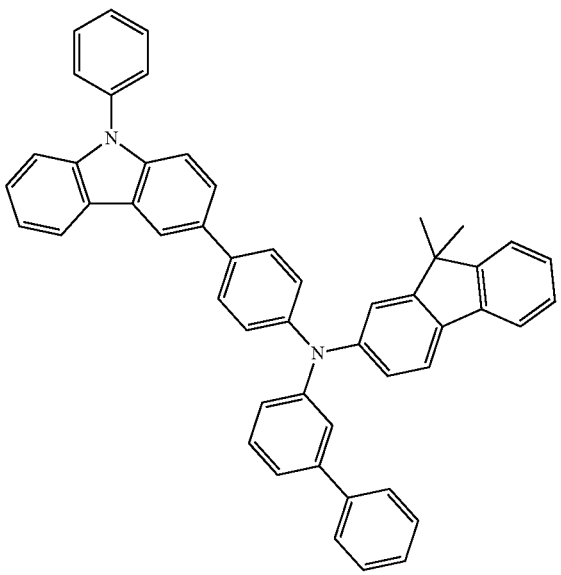

-continued
HT3
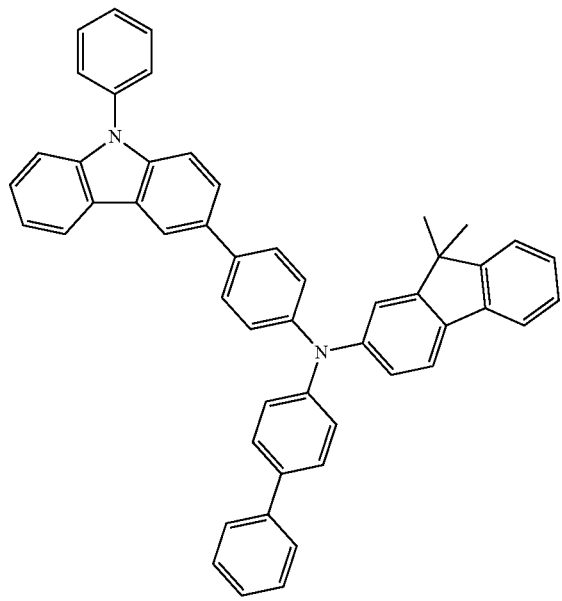
HT5
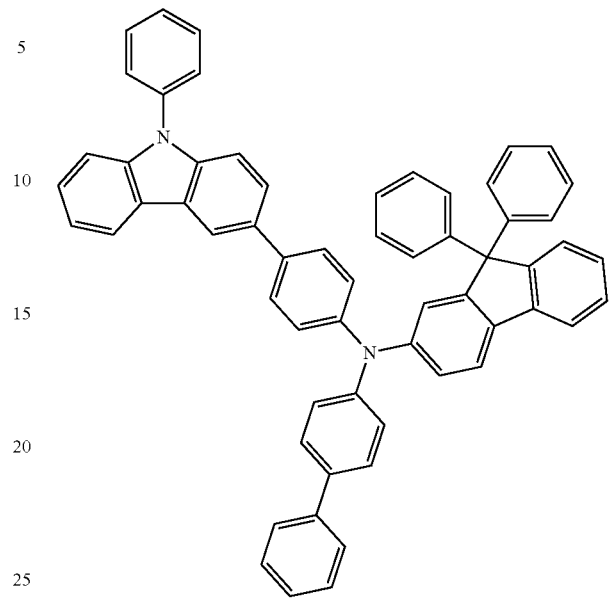
HT4
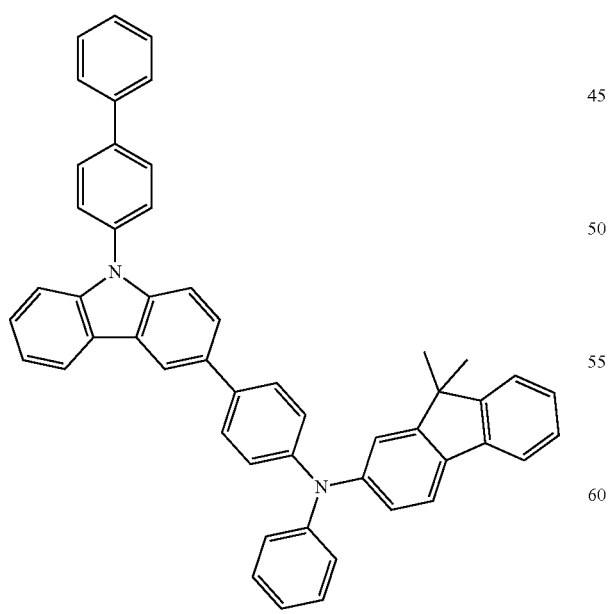
HT6

-continued
HT7
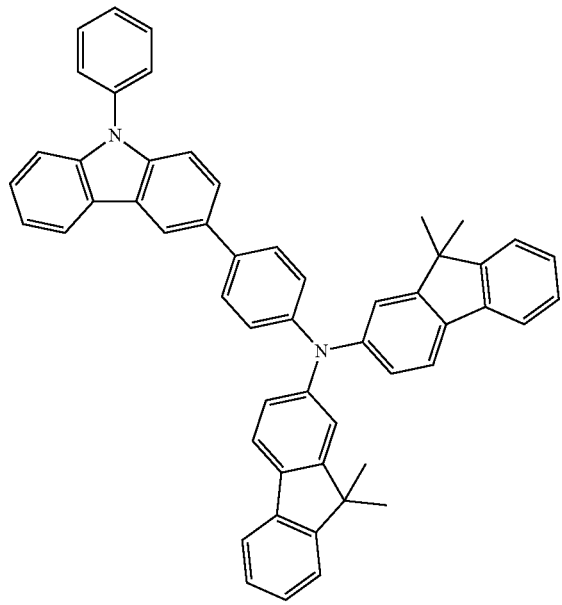
HT8
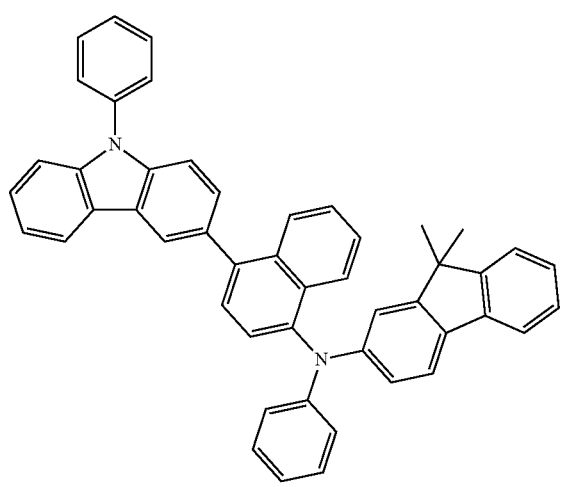
HT9
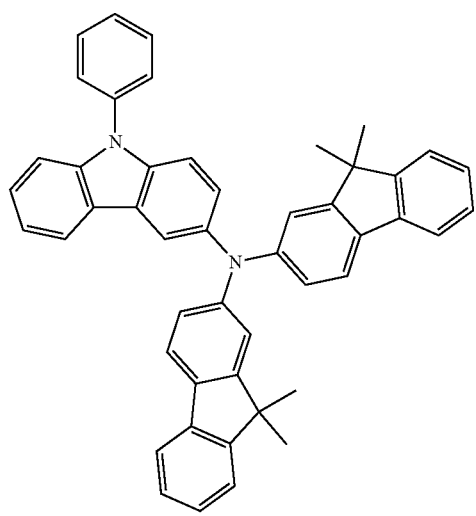
-continued
HT10
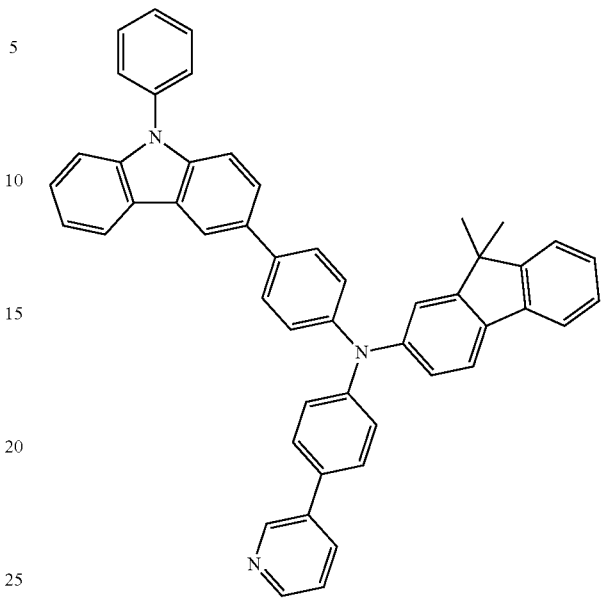
HT11
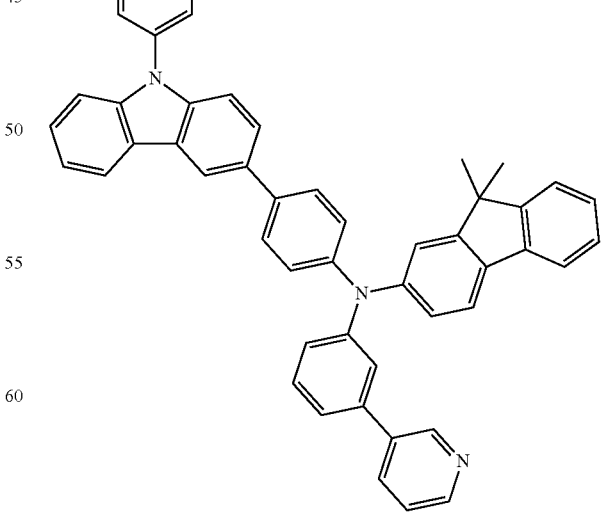

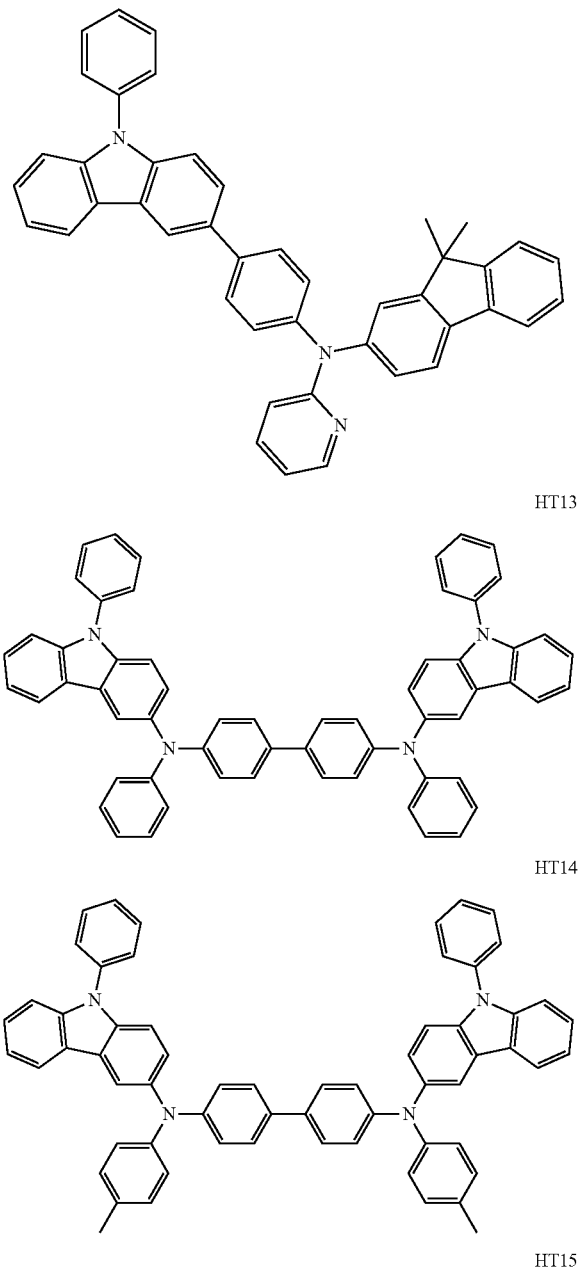
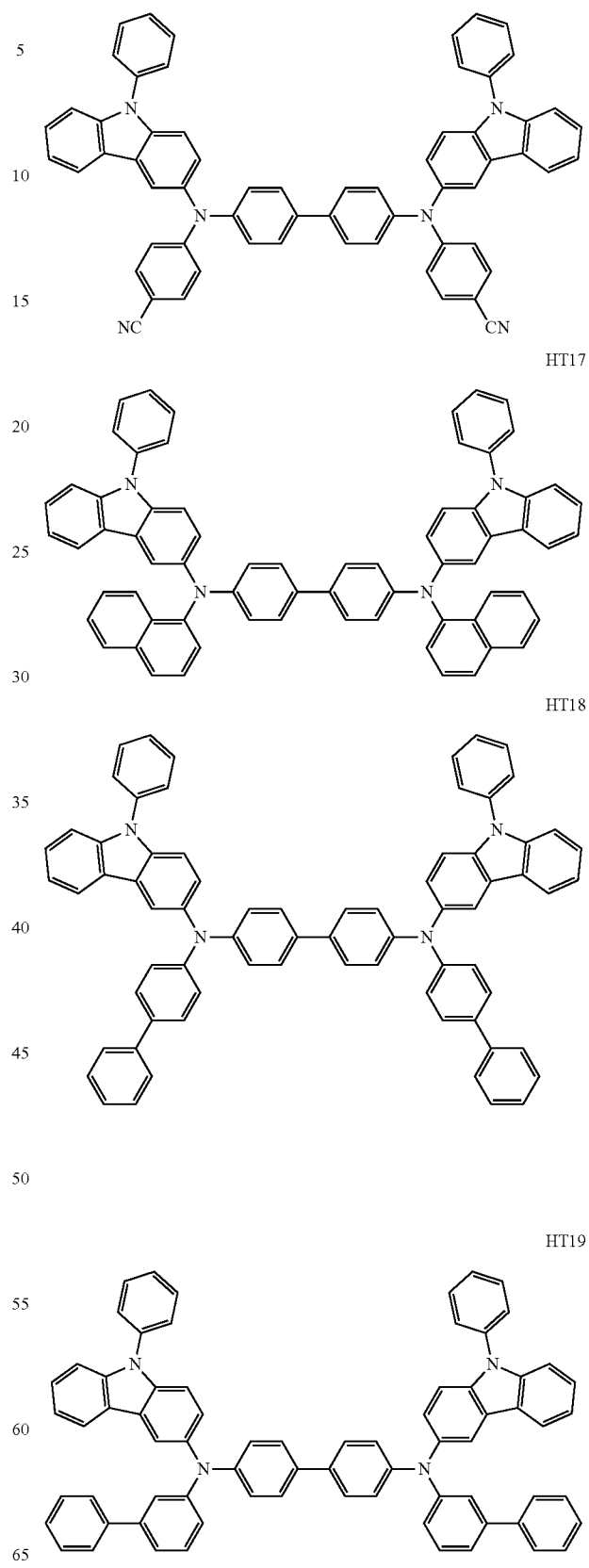

HT20

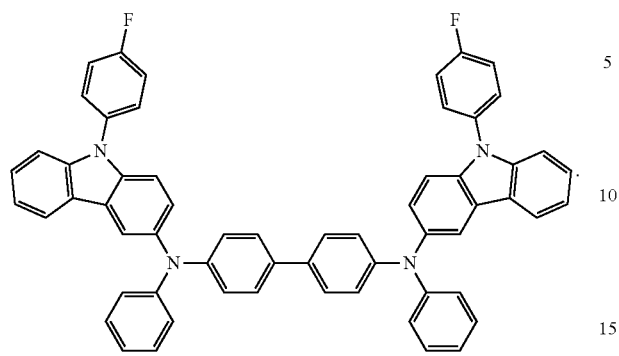

The hole transport layer may include the condensed cyclic compound represented by Formula 1.

A thickness of the hole transport region may be in a range of about 100 Angstroms (Å) to about 10,000 Å, for example, about 100 Å to about 1,000 Å. When the hole transport region includes at least one of a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example about 100 Å to about 1,500 Å. While not wishing to be bound by theory, it is understood that when the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or non-homogeneously dispersed in the hole transport region.

The charge-generation material may be, for example, a p-dopant. The p-dopant may be one selected from a quinone derivative, a metal oxide, and a cyano group-containing compound, but embodiments of the present disclosure are not limited thereto. Non-limiting examples of the p-dopant are a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 or HP-1, but are not limited thereto.

Compound HT-D1 F4-TCNQ

Compound HT-D1

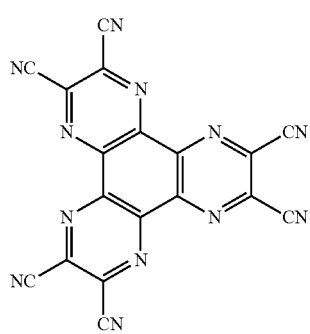

F4-TCNQ

HP-1

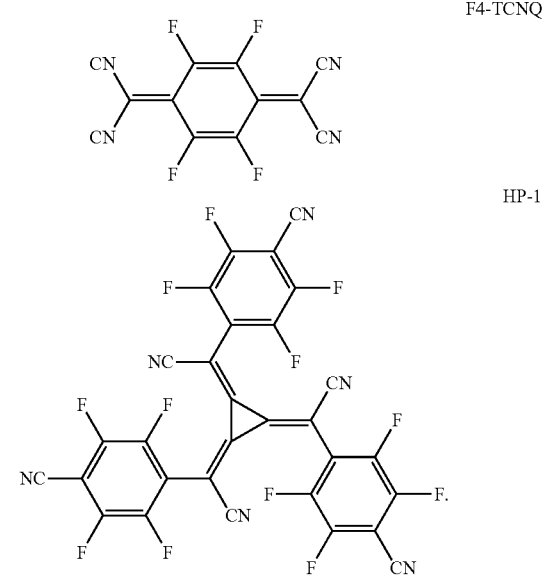

The hole transport region may include a buffer layer.

Also, the buffer layer may compensate for an optical resonance distance according to a wavelength of light emitted from the emission layer, and thus, efficiency of a formed organic light-emitting device may be improved.

Then, an emission layer may be formed on the hole transport region by vacuum deposition, spin coating, casting, LB deposition, or the like. When the emission layer is formed by vacuum deposition or spin coating, the deposition or coating conditions may be similar to those applied in forming the hole injection layer although the deposition or coating conditions may vary according to a material that is used to form the emission layer.

The electron transport region may further include an electron blocking layer. The electron blocking layer may include, for example, mCP, but a material therefor is not limited thereto:

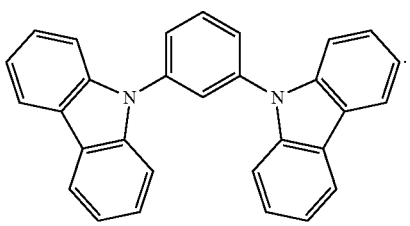

mCP

For example, the hole transport region may include the electron blocking layer, wherein the electron blocking layer includes the condensed cyclic compound represented by Formula 1.

A thickness of the electron blocking layer may be in a range of about 50 Å to about 1,000 Å, for example, about 70 Å to about 500 Å. While not wishing to be bound by theory, it is understood that when the thickness of the electron blocking layer is within the range described above, the electron blocking layer may have satisfactory electron blocking characteristics without a substantial increase in driving voltage.

When the organic light-emitting device is a full-color organic light-emitting device, the emission layer may be patterned into a red emission layer, a green emission layer, and a blue emission layer. In one or more embodiments, due to a stacked structure including a red emission layer, a green emission layer, and/or a blue emission layer, the emission layer may emit white light.

The emission layer may include the condensed cyclic compound represented by Formula 1. For example, the emission layer may include the compound represented by Formula 1 alone. In one or more embodiment, the emission layer may include a host and a dopant, and the host may include the condensed cyclic compound represented by Formula 1. In one or more embodiment, the emission layer may include a host and a dopant, and the dopant may include the condensed cyclic compound represented by Formula 1.

In one or more embodiment, the dopant in the emission layer may be a phosphorescent dopant, and the phosphorescent dopant may include an organometallic compound represented by Formula 81 below:

Formula 81

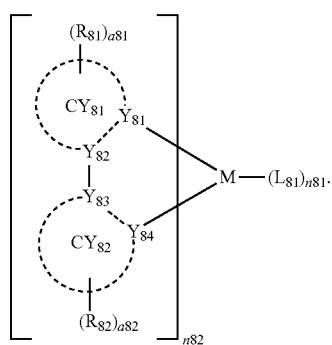

In Formula 81,

M may be selected from iridium (Ir), platinum (Pt), osmium (Os), titanium (Ti), zirconium (Zr), hafnium (Hf), europium (Eu), terbium (Tb), thulium (Tm), rhenium (Re), and rhodium (Rh), $Y_{81}$ to $Y_{84}$ may each independently be C or N, $Y_{81}$ and $Y_{82}$ may be linked each other via a single bond or a double bond, and $Y_{83}$ and $Y_{84}$ may be linked each other via a single bond or a double bond, $CY_{81}$ and $CY_{82}$ may each independently be selected from a benzene group, a naphthalene group, a fluorene group, a spiro-bifluorene group, an indene group, a pyrrole group, a thiophene group, a furan group, an imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, or a dibenzothiophene group, wherein $CY_{81}$ and $CY_{82}$ may optionally be further linked each other via an organic linking group, $R_{81}$ and $R_{82}$ may each independently be selected from hydrogen, deuterium, —F, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SFS, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_5$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), a81 and a82 may each independently be an integer of 1 to 5, n81 may be an integer of 0 to 4, n82 may be 1, 2, or 3, $L_{81}$ may be a monovalent, divalent, or trivalent organic ligand, $Q_1$ to $Q_7$ may respectively be the same as $Q_1$ to $Q_3$ of —Si($Q_1$)($Q_2$)($Q_3$) in Formula 1, and $R_{81}$ and $R_{82}$ may respectively be the same as described in connection with $R_{11}$.

The phosphorescent dopant may include at least one selected from Compounds PD1 to PD78 and $Fir_6$, but embodiments of the present disclosure are not limited thereto:

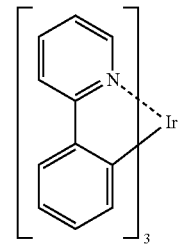

PD1

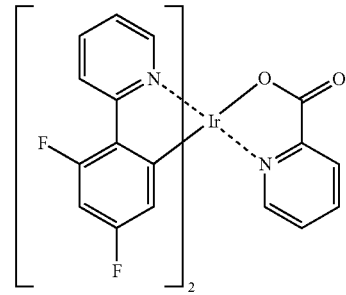

PD2

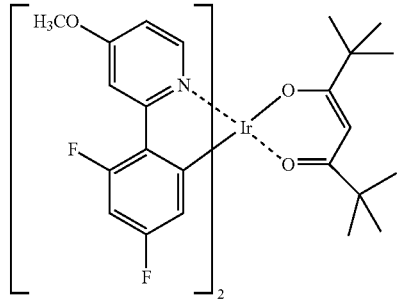

PD3

PD4
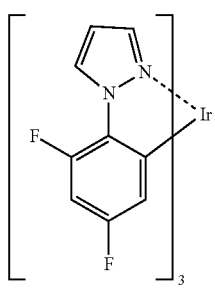
PD5
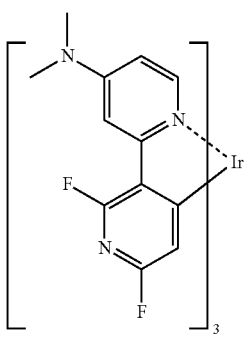
PD6
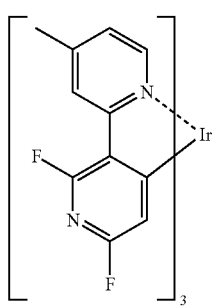
PD7
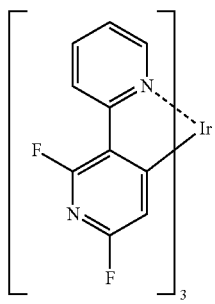
PD8
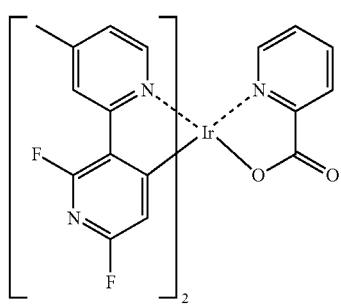
PD9
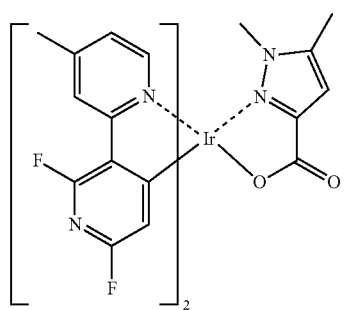
PD10
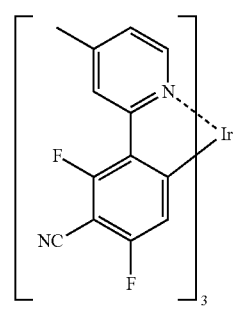
PD11
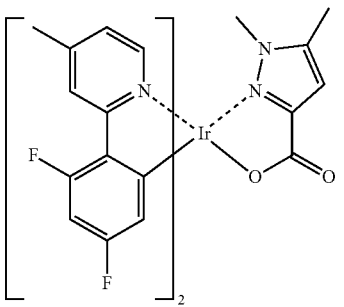
PD12
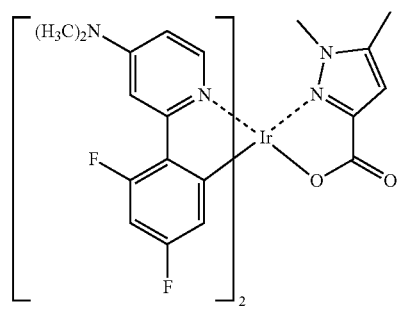
PD13
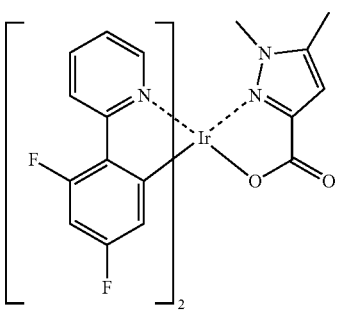

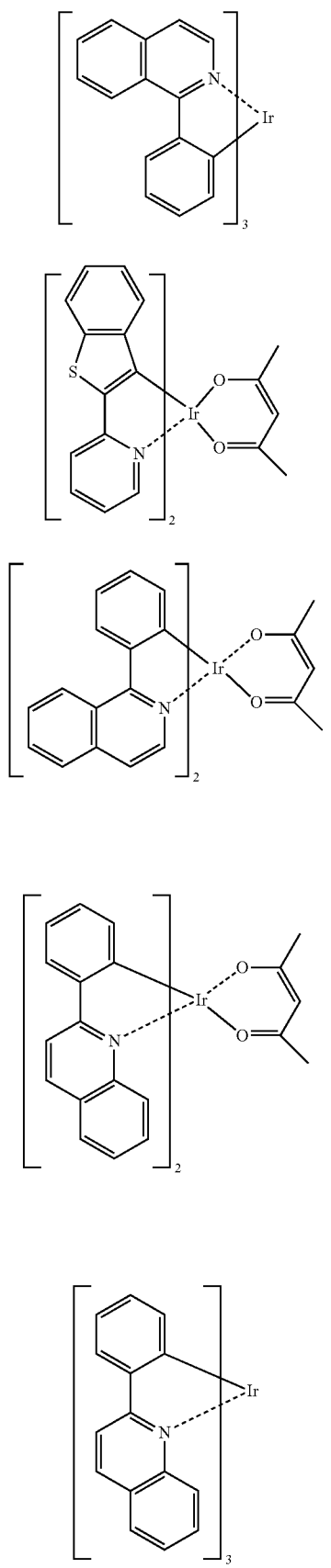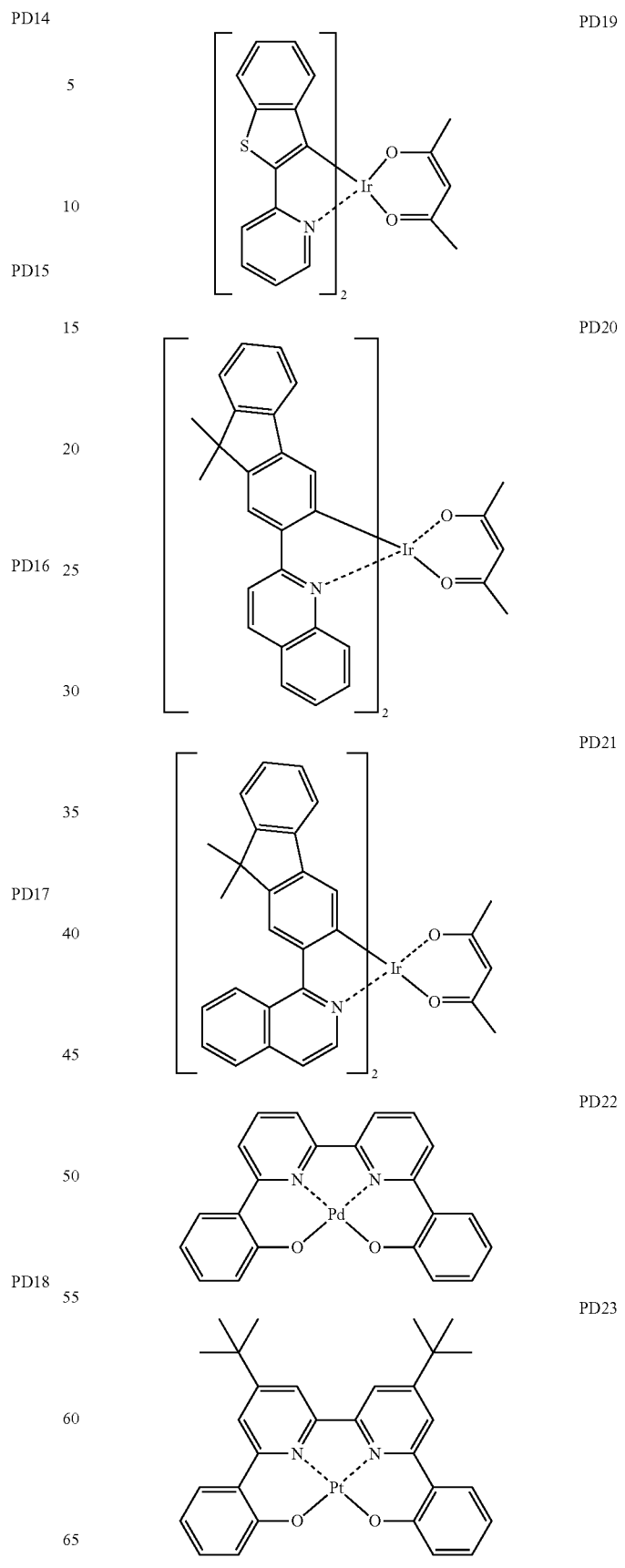

-continued
PD24
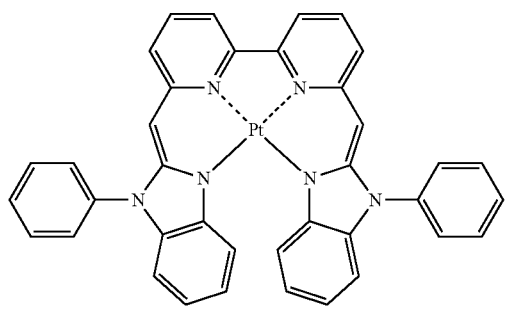
PD25
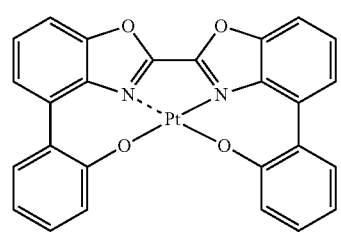
PD26
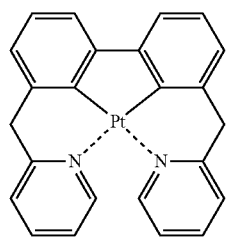
PD27
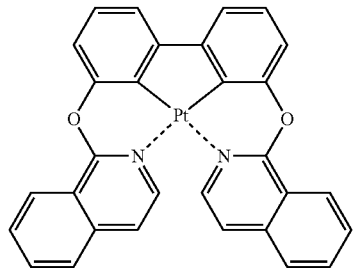
PD28
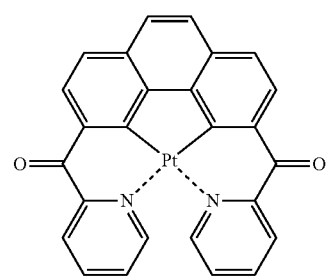
PD29
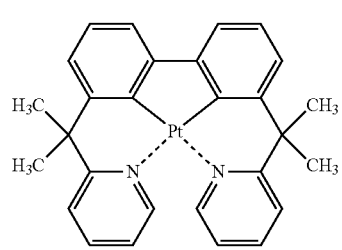
-continued
PD30
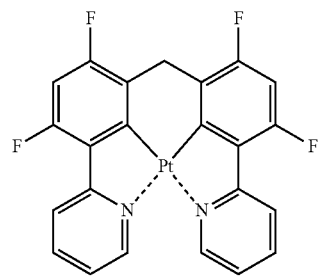
PD31
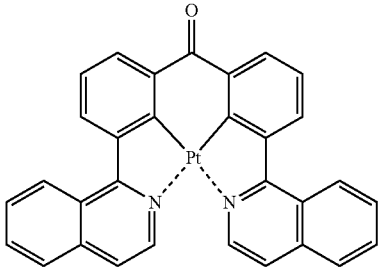
PD32
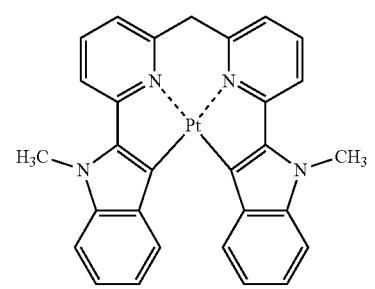
PD33
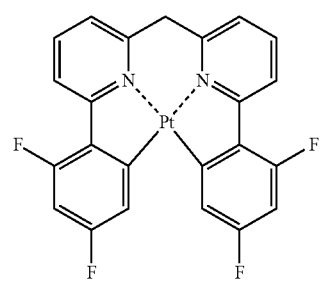
PD34
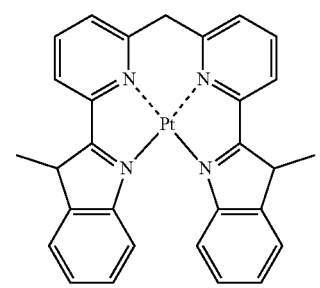

-continued
PD35
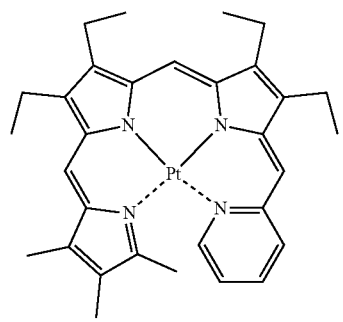
PD36
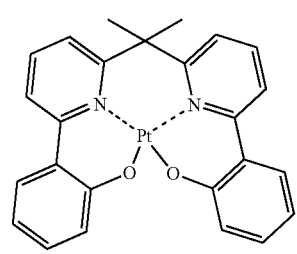
PD37
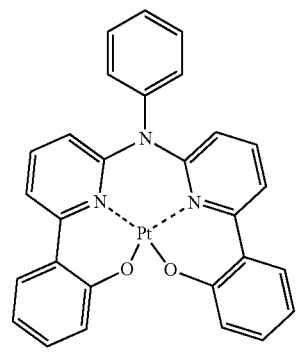
PD38
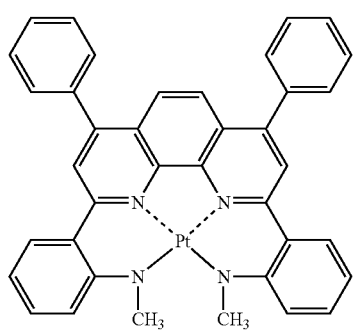
PD39
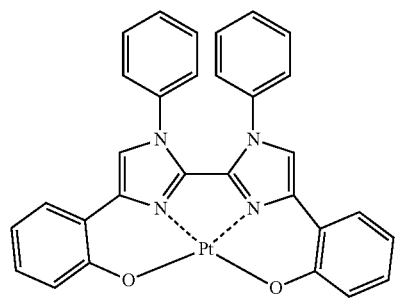
-continued
PD40
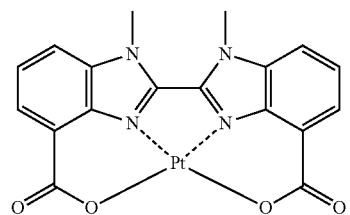
PD41
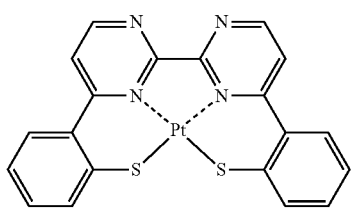
PD42
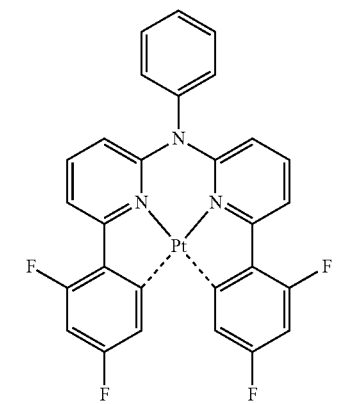
PD43
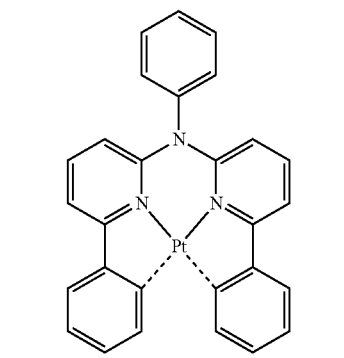
PD44
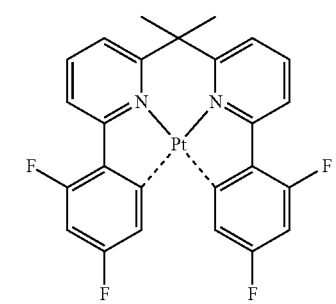

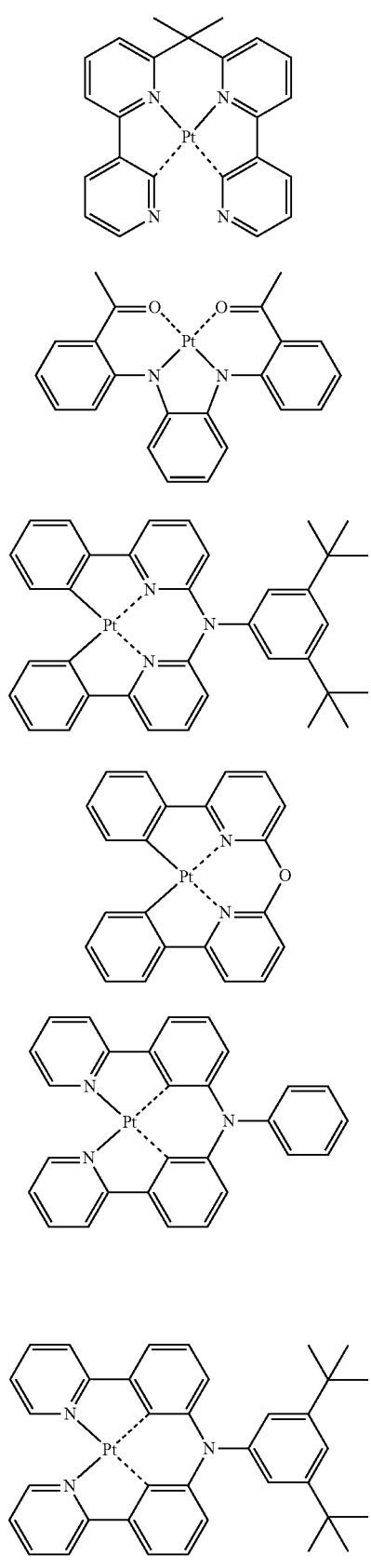
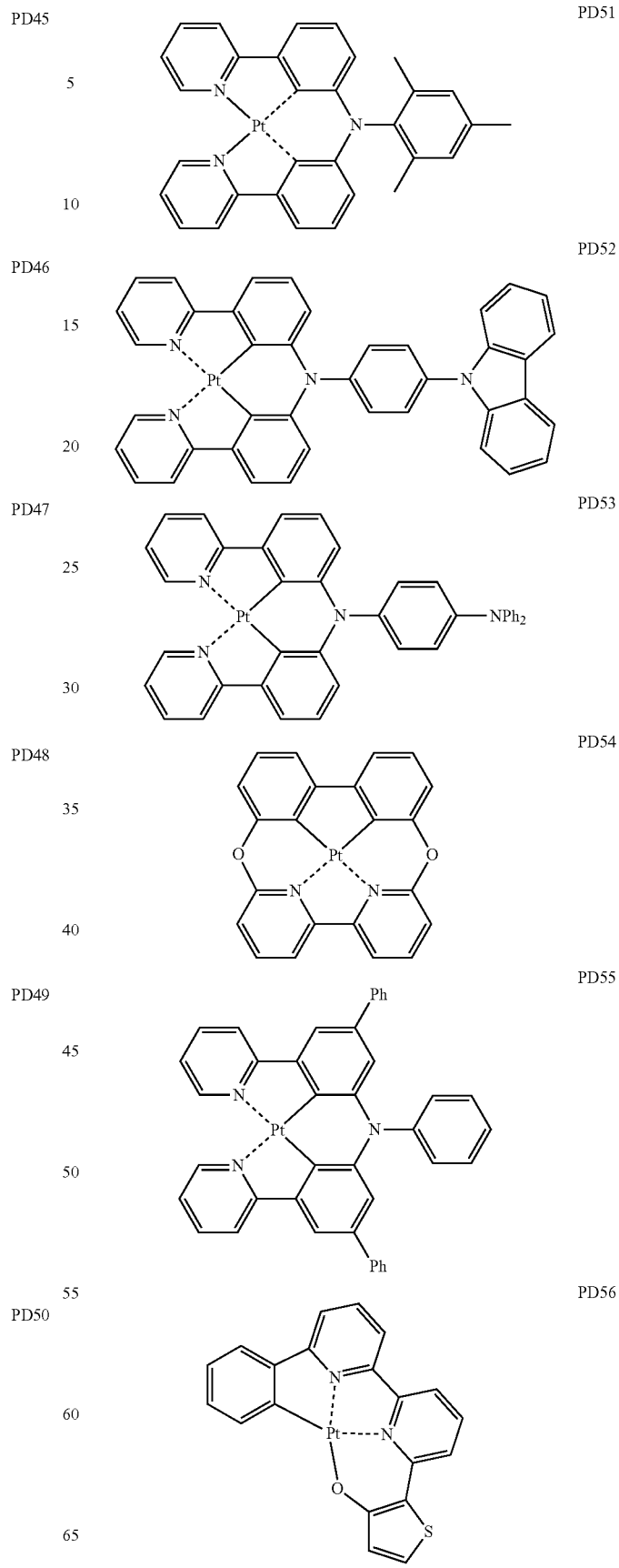

PD57
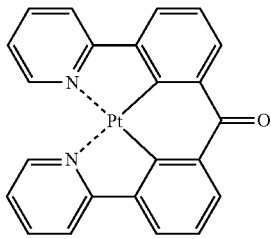
PD58
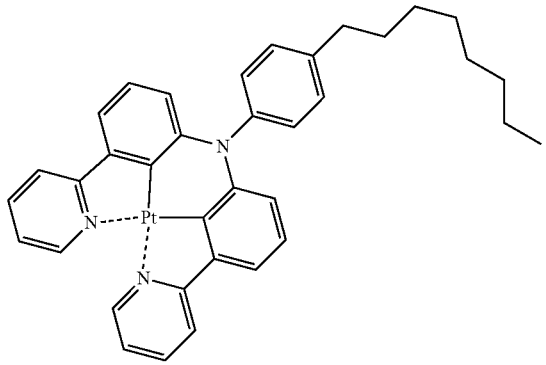
PD59
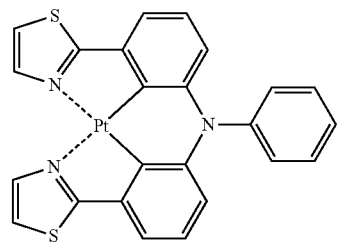
PD60
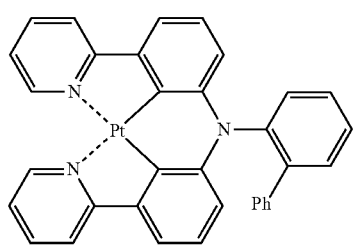
PD61
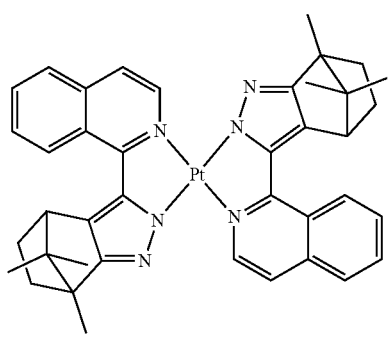
PD62
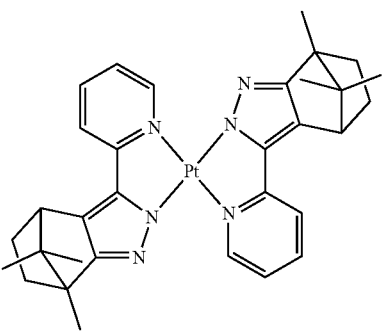
PD63
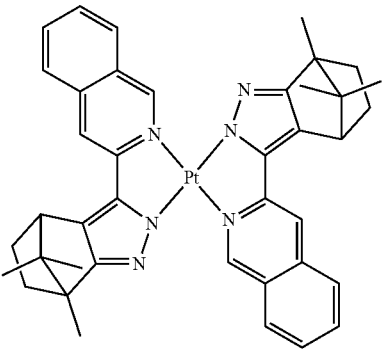
PD64
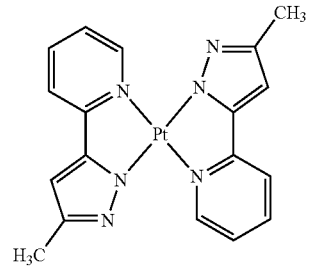
PD65
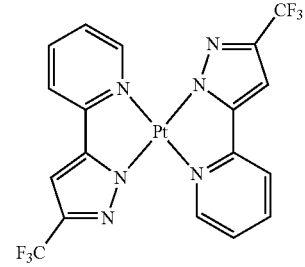
PD66
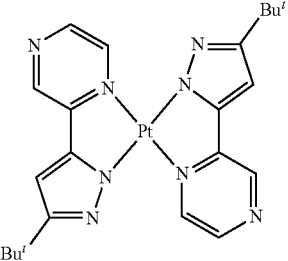

PD67
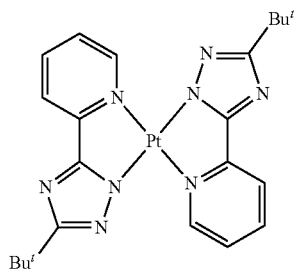
PD68
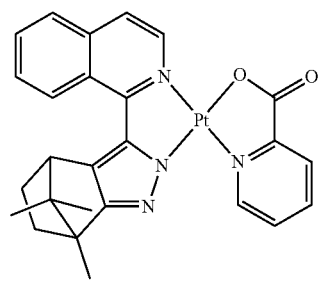
PD69
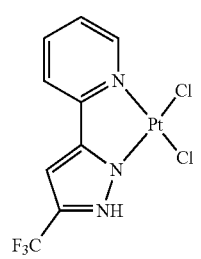
PD70
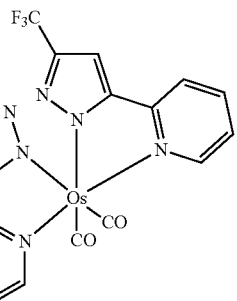
PD71
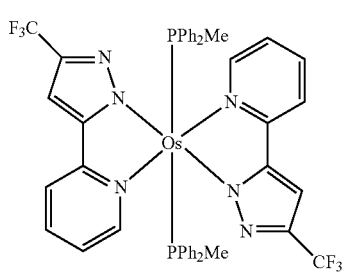
PD72
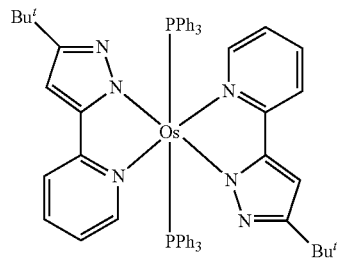
PD73
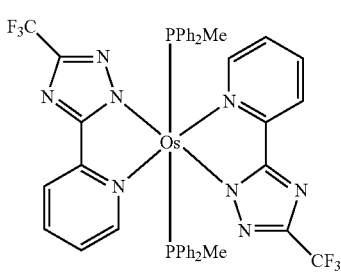
PD74
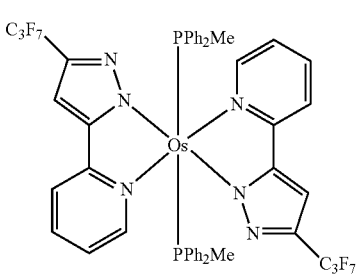
PD75
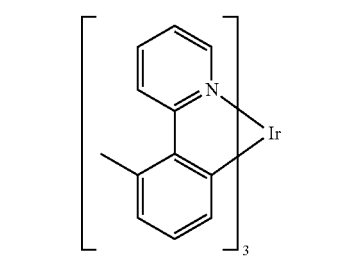
PD76
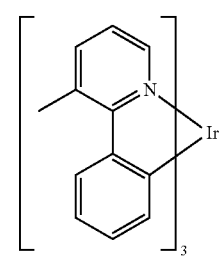
PD77
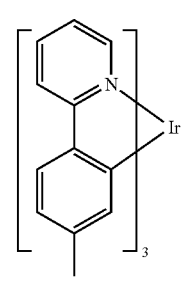

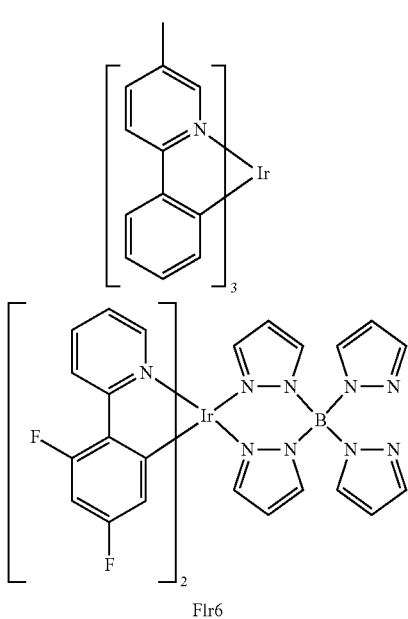

Flr6

In one or more embodiments, the phosphorescent dopant may include PtOEP:

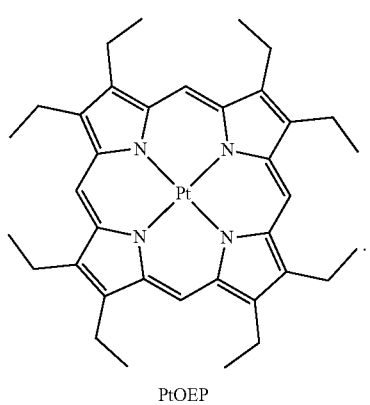

PtOEP

When the emission layer includes a host and a dopant, an amount of the dopant may be in a range of about 0.01 parts by weight to about 20 parts by weight based on 100 parts by weight of the host, but embodiments of the present disclosure are not limited thereto.

A thickness of the emission layer may be in a range of about 100 Å to about 1,000 Å, for example, about 200 Å to about 600 Å. While not wishing to be bound by theory, it is understood that when the thickness of the emission layer is within this range, excellent light-emission characteristics may be obtained without a substantial increase in driving voltage.

Then, an electron, transport region may be disposed on the emission layer.

The electron transport region may include at least one selected from a hole blocking layer, an electron transport layer, and an electron injection layer.

For example, the electron transport region may have a hole blocking layer/electron transport layer/electron injection layer structure or an electron transport layer/electron injection layer structure, but the structure of the electron transport region is not limited thereto. The electron transport layer may have a single-layered structure or a multi-layered structure including two or more different materials.

Conditions for forming the hole blocking layer, the electron transport layer, and the electron injection layer which constitute the electron transport region may be understood by referring to the conditions for forming the hole injection layer.

When the electron transport region includes a hole blocking layer, the hole blocking layer may include, for example, at least one of BCP and Bphen, but may also include other materials.

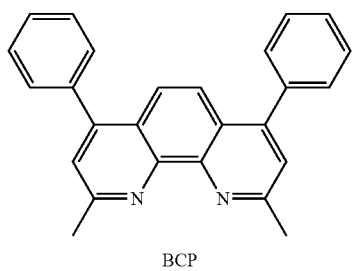

BCP

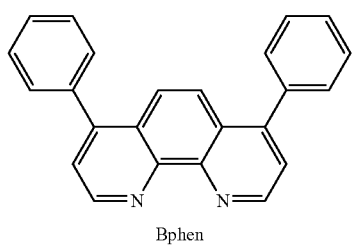

Bphen

A thickness of the hole blocking layer may be in a range of about 20 Å to about 1,000 Å, for example, about 30 Å to about 300 Å. While not wishing to be bound by theory, it is understood that when the thickness of the hole blocking layer is within these ranges, the hole blocking layer may have excellent hole blocking characteristics without a substantial increase in driving voltage.

The electron transport layer may further include at least one selected from BCP, Bphen, $Alq_3$, BAlq, TAZ, and NTAZ.

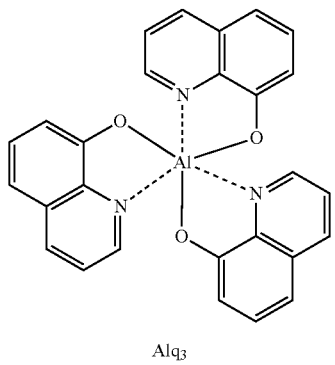

$Alq_3$

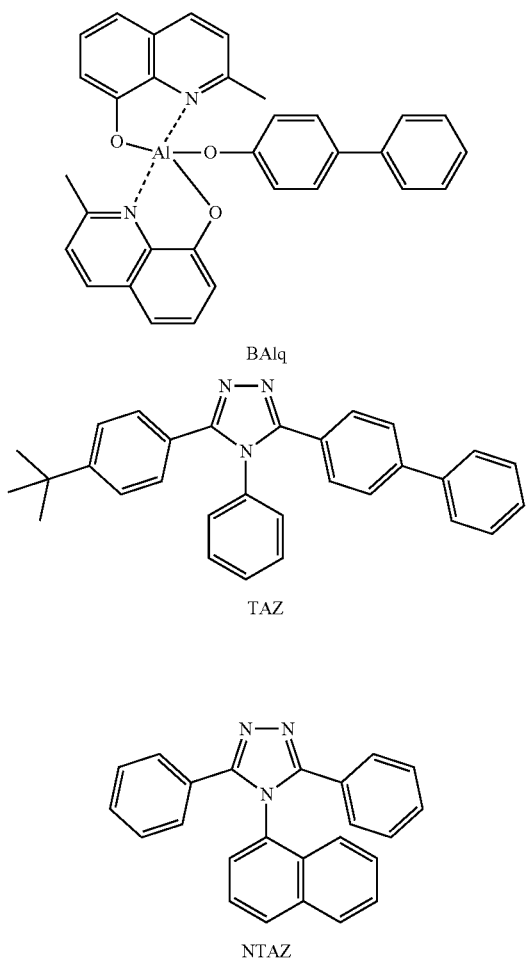

BAlq

TAZ

NTAZ

In one or more embodiments, the electron transport layer may include at least one selected from Compounds ET1, ET2, and ET3, but embodiments of the present disclosure are not limited thereto:

ET1

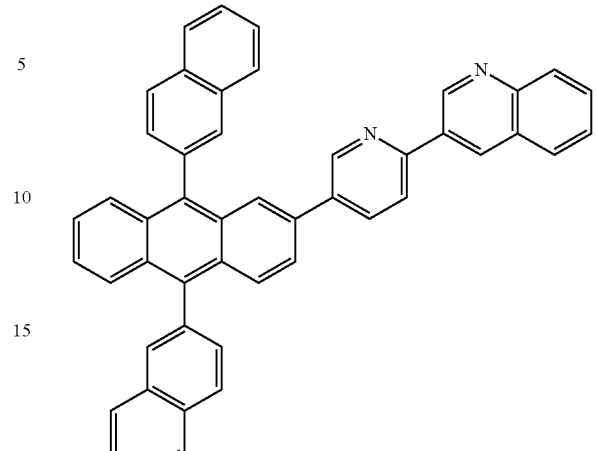

ET2

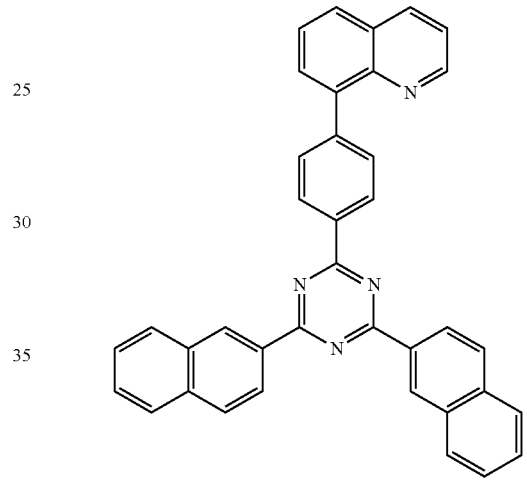

ET3

A thickness of the electron transport layer may be in a range of about 100 Å to about 1,000 Å, for example, about 150 Å to about 500 Å. While not wishing to be bound by theory, it is understood that when the thickness of the electron transport layer is within the range described above, the electron transport layer may have satisfactory electron transport characteristics without a substantial increase in driving voltage.

Also, the electron transport layer may further include, in addition to the materials described above, a metal-containing material.

The metal-containing material may include a $L_1$ complex. The $L_1$ complex may include, for example, Compound ET-D1 (lithium 8-hydroxyquinolate, LiQ) or ET-D2.

ET-D1

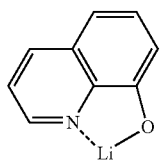

ET-D2

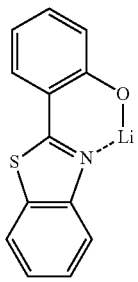

The electron transport region may include an electron injection layer (EIL) that promotes flow of electrons from the second electrode 19 thereinto.

The electron injection layer may include at least one selected from LiQ, LiF, NaCl, CsF, $Li_2O$, and BaO.

A thickness of the electron injection layer may be in a range of about 1 Å to about 100 Å, for example, about 3 Å to about 90 Å. While not wishing to be bound by theory, it is understood that when the thickness of the electron injection layer is within the range described above, the electron injection layer may have satisfactory electron injection characteristics without a substantial increase in driving voltage.

The second electrode 19 is disposed on the organic layer 15. The second electrode 19 may be a cathode. A material for forming the second electrode 19 may be metal, an alloy, an electrically conductive compound, or a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be formed as the material for forming the second electrode 19. To manufacture a top-emission type light-emitting device, a transmissive electrode formed using ITO or IZO may be used as the second electrode 19.

In an embodiment, the organic layer 15 of the organic light-emitting device 10 may include a hole transport region and an emission layer, and the hole transport region and the emission layer may each include the condensed cyclic compound represented by Formula 1. Here, the condensed cyclic compound represented by Formula 1 included in the hole transport region may be identical to the condensed cyclic compound represented by Formula 1 included in the emission layer.

In one or more embodiments, the organic layer 15 of the organic light-emitting device 10 may include a hole transport region and an emission layer, and the hole transport region and the emission layer may each include the condensed cyclic compound represented by Formula 1. Here, the condensed cyclic compound represented by Formula 1 included in the hole transport region may be different from the condensed cyclic compound represented by Formula 1 included in the emission layer.

Here, the hole transport region may include at least one selected from a hole transport layer and an electron blocking layer, and the condensed cyclic compound represented by Formula 1 may be included: i) in the hole transport layer, ii) in the electron blocking layer, or iii) in both the hole transport layer and the electron blocking layer. The electron blocking layer may directly contact the emission layer.

Hereinbefore, the organic light-emitting device has been described with reference to the FIGURE, but embodiments of the present disclosure are not limited thereto.

The term "$C_1$-$C_{60}$ alkyl group" as used herein refers to a linear or branched aliphatic saturated hydrocarbon monovalent group having 1 to 60 carbon atoms, and examples thereof include a methyl group, an ethyl group, a propyl group, an iso-butyl group, a sec-butyl group, a tert-butyl group, a pentyl group, an iso-amyl group, and a hexyl group. The term "$C_1$-$C_{60}$ alkylene group" as used herein refers to a divalent group having the same structure as the $C_1$-$C_{60}$ alkyl group.

The term "$C_1$-$C_{60}$ alkoxy group" as used herein refers to a monovalent group represented by—$OA_{101}$ (wherein $A_{101}$ is the $C_1$-$C_{60}$ alkyl group), and examples thereof include a methoxy group, an ethoxy group, and an iso-propyloxy group.

The term "$C_2$-$C_{60}$ alkenyl group" as used herein refers to a hydrocarbon group having at least one carbon-carbon double bond in the middle or at the terminus of the $C_2$-$C_{60}$ alkyl group, and examples thereof include an ethenyl group, a propenyl group, and a butenyl group. The term "$C_2$-$C_{60}$ alkenylene group" as used herein refers to a divalent group having the same structure as the $C_2$-$C_{60}$ alkenyl group.

The term "$C_2$-$C_{60}$ alkynyl group" as used herein refers to a hydrocarbon group having at least one carbon-carbon triple bond in the middle or at the terminus of the $C_2$-$C_{60}$ alkyl group, and examples thereof include an ethynyl group, and a propynyl group. The term "$C_2$-$C_{60}$ alkynylene group" as used herein refers to a divalent group having the same structure as the $C_2$-$C_{60}$ alkynyl group.

The term "$C_3$-$C_{10}$ cycloalkyl group" as used herein refers to a monovalent saturated hydrocarbon monocyclic group having 3 to 10 carbon atoms, and non-limiting examples thereof include a cyclopropyl group, a cyclobutyl group, a cyclopentyl group, a cyclohexyl group, and a cycloheptyl group. The term "$C_3$-$C_{10}$ cycloalkylene group" as used herein refers to a divalent group having the same structure as the $C_3$-$C_{10}$ cycloalkyl group.

The term "$C_1$-$C_{10}$ heterocycloalkyl group" as used herein refers to a monovalent saturated monocyclic group having at least one heteroatom selected from N, O, P, Si and S as a ring-forming atom and 1 to 10 carbon atoms, and non-limiting examples thereof include a tetrahydrofuranyl group, and a tetrahydrothiophenyl group. The term "$C_1$-$C_{10}$ heterocycloalkylene group" as used herein refers to a divalent group having the same structure as the $C_1$-$C_{10}$ heterocycloalkyl group.

The term "$C_3$-$C_{10}$ cycloalkenyl group" as used herein refers to a monovalent monocyclic group that has 3 to 10 carbon atoms and at least one carbon-carbon double bond in the ring thereof and no aromaticity, and non-limiting examples thereof include a cyclopentenyl group, a cyclohexenyl group, and a cycloheptenyl group. The term "$C_3$-$C_{10}$ cycloalkenylene group" as used herein refers to a divalent group having the same structure as the $C_3$-$C_{10}$ cycloalkenyl group.

The term "$C_1$-$C_{10}$ heterocycloalkenyl group" as used herein refers to a monovalent monocyclic group that has at least one heteroatom selected from N, O, P, Si, and S as a ring-forming atom, 1 to 10 carbon atoms, and at least one carbon-carbon double bond in its ring. Non-limiting examples of the $C_2$-$C_{10}$ heterocycloalkenyl group include a 2,3-dihydrofuranyl group, and a 2,3-dihydrothiophenyl group. The term "$C_1$-$C_{10}$ heterocycloalkenylene group" as used herein refers to a divalent group having the same structure as the $C_1$-$C_{10}$ heterocycloalkenyl group.

The term "$C_6$-$C_{60}$ aryl group" as used herein refers to a monovalent group having a carbocyclic aromatic system having 6 to 60 carbon atoms, and the term "$C_6$-$C_{60}$ arylene group" as used herein refers to a divalent group having a carbocyclic aromatic system having 6 to 60 carbon atoms. Non-limiting examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

The term "$C_1$-$C_{60}$ heteroaryl group" as used herein refers to a monovalent group having a heterocyclic aromatic system that has at least one heteroatom selected from N, O, P, and S as a ring-forming atom, and 1 to 60 carbon atoms. The term $C_1$-$C_{60}$ heteroarylene group" as used herein refers to a divalent group having a heterocyclic aromatic system that has at least one heteroatom selected from N, O, P, and S as a ring-forming atom, and 1 to 60 carbon atoms. Non-limiting examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

The term "$C_6$-$C_{60}$ aryloxy group" as used herein refers to —$OA_{102}$ (wherein $A_{102}$ is the $C_6$-$C_{60}$ aryl group), and a $C_6$-$C_{60}$ arylthio group as used herein indicates—$SA_{103}$ (wherein $A_{103}$ is the $C_6$-$C_{60}$ aryl group).

The term "monovalent non-aromatic condensed polycyclic group" as used herein refers to a monovalent group having two or more rings condensed to each other, only carbon atoms (for example, the number of carbon atoms may be in a range of 8 to 60) as a ring-forming atom, and no aromaticity in its entire molecular structure. Non-limiting examples of the monovalent non-aromatic condensed polycyclic group include a fluorenyl group. The term "divalent non-aromatic condensed polycyclic group" as used herein refers to a divalent group having the same structure as the monovalent non-aromatic condensed polycyclic group.

The term "monovalent non-aromatic condensed heteropolycyclic group" as used herein refers to a monovalent group having two or more rings condensed to each other, a heteroatom selected from N, O, P, Si, and S, other than carbon atoms (for example, the number of carbon atoms may be in a range of 2 to 60), as a ring-forming atom, and no aromaticity in its entire molecular structure. Non-limiting examples of the monovalent non-aromatic condensed heteropolycyclic group include a carbazolyl group. The term "divalent non-aromatic condensed heteropolycyclic group" as used herein refers to a divalent group having the same structure as the monovalent non-aromatic condensed heteropolycyclic group.

In Formula 1, at least one substituent of the substituted $C_1$-$C_{60}$ alkyl group, the substituted $C_2$-$C_{60}$ alkenyl group, the substituted $C_2$-$C_{60}$ alkynyl group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from:

deuterium, —$CD_3$, —$CD_2H$, —$CDH_2$, a hydroxyl group, a cyano group, a nitro group, an amino group, an am idino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —$CD_3$, —$CD_2H$, —$CDH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{11})(Q_{12})(Q_{13})$, —$N(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —$CD_3$, —$CD_2H$, —$CDH_2$, a hydroxyl group, a cyano group, a nitro group, an amino group, an amidino group, a hydrazine, group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_6$° alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$Si(Q_{21})(Q_{22})(Q_{23})$, —$N(Q_{24})(Q_{25})$, and —$B(Q_{26})(Q_{27})$; and —$Si(Q_{31})(Q_{32})(Q_{33})$, —$N(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may each independently be selected from hydrogen, deuterium, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

The term "biphenyl group" refers to a monovalent group in which two benzene groups are linked via a single bond.

The term "terphenyl group" refers to a monovalent group in which two benzene groups are linked via a single bond.

Hereinafter, a compound and an organic light-emitting device according to embodiments are described in detail with reference to Synthesis Example and Examples. However, the organic light-emitting device is not limited thereto. The wording "'B' was used instead of 'A'" used in describing Synthesis Examples means that a molar equivalent of 'A' was identical to a molar equivalent of 'B'.

EXAMPLES

Synthesis Example 1: Synthesis of Compound 258

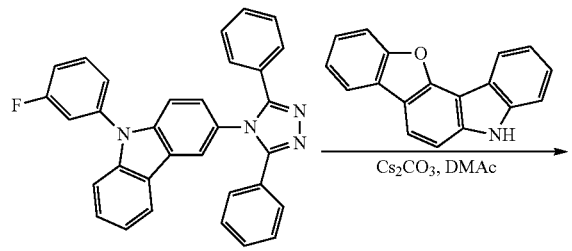

258

10.04 grams (g) (20.90 millimoles, mmol) of 3-(3,5-diphenyl-4H-1,2,4-triazol-4-yl)-9-(3-fluorophenyl)-9H-carbazole, 6.45 g (25.08 mmol) of 5H-benzofuro[3,2-c]carbazole, and 13.62 g (41.79 mmol) of caesium carbonate were dissolved in 52 milliliters (mL) of dimethylacetamide and stirred for 24 hours under reflux. After the reaction was completed, the reaction product was cooled to room temperature and added to a solution in which methanol and water were mixed at a ratio of 1:1. The mixture was precipitated, filtered, and dried. The product obtained therefrom was separated by silica gel column chromatography and recrystallized in a dichloromethane/n-hexane condition to obtain 6.40 g (yield of 43%) of Compound 258.

LC-Mass (Calcd: 717.25 g/mol, Found: M+1=718 g/mol)

Synthesis Example 2: Synthesis of Compound 327

1) Synthesis of Intermediate (A)

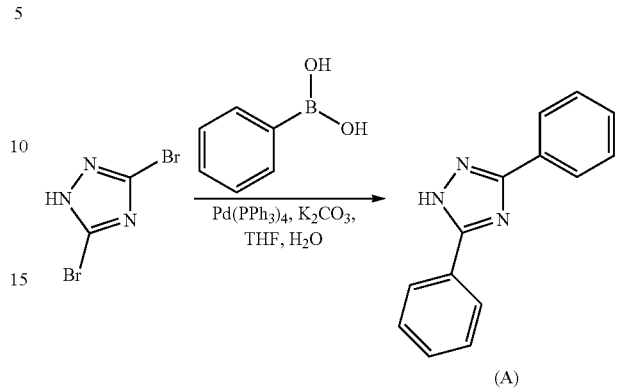

(A)

15.38 g (67.79 mmol) of 3,5-dibromo-1H-1,2,4-triazole, 24.80 g (203.38 mmol) of phenylboronic acid, 7.83 g (6.78 mmol) of tetrakis(triphenylphosphine)palladium(0), and 18.74 g (135.59 mmol) of potassium carbonate were added to a mixed solution including 170 mL of tetrahydrofuran and 70 mL of water and stirred under reflux. After the reaction was completed, the reaction product was cooled to room temperature, and an aqueous solution layer was removed therefrom by extraction. The resultant was filtered under reduced pressure through silica gel, and the filtrate was concentrated under reduced pressure. The product obtained therefrom was separated by silica gel column chromatography to obtain 9.20 g (yield of 61%) of Intermediate (A).

LC-Mass (Calcd: 221.10 g/mol, Found: M+1=222 g/mol)

2) Synthesis of Intermediate (B)

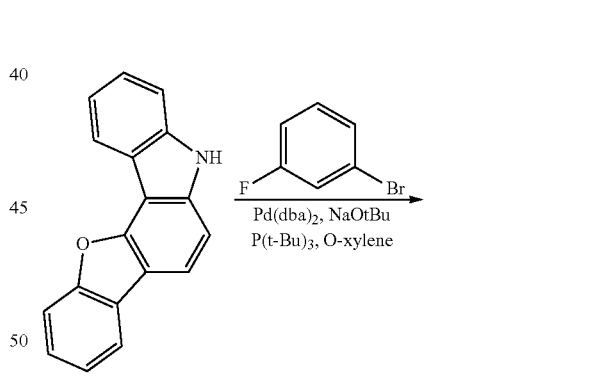

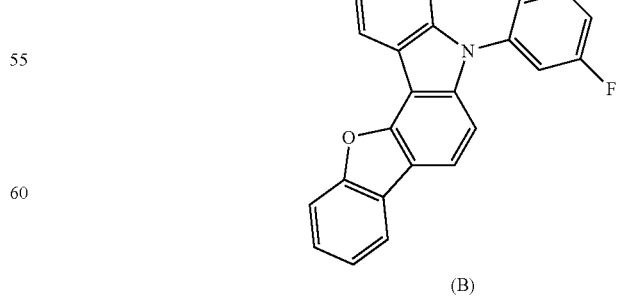

(B)

26.36 g (102.46 mmol) of 5H-benzofuro[3,2-c]carbazole, 23.31 g (133.19 mmol) of 1-bromo-3-fluorobenzene, 5.89 g (10.25 mmol) of bis(dibenzylideneacetone)palladium (0), 19.69 g (204.91 mmol) of sodium tert-butoxide, and 8.29 g (20.49 mmol) of tri-tert-butylphosphine solution (50%) were dissolved in 260 mL of O-xylene and stirred for 24 hours under reflux. After the reaction was completed, the reaction product was cooled to room temperature and filtered under reduced pressure through silica gel. The filtrate was concentrated under reduced pressure. The product obtained therefrom was separated by silica gel column chromatography to obtain 27.31 g (yield of 76%) of Intermediate (B).

LC-Mass (Calcd: 351.11 g/mol, Found: M+1=352 g/mol)

3) Synthesis of Intermediate (C)

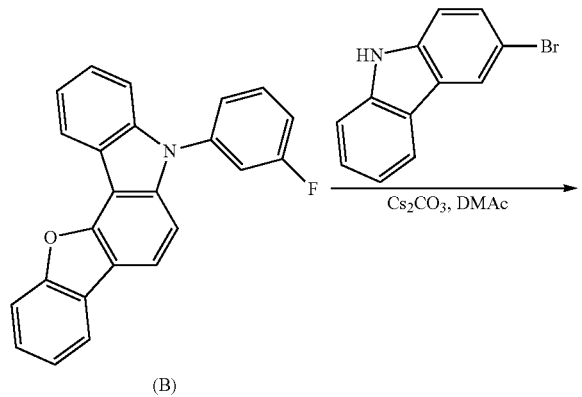

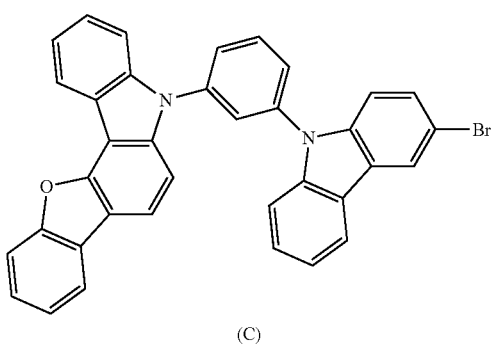

26.10 g (74.29 mmol) of Intermediate (B), 14.06 g (57.15 mmol) of 3-bromo-9H-carbazole, and 37.24 g (114.29 mmol) of caesium carbonate were dissolved in 145 mL of dimethylacetamide and stirred for 24 hours under reflux. After the reaction was completed, the reaction product was cooled to room temperature, precipitated in methanol, filtered, and then dried. The product obtained therefrom was dissolved in dichlorobenzene and filtered under reduced pressure through silica gel. The filtrate was concentrated under reduced pressure and taken out in a state in which a small amount of solvent remained. The resultant obtained therefrom was stirred at room temperature for a day, and recrystallized to obtain 25.60 g (yield of 78%) of Compound (C).

LC-Mass (Calcd: 576.08 g/mol, Found: M+1=577 g/mol)

4) Synthesis of Compound 327

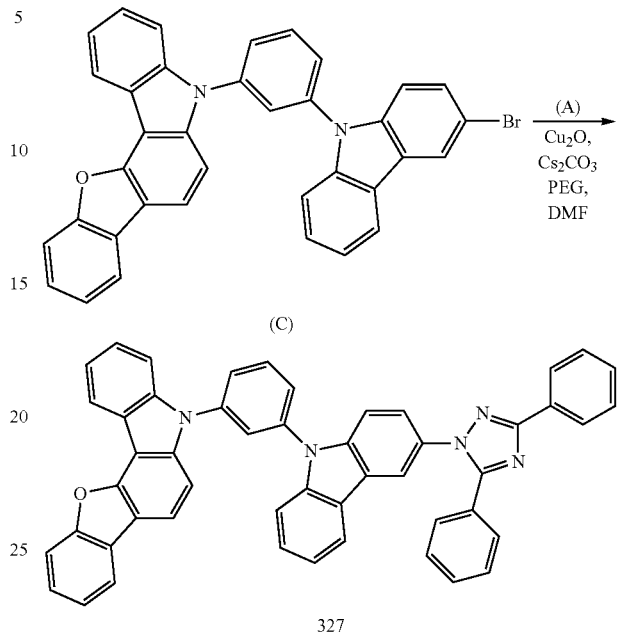

12.07 g (20.90 mmol) of Intermediate (C), 6.01 g (27.17 mmol) of Intermediate (A), 0.15 g (1.04 mmol) of copper(I) oxide, 9.53 g (29.26 mmol) of caesium carbonate, 0.75 g (3.13 mmol) of ligand, and 5.09 g (10.45 mmol) of PEG were dissolved in 25 mL of dimethylformamide and stirred for 24 hours under reflux. After the reaction was completed, the reaction product was cooled to room temperature and added to a mixed solution in which methanol and water were mixed at a ratio of 1:1. The mixture was precipitated, filtered, and then dried. The product obtained therefrom was separated by silica gel column chromatography and recrystallized in a dichloromethane/n-hexane condition to obtain 2.30 g (yield of 15%) of Compound 327.

LC-Mass (Calcd: 717.25 g/mol, Found: M+1=718 g/mol)

Synthesis Example 3: Synthesis of Compound 322

1) Synthesis of Intermediate (D)

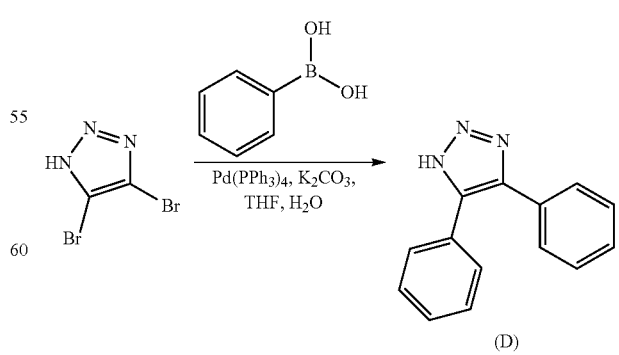

15.38 g (67.79 mmol) of 4,5-dibromo-1H-1,2,3-triazole, 24.80 g (203.38 mmol) of phenylboronic acid, 7.83 g (6.78 mmol) of tetrakis(triphenylphosphine)palladium(0), and 18.74 g (135.59 mmol) of potassium carbonate were added to a mixed solution including 170 mL of tetrahydrofuran and 70 mL of water, and stirred under reflux. After the reaction was completed, the reaction product was cooled to room temperature, and an aqueous solution layer was removed therefrom by extraction. The resultant was filtered under reduced pressure through silica gel, and the filtrate was concentrated under reduced pressure. The product obtained therefrom was separated by silica gel column chromatography to obtain 7.31 g (yield of 49%) of Intermediate (D).

LC-Mass (Calcd: 221.10 g/mol, Found: M+1=222 g/mol)

2) Synthesis of Compound 322

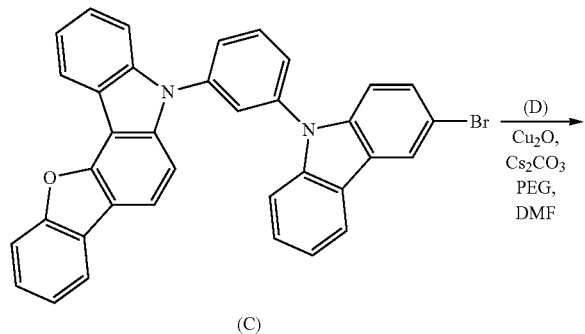

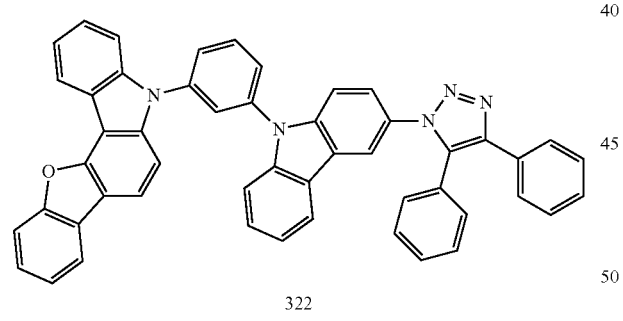

12.07 g (20.90 mmol) of Intermediate (C), 6.01 g (27.17 mmol) of Intermediate (D), 0.15 g (1.04 mmol) of copper(I) oxide, 9.53 g (29.26 mmol) of caesium, carbonate, 0.75 g (3.13 mmol) of ligand, and 5.09 g (10.45 mmol) of PEG were dissolved in 25 mL of dimethylformamide and stirred for 24 hours under refluxed. After the reaction was completed, the reaction product was cooled to room temperature and added to a mixed solution in which. Methanol and water were mixed at a ratio of 1:1. The mixture was precipitated, filtered, and then dried. The product obtained therefrom was separated by silica gel column chromatography and recrystallized in a dichloromethane/n-hexane condition to obtain 1.32 g (yield of 9%) of Compound 322.

LC-Mass (Calcd: 717.25 g/mol, Found: M+1=718 g/mol)

Synthesis Example 4: Synthesis of Compound 238

1) Synthesis of Intermediate (E)

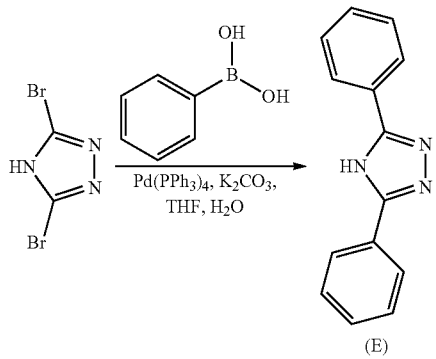

3,5-dibromo-4H-1,2,4-triazole 45.63 g (201.22 mmol), 73.57 g (603.36 mmol) of phenylboronic acid, 23.24 g (20.11 mmol) of tetrakis(triphenylphosphine)palladium(0), and 55.59 g (402.24 mmol) of potassium carbonate were added to a mixed solution including 500 mL of tetrahydrofuran and 200 mL of water and stirred under reflux. After the reaction was completed, the reaction product was cooled to room temperature, and an aqueous solution layer was removed therefrom by extraction. The resultant was filtered under reduced pressure through silica gel, and the filtrate was concentrated under reduced pressure. The product obtained therefrom was separated by silica gel column chromatography to obtain 26.10 g (yield of 59%) of Intermediate (E).

LC-Mass (Calcd: 221.10 g/mol, Found: M+1=222 g/mol)

2) Synthesis of Intermediate (F)

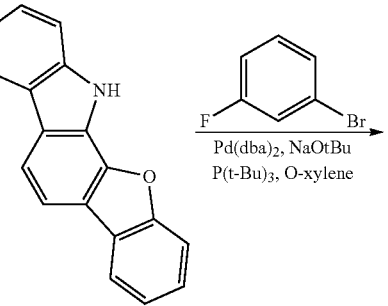

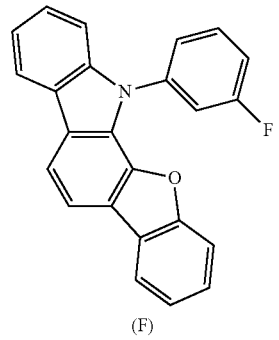

13.18 g (51.23 mmol) of 12H-benzofuro[2,3-a]carbazole, 11.65 g (66.60 mmol) of 1-bromo-3-fluorobenzene, 2.95 g (5.12 mmol) of bis(dibenzylideneacetone)palladium(0), 9.85 g (102.46 mmol) of sodium tert-butoxide, and 4.15 g (10.25 mmol) of tri-tert-butylphosphine solution (50%) were dissolved in 130 mL of O-xylene and stirred for 24 hours under reflux. After the reaction was completed, the reaction product was cooled to room temperature and filtered under reduced pressure through silica gel. The filtrate was concentrated under reduced pressure. The product obtained therefrom was separated by silica gel column chromatography to obtain 13.21 g (yield of 73%) of Intermediate (F).

LC-Mass (Calcd: 351.11 g/mol, Found: M+1=352 g/mol)

3) Synthesis of Intermediate (G)

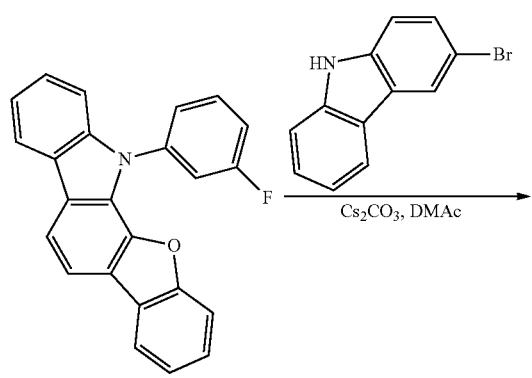

(F)

4) Synthesis of Compound 238

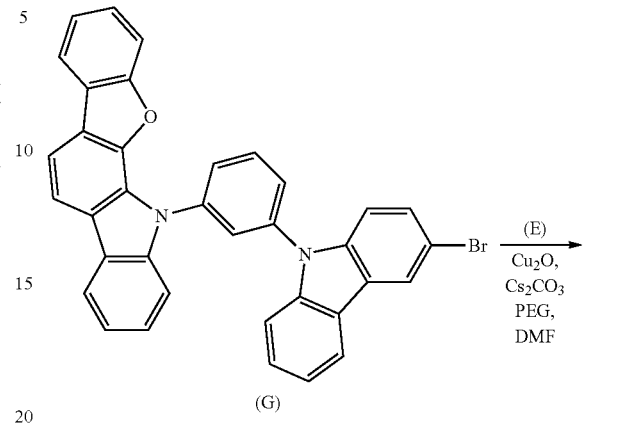

(G)

13.45 g (38.27 mmol) of Intermediate (F), 7.25 g (29.44 mmol) of 3-bromo-9H-carbazole, and 19.18 g (58.88 mmol) of caesium carbonate were dissolved in 75 mL of dimethylacetamide and stirred for 24 hours under reflux. After the reaction was completed, the reaction product was cooled to room temperature, precipitated in methanol, filtered, and then dried. The product obtained therefrom was dissolved in dichlorobenzene and filtered under reduced pressure through silica gel. The filtrate was concentrated under reduced pressure and taken out in a state in which a small amount of solvent remained. The resultant obtained therefrom was stirred at room temperature for a day, nd recrystallized to obtain 12.68 g (yield of 75%) of Compound (G).

LC-Mass (Calcd: 576:08 g/mol, Found: M+1=577 g/mol)

12.07 g (20.90 mmol) of Intermediate (G), 6.01 g (27.17 mmol) of Intermediate (E), 0.15 g (1.04 mmol) of copper(I) oxide, 9.53 g (29.26 mmol) of caesium carbonate, 0.75 g (3.13 mmol) of ligand, and 5.09 g (10.45 mmol) of PEG were dissolved in 26 mL of dimethylformamide and stirred for 24 hours under reflux. After the reaction was completed, the reaction product was cooled to room temperature and added to a mixed solution in which methanol and water were mixed at a ratio of 1:1. The mixture was precipitated, filtered, and then dried. The product obtained therefrom was separated by silica gel column chromatography and recrystallized in a dichloromethane/n-hexane condition to obtain 3.22 g (yield of 21%) of Compound 238.

LC-Mass (Calcd: 717.25 g/mol, Found: M+1=718 g/mol)'

Synthesis Example 5: Synthesis of Compound 67

1) Synthesis of Intermediate (H)

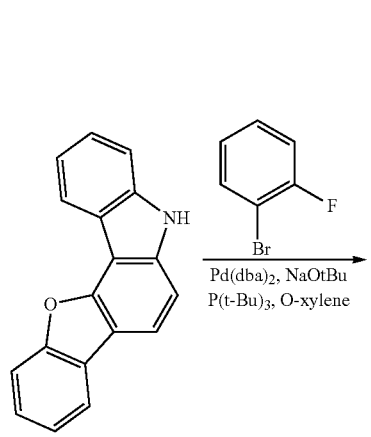

2) Synthesis of Intermediate (I)

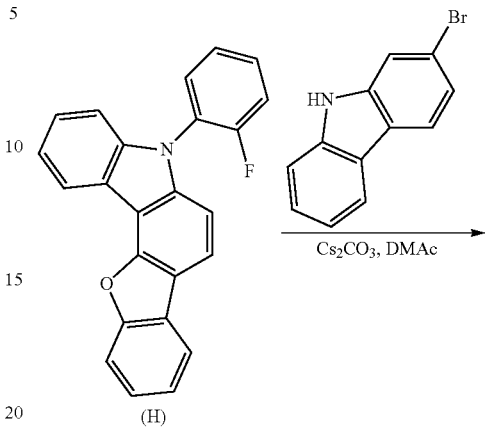

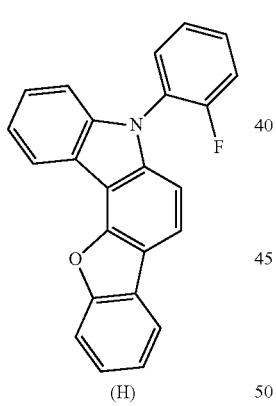

(H)

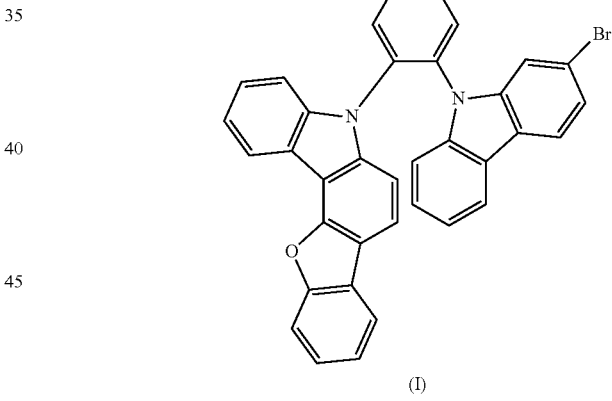

(I)

23.43 g (91.07 mmol) of 5H-benzofuro[3,2-c]carbazole, 20.72 g (118.39 mmol) of 1-bromo-2-fluorobenzene, 5.24 g (9.11 mmol) of bis(dibenzylideneacetone)palladium(0), 17.50 g (182.14 mmol) of sodium tert-butoxide, and 7.37 g (18.21 mmol) of tri-tert-butylphosphine solution (50%) were dissolved in 230 mL of O-xylene and stirred for 24 hours under reflux. After the reaction was completed, the reaction product was cooled to room temperature and filtered under reduced pressure through silica gel. The filtrate was concentrated under reduced pressure. The product obtained therefrom was separated by silica gel column chromatography to obtain 18.60 g (yield of 58%) of Intermediate (H).

LC-Mass (Calcd: 351.11 g/mol, Found: M+1=352 g/mol)

15.82 g (45.02 mmol) of Intermediate (H), 8.52 g (34.63 mmol) of 2-bromo-9H-carbazole, and 22.57 g (69.27 mmol) of caesium carbonate were dissolved in 90 mL of dimethylacetamide and stirred for 24 hours under reflux. After the reaction was completed, the reaction product was cooled to room temperature, precipitated in methanol, filtered, and then dried. The product obtained therefrom was dissolved in dichlorobenzene and filtered under reduced pressure through silica gel. The filtrate was concentrated under reduced pressure and taken out in a state in which a small amount of solvent remained. The resultant obtained therefrom was stirred at room temperature for a day and recrystallized to obtain 9.87 g (yield of 49%) of Compound (I).

LC-Mass (Calcd: 576.08 g/mol, Found: M+1=577 g/mol)

3) Synthesis of Compound 67

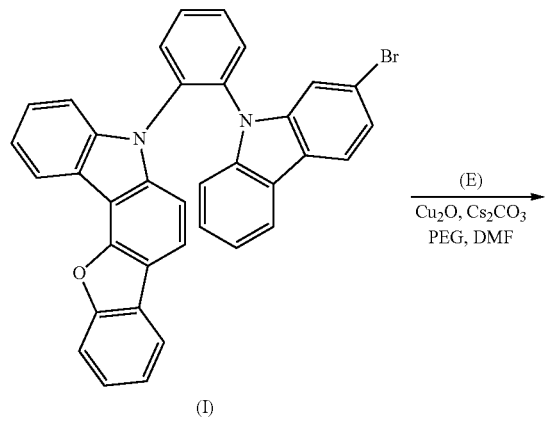

(I)

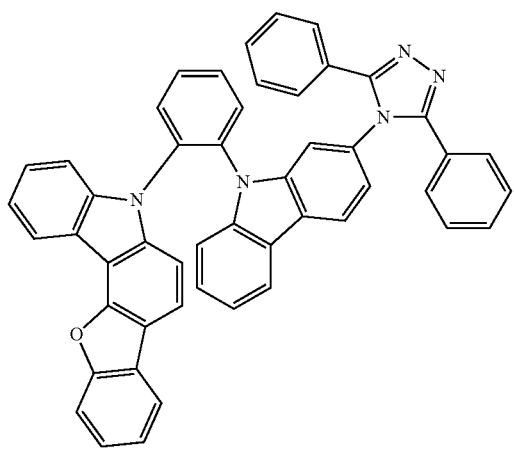

67

9.65 g (16.72 mmol) of Intermediate (I), 4.81 g (21.73 mmol) of Intermediate (E), 0.12 g (0.84 mmol) of copper(I) oxide, 7.63 g (23.40 mmol) of caesium carbonate, 0.60 g (2.51 mmol) of ligand, and 4.07 g (8.36 mmol) of PEG were dissolved in 21 mL of dimethylformamide and stirred for 24 hours under reflux. After the reaction was completed, the reaction product was cooled to room temperature and added to a mixed solution in which methanol and water were mixed at a ratio of 1:1. The mixture was precipitated, filtered, and then dried. The product obtained therefrom was separated by silica gel column chromatography and recrystallized in a dichloromethane/n-hexane condition to obtain 2.33 g (yield of 19%) of Compound 67.

LC-Mass (Calcd: 717.25 g/mol, Found: M+1=718 g/mol)

Comparative Synthesis Example 1: Synthesis of Compound A

1) Synthesis of Intermediate (J)

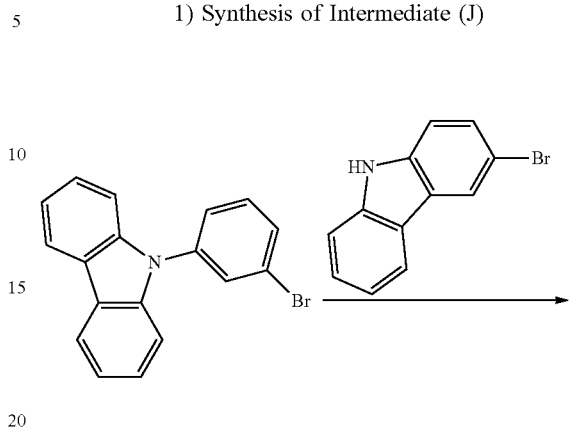

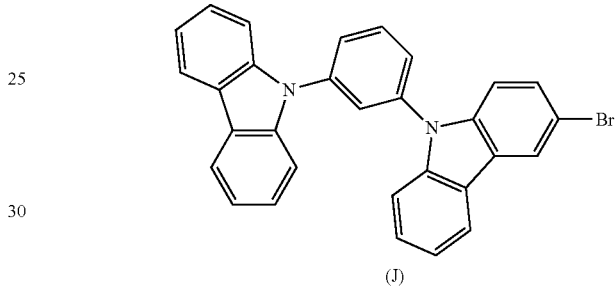

(J)

10.51 g (42.69 mmol) of 3-bromo-9H-carbazole, 20.63 g (64.04 mmol) of 9-(3-bromophenyl)-9H-carbazole, 8.13 g (42.69 mmol) of copper(I) iodide, 23.60 g (170.76 mmol) of potassium carbonate, and 15.39 g (85.38 mmol) of 1,10-phenantholine were dissolved in 110 mL of O-xylene and stirred for 24 hours under reflux. After the reaction was completed, the reaction product was cooled to room temperature and filtered under reduced pressure through silica gel. The filtrate was concentrated under reduced pressure. The product obtained therefrom was separated by silica gel column chromatography to obtain 10.96 g (yield of 73%) of Intermediate (J).

LC-Mass (Calcd: 486.07 g/mol, Found: M+1=487 g/mol)

2) Synthesis of Compound A

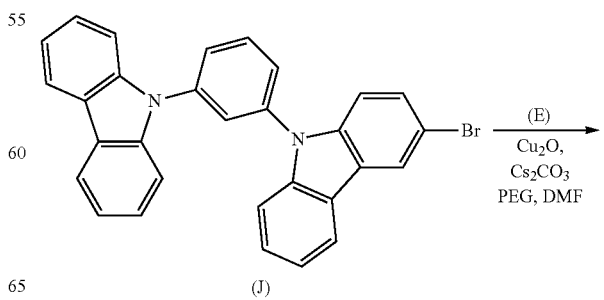

(J)

-continued

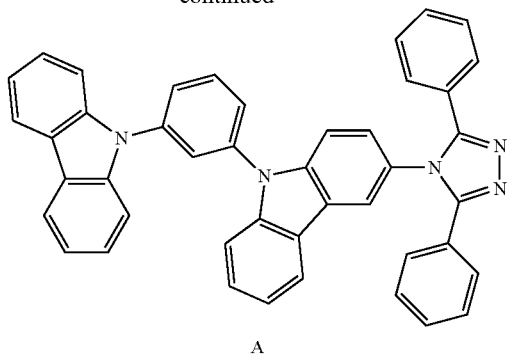

A 9.32 g (19.12 mmol) of Intermediate (J), 5.50 g (24.85 mmol) of Intermediate (E), 0.14 g (0.96 mmol) of copper(I) oxide, 8.72 g (26.76 mmol) of caesium carbonate, 0.69 g (2.87 mmol) of ligand, and 4.66 g (9.56 mmol) of PEG were dissolved in 24 mL of dimethylformamide and stirred for 24 hours under reflux. After the reaction was completed, the reaction product was cooled to room temperature and added to a mixed solution in which methanol and water were mixed at a ratio of 1:1. The mixture was precipitated, filtered, and then dried. The product obtained therefrom was separated by silica gel column chromatography and recrystallized in a dichloromethane/n-hexane condition to obtain 5.87 g (yield of 49%) of Compound A.

LC-Mass (Calcd: 627.24 g/mol, Found: M+1=628 g/mol)

Example 1

A glass substrate, on which a 1,500 Angstrom (Å) ITO electrode (first electrode, anode) was formed, was washed with distilled water sonification. When the washing with distilled water was completed, sonification washing was performed using a solvent, such as iso-propyl alcohol, acetone, or methanol. The resultant was dried and then transferred to a plasma washer, and the resultant substrate was washed with oxygen plasma for 5 minutes and then, transferred to a vacuum depositing device.

Compound HT3 and Compound HP-1 were co-deposited on the ITO electrode of the glass substrate to form a hole injection layer having a thickness of 100 Å, Compound HT3 was deposited on the hole injection layer to form a hole transport layer having a thickness of 1,300 Å, and mCP was deposited on the hole transport layer to form an electron blocking layer having a thickness of 100 Å, thereby forming a hole transport region.

Compound 258 (host) and FIr6 (dopant, 10 weight %) were co-deposited on the hole transport region to form an emission layer having a thickness of 400 Å.

BCP was vacuum-deposited on the emission layer to form a hole blocking layer having a thickness of 100 Å, Compound ET3 and LiQ were vacuum-deposited on the hole blocking layer to form an electron transport layer having a thickness of 300 Å, LiQ was deposited on the electron transport layer to form an electron injection layer having a thickness of 10 Å, and Al was vacuum-deposited on the electron injection layer to form an Al second electrode (cathode) having a thickness of 1,200 Å, thereby completing the manufacture of an organic light-emitting device.

Examples 2 to 5 and Comparative Example 1

Organic light-emitting devices were manufactured, in the same manner as in Example 1, except that Compounds shown in Table 2 were each used instead of Compound 1 as a host in forming an emission layer.

Evaluation Example 1: Evaluation of Characteristics of Organic Light-Emitting Devices The change in current density, the change in luminance, and luminescent efficient with respect to the voltage in the organic light-emitting devices manufactured according to Examples 1 to 5 and Comparative Example 1 were measured. Specific measurement methods are as follows, and results thereof are shown in Table 2.

(1) Change in Current Density According to Voltage

Regarding the manufactured organic light-emitting device, a current flowing in a unit device was measured by using a current-voltage meter while a voltage was raised from 0 volts (V) to 10 V, and the measured current value was divided by an area.

(2) Measurement of Change in Luminance According to Voltage

Regarding the manufactured organic light-emitting device, luminance was measured by using Minolta Cs-1, 000A while a voltage was raised from 0 V to 10 V.

(3) Measurement of Luminescent Efficiency

Current efficiency (cd/A) was measured at the same current density (10 mA/cm$^2$) by using luminance, current density, and voltage measured according to (1) and (2).

(4) Measurement of Durability

The time that lapsed when luminance was 95% of initial luminance (100%) was evaluated.

The driving voltage, current efficiency, and durability in Table 2 were relative values when the driving voltage, current efficiency, and durability of the organic light-emitting device manufactured according to Comparative Example 1 were 100%.

TABLE 2

| | Host | Driving voltage (relative value) | Current efficiency (relative value) | Durability (relative value) | Emission color |
|---|---|---|---|---|---|
| Example 1 | Compound 258 | 95 | 115 | 123 | Blue |
| Example 2 | Compound 327 | 95 | 103 | 120 | Blue |
| Example 3 | Compound 322 | 102 | 107 | 108 | Blue |
| Example 4 | Compound 238 | 100 | 102 | 105 | Blue |
| Example 5 | Compound 67 | 98 | 112 | 121 | Blue |
| Comparative Example 1 | Compound A | 100 | 100 | 100 | Blue |

Evaluation Example 2: Evaluation of Thermal Characteristics

Thermal analysis (N$_2$ atmosphere, temperature range: room temperature ID 800° C. (10° C./min)-TGA, room temperature to 400° C.-DSC, pan type: Pt Pan in disposable Al Pan (TGA), disposable Al pan (DSC)) was performed on Compound 258, Compound A, and Compound B by using thermogravimetric analysis (TGA) and differential scanning calorimetry (DSC), and results thereof are shown in Table 3. Referring to Table 3, it is confirmed that Compound 258 has excellent thermal stability.

Table 3

| Compound | Tg (° C.) | T_d (° C.) |
|---|---|---|
| Compound 258 | 175 | 420 |
| Compound A | 125 | 385 |
| Compound B | 85 | — |

A

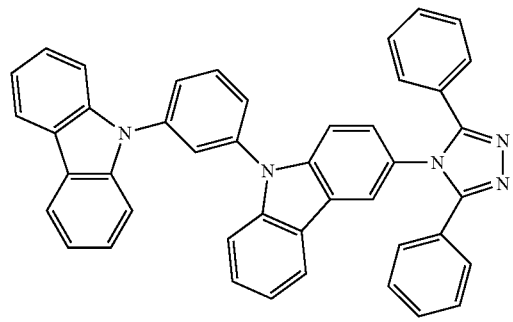 [SMILES: c1ccc(-c2nnc(-c3ccccc3)n2-c2ccc3c(c2)c2ccccc2n3-c2cccc(-n3c4ccccc4c4ccccc43)c2)cc1]

B

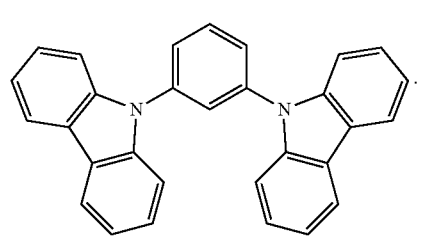 [SMILES: c1cc(-n2c3ccccc3c3ccccc32)cc(-n2c3ccccc3c3ccccc32)c1]

In one or more embodiments, a condensed cyclic compound has excellent electric characteristics and thermal stability. Accordingly, an organic light-emitting device including the condensed cyclic compounds has a low driving voltage, high efficiency, high brightness, a long lifespan, and high color purity.

It should be understood that embodiments described herein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present description as defined by the following claims.

What is claimed is:

1. A condensed cyclic compound represented by Formula 1:

Ar₁——(L₁)ₘ₁—Ar₂    Formula 1

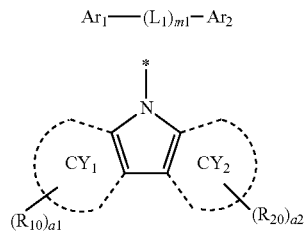

Formula 2

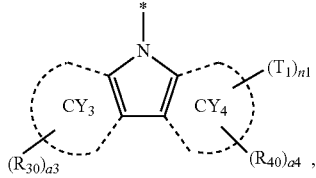

Formula 3 wherein, in Formulae 1 to 3,
$L_1$ is a substituted or unsubstituted $C_5$-$C_{60}$ carbocyclic group or a $C_2$-$C_{60}$ heterocyclic group,
m1 is an integer of 1 to 5,
$Ar_1$ is a group represented by Formula 2,
$Ar_2$ is a group represented by Formula 3,
$T_1$ is a group represented by one selected from Formulae 5-1 to 5-7:

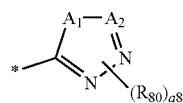 5-1

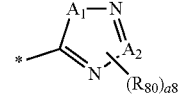 5-2

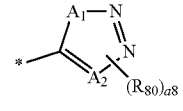 5-3

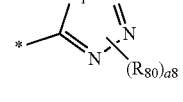 5-4

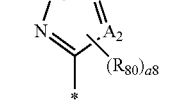 5-5

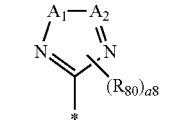 5-6

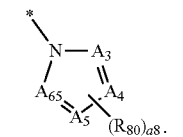 5-7 wherein, in formulae 5-1 to 5-7,
$A_1$ is O, S, or N,
$A_2$ is C or Si,
$A_3$ to $A_6$ is N, C, or Si, wherein at least two selected from $A_3$ to $A_6$ are each N,
$R_{80}$ is selected from:
hydrogen, deuterium, —F, —Cl, —Br, —I, a cyano group, a $C_1$-$C_{20}$ alkyl group, and a $C_1$-$C_{20}$ alkoxy group;
a $C_1$-$C_{20}$ alkyl group one a $C_1$-$C_{20}$ alkoxy group, each substituted with at least one selected from deuterium, a cyano group, a phenyl group, a biphenyl group, a terphenyl group, and a naphthyl group, a phenyl group, a biphenyl group, a terphenyl group, a naphthyl group, a fluorenyl group, a carbazolyl group, a dibenzofuranyl group, and a dibenzothiophenyl group, and a phenyl group, a biphenyl group, a terphenyl group, a naphthyl group, a group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, and a naphthyl group, a8 an integer of 1 to 3, and

* indicates a binding see to a neighboring atom, n1 is an integer of 1 to 5, ring $CY_1$ to ring $CY_4$ are each independently a $C_6$-$C_{60}$ carbocyclic group or a $C_2$-$C_{60}$ heterocyclic group, wherein ring $CY_1$ is a $C_6$-$C_{60}$ carbocyclic group having two or more rings or a $C_2$-$C_{60}$ heterocyclic group having two or more rings, $R_{10}$, $R_{20}$, $R_{30}$, and $R_{40}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_1$)($Q_2$)($Q_3$), —N($Q_4$)($Q_5$), and —B($Q_6$)($Q_7$), a1 to a4 are each independently an integer of 1 to 10,

* indicates a binding site to a neighboring atom, at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group is selected from:

deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from deuterium, —F, —Cl, —Br, —I, —$CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{11}$)($Q_{12}$)($Q_{13}$), —N($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from deuterium, —F, —Cl, —Br, —I, $CD_3$, —$CD_2H$, —$CDH_2$, —$CF_3$, —$CF_2H$, —$CFH_2$, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —Si($Q_{21}$)($Q_{22}$)($Q_{23}$), —N($Q_{24}$)($Q_{25}$), and —B($Q_{26}$)($Q_{27}$); and —Si($Q_{31}$)($Q_{32}$)($Q_{33}$), —N($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

2. The condensed cyclic compound of claim 1, wherein $L_1$ is a group represented by one selected from Formulae 4-1 to 4-3:

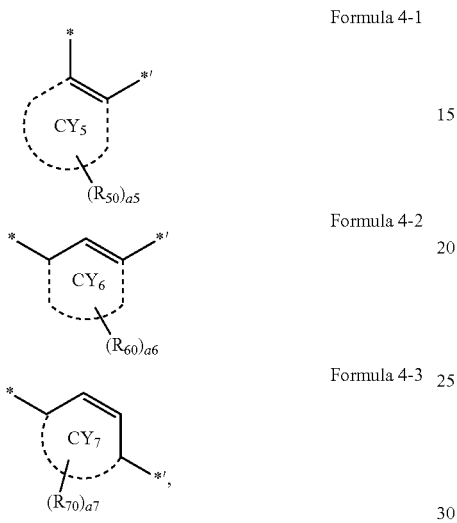

Formula 4-1

Formula 4-2

Formula 4-3 wherein, in Formulae 4-1 to 4-3,

CY$_5$ to CY$_7$ are each independently selected from a $C_5$-$C_{30}$ carbocyclic group and a $C_2$-$C_{60}$ heterocyclic group, $R_{50}$, $R_{60}$, and $R_{70}$ are each independently selected from hydrogen, deuterium, —F, —Cl, —Br, —I, a hydroxyl group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_{41}$)($Q_{42}$)($Q_{43}$), —N($Q_{44}$)($Q_{45}$), and —B($Q_{46}$)($Q_{47}$), $Q_{41}$ to $Q_{47}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group, and a5 to a7 are each independently an integer of 0 to 10, and * and *' each indicate a binding site to a neighboring atom.

3. The condensed cyclic compound of claim 2, wherein CY$_5$ to CY$_7$ are each independently selected from a benzene group, a naphthalene group, a fluorene group, a carbazole group, a dibenzofuran group, and a dibenzothiophene group.

4. The condensed cyclic compound of claim 1, wherein $L_1$ is a group represented by one selected from Formulae 40-1 to 40-12:

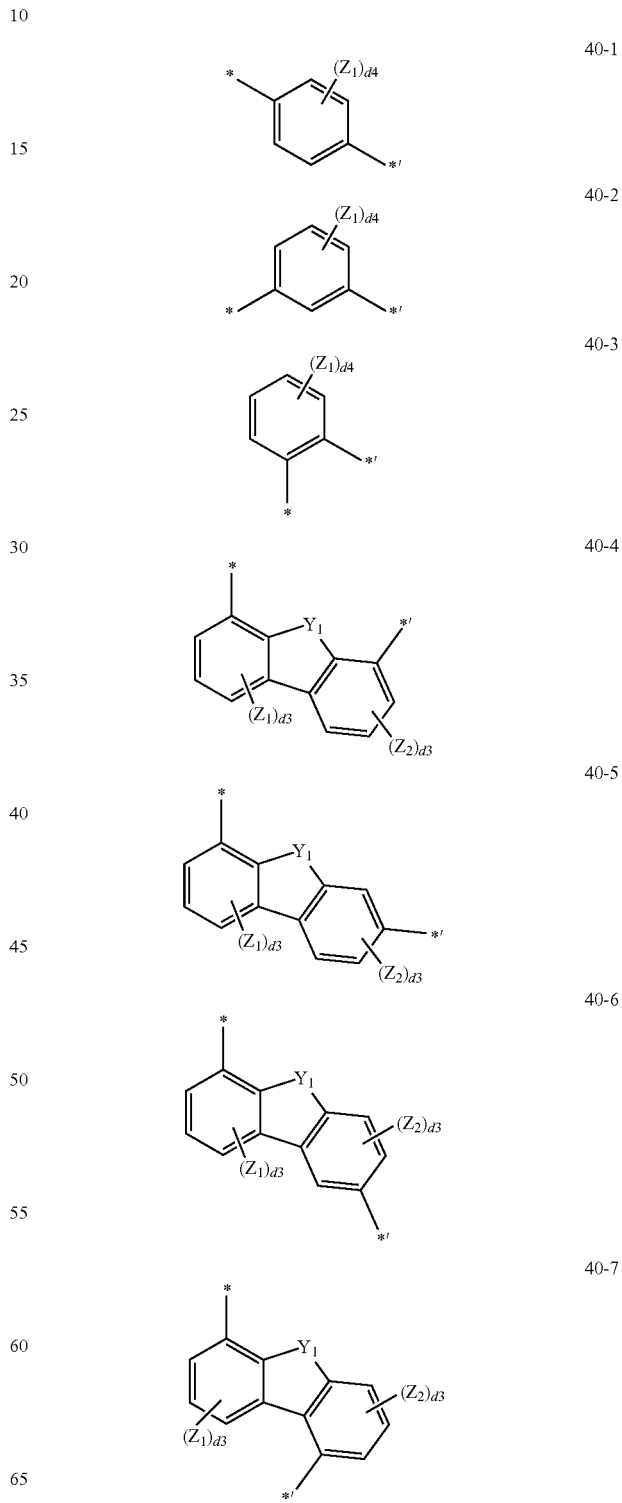

40-1

40-2

40-3

40-4

40-5

40-6

40-7

-continued

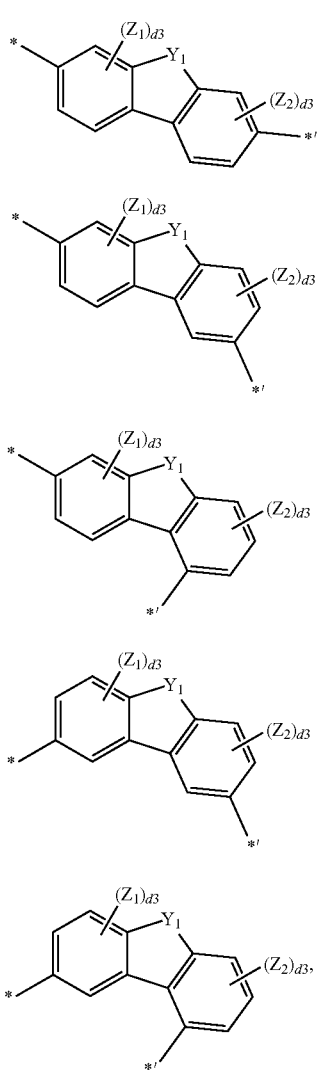

40-8

40-9

40-10

40-11

40-12 wherein, in Formulae 40-1 to 40-12, $Y_1$ is O, S, $C(Z_3)(Z_4)$, $N(Z_5)$, or $Si(Z_6)(Z_7)$, $Z_1$ to $Z_7$ are each independently selected from hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a biphenyl group, a terphenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, and —$Si(Q_{53})(Q_{54})(Q_{55})$, $Q_{53}$ to $Q_{55}$ are each independently selected from a $C_1$-$C_{10}$ alkyl group, a $C_1$-$C_{10}$ alkoxy group, a phenyl group, a biphenyl group, a terphenyl group, and a naphthyl group, d3 is an integer of 1 to 3, d4 is an integer of 1 to 4, and

* and *' each indicate a binding site to a neighboring atom.

5. The condensed cyclic compound of claim 1, wherein m1 is 1 to 3.

6. The condensed cyclic compound of claim 1, wherein $T_1$ is a group represented by one selected from Formulae 6-1 to 6-8:

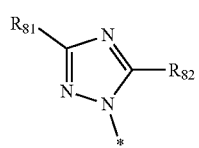

6-1

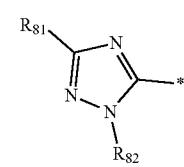

6-2

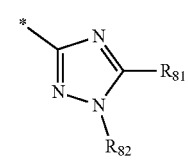

6-3

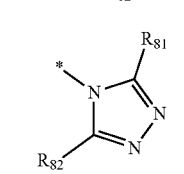

6-4

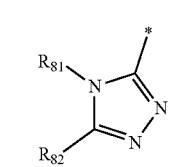

6-5

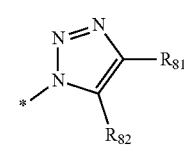

6-6

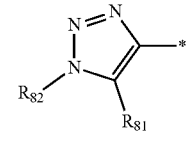

6-7

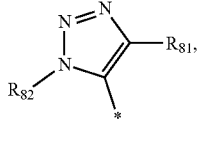

6-8 wherein, in Formulae 6-1 to 6-8, $R_{81}$ and $R_{82}$ are each independently selected from:

hydrogen, deuterium, —F, —Cl, —Br, —I, a cyano group, a $C_1$-$C_{20}$ alkyl group, and a alkoxy group;

a $C_1$-$C_{20}$ alkyl group and a $C_1$-$C_{20}$ alkoxy group, each substituted with at least one selected from deuterium, a cyano group, a phenyl group, a biphenyl group, a terphenyl group, and a naphthyl group;

a phenyl group, a biphenyl group, a terphenyl group, a naphthyl group, a fluorenyl group, a carbazolyl group, a dibenzofuranyl group, and a dibenzothiophenyl group; and a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, —F, —Cl, —Br, —I, a cyano group, a $C_1$-$C_{20}$ alkyl group, a $C_1$-$C_{20}$ alkoxy group, a phenyl group, a biphenyl group, a terphenyl group, and a naphthyl group, and

* indicates a binding site to a neighboring atom.

7. The condensed cyclic compound of claim 1, wherein n1 is 1.

8. The condensed cyclic compound of claim 1, wherein $CY_1$ is selected from a naphthalene group, a fluorene group, a carbazole group, a dibenzofuran group, and a dibenzothiophene group, and $CY_2$ and $CY_3$ are each independently selected from a benzene group, a naphthalene group, a fluorene group, a carbazole group, a dibenzofuran group, and a dibenzothiophene group.

9. The condensed cyclic compound of claim 1, wherein $CY_4$ is a benzene group.

10. The condensed cyclic compound of claim 1, wherein $A_1$ is selected from groups represented by Formulae 2-1 to 2-6, and $Ar_2$ is selected from groups represented by Formulae 3-1 to 3-7:

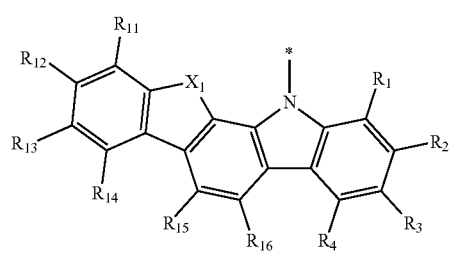

2-1

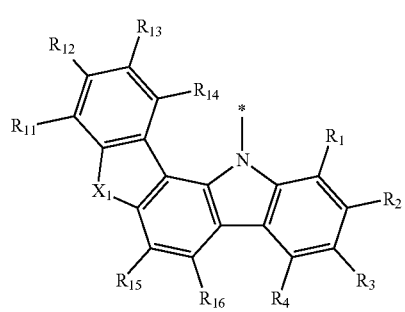

2-2

-continued

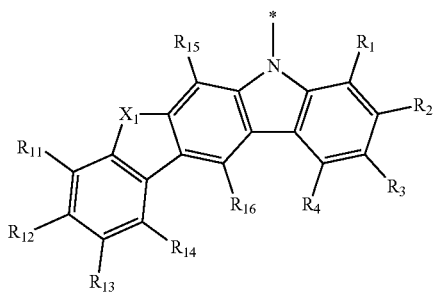

2-3

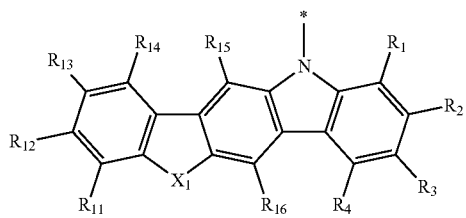

2-4

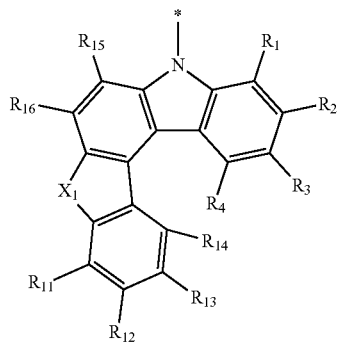

2-5

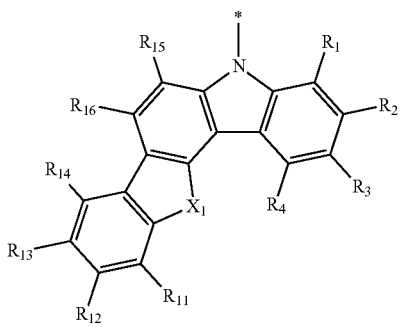

2-6

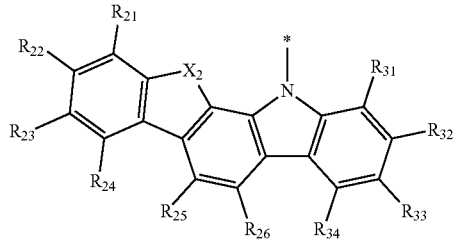

3-1

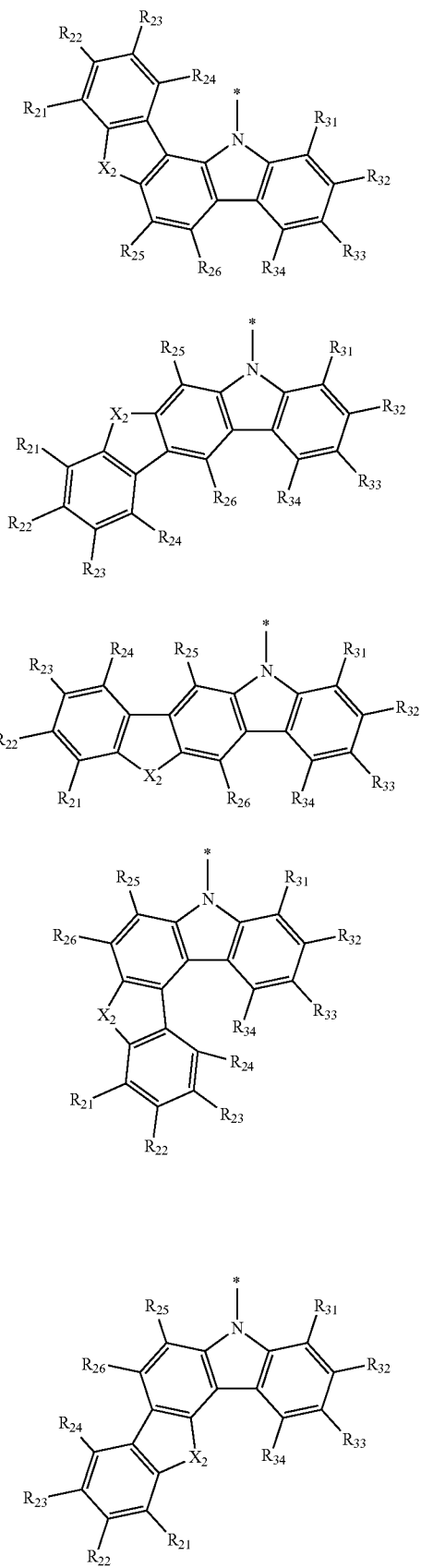

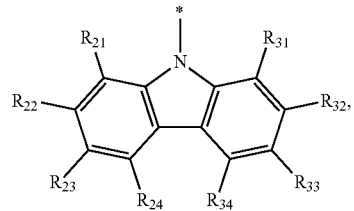

wherein, in Formulae 2-1 to 2-7 and 3-1 to 3-7,
$X_1$ is $C(R_{17})(R_{18})$, $N(R_{19})$, O, or S,
$X_2$ is $C(R_{27})(R_{28})$, $N(R_{29})$, O, or S,
$Z_5$ is $C(R_5)(R_6)$,
$R_1$ to $R_6$, $R_{11}$ to $R_{19}$, $R_{21}$ to $R_{29}$, and $R_{31}$ to $R_{34}$ are each independently selected from:

hydrogen, deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienoyrimidinyl group, a phenoxazinyl group, a pyridobenzoxazinyl group, and a pyridobenzothiazinyl group;

a cyclopentyl group, a cyclohexyl group, a cyclopentenyl group, a cyclohexenyl group, a cycloheptenyl group, a phenyl group, a biphenyl group, a terphenyl group, a pentalenyl group, an indenyl group, a naphthyl group, an azulenyl group, a heptalenyl group, an indacenyl group, an acenaphthyl group, a fluorenyl group, a spiro-bifluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienoyrimidinyl group, a phenoxazinyl group, a pyridobenzoxazinyl group, and a pyridobenzothiazinyl group, each substituted with at least one selected from deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a biphenyl group, a terphenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —Si($Q_{31}$)($Q_{32}$)($Q_{33}$), —N($Q_{34}$)($Q_{35}$), and —B($Q_{36}$)($Q_{37}$); and —Si($Q_1$)($Q_2$)($Q_3$), —N($Q_4$)($Q_5$), and —B($Q_6$)($Q_7$), $Q_1$ to $Q_7$ and $Q_{31}$ to $Q_{37}$ are each independently selected from hydrogen, a $C_{20}$ alkyl group, a $C_1$-$C_{20}$ alkoxy group, a phenyl group, a biphenyl group, a terphenyl group, a naphthyl group, a fluorenyl group, a carbazolyl group, a dibenzofuranyl group, and a dibenzothiophenyl group, and

* indicates a binding site to a neighboring atom.

11. The condensed cyclic compound of claim 10, wherein $R_1$ to $R_6$, $R_{11}$ to $R_{19}$, $R_{21}$ to $R_{29}$, and $R_{31}$ to $R_{34}$ are each independently selected from:

hydrogen, deuterium, —F, —Cl, —Br, —I, a cyano group, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from deuterium, —F, —Cl, —Br, —I, a cyano group, a phenyl group, a biphenyl group, a terphenyl group, and a naphthyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group;

a cyclopentyl group, a cyclohexyl group, a cyclopentenyl group, a cyclohexenyl group, a cycloheptenyl group, a phenyl group, a biphenyl group, a terphenyl group, a naphthyl group, a fluorenyl group, a carbazolyl group, a dibenzofuranyl group, and a dibenzothiophenyl group, each substituted with at least one selected from deuterium, a cyano group, a $C_1$-$C_{20}$ alkyl group, a $C_1$-$C_{20}$ alkoxy group, a phenyl group, a biphenyl group, a terphenyl group, a naphthyl group, and —Si($Q_{31}$)($Q_{32}$)($Q_{33}$); and —Si($Q_1$)($Q_2$)($Q_3$), and $Q_1$ to $Q_3$ and $Q_{31}$ to $Q_{33}$ are each independently selected from hydrogen, a $C_1$-$C_{20}$ alkyl group, a $C_1$-$C_{20}$ alkoxy group, a phenyl group, a biphenyl group, a terphenyl group, and a naphthyl group.

12. The condensed cyclic compound of claim 10, wherein $X_1$ is N($R_{19}$), O, or S.

13. The condensed cyclic compound of claim 10, wherein $Ar_2$ is a group represented by Formula 3-7.

14. An organic light-emitting device comprising:
a first electrode;
a second electrode; and
an organic layer disposed between the first electrode and the second electrode and comprising an emission layer,
wherein the organic layer comprises at least one of the condensed cyclic compound represented by Formula 1 in claim 1.

15. The organic light-emitting device of claim 14, wherein the first electrode is an anode,
the second electrode is a cathode,
the organic layer comprises a hole transport region between the first electrode and the emission layer and an electron transport region between the emission layer and the second electrode,
the hole transport region comprises at least one selected from a hole injection layer, a hole transport layer, and an electron blocking layer, and
the electron transport region comprises at least one selected from a hole blocking layer, an electron transport layer, and an electron injection layer.

16. The organic light-emitting device of claim 14, wherein the emission layer comprises the condensed cyclic compound represented by Formula 1.

17. The organic light-emitting device of claim 14, wherein the emission layer comprises a host and a dopant,
the host comprises the condensed cyclic compound represented by Formula 1, and
an amount of the host is larger than an amount of the dopant.

18. The organic light-emitting device of claim 15, wherein the hole transport region comprises the condensed cyclic compound represented by Formula 1.

19. The organic light-emitting device of claim 15, wherein the organic light-emitting device further comprises an electron transport region comprising the condensed cyclic compound represented by Formula 1.

\* \* \* \* \*